(12) United States Patent
Nishimura et al.

(10) Patent No.: US 8,710,174 B2
(45) Date of Patent: Apr. 29, 2014

(54) TRIAZINE RING-CONTAINING POLYMER AND FILM-FORMING COMPOSITION COMPRISING SAME

(71) Applicant: Nissan Chemical Industries, Ltd., Tokyp (JP)

(72) Inventors: Naoya Nishimura, Funabashi (JP); Taku Kato, Funabashi (JP); Masaaki Ozawa, Funabashi (JP); Masahiro Hida, Funabashi (JP); Yasuyuki Koide, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/019,896

(22) Filed: Sep. 6, 2013

(65) Prior Publication Data

US 2014/0008751 A1 Jan. 9, 2014

Related U.S. Application Data

(62) Division of application No. 13/318,792, filed as application No. PCT/JP2010/057761 on May 6, 2010.

(30) Foreign Application Priority Data

| May 7, 2009 | (JP) | 2009-112880 |
| Jun. 15, 2009 | (JP) | 2009-142249 |
| Jul. 24, 2009 | (JP) | 2009-173329 |
| Jul. 29, 2009 | (JP) | 2009-176265 |
| Mar. 29, 2010 | (JP) | 2010-074628 |
| Mar. 29, 2010 | (JP) | 2010-074651 |

(51) Int. Cl.
| *C08G 63/44* | (2006.01) |
| *C08G 73/00* | (2006.01) |
| *C08G 73/06* | (2006.01) |
| *C08K 5/3492* | (2006.01) |
| *C07D 401/12* | (2006.01) |
| *C07D 403/00* | (2006.01) |
| *C08K 5/34* | (2006.01) |

(52) U.S. Cl.
CPC ............ *C08G 73/00* (2013.01); *C08G 73/0644* (2013.01); *C08K 5/3492* (2013.01); *C07D 401/12* (2013.01); *C07D 403/00* (2013.01)
USPC ........... 528/362; 257/432; 514/241; 524/100; 544/211

(58) Field of Classification Search
CPC .. C08G 73/00; C08G 73/0644; C08K 5/3492; C07D 401/12; C07D 403/00
USPC ........... 257/432; 514/241; 524/100; 528/362; 544/211
See application file for complete search history.

(56) References Cited

U.S. PATENT DOCUMENTS

| 5,886,130 A | 3/1999 | Trimmer et al. |
| 5,925,746 A | 7/1999 | Lauk et al. |
| 8,263,541 B2 | 9/2012 | Penninger et al. |
| 2009/0318725 A1 | 12/2009 | Takeuchi |

FOREIGN PATENT DOCUMENTS

| EP | 0 925 319 B1 | 6/1999 |
| JP | 32-3145 B1 | 5/1957 |
| JP | 7-113009 A | 5/1995 |
| JP | 11-71533 A | 3/1999 |
| JP | 2000-53659 A | 2/2000 |
| JP | 2001-503077 A | 3/2001 |
| JP | 2001-167885 A | 6/2001 |
| JP | 2003-301120 A | 10/2003 |
| JP | 2004-156001 A | 6/2004 |
| JP | 2007-246877 A | 9/2007 |
| JP | 2008-24832 A | 2/2008 |
| JP | 2009-263570 A | 11/2009 |

OTHER PUBLICATIONS

Mahapatra et al., "Hyperbranched Aromatic Polyamines with s-Triazine rings," Journal of Applied Polymer Science (2007) vol. 106, pp. 95-102.
Salisu et al., "New Liquid Crystals in the Series of 1,3,5, Triazine Compounds Containing Azobenzene at the Peripheral Arms", Bayero Journal of Pure and Applied Sciences, 3(1), pp. 54-58, Jan. 2010 (accepted Mar. 2010).

*Primary Examiner* — Terressa Boykin
(74) *Attorney, Agent, or Firm* — Birch, Stewart, Kolasch & Birch, LLP

(57) ABSTRACT

A polymer containing a triazine ring-containing repeating unit structure represented by, for example, formula (23) or (24), which alone can achieve high heat resistance, high transparency, high refraction index, high solubility, and low volume shrinkage, without adding a metal oxide.

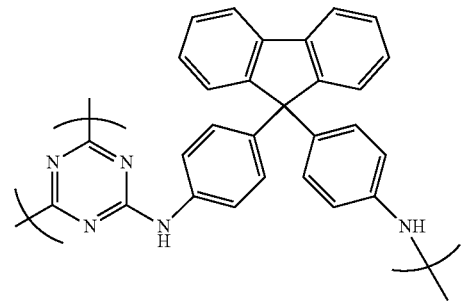

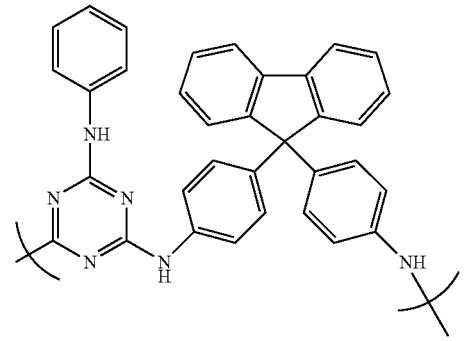

14 Claims, 51 Drawing Sheets

TRIAZINE RING-CONTAINING POLYMER AND FILM-FORMING COMPOSITION COMPRISING SAME

CROSS REFERENCE

The present application is a 37 C.F.R. §1.53(b) divisional of, and claims priority to, U.S. application Ser. No. 13/318, 792, filed Nov. 4, 2011. Application No. 13/318,792 is the national phase under 35 U.S.C. §371 of International Application No. PCT/JP2010/057761, filed on May 6, 2010. Priority is also claimed to Japanese Application No. 2009-112880 filed on May 7, 2009, Japanese Application No. 2009-142249 filed on Jun. 15, 2009, Japanese Application No. 2009-173329 filed on Jul. 24, 2009, Japanese Application No. 2009-176265 filed on Jul. 29, 2009, Japanese Application No. 2010-074628 filed on Mar. 29, 2010 and Japanese Application No. 2010-074651 filed on Mar. 29, 2010. The entire contents of each of these applications is hereby incorporated by reference.

TECHNICAL FIELD

The present invention relates to a triazine ring-containing polymer, and also to a film-forming composition containing it.

BACKGROUND ART

To provide high-molecular compounds with high function, a variety of attempts have been made to date. As a method for providing a high-molecular compound with a high refractive index, for example, it has been practiced to introduce aromatic rings, halogen atoms or sulfur atoms. In particular, high-molecular episulfide compounds with sulfur atoms and high-molecular thiourethane compounds introduced therein have been put into practical use as spectacle lenses of high refractive index.

With a polymer alone, however, it is difficult to design a material of a refractive index higher than 1.7. A method making use of an inorganic metal oxide is, therefore, known as a most promising method for achieving a still higher refractive index.

Methods reported include, for example, a method that achieves an increase in refractive index by using a hybrid material formed by mixing a siloxane polymer with a microparticle-dispersed material in which zirconia, titania or the like is dispersed (Patent Document 1).

Also reported is a method that introduces fused ring skeletons of high refractive index in parts of a siloxane polymer (Patent Document 2).

Numerous attempts have also been made to impart heat resistance to high-molecular compounds. Specifically, it is well known that the heat resistance of a high-molecular compound can be improved by introducing aromatic rings. For example, a polyarylene copolymer with substituted arylene repeating units contained in the backbone thereof has been reported (Patent Document 3). This high-molecular compound is expected to find utility primarily as heat-resistant plastics.

On the other hand, melamine resins are well-known as triazine-based resins. However, they are far lower in decomposition temperature compared with heat-resistant materials such as graphite.

As heat-resistant organic materials formed of carbon and nitrogen, aromatic polyimides and aromatic polyamides have been primarily used to date. However, these materials are not very high in heat-resistant temperature as they have a linear structure.

As nitrogen-containing high-molecular materials having heat resistance, triazine-based fused materials have also been reported (Patent Document 4).

In the meantime, a demand has arisen in recent years for high-functionality, high-molecular materials upon development of electronic devices such as liquid crystal displays, organic electroluminescence (EL) displays, optical semiconductor (LED) devices, solid-state imaging devices, organic thin-film solar cells, dye-sensitized solar cells, and organic thin-film transistors (TFT).

Specific properties to be required include, for example, 1) heat resistance, 2) transparency, 3) high refractive index, 4) high solubility, and 5) lower volume shrinkage rate.

Nonetheless, the above-mentioned spectacle lens materials of high refractive index are generally low in heat resistance, and need to be produced in a temperature range of 200° C. and lower. They are, hence, not suited for processing such as baking at 300° C. under the atmosphere.

Further, high-molecular compounds with aromatic rings or triazine rings introduced therein are generally insufficient in the solubility in solvents, and therefore, are insoluble in resist solvents as safety solvents. On the other hand, materials that exhibit high solubility are generally low in transparency.

On the other hand, materials making use of an inorganic metal oxide can be hardly provided with improved transparency while retaining high refractive index, because refractive index and transparency are in a trade-off correlation.

These materials contain microparticles of different properties, and therefore, involve a problem in that, when subjected to dry processing such as etching or ashing, the etch rate may become unstable, thereby making it difficult to obtain a film of uniform thickness, and upon fabrication of a device, the process margin may become narrow.

Now, highly branched polymers can be roughly divided into hyperbranched polymers and dendrimers.

The term "hyperbranched polymer" means a highly branched polymer having an irregular branched structure obtained by polymerizing, for example, an ABx-type polyfunctional monomer in which A and B are functional groups reactable to each other and the number X of B is 2 or greater.

On the other hand, the term "dendrimer" means a highly branched polymer having a regular branched structure. Hyperbranched polymers are characterized in that compared with dendrimers, they can be easily synthesized and can be readily synthesized in high-molecular forms.

There is an exemplary report that hyperbranched polymers with triazine rings contained therein were synthesized for use as flame retardants (Non-Patent Document 1).

PRIOR ART DOCUMENTS

Patent Documents

Patent Document 1: JP-A 2007-246877
Patent Document 2: JP-A 2008-24832
Patent Document 3: U.S. Pat. No. 5,886,130
Patent Document 4: JP-A 2000-53659

Non-Patent Document

Non-Patent Document 1: Journal of Applied Polymer Science, 106, pp. 95 to 102 (2007)

SUMMARY OF THE INVENTION

Problems to be Solved by the Invention

With the foregoing circumstances in view, the present invention has as objects thereof the provision of a triazine ring-containing polymer capable of achieving high heat resistance, high transparency, high refractive index, high solubility and low volume shrinkage by itself without addition of a metal oxide and a film-forming composition containing the triazine ring-containing polymer.

Means for Solving the Problems

To achieve the above-described objects, the present inventors have enthusiastically conducted research. As a result, it has been found that a polymer containing repeating units having a triazine ring and an aromatic ring can achieve high heat resistance, high transparency, high refractive index, high solubility and low volume shrinkage by itself and is suited as a film-forming composition upon fabrication of an electronic device, leading to the completion of the present invention.

Described specifically, the present invention provides:

1. A triazine ring-containing polymer characterized by including repeating unit structures represented by the following formula (1) or (2):

[Chemical Formula 1]

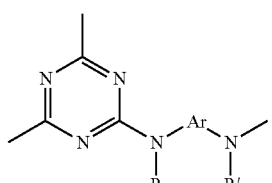

(1)

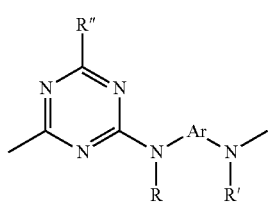

(2)

wherein R and R' independently from each other mean a hydrogen atom or an alkyl, alkoxy, aryl or aralkyl group, R" means an alkyl, aralkyl, aryl, alkylamino, alkoxysilyl-containing alkylamino, aralkylamino, arylamino, alkoxy, aralkyloxy or aryloxy group, and Ar means at least one selected from the group consisting of groups represented by the following formulas (3) to (19):

[Chemical Formula 2]

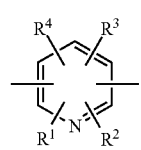

(3)

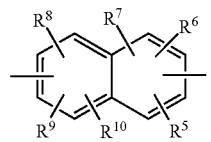

(4)

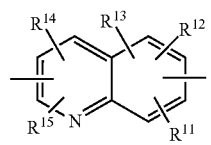

(5)

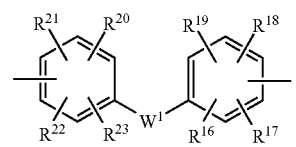

(6)

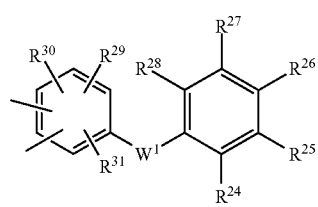

(7)

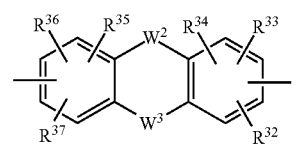

(8)

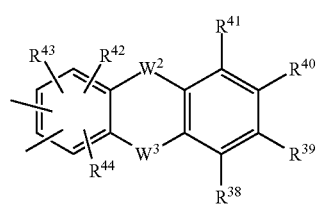

(9)

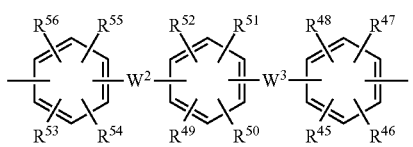

(10)

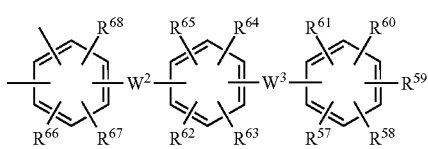

(11)

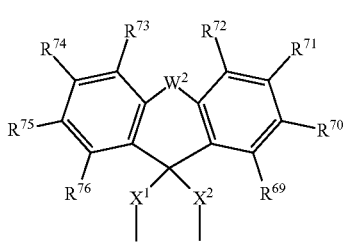

(12)

-continued

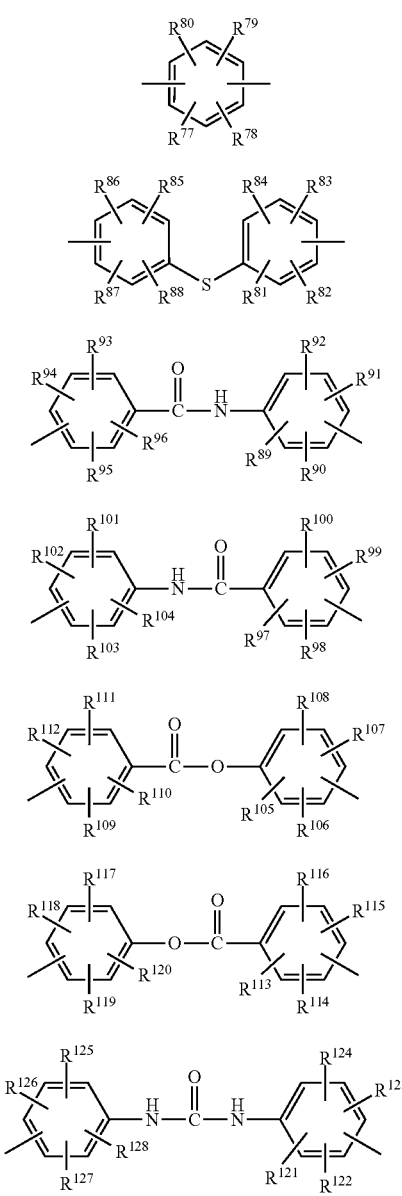

(13)
(14)
(15)
(16)
(17)
(18)
(19)

wherein $R^1$ to $R^{128}$ independently from each other mean a hydrogen or halogen atom, or a carboxyl, sulfone, branched or unbranched C1 to C10 alkyl or branched or unbranched C1 to C10 alkoxy group, $W^1$ means a single bond, C=O or $NR^{129}$ in which $R^{129}$ means a hydrogen atom or a branched or unbranched C1 to C10 alkyl group, $W^2$ and $W^3$ independently from each other mean a single bond, $CR^{130}R^{131}$ in which $R^{130}$ and $R^{131}$ independently from each other mean a hydrogen atom or a branched or unbranched C1 to C10 alkyl group with a proviso that these alkyl groups may be fused together to form a ring, C=O, O, S, SO, $SO_2$, or $NR^{129}$ in which $R^{129}$ has the same meaning as defined above, $X^1$ and $X^2$ independently from each other mean a single bond, a branched or unbranched C1 to C10 alkylene group, or the following formula (20):

[Chemical Formula 3]

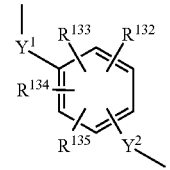

(20)

wherein $R^{132}$ to $R^{135}$ independently from each other mean a hydrogen or halogen atom, or a carboxyl, sulfone, branched or unbranched C1 to C10 alkyl or branched or unbranched C1 to C10 alkoxy group, and $Y^1$ and $Y^2$ independently from each other mean a single bond, or a branched or unbranched C1 to C10 alkylene group.

2. The triazine ring-containing polymer as described above in 1, wherein Ar is at least one selected from the group consisting of the groups represented by the formulas (6) to (12).

3. The triazine ring-containing polymer as described above in 1, wherein Ar is at least one selected from the group consisting of the groups represented by the formulas (8), (9) and (12).

4. The triazine ring-containing polymer as described above in 1, wherein Ar is at least one selected from the group consisting of the groups represented by the formulas (6), (13), and (15) to (19).

5. The triazine ring-containing polymer as described above in 1, wherein Ar is represented by the following formula (21) or (22):

[Chemical Formula 4]

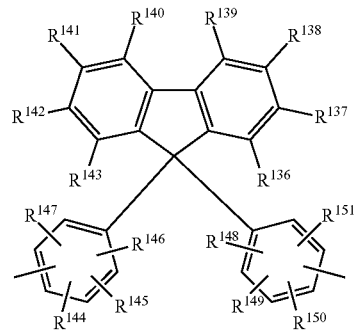

(21)

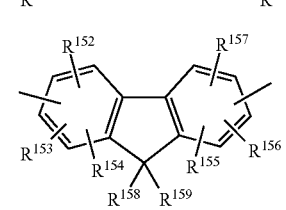

(22)

wherein $R^{136}$ to $R^{159}$ independently from each other mean a hydrogen or halogen atom, a carboxyl or sulfone group, a branched or unbranched C1 to C10 alkyl group with a proviso that $R^{158}$ and $R^{159}$ may be fused together to form a ring, or a branched or unbranched C1 to C10 alkoxy group.

6. The triazine ring-containing polymer as described above in 1, wherein the repeating unit structures are represented by the following formula (23):

[Chemical Formula 5]

(23)

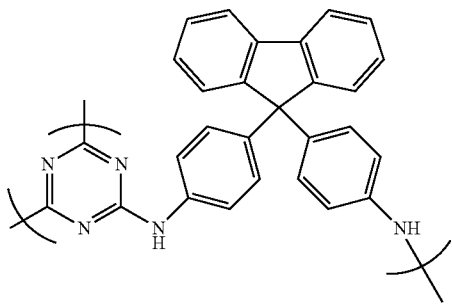

7. The triazine ring-containing polymer as described above in 1, wherein the repeating unit structures are represented by the following formula (24):

[Chemical Formula 6]

(24)

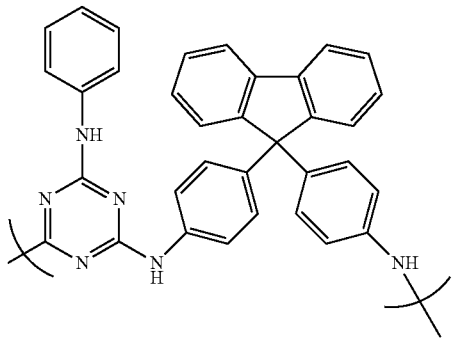

8. The triazine ring-containing polymer as described above in 1, including repeating unit structures represented by the following formula (25):

[Chemical Formula 7]

(25)

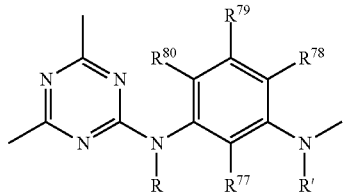

wherein R, R' and $R^{77}$ to $R^{80}$ have the same meanings as defined above.

9. The triazine ring-containing polymer as described above in claim 8, including repeating unit structures represented by the following formula (26):

[Chemical Formula 8]

(26)

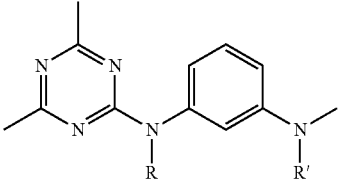

wherein R and R' have the same meanings as defined above.

10. The triazine ring-containing polymer as described above in 8, wherein the repeating unit structures are represented by the following formula (27):

[Chemical Formula 9]

(27)

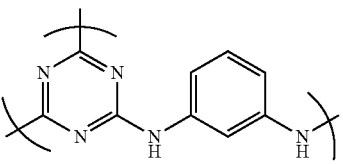

11. The triazine ring-containing polymer as described above in any one of 1 to 10, wherein at least one end thereof is capped by alkyl, aralkyl, aryl, alkylamino, alkoxysilyl-containing alkylamino, aralkylamino, arylamino, alkoxy, aralkyloxy, aryloxy or ester groups.

12. The triazine ring-containing polymer as described above in 11, including at least one terminal triazine ring, which is capped by alkyl, aralkyl, aryl, alkylamino, alkoxysilyl-containing alkylamino, aralkylamino, arylamino, alkoxy, aralkyloxy, aryloxy or ester groups.

13. A film-forming composition including the triazine ring-containing polymer as described above in any one of 1 to 12.

14. A film including the triazine ring-containing polymer as described above in any one of 1 to 12.

15. An electronic device provided with a substrate and the film as described above in 14 formed on the substrate.

16. An optical member provided with a substrate and the film as described above in 14 formed on the substrate.

17. A solid-state imaging device including a charge-coupled device or complementary metal oxide film semiconductor provided with at least one film as described above in 14.

18. A solid-state imaging device provided with the film as described above in 14 as a planarization layer on a color is filter.

19. A process for producing a triazine ring-containing hyperbranched polymer, characterized by heating at from 60 to 150° C. a solution of a cyanuric halide or diaminoaryl compound and an organic solvent contained therein, and adding the diaminoaryl compound or cyanuric halide to the solution at the temperature to obtain the triazine ring-containing hyperbranched polymer in a single step.

20. A process for producing a triazine ring-containing hyperbranched polymer, characterized by including a first step of reacting a cyanuric halide and a diaminoaryl compound at from −50 to 50° C. in an organic solvent, and subsequent to the step, a second step of conducting a reaction at from 60 to 150° C.

21. A process for producing a triazine ring-containing hyperbranched polymer, characterized by polymerizing a cyanuric halide compound and a diaminoaryl compound in the presence of from 0.05 to 500 equivalents, based on the cyanuric halide compound, of an organic monoamine.

22. The triazine ring-containing hyperbranched polymer obtained by the production process as described above in 21.

23. A composition including the triazine ring-containing hyperbranched polymer as described above in 22 and a crosslinking agent.

24. A composition characterized by including a triazine ring-containing hyperbranched polymer, which includes repeating unit structures represented by the following formula (1'):

[Chemical Formula 10]

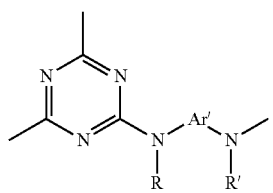
(1')

wherein R and R' independently from each other mean a hydrogen atom or an alkyl, alkoxy, aryl or aralkyl group, and Ar' means a divalent organic group containing at least one of an aromatic ring and a heteroring, and a crosslinking agent.

25. The composition as described above in 24, wherein Ar' means at least one selected from the group consisting of groups represented by the following formulas (3) to (6') and (7') to (19):

[Chemical Formula 11]

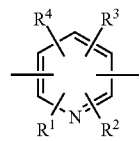
(3)

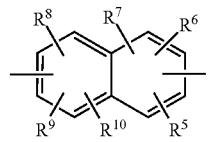
(4)

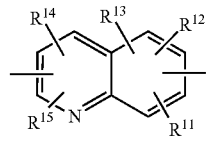
(5)

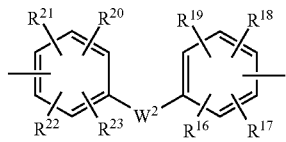
(6')

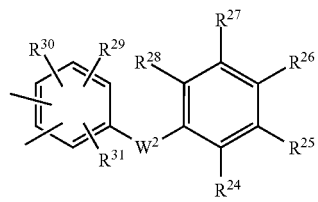
(7')

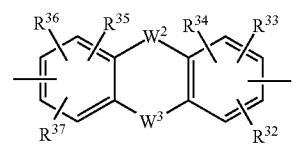
(8)

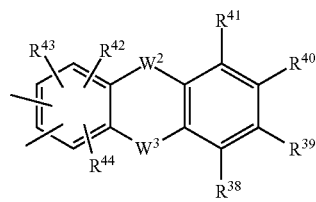
(9)

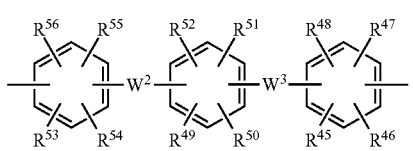
(10)

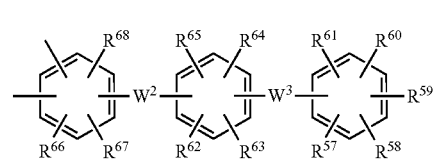
(11)

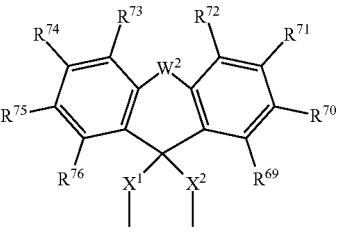
(12)

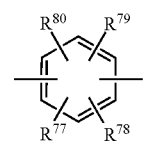
(13)

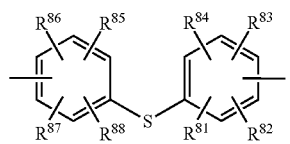
(14)

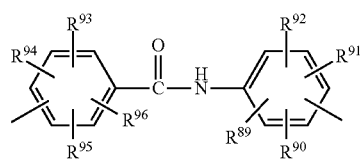
(15)

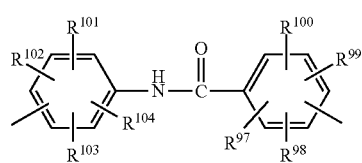
(16)

-continued

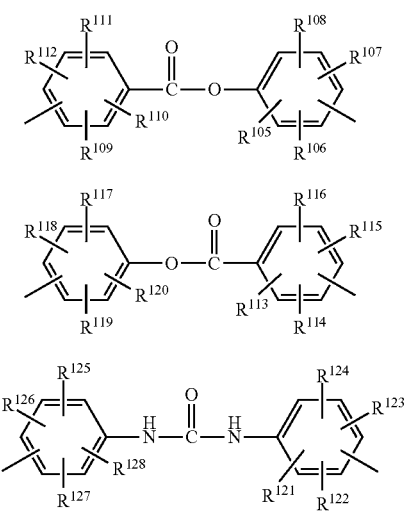

wherein $R^1$ to $R^{129}$ independently from each other mean a hydrogen or halogen atom, or a carboxyl, sulfone, branched or unbranched C1 to C10 alkyl or branched or unbranched C1 to C10 alkoxy group, $W^2$ and $W^3$ independently from each other mean a single bond, $CR^{130}R^{131}$ in which $R^{130}$ and $R^{131}$ independently from each other mean a hydrogen atom or a branched or unbranched C1 to C10 alkyl group with a proviso that these alkyl groups may be fused together to form a ring, C=O, O, S, SO, $SO_2$, or $NR^{129}$ in which $R^{129}$ has the same meaning as defined above, $X^1$ and $X^2$ independently from each other mean a single bond, a branched or unbranched C1 to C10 alkylene group, or the following formula (20):

[Chemical Formula 12]

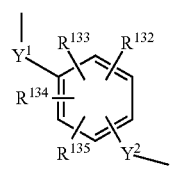

wherein $R^{132}$ to $R^{135}$ independently from each other mean a hydrogen or halogen atom, or a carboxyl, sulfone, branched or unbranched C1 to C10 alkyl or branched or unbranched C1 to C10 alkoxy group, and $Y^1$ and $Y^2$ independently from each other mean a single bond, or a branched or unbranched C1 to C10 alkylene group.
26. A polymer characterized by having a weight average molecular weight of from 500 to 500,000 and a refractive index at 550 nm of at least 1.70, and being free of any sulfur atom in a molecule thereof.
27. The polymer as described above in 26, which is a hyperbranched polymer.

Advantageous Effect of the Invention

According to the present invention, it is possible to provide a triazine ring-containing polymer capable of achieving high heat resistance, high transparency, high refractive index, high solubility and low volume shrinkage by itself without using a metal oxide.

The inclusion of the polymer skeleton according to the present invention makes it possible to retain high heat resistance and high transparency even when 1) a secondary amine is used as a spacer in the polymer and 2) a primary amine is substituted to an end. Further, the change of a polymer skeleton to a highly-branched or linear, preferably hyperbranched polymer skeleton according to the present invention makes it possible to control physical properties even when monomer units which have heretofore been considered to impair heat resistance and transparency are used.

The exhibition of a high refractive index by the hyperbranched polymer according to the present invention is presumably attributable to an increase in electron density as a result of close gathering of triazine rings and aryl (Ar) moieties owing to the adoption of a hyperbranched structure.

Especially when R and/or R' is a hydrogen atom, the adoption of the hyperbranched structure is considered to induce hydrogen bonding between the nitrogen atoms on triazine rings and the hydrogen atoms at amine sites, whereby the triazine rings and aryl (Ar) moieties more closely gather to result in an increased electron density.

Even in the case of a polymer having no sulfur atom in its molecule, a high refractive index as high as, for example, 1.70 (when measured at 550 nm) is exhibited.

The range of such refractive indexes may have, as a lower limit, preferably 1.70 or higher, more preferably 1.75 or higher, still more preferably 1.80 or higher although this range varies depending on the use situation. Its upper limit is not specifically limited, and may be approximately from 2.00 to 1.95 or lower.

Further, despite the use of rigid sites such as fluorene skeletons as principal repeating units in the polymer, the solubility is not impaired, thereby making it possible to prepare a varnish which is soluble in a resist solvent of high safety.

The triazine ring-containing polymer has a low viscosity when dissolved in a solvent although it is a high-molecular compound. In particular, a polymer having methaphenylene diamine sites is excellent in handling properties owing to its superb solubility in various organic solvents.

As no metal oxide is contained and a high refractive index can be exhibited by the polymer alone, the etch rate becomes constant even when subjected to dry processing such as etching or ashing. Therefore, a film of uniform thickness can be obtained, leading to an enlarged process margin upon fabrication of a device.

Various properties which the triazine ring-containing polymer according to the present invention has can be controlled by changing the kinds of monomers as its starting raw materials upon synthesis.

According to the process of the present invention for the production of the triazine ring-containing polymer, the polymer can be obtained without gelation in a single heating step. Because the polymer can be obtained without gelation even by using the cyanuric halide compound and diaminoaryl compound as raw materials at a molar ratio other than 2:3, it is possible to control the compositions of triazine parts and diamine parts and the molecular weight of the resulting polymer as desired.

According to the production process described in Non-Patent Document 1 cited above, it is described necessary to charge the cyanuric halide compound and diaminoaryl compound at the molar ratio of 2:3 and to react them at different temperatures in three stages. By this process, however, the molecular weight of the resulting polymer cannot be controlled. Further, the polymer is prone to coloring, as the cyanuric halide compound dissolved in dimethylacetamide is added dropwise at room temperature.

The triazine ring-containing polymer according to the present invention can be suitably used as a highly heat-resistant, insulating material or as a lens member required to have high refractive index.

Films, which have been prepared by using the triazine ring-containing polymer of the present invention having such properties as described above, can be suitably used as members upon fabrication of electronic devices such as liquid crystal displays, organic electroluminescence (EL) displays, optical semiconductor (LED) devices, solid-state imaging devices, organic thin-film solar cells, dye-sensitized solar cells, and organic thin-film transistors (TFT).

Solid-state imaging devices include members required to have a particularly high refractive index, such as filling films and planarization films on photodiodes, front and rear planarization films for color filters, microlenses, and planarization films and conformal films on microlenses. The triazine ring-containing polymer according to the present invention can be suitably used as these members.

BRIEF DESCRIPTION OF THE DRAWINGS

FIG. 120 is a diagram showing a $^1$H-NMR spectrum of the high-molecular compound [17] obtained in Example 234.

EMBODIMENT FOR CARRYING OUT THE INVENTION

Figure 1:
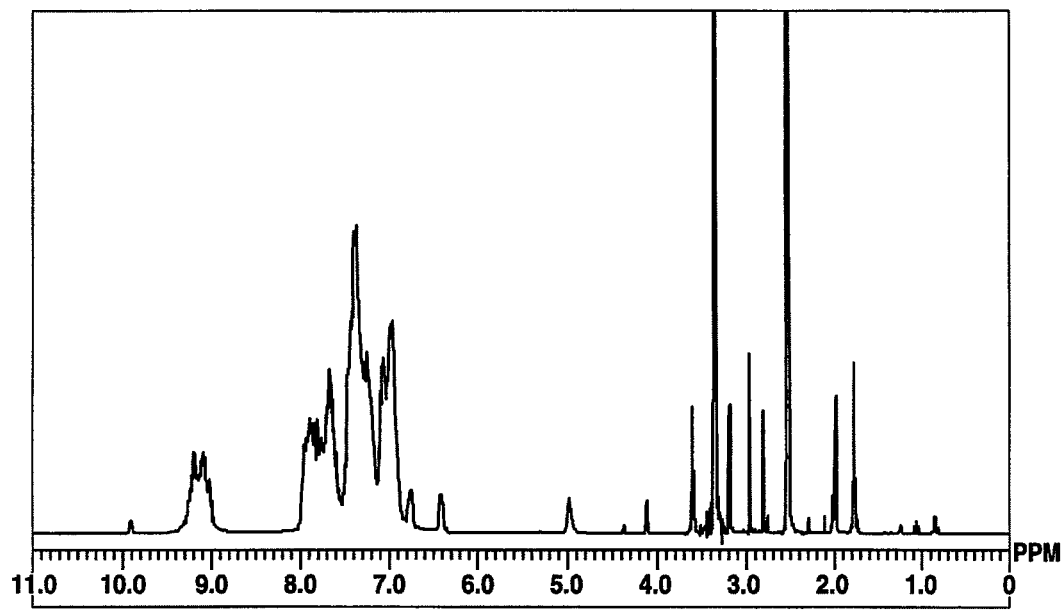
FIG. 1 is a diagram showing a $^1$H-NMR spectrum of the high-molecular compound [3] obtained in Example 1.

The present invention will hereinafter be described in further detail.

The triazine ring-containing polymer according to the present invention contains repeating unit structures represented by the following formula (1) or (2).

[Chemical Formula 13]

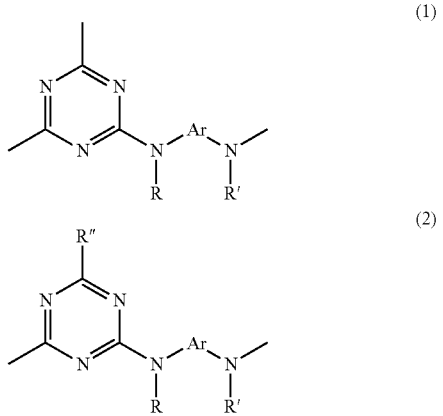

In the above formulas, R and R' independently from each other mean a hydrogen atom, an alkyl, alkoxy, aryl or aralkyl group, R" means an alkyl, aralkyl, aryl, alkylamino, alkoxysilyl-containing alkylamino, aralkylamino, arylamino, alkoxy, aralkyloxy or aryloxy group.

In the present invention, the carbon number of the alkyl group is not specifically limited, but may preferably be from 1 to 20. Taking into consideration a further increase in the heat resistance of the polymer, the carbon number may be more preferably from 1 to 10, still more preferably from 1 to 3. Further, its structure may be any of linear, branched and cyclic.

Specific examples of the alkyl group include methyl, ethyl, n-propyl, isopropyl, cyclopropyl, n-butyl, isobutyl, s-butyl, t-butyl, cyclobutyl, 1-methyl-cyclopropyl, 2-methyl-cyclopropyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, cyclopentyl, 1-methyl-cyclobutyl, 2-methyl-cyclobutyl, 3-methyl-cyclobutyl, 1,2-dimethyl-cyclopropyl, 2,3-dimethyl-cyclopropyl, 1-ethyl-cyclopropyl, 2-ethyl-cyclopropyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3,-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, cyclohexyl, 1-methyl-cyclopentyl, 2-methyl-cyclopentyl, 3-methyl-cyclopentyl, 1-ethyl-cyclobutyl, 2-ethyl-cyclobutyl, 3-ethyl-cyclobutyl, 1,2-dimethyl-cyclobutyl, 1,3-dimethyl-cyclobutyl, 2,2-dimethyl-cyclobutyl, 2,3-dimethyl-cyclobutyl, 2,4-dimethylcyclobutyl, 3,3-dimethyl-cyclobutyl, 1-n-propyl-cyclopropyl, 2-n-propyl-cyclopropyl, 1-isopropyl-cyclopropyl, 2-isopropyl-cyclopropyl, 1,2,2-trimethyl-cyclopropyl, 1,2,3-trimethyl-cyclopropyl, 2,2,3-trimethyl-cyclopropyl, 1-ethyl-2-methyl-cyclopropyl, 2-ethyl-1-methyl-cyclopropyl, 2-ethyl-2-methyl-cyclopropyl, 2-ethyl-3-methyl-cyclopropyl, and the like.

The carbon number of the alkoxy group is not specifically limited, but may preferably be from 1 to 20. Taking into consideration a further increase in the heat resistance of the polymer, the carbon number may be more preferably from 1 to 10, still more preferably from 1 to 3. Further, the structure of its alkyl moiety may be any of linear, branched and cyclic.

Specific examples of the alkoxy group include methoxy, ethoxy, n-propoxy, isopropoxy, n-butoxy, isobutoxy, s-butoxy, t-butoxy, n-pentoxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3,-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, and the like.

The carbon number of the aryl group is not specifically limited, but may preferably be from 6 to 40. Taking into consideration a further increase in the heat resistance of the polymer, the carbon number may be more preferably from 6 to 16, still more preferably from 6 to 13.

Specific examples of the aryl group include phenyl, o-chlorophenyl, m-chlorophenyl, p-chlorophenyl, o-fluorophenyl, p-fluorophenyl, o-methoxyphenyl, p-methoxyphenyl, p-nitrophenyl, p-cyanophenyl, α-naphthyl, β-naphthyl, o-biphenylyl, m-biphenylyl, p-biphenylyl, 1-anthryl, 2-anthryl, 9-anthryl, 1-phenanthryl, 2-phenanthryl, 3-phenanthryl, 4-phenanthryl, 9-phenanthryl, and the like.

The carbon number of the aralkyl group is not specifically limited, but may preferably be from 7 to 20. Its alkyl moiety may be any of linear, branched and cyclic.

Its specific examples include benzyl, p-methylphenylmethyl, m-methylphenylmethyl, o-ethylphenylmethyl, m-ethylphenylmethyl, p-ethylphenylmethyl, 2-propylphenylmethyl, 4-isopropylphenylmethyl, 4-isobutylphenylmethyl, α-naphthylmethyl, and the like.

Specific examples of the alkylamino group include methylamino, ethylamino, n-propylamino, isopropylamino, n-butylamino, isobutylamino, s-butylamino, t-butylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, and the like.

Specific examples of the aralkylamino group include benzylamino, methoxycarbonylphenylmethylamino, ethoxycarbonylphenylmethylamino, p-methylphenylmethylamino, m-methylphenylmethylamino, o-ethylphenylmethylamino, m-ethylphenylmethylamino, p-ethylphenylmethylamino, 2-propylphenylmethylamino, 4-isopropylphenylmethylamino, 4-isobutylphenylmethylamino, naphthylmethylamino, methoxycarbonylnaphthylmethylamino, ethoxycarbonylnaphthylmethylamino, and the like.

Specific examples of the arylamino group include phenylamino, methoxycarbonylphenylamino, ethoxycarbonylphenylamino, naphthylamino, methoxycarbonylnaphthylamino, ethoxycarbonylnaphthylamino, anthranylamino, pyrenylamino, biphenylamino, terphenylamino, fluorenylamino, and the like.

The alkoxysilyl-containing alkylamino group may be any of a monoalkoxysilyl-containing alkylamino group, a dialkoxysilyl-containing alkylamino group, and a trialkoxysilyl-containing alkylamino group. Its specific examples include 3-trimethoxysilylpropylamino, 3-triethoxysilylpropylamino, 3-dimethylethoxysilylpropylamino, 3-methyldiethoxysilylpropylamino, N-(2-aminoethyl)-3-dimethylmethoxysilylpropylamino, N-(2-aminoethyl)-3-methyldimethoxysilylpropylamino, N-(2-aminoethyl)-3-trimethoxysilylpropylamino, and the like.

Specific examples of the aryloxy group include phenoxy, naphthoxy, anthranyloxy, pyrenyloxy, biphenyloxy, terphenyloxy, fluorenyloxy, and the like.

Specific examples of the aralkyloxy group include benzyloxy, p-methylphenylmethyloxy, m-methylphenylmethyloxy, o-ethylphenylmethyloxy, m-ethylphenylmethyloxy, p-ethylphenylmethyloxy, 2-propylphenylmethyloxy, 4-isopropylphenylmethyloxy, 4-isobutylphenylmethyloxy, α-naphthylmethyloxy, and the like.

Ar means at least one of the groups represented by the formulas (3) to (19), with at least one of the groups represented by the formulas (6) to (19) being preferred, and at least one of the groups represented by the formulas (6), (8), (9), (12), (13), and (15) to (19) being more preferred.

[Chemical Formula 14]

(3)

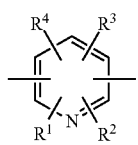

(4)

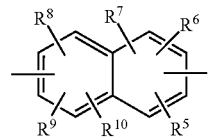

(5)

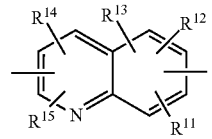

(6)

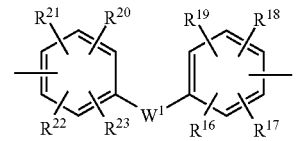

(7)

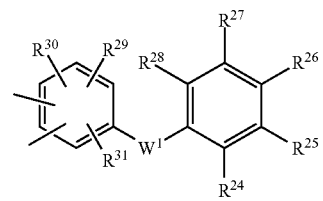

(8)

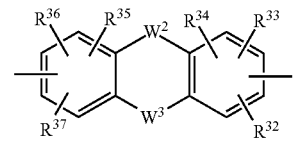

(9)

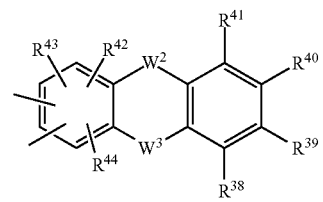

(10)

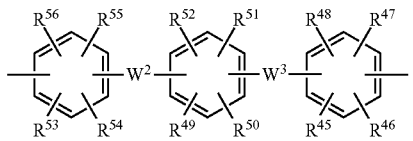

(11)

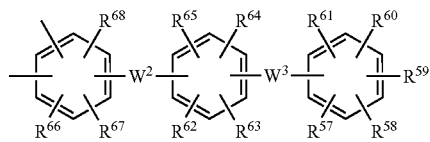

(12)

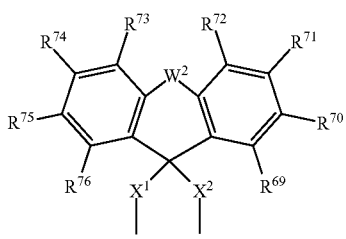

$R^1$ to $R^{128}$ independently from each other mean a hydrogen atom, halogen atom, carboxyl, sulfone, branched or unbranched C1 to C10 alkyl or branched or unbranched C1 to C10 alkoxy group, $W^1$ means a single bond, C=O or $NR^{129}$ in which $R^{129}$ means a hydrogen atom or a branched or unbranched C1 to C10 alkyl group, $W^2$ and $W^3$ independently from each other mean a single bond, $CR^{130}R^{131}$ in which $R^{130}$ and $R^{131}$ independently from each other mean a hydrogen atom or a branched or unbranched C1 to C10 alkyl group with a proviso that these alkyl groups may be fused together to form a ring, C=O, O, S, SO, $SO_2$, or $NR^{129}$ in which $R^{129}$ has the same meaning as defined above.

As these alkyl groups and alkoxy groups, those exemplified above can be mentioned.

As the halogen atom, a fluorine, chlorine, bromine or iodine atom can be mentioned.

Further, $X^1$ and $X^2$ independently from each other mean a single bond, a branched or unbranched C1 to C10 alkylene group, or a group represented by the following formula (20).

$R^{132}$ to $R^{125}$ independently from each other mean a hydrogen atom, halogen atom, carboxyl, sulfone, branched or is unbranched C1 to C10 alkyl or branched or unbranched C1 to C10 alkoxy group, and $Y^1$ and $Y^2$ independently from each other mean a single bond, or a branched or unbranched C1 to C10 alkylene group.

As these halogen atom, alkyl group and alkoxy group, those exemplified above can be mentioned.

As the branched or unbranched C1 to C10 alkylene group, methylene, ethylene, propylene, trimethylene, tetramethylene, pentamethylene or the like can be mentioned.

As Ar suited in the present invention, a divalent organic group containing a fluorene ring can be mentioned. For example, a divalent organic group represented by the following formula (21) or (22) is suited.

wherein $R^{136}$ to $R^{159}$ independently from each other mean a hydrogen atom, halogen atom, carboxyl, sulfone, branched or unbranched C1 to C10 alkyl group with a proviso that $R^{158}$ and $R^{159}$ may be fused together to form a ring, or a branched or unbranched C1 to C10 alkoxy group.

As the halogen atom, a similar halogen atom as exemplified above can be mentioned.

As the branched or unbranched C1 to C10 alkyl group, a similar, branched or unbranched C1 to C10 alkyl group as exemplified above can be mentioned.

As the ring which may be formed by the fusion of $R^{158}$ and $R^{159}$, a cyclopentyl ring, cyclohexyl ring or the like can be mentioned.

As the branched or unbranched C1 to C10 alkoxy group, a similar, branched or unbranched C1 to C10 alkoxy group as exemplified above can be mentioned.

Of these, a hydrogen atom is preferred as each of $R^{136}$ to $R^{159}$.

Specific examples of the aryl groups represented by the formulas (3) to (19), (21) and (22) include, but are not limited to, those represented by the following formulas.

[Chemical Formula 17]

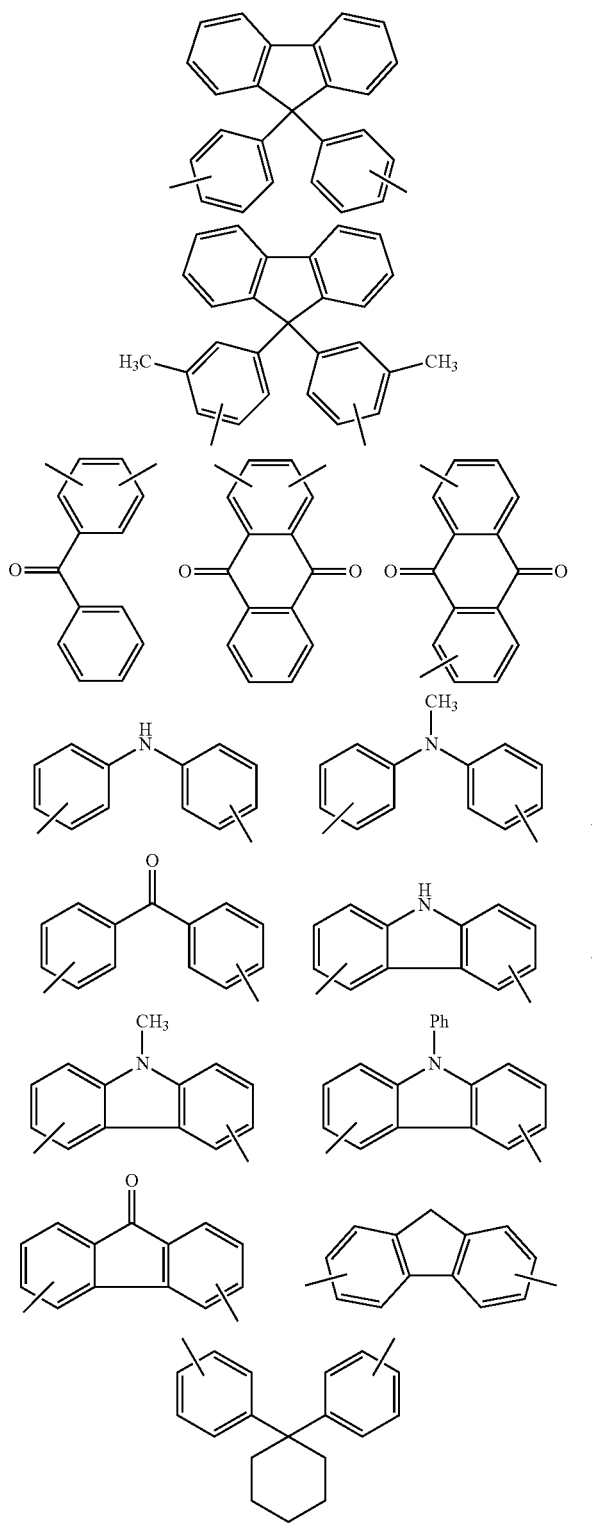

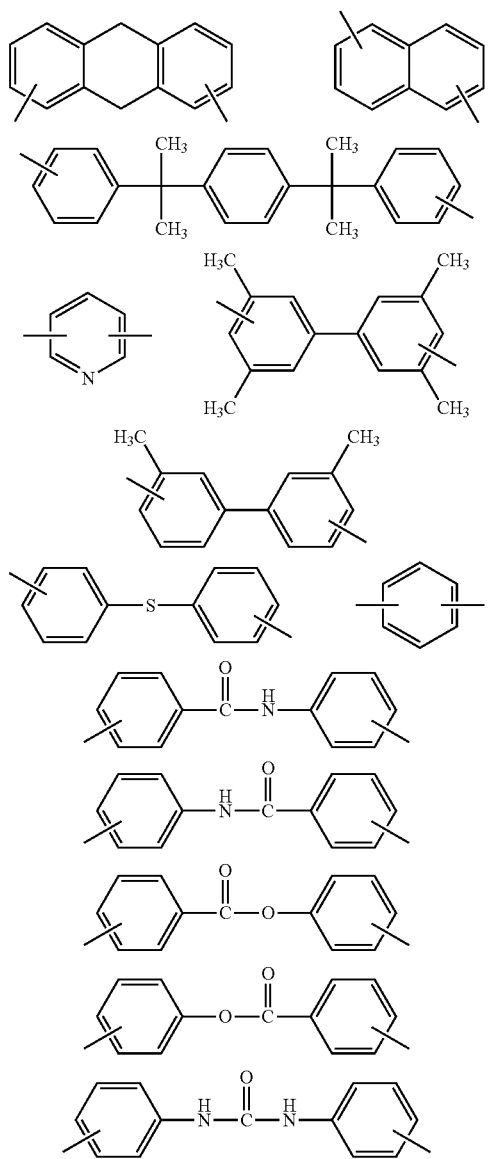

Among these, the aryl groups represented by the following formulas are more preferred for the availability of polymers having higher refractive index.

[Chemical Formula 18]

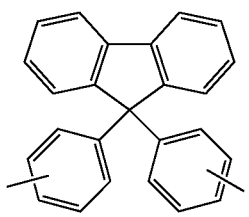

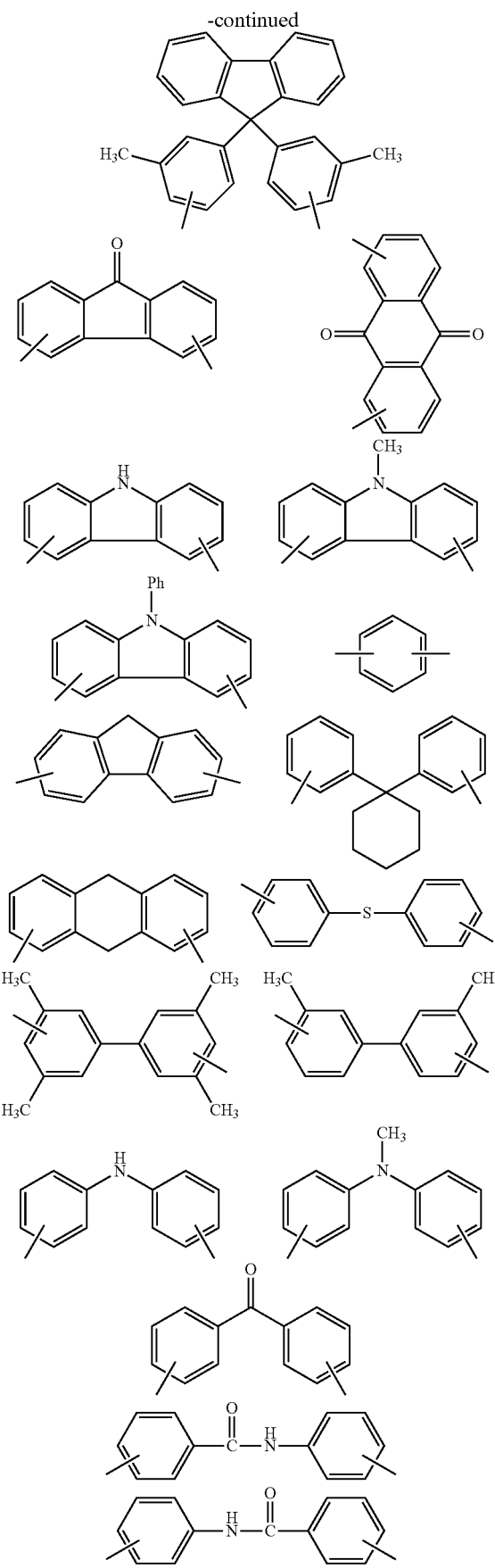

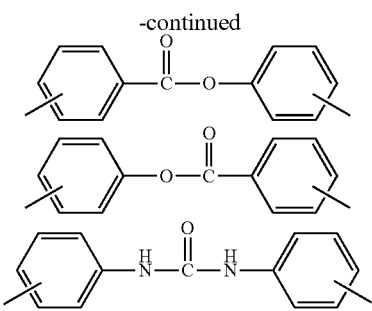

From the standpoint of exhibition of high refractive index, a rigid structure having a ring skeleton such as the fluorene skeleton or carbazole skeleton is suited as the aryl (Ar) moiety because aryl (Ar) moieties tend to closely gather to provide an increased electron density. In addition, the simple benzene ring is also suited, because it has a small structure so that aryl (Ar) moieties tend to closely gather to provide an increased electron density.

As the connecting group such as $W^1$ for benzene rings, a functional group having high hydrogen bonding ability, such as a carbonyl-containing group or an amine, is suited, because the functional group forms a hydrogen bond with a hydrogen atom in an amine moiety (when R and/or R' is a hydrogen atom) so that aryl (Ar) moieties tend to more closely gather to provide an increased electron density.

From such viewpoints as described above, aryl groups represented by the following formulas are preferred.

[Chemical Formula 19]

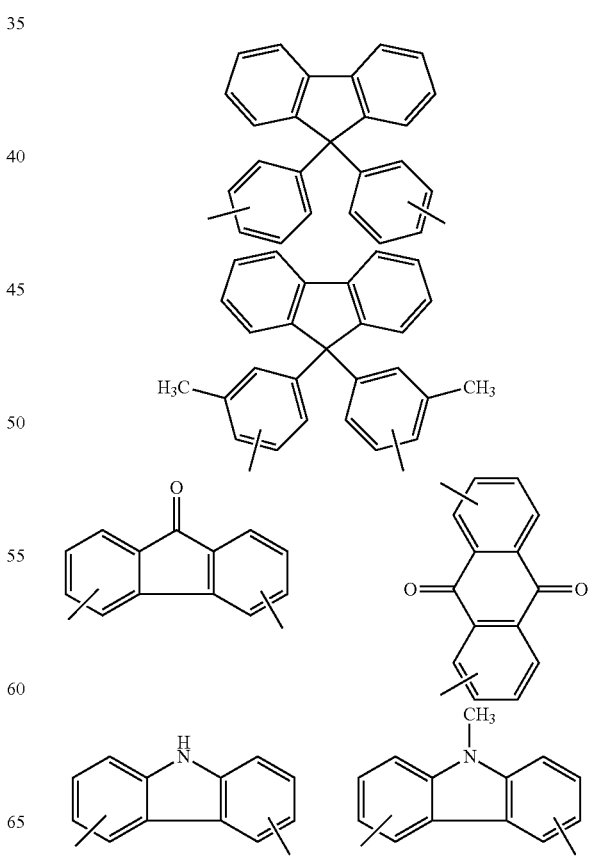

-continued

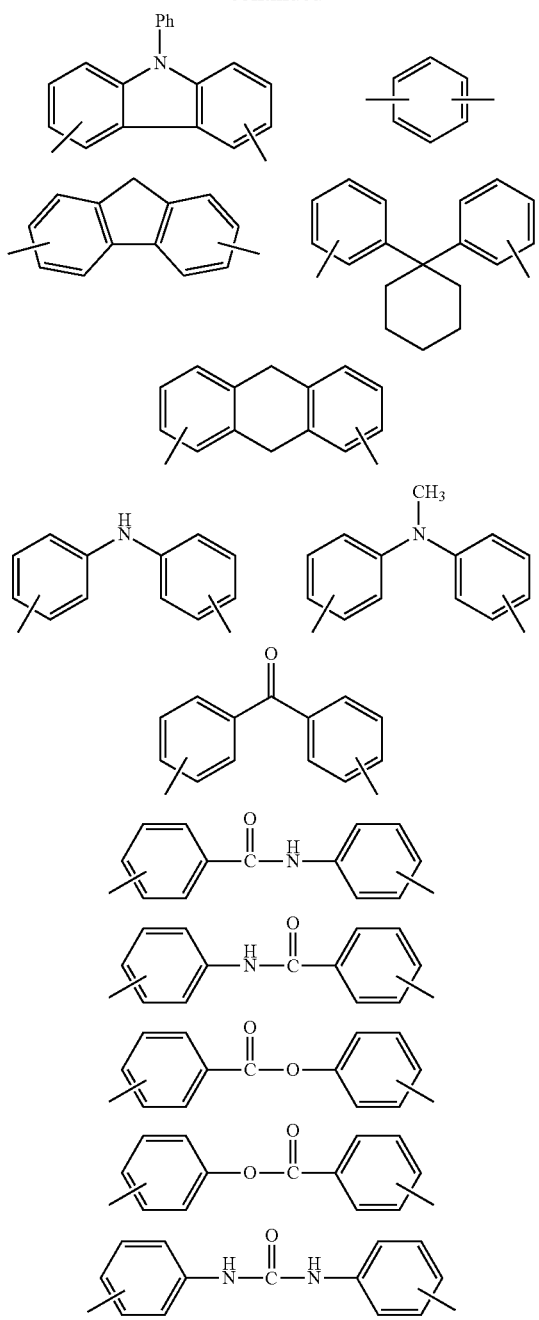

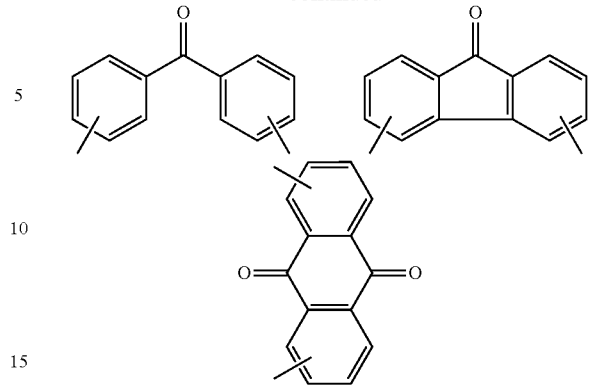

Suited repeating unit structures include, but are not limited to, those represented by the following formula (23) or (24).
[Chemical Formula 21]

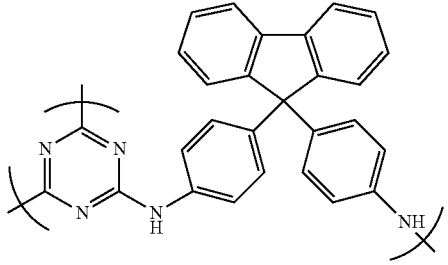

(23)

(24)

Considering to provide the polymer according to the present invention with still higher solubility in a high-safety solvent such as a resist solvent when the polymer is a hyperbranched polymer, it is preferred to contain repeating unit structures represented by the following formula (25):
[Chemical Formula 22]

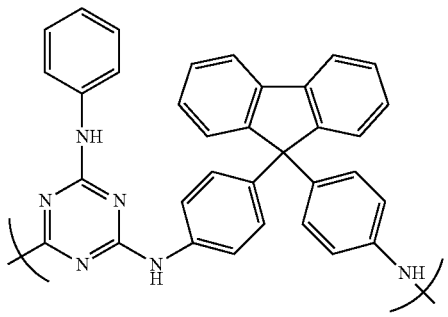

From the standpoint of exhibition of higher refractive index, aryl groups represented by the following formulas are more preferred.
[Chemical Formula 20]

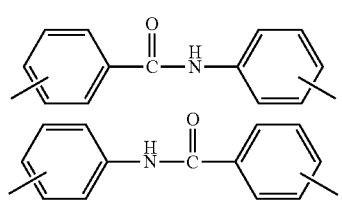

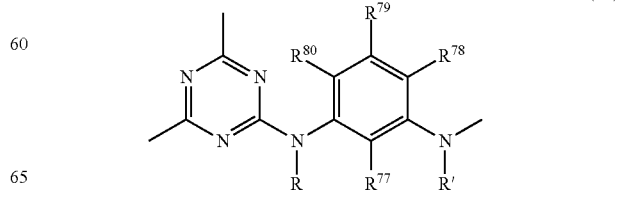

(25)

wherein R, R' and $R^{77}$ to $R^{80}$ have the same meanings as defined above.

From such a viewpoint as described above, particularly suited, repeating unit structures include those represented by the following formula (26), and a highly-branched polymer (hyperbranched polymer) represented by the following formula (27) is most suited.

[Chemical Formula 23]

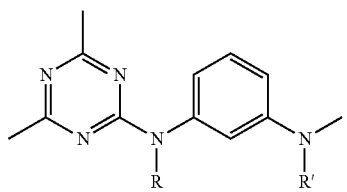

(26)

wherein R and R' have the same meanings as defined above.

[Chemical Formula 24]

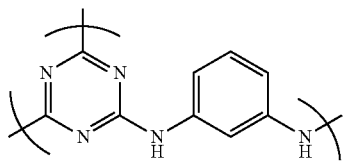

(27)

Although no particular limitation is imposed on the weight average molecular weight of the polymer in the present invention, it may be preferably from 500 to 500,000, more preferably from 500 to 100,000. From the standpoints of still higher heat resistance and still lower shrinkage rate, 2,000 or higher is preferred. From the standpoints of still higher solubility and still lower viscosity of a resulting solution, 50,000 or lower is preferred, with 30,000 or lower being more preferred and 10,000 or lower being still more preferred.

It is to be noted that the term "weight average molecular weight" as used herein means an average molecular weight as measured by gel permeation chromatography (hereinafter called "GPC") and calibrated against standard polystyrene.

About the processes of the present invention for the production of the triazine ring-containing polymer, a description will now be made based on examples.

These production processes will be classified into schemes 1, 2, 3 and 4. When each scheme needs to be classified further, "a" and "b" will be added. As will be shown in the below-described scheme 1-a, for example, a highly-branched polymer (hyperbranched polymer) with repeating structures (23') contained therein can be obtained by reacting a cyanuric halide (28) and an amino-containing bisaminophenylfluorene compound (29) in an appropriate organic solvent.

As will be shown in the below-described scheme 1-b, a highly-branched polymer (hyperbranched polymer) with repeating structures (27') contained therein can be obtained by reacting the cyanuric halide (28) and a m-phenylenediamine compound (30) in an appropriate organic solvent.

[Chemical Formula 25]

Scheme 1-a

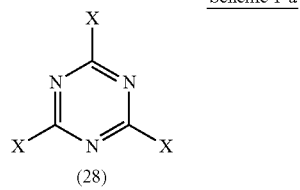

(28)

+

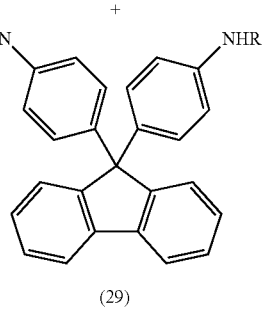

(29)

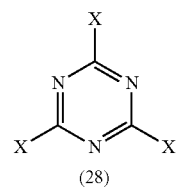

(23')

Scheme 1-b

(28)

+

(30)

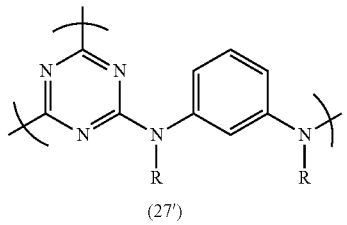

(27')

wherein Xs independently from each other mean a halogen atom, and R has the same meaning as defined above.

As will be shown in the below-described scheme 2-a, a highly-branched polymer (hyperbranched polymer) with the repeating structures (23') contained therein can also be synthesized from a compound (31) obtained by using and reacting the cyanuric halide (28) and the amino-containing bisaminophenylfluorene compound (29) in equivalent amounts in an appropriate organic solvent.

As will be shown in the below-described scheme 2-b, the highly-branched polymer (hyperbranched polymer) with repeating structures (27') contained therein can also be synthesized from a compound (32) obtained by using and reacting the cyanuric halide (28) and the m-phenylenediamine compound (30) in an appropriate organic solvent.

[Chemical Formula 26]

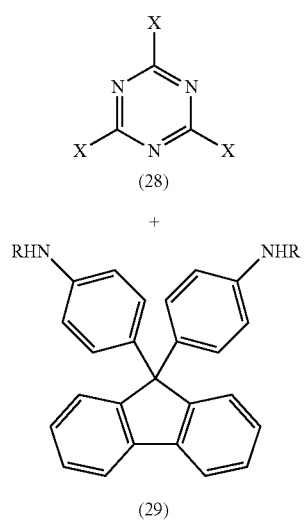

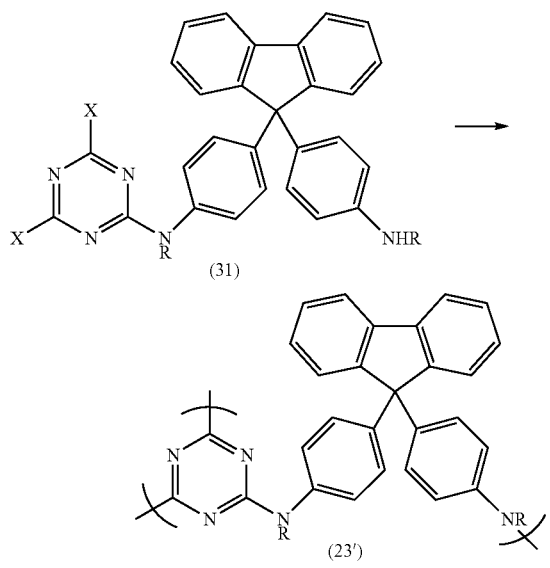

Scheme 2-a

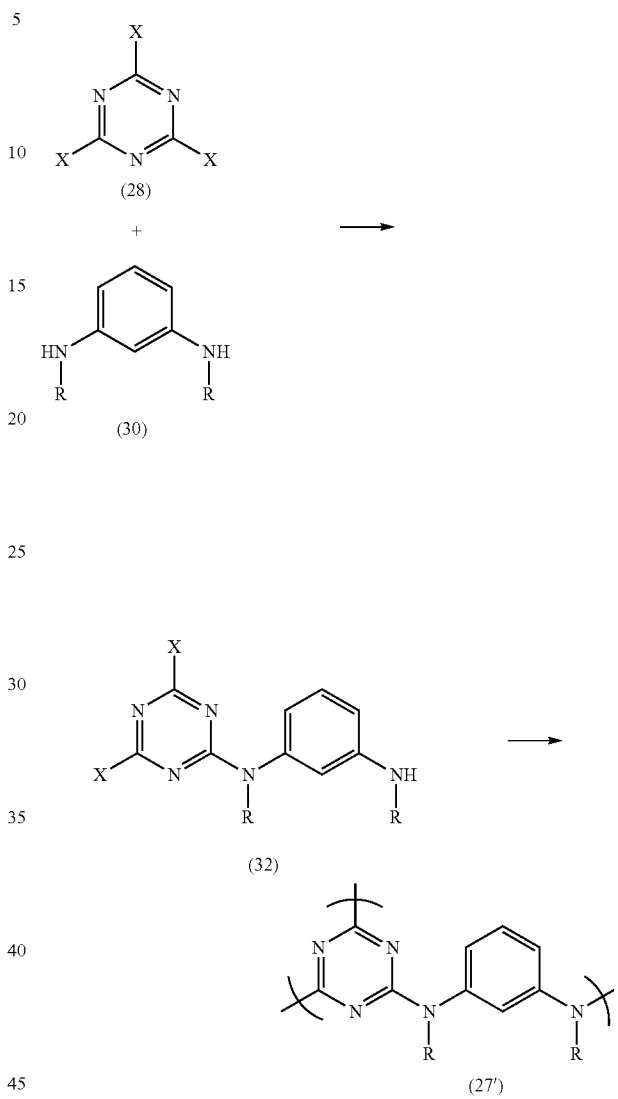

Scheme 2-b wherein Xs independently from each other mean a halogen atom, and R has the same meaning as defined above.

As will be shown in the below-described scheme 3, a linear polymer with repeating structures (24') contained therein can be obtained by reacting a phenylamino-containing triazine dihalogenide (33) and the amino-containing bisaminophenylfluorene compound (29) in an appropriate organic solvent.

It is to be noted that the above-described compounds represented by the formula (28), formula (29), formula (30) and formula (33) are available as commercial products, for example, from Aldrich Corporation or Tokyo Chemical Industry Co., Ltd.

[Chemical Formula 27]

Scheme 3

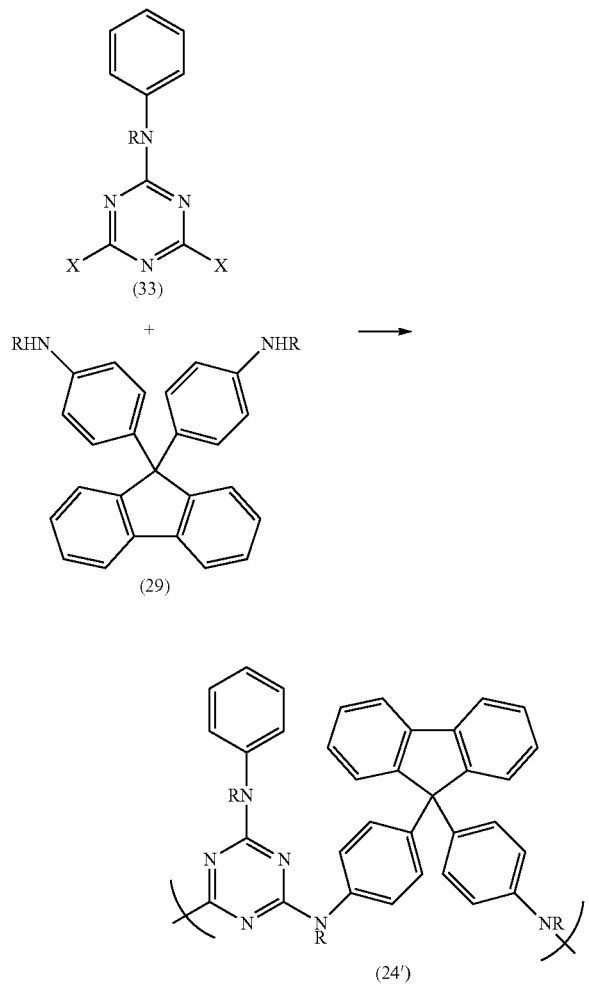

wherein Xs independently from each other mean a halogen atom, and R has the same meaning as defined above.

By using any of the above-described methods, the polymer according to the present invention can be produced at low cost, and moreover, easily and safely. These production methods are significantly shorter in reaction time than general polymer syntheses, and therefore, are in conformity with the considerations to the environment in recent years and can decrease $CO_2$ emissions. Further, these production methods can perform stable production even when the production scale is substantially increased, and hence, do not impair a stable supply system on the industrial level.

Especially taking into consideration the stability of the cyanuric chloride as a raw material and an industrial viewpoint, the production method of the scheme 2 is more preferred.

In the method of each of the schemes 1 and 2, the charge amounts of the individual raw materials are optional insofar as the target polymer can be obtained. It is, however, preferred to use from 0.01 to 10 equivalents of the diamino compound (29) or (30) per equivalent of the triazine compound (28).

Especially in the method of each scheme 1, it is preferred to avoid using 3 equivalents of the diamino compound (29) or (30) per 2 equivalents of the cyanuric halide (28). By shifting the equivalent amounts of their functional groups, the formation of gelled matter can be avoided.

To obtain highly-branched polymers (hyperbranched polymers) having various molecular weights and containing many triazine rings as terminal moieties, it is preferred to use the diamino compound (29) or (30) in an amount of smaller than 3 equivalents per 2 equivalents of the cyanuric halide (28).

To obtain highly-branched polymers (hyperbranched polymers) having various molecular weights and containing many amine terminal moieties, on the other hand, it is preferred to use the cyanuric halide (28) or (30) in an amount of smaller than 2 equivalents per 3 equivalents of the diamino compound (29).

A highly-branched polymer (hyperbranched polymer) with many triazine rings contained as terminal moieties therein is preferred in that excellent transparency and light resistance are available, for example, when formed into a thin film.

As has been described above, the molecular weight of the resulting highly-branched polymer (hyperbranched polymer) can be readily controlled by adjusting the amount of the diamino compound (29) or (30) or the cyanuric halide (28) as desired.

As the above-described organic solvents, various solvents commonly employed in reactions of this type can be used. Illustrative are tetrahydrofuran, dioxane, and dimethyl sulfoxide; amide solvents such as N,N-dimethylformamide, N-methyl-2-pyrrolidone, tetramethylurea, hexamethylphosphoramide, N,N-dimethylacetamide, N-methyl-2-piperidone, N,N-dimethylethyleneurea, N,N,N',N'-tetramethylmalonamide, N-methylcaprolactam, N-acetylpyrrolidine, N,N-diethylacetamide, N-ethyl-2-pyrrolidone, N—N-dimethylpropionamide, N,N-dimethylisobutylamide, N-methylformamide, and N,N'-dimethylpropyleneurea; and their mixed solvents.

Among these, N,N-dimethylformamide, dimethyl sulfoxide, N-methyl-2-pyrrolidone, N,N-dimethylacetamide, and their mixed systems are preferred, with N,N-dimethylacetamide and N-methyl-2-pyrrolidone being particularly suited.

In the reactions of each scheme 1 and the scheme 3 and the reaction in a second stage of each scheme 2, the reaction temperatures may each be set as desired in a range of from the melting point of the solvent to be used to the boiling point of the solvent. In particular, from 0 to 150° C. or so is preferred, and from 60 to 100° C. is more preferred.

Especially in the reaction of each scheme 1, the reaction temperature may be preferably from 60 to 150° C., more preferably from 80 to 150° C., still more preferably form 80 to 120° C. from the standpoints of minimizing the linearity and increasing the degree of branching.

In the method of a first stage of each scheme 2, the reaction temperature may be set as desired in a range of from the melting point of the solvent to be used to the boiling point of the solvent. In particular, from −50 to 50° C. or so is preferred, from −20 to 50° C. or so is more preferred, from −10 to 50° C. is still more preferred, and from −10 to 10° C. is even still more preferred.

Especially for the method of each scheme 2, it is preferred to adopt two-stage steps including a first step of reacting at from −50 to 50° C., and following this step, a second step of reacting at from 60 to 150° C.

In each of the reactions described above, the order of addition of the individual reactants is optional. For the reaction of each scheme 1, however, most suited is a method that includes heating the solution of the cyanuric halide (28) or diamino compound (29) or (30) in the organic solvent to from 60 to 150° C., preferably from 80 to 150° C., and then adding at this temperature the diamino compound (29) or (30) or the cyanuric halide (28) to the solution.

In this case, the reactant to be dissolved beforehand in the solvent and the reactant to be added subsequently can be chosen as desired, but preferred is a method that adds the cyanuric halide (28) to the heated solution of the diamino compound (29) or (30).

In the reaction of each scheme 2, the reactant to be dissolved beforehand in the solvent and the reactant to be added subsequently can also be chosen as desired, but preferred is a method that adds the diamino compound (29) or (30) to the chilled solution of the cyanuric halide (28).

The reactant to be added subsequently may be added either neat, or as mentioned above, in the form of a solution in the organic solvent. However, the latter method is suited when the ease of operation and the readiness of control of the reaction are taken into account.

The addition can be conducted gradually by dropwise addition or the like, or can be conducted by adding the reactant at once in its entirety.

In each scheme 1, the target, triazine ring-containing, highly-branched polymer (hyperbranched polymer) can be obtained without gelation even when both the compounds are reacted in a single step (without raising the temperature stepwise) after mixing them in a heated state.

It is to be noted that the method of each scheme 1 is not limited to the use of the above-mentioned diamine component adapted to afford aryl (Ar) groups but is applicable to processes for the production of the hyperbranched polymer, which use desired diaminoaryl compounds, respectively.

The method of each scheme 1 can also be applied, for example, upon using a diamine compound capable of affording, as $W^1$, an aryl group such as $CR^{130}R^{131}$ ($R^{130}$ and $R^{131}$ are the same as defined above), O, SO or $SO_2$ in addition to a single bond and C=O.

In the reactions of each scheme 1 and the scheme 3 and the reaction in the second stage of the scheme 2, various bases which are commonly employed upon polymerization or after polymerization may be added.

Specific examples of these bases include potassium carbonate, potassium hydroxide, sodium carbonate, sodium hydroxide, sodium hydrogencarbonate, sodium ethoxide, sodium acetate, lithium carbonate, lithium hydroxide, lithium oxide, potassium acetate, magnesium oxide, calcium oxide, barium hydroxide, trilithium phosphate, trisodium phosphate, tripotassium phosphate, cesium fluoride, aluminum oxide, ammonia, trimethylamine, triethylamine, diisopropylamine, diisopropylethylamine, N-methylpiperidine, 2,2,6,6-tetramethyl-N-methylpiperidine, pyridine, 4-dimethylaminopyridine, N-methylmorpholine, and the like.

These bases may be added in an amount of preferably from 1 to 100 equivalents, more preferably from 1 to 10 equivalents per equivalent of the cyanuric halide (28) or (33). These bases may be used as aqueous solutions.

Preferably, no raw material components remain in the resultant polymer. However, some of the raw materials may remain unless they impair the advantageous effects of the present invention.

In the method of each scheme, the product can be readily purified by reprecipitation or the like after the completion of the reaction.

It is to be noted that in the present invention, some of the halogen atoms of at least one terminal triazine ring may be capped by alkyl, aralkyl, aryl, alkylamino, alkoxysilyl-containing alkylamino, aralkylamino, arylamino, alkoxy, aralkyloxy, aryloxy, or ester groups.

Of these, alkylamino, alkoxysilyl-containing alkylamino, aralkylamino, or arylamino groups are preferred, with alkylamino or arylamino groups being more preferred, and arylamino groups being still more preferred.

As the ester groups, methoxycarbonyl, ethoxycarbonyl and the like can be mentioned. As the alkyl, aralkyl, aryl, alkylamino, alkoxysilyl-containing alkylamino, aralkylamino, arylamino, alkoxy, aralkyloxy and aryloxy groups, those exemplified above can be mentioned.

These groups can each be easily introduced by substituting a compound, which affords the corresponding substituent group, for desired one of the halogen atoms on the triazine ring. As shown by the below-described schemes 4-a and 4-b, for example, highly-branched polymers (34) and (35), each of which contains a phenylamino group at at least one end thereof, can be obtained by adding and reacting an aniline derivative.

[Chemical Formula 28]

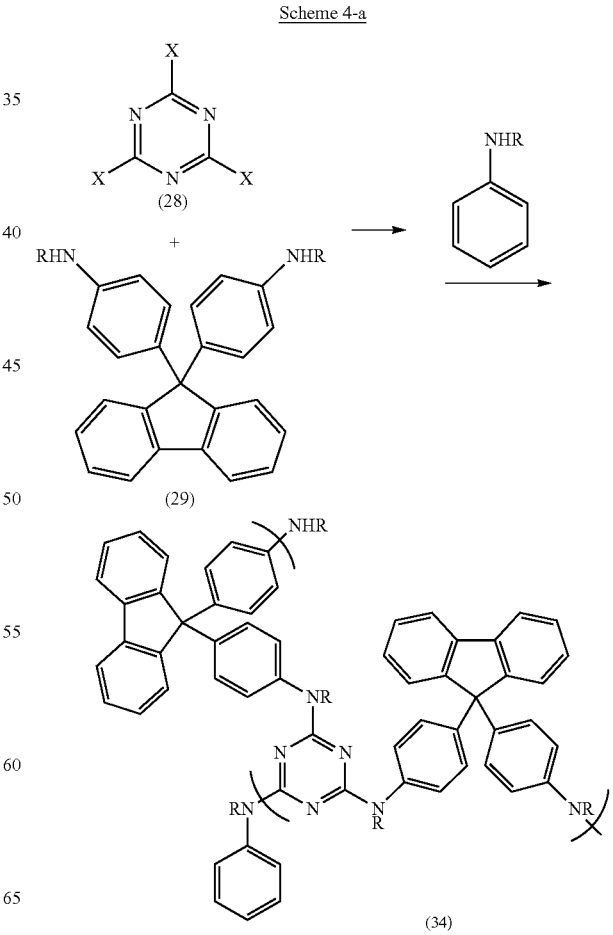

Scheme 4-a

-continued
Scheme 4-b

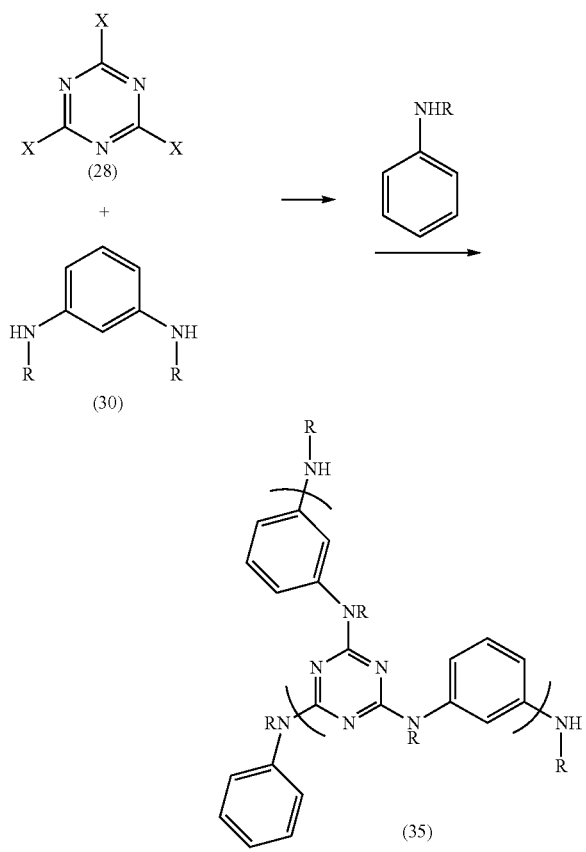

wherein X and R have the same meanings as defined above.

A hyperbranched polymer, which is reduced in rigidity, lower in the degree of branching and softer compared with general hyperbranched polymers, can be obtained by conducting the concurrent charging of an organic monoamine, in other words, reacting the cyanuric halide compound and the diaminoaryl compound in the presence of the organic monoamine in each of the above-described schemes.

Hyperbranched polymers obtained by the above-described method are provided with excellent solubility in solvents (excellent resistance to aggregation) and superb crosslinkability with crosslinking agents, and therefore, are especially advantageous when used as compositions in combination with the crosslinking agents to be described subsequently herein.

As the organic monoamine, alkylmonoamines, aralkylmonoamines and arylmonoamines are each usable.

The alkylmonoamines include methylamine, ethylamine, n-propylamine, isopropylamine, n-butylamine, isobutylamine, s-butylamine, t-butylamine, n-pentylamine, 1-methyl-n-butylamine, 2-methyl-n-butylamine, 3-methyl-n-butylamine, 1,1-dimethyl-n-propylamine, 1,2-dimethyl-n-propylamine, 2,2-dimethyl-n-propylamine, 1-ethyl-n-propylamine, n-hexylamine, 1-methyl-n-pentylamine, 2-methyl-n-pentylamine, 3-methyl-n-pentylamine, 4-methyl-n-pentylamine, 1,1-dimethyl-n-buytlamine, 1,2-dimethyl-n-butylamine, 1,3-dimethyl-n-butylamine, 2,2-dimethyl-n-butylamine, 2,3-dimethyl-n-butylamine, 3,3-dimethyl-n-butylamine, 1-ethyl-n-butylamine, 2-ethyl-n-butylamine, 1,1,2-trimethyl-n-propylamine, 1,2,2-trimethyl-n-propylamine, 1-ethyl-1-methyl-n-propylamine, 1-ethyl-2-methyl-n-propylamine, 2-ethylhexylamine, and the like.

Specific examples of the aralkylmonoamines include benzylamine, p-methoxycarbonylbenzylamine, p-ethoxycarbonylphenylbenzylamine, p-methylbenzylamine, m-methylbenzylamine, o-methoxybenzylamine, and the like.

Specific examples of the arylmonoamines include aniline, p-methoxycarbonylaniline, p-ethoxycarbonylaniline, p-methoxyaniline, 1-naphthylamine, 2-napthylamine, anthranylamine, 1-aminopyrene, 4-biphenylamine, o-phenylaniline, 4-amino-p-terphenyl, 2-aminofluorene, and the like.

In each of the above-described schemes, the organic monoamine may be used in an amount of preferably from 0.05 to 500 equivalents, more preferably from 0.05 to 120 equivalents, still more preferably from 0.05 to 50 equivalents per the cyanuric halide compound.

The reaction temperature in this scheme may also be set at preferably from 60 to 150° C., more preferably from 80 to 150° C., still more preferably from 80 to 120° C. from the standpoints of minimizing the linearity and increasing the degree of branching.

However, the mixing of the three reactants of the organic monoamine, cyanuric halide compound and diaminoaryl compound may be conducted at low temperature. The temperature in the mixing may be preferably from −50 to 50° C. or so, more preferably from −20 to 50° C. or so, still more preferably from −20 to 10° C. It is preferred to conduct the reaction by raising the temperature to a polymerization temperature at once (in a single stage) after the low-temperature charging.

As an alternative, the mixing of the two reactants of the cyanuric halide compound and diaminoaryl compound may be conducted at low temperature. The temperature during the mixing may be preferably from −50 to 50° C. or so, more preferably from −20 to 50° C. or so, still more preferably from −20 to 10° C. It is preferred to add the organic monoamine after the low-temperature charging and then to raise the temperature at once (in a single stage) to a polymerization temperature to conduct the reaction.

The reaction that reacts the cyanuric halide compound and diaminoaryl compound in the presence of such an organic monoamine may be conducted using a similar organic solvent as that mentioned above.

The method of each of the schemes 1 to 4 is not limited to the above-mentioned reaction that uses the diamine component capable of affording the above-mentioned aryl (Ar) group, but can be applied to processes that produce hyperbranched polymers by using desired diaminoaryl compounds.

The method of each of the schemes 1 to 4 can also be applied, for example, upon using a diamine compound capable of affording, as $W^1$, an aryl group such as $CR^{130}R^{131}$ ($R^{130}$ and $R^{131}$ are the same as defined above), O, SO or $SO_2$ in addition to a single bond and C=O.

The above-described polymers according to the present invention can be used as compositions in combination with other compounds. Examples of such compositions include compositions with leveling agents, surfactants, crosslinking agents, resins or the like.

These compositions can be used as film-forming compositions, and can be suitably used as film-forming compositions (also called "polymer varnishes") with the polymers dissolved in various solvents.

The solvents to be used to dissolve the polymers may be the same as or different from the solvents employed upon polymerization. No particular limitation is imposed on these solvents insofar as the compatibility with the polymers is not impaired, and these solvents can be selectively used either singly or in combination.

Specific examples of these solvents include toluene, p-xylene, o-xylene, m-xylene, ethylbenzene, styrene, ethylene glycol dimethyl ether, propylene glycol monomethyl ether, ethylene glycol monomethyl ether, propylene glycol, propylene glycol monoethyl ether, ethylene glycol monoethyl ether, ethylene glycol monoisopropyl ether, ethylene glycol methyl ether acetate, propylene glycol monomethyl ether acetate, ethylene glycol ethyl ether acetate, diethylene glycol dimethyl ether, propylene glycol monobutyl ether, ethylene glycol monobutyl ether, diethylene glycol diethyl ether, dipropylene glycol monomethyl ether, diethylene glycol monomethyl ether, dipropylene glycol monoethyl ether, diethylene glycol monoethyl ether, triethylene glycol dimethyl ether, diethylene glycol monoethyl ether acetate, diethylene glycol, 1-octanol, ethylene glycol, hexylene glycol, trimethylene glycol, 1-methoxy-2-butanol, cyclohexanol, diacetone alcohol, furfuryl alcohol, tetrahydrofurfuryl alcohol, propylene glycol, benzyl alcohol, 1,3-butanediol, 1,4-butanediol, 2,3-butanediol, γ-butyrolactone, acetone, methyl ethyl ketone, methyl isopropyl ketone, diethyl ketone, methyl isobutyl ketone, methyl normal butyl ketone, cyclohexanone, ethyl acetate, isopropyl acetate, normal propyl acetate, isobutyl acetate, normal butyl acetate, ethyl lactate, methanol, ethanol, isopropanol, tert-butanol, allyl alcohol, normal propanol, 2-methyl-2-butanol, isobutanol, normal butanol, 2-methyl-1-butanol, 1-pentanol, 2-methyl-1-pentanol, 2-ethylhexanol, 1-octanol, ethylene glycol, hexylene glycol, trimethylene glycol, 1-methoxy-2-butanol, diacetone alcohol, furfuryl alcohol, tetrahydrofurfuryl alcohol, propylene glycol, benzyl alcohol, tetrahydrofuran, 1,4-dioxane, N,N-dimethylformamide, N,N-dimethylacetamide, N-methylpyrrolidone, 1,3-dimethyl-2-imidazolidinone, dimethyl sulfoxide, N-cyclohexyl-2-pyrrolidinone, and the like. From the viewpoints of the solubility and storage stability of polymers, more preferred are propylene glycol monomethyl ether, propylene glycol monoethyl ether, propylene glycol monomethyl ether acetate, propylene glycol monobutyl ether, cyclohexanone, and the like.

The concentration of solids in each film-forming composition is not particularly limited insofar as it is in a range that does not affect the storage stability, and can be set as desired depending on the thickness of a film to be is formed. Described specifically, the solids concentration may be preferably from 0.1 to 50% by mass, more preferably from 0.1 to 20% by mass from the viewpoints of solubility and storage stability.

In the present invention, components other than the polymer and solvent, for example, a leveling agent, surfactant, crosslinking agent and the like may be contained to such extents as not to impair the advantageous effects of the present invention.

Examples of the surfactant include nonionic surfactants, e.g., polyoxyethylene alkyl ethers such as polyoxyethylene lauryl ether, polyoxyethylene stearyl ether, polyoxyethylene cetyl ether and polyoxyethylene oleyl ether, polyoxyethylene alkylaryl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate and sorbitan tristearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan tri-oleate and polyoxyethylene sorbitan tristearate; fluorine-containing surfactants such as trade names "F-TOP EF301, EF303, EF352" (product of Mitsubishi Materials Electronic Chemicals Co., Ltd. (formerly, products of Jemco Co.)), "MEGAFAC F171, F173, R-08, R-30" (products of DIC Corporation), "FLUORAD FC430, FC431" (products of Sumitomo 3M Limited) and trade names "ASAHIGUARD AG710," "SURFLON S-382, SC101, SC102, SC103, SC104, SC105, SC106" (products of Asahi Glass Co., Ltd.); "ORGANOSILOXANE POLYMER KP341" (product of Shin-Etsu Chemical Co., Ltd.); "BYK-302," "BYK-307," "BYK-322," "BYK-323," "BYK-330," "BYK-333," "BYK-370," "BYK-375" and "BYK-378" (products of BYK Japan K.K.).

These surfactants may be used either singly or in combination. The surfactant may be used in an amount of preferably from 0.0001 to 5 parts by mass, more preferably from 0.001 to 1 parts by mass, still more preferably from 0.01 to 0.5 parts by mass per 100 parts by mass of the polymer.

Further, a composition of a hyperbranched polymer represented by the below-described formula (1'), which includes especially such a triazine ring-containing, hyperbranched polymer as mentioned above, and a crosslinking agent is useful as a film-forming or like composition.

[Chemical Formula 29]

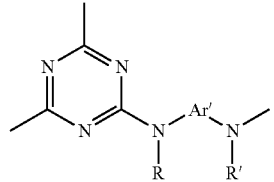

(1')

wherein R and R' have the same meanings as defined above, and Ar' means a divalent organic group containing at least one of an aromatic ring and a heteroring.

Ar' can be a desired group insofar as it is a divalent organic group containing an aromatic ring and/or a heteroring. Preferably, however, divalent organic groups such as the above-mentioned ones represented by the formulas (3) to (19) can be mentioned. It is to be noted that the hyperbranched polymer represented by the above-described formula (1') can also be applied upon using a diamine compound capable of affording, as $W^1$, an aryl group such as $CR^{130}R^{131}$ ($R^{130}$ and $R^{131}$ are the same as defined above), O, SO or $SO_2$ in the formulas (6) and (7) in addition to a single bond and C═O. Further, the aromatic ring can be a fused ring such as an anthracene ring or pyrene ring, and the heteroring can be a fused ring such as a quinoline ring or indole ring.

As a more preferred range of Ar', a similar range as the above-described Ar can be mentioned.

It is to be noted that the hyperbranched polymer represented by the formula (1') can also be synthesized likewise by the methods of the schemes 1 to 4.

No particular limitation is imposed on the crosslinking agent insofar as it is a compound containing one or more substituent groups capable of reacting with the polymer according to the present invention.

Such compounds include melamine compounds containing one or more crosslink-forming substituent groups such as methylol groups or methoxymethyl groups, substituted urea compounds, compounds containing two or more crosslink-forming substituent groups such as epoxy groups or oxetane groups, compounds containing one or more blocked isocyanato, compounds containing one or more acid anhydride, compounds containing one or more (meth)acryl groups, phenoplast compounds, and the like. From the viewpoints of heat resistance and storage stability, however, compounds containing one or more epoxy groups, blocked isocyanato groups or (meth)acryl groups are preferred.

A blocked isocyanato group is also preferred in that it can be crosslinked via a urea bond and does not lower the refractive index owing to the inclusion of a carbonyl group.

These compounds are required to contain at least one crosslink-forming substituent group when used for the end group treatment of a polymer, but are also required to contain at least two crosslink-forming substituent groups when used for the crosslinking treatment of polymers themselves.

The epoxy-containing compounds each contain two or more epoxy groups in a molecule. When exposed to high temperature upon thermal curing, epoxy rings are opened so that a crosslinking reaction proceeds through an addition reaction between the epoxy-containing compound and the polymer according to the present invention.

Specific examples of such crosslinking agents include tris (2,3-epoxypropyl) isocyanurate, 1,4-butanediol diglycidyl ether, 1,2-epoxy-4-(epoxyethyl)cyclohexane, glycerol triglycidyl ether, diethylene glycol diglycidyl ether, 2,6-diglycidylphenyl glycidyl ether, 1,1,3-tris[p-(2,3-epoxypropoxy) phenyl]propane, diglycidyl 1,2-cyclohexanedicarboxylate, 4,4'-methylenebis(N,N-diglycidylaniline), 3,4-epoxycyclohexylmethyl 3,4-epoxycyclohexanecarboxylate, trimethylolethane triglycidyl ether, bisphenol-A diglycidyl ether, pentaerythritol polyglycidyl ether, and the like.

Usable commercial products include "YH-434" and "YH434L," epoxy resins containing at least two epoxy groups (products of Tohto Kasei Co., Ltd.); "EPOLEAD GT-401, GT-403, GT-301, GT-302," "CELLOXIDE 2021" and "CELLOXIDE 3000," epoxy resins having a cyclohexane oxide structure (products of Daicel Chemical Industries, Ltd.); "EPIKOTE (now, JER) 1001, 1002, 1003, 1004, 1007, 1009, 1010, 828," bisphenol A epoxy resins (products of Japan Epoxy Resins Co., Ltd.); "EPIKOTE (now, JER) 807," bisphenol F epoxy resin (product of Japan Epoxy Resins Co., Ltd.; "EPIKOTE (now, JER) 152, 154," phenol novolak epoxy resins (products of Japan Epoxy Resins Co., Ltd.; "EPPN 201, 202," phenol novolak epoxy resins (products of Nippon Kayaku Co., Ltd.); "EOCN-102," "EOCN-103S," "EOCN-104S," "EOCN-1020," "EOCN-1025" and "EOCN-1027," cresol novolak epoxy resins (products of Nippon Kayaku Co., Ltd.); "EPIKOTE (now JER) 180S75," cresol novolak epoxy resin (product of Japan Epoxy Resins Co., Ltd.); "DENACOL EX-252," alicyclic epoxy resin (product of Nagase ChemteX Corporation); "CY175," "CY177," "CY179" (products of Ciba-Geigy AG) and "ARALDITE CY-182, CY-192, CY-184," alicyclic epoxy resins (products of Ciba-Geigy AG); "EPICLON 200, 400," alicyclic epoxy resins (products of DIC Corporation); "EPIKOTE (now JER) 871, 872," alicyclic epoxy resins (products of Japan Epoxy Resins Co., Ltd.); "ED-5661" and "ED-5662," alicyclic epoxy resins (products of Celanese Coating); "DENACOL EX-611, EX-612, EX-614, EX-622, EX-411, EX-512, EX-522, EX-421, EX-313, EX-314, EX-321," aliphatic polyglycidyl ethers (products of Nagase ChemteX Corporation); and the like.

Such acid anhydride compounds are each a carboxylic to acid anhydride obtained by dehydrating condensation of two molecules of a carboxylic acid. When exposed to high temperature upon thermal curing, anhydride rings are opened so that a crosslinking reaction proceeds through an addition reaction with the polymer according to the present invention.

Specific examples of such acid anhydride compounds include those containing one acid anhydride group in a molecule, such as phthalic anhydride, tetrahydrophthalic anhydride, hexahydrophthalic anhydride, methyltetrahydrophthalic anhydride, methylhexahydrophthalic anhydride, nadic anhydride, methylnadic anhydride, maleic anhydride, succinic anhydride, octylsuccinic anhydride and dodecenylsuccinic anhydride; those containing two acid anhydride groups in a molecule, such as 1,2,3,4-cyclobutanetetracarboxylic dianhydride, pyromellitic anhydride, 3,4-dicarboxy-1,2,3,4-tetrahydro-1-naphthalenesuccinic dianhydride, bicycle[3.3.0]octane-2,4,6,8-tetracarboxylic dianhydride, 5-(2,5-dioxotetrahydro-3-furanyl)-3-methyl-3-cyclohexene-1,2-dicarboxylic anhydride, 1,2,3,4-butanetetracarboxylic dianhydride, 3,3',4,4'-benzophenonetetracarboxylic dianhydride, 3,3',4,4'-biphenyltetracarboxylic dianhydride, 2,2-bis (3,4-dicarboxyphenyl)hexafluoropropane dianhydride and 1,3-dimethyl-1,2,3,4-cyclobutanetetracarboxylic dianhydride; and the like.

Such (meth)acrylic compounds each contain two or more (meth)acryl groups in a molecule. When exposed to high temperature upon thermal curing, a crosslinking reaction proceeds through an addition reaction with the polymer according to the present invention.

Examples of the (meth)acryl-containing compounds include ethylene glycol diacrylate, ethylene glycol dimethacrylate, polyethylene glycol diacrylate, polyethylene glycol dimethacrylate, ethoxylated bisphenol A diacrylate, ethoxylated bisphenol A dimethacrylate, ethoxylated trimethylol propane triacrylate, ethoxylated trimethylol propane trimethacrylate, ethoxylated glyceryl triacrylate, ethoxylated glyceryl trimethacrylate, ethoxylated pentaerythritol tetraacrylate, ethoxylated pentaerythritol tetramethacrylate, ethoxylated dipentaerythritol hexaacrylate, polyglyceryl monoethylene oxide polyacrylate, polyglyceryl polyethylene glycol polyacrylate, dipentaerythritol hexaacrylate, dipentaerythritol hexamethacrylate, neopentyl glycol diacrylate, neopentyl glycol dimethacrylate, pentaerythritol triacrylate, pentaerythritol trimethacrylate, trimethylol propane triacrylate, trimethylol propane trimethacrylate, tricyclodecane dimethanol diacrylate, tricyclodecane dimethanol dimethacrylate, 1,6-hexanediol diacrylate, 1,6-hexanediol dimethacrylate, and the like.

The above-described (meth)acryl-containing compounds are available as commercial products. Specific examples include "NK ESTER A-200, A-400, A-600, A-1000, A-TMPT, UA-53H, 1G, 2G, 3G, 4G, 9G, 14G, 23G, ABE-300, A-BPE-4, A-BPE-6, A-BPE-10, A-BPE-20, A-BPE-30, BPE-80N, BPE-100N, BPE-200, BPE-500, BPE-900, BPE-1300N, A-GLY-3E, AGLY-9E, A-GLY-20E, A-TMPT-3E0, A-TMPT-9EO, ATM-4E, ATM-35E" (products of Shin-Nakamura Chemical Co., Ltd.); "KAYARAD (registered trademark) DPEA-12, PEG400DA, THE-330, RP-1040" (products of Nippon Kayaku Co., Ltd.); "M-210" and "M-350" (products of Toagosei Co., Ltd.); "KAYARAD (registered trademark) DPHA, NPGDA, PET30" (products of Nippon Kayaku Co., Ltd.); "NK ESTER A-DPH, A-TMPT, A-DCP, A-HD-N, TMPT, DCP, NPG, HD-N" (products of Shin-Nakamura Chemical Co., Ltd.); and the like.

The blocked isocyanato-containing compounds each contain in a molecule two or more blocked isocyanato groups, which are isocyanato (—NCO) groups blocked by appropriate protective groups, respectively. When exposed to high temperature upon thermal curing, the protective groups (blocking parts) are removed through thermal dissociation, and the resulting isocyanato groups induce a crosslinking reaction with the resin. Illustrative are compounds each containing in a molecule one or more groups represented by the following formula (note: these groups may be the same or different).

[Chemical Formula 30]

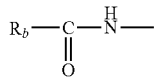

wherein $R_b$ means an organic group in the blocked moiety.

Such compounds can each be obtained, for example by reacting an appropriate blocking agent to a corresponding compound which contains two or more isocyanato groups in a molecule.

Examples of the compound, which contains two or more isocyanato groups in a molecule, include polyisocyanates such as isophorone diisocyanate, 1,6-hexamethylene diisocyanate, methylene bis(4-cyclohexylisocyanate) and trimethyl hexamethylene diisocyanate, and their dimers and trimers; their reaction products with diols, triols, diamines and triamines; and the like.

Illustrative of the blocking agent includes alcohols such as methanol, ethanol, isopropanol, n-butanol, 2-ethoxyhexanol, 2-N,N-dimethylaminoethanol, 2-ethoxyethanol and cyclohexanol; phenols such as phenol, o-nitrophenol, p-chlorophenol and o-, m- and p-cresols; lactams such as ε-caprolactam; oximes such as acetone oxime, methyl ethyl ketone oxime, methyl isobutyl ketone oxime, cyclohexanone oxime, acetophenone oxime and benzophenone oxime; pyrazoles such as pyrazole, 3,5-dimethylpyrazole and 3-methylpyrazole; thiols such as dodecanethiol and benzenethiol; and the like.

Such blocked isocyanato-containing compounds are also available as commercial products. Specific examples include "B-830," "B-815N," "B-842N," "B-870N," "B-874N," "B-882N," "B-7005," "B-7030," "B-7075" and "B-5010" (products of Mitsui Chemicals Polyurethanes Co., Ltd.); "DURANATE (registered trademark) 17B-60PX, TPA-B80E, MF-B60X, MF-K60X, E402-B80T" (products of Asahi Kasei Chemicals Corporation); "KARENZ (registered trademark) MOI-BM" (product of Showa Denko K.K.); and the like.

As aminoplast compounds, those containing two or more methoxymethylene groups in a molecule can be mentioned. When exposed to high temperature upon thermal curing, a crosslinking reaction proceeds through a demethanolation condensation reaction with the polymer according to the present invention.

Examples of the melamine compounds include CYMEL series such as "CYMEL (registered trademark) 303," hexamethoxymethylmelamine, "CYMEL 1170," tetrabutoxymethylglycoluril and "CYMEL 1123," tetramethoxymethylbenzoguanamine (products of Nihon Cytec Industries, Inc.); "NIKALAC (registered trademark) MW-30HM, MW-390, MW-100LM, MX-750LM," methylated melamine resins, and "NIKALAC MX-270, MX-280, MX-290," methylated urea resins (products of Sanwa Chemical Co., Ltd.); and the like.

Such oxetane compounds each contain two or more oxetanyl groups in a molecule. When exposed to high temperature upon thermal curing, a crosslinking reaction proceeds through an addition reaction with the polymer according to the present invention.

Examples of the oxetanyl-containing compounds include "OXT-221," "OX-SQ-H" and "OX-SC" all of which contain oxetanyl groups (products of Toagosei Co., Ltd.).

The phenoplast compounds each contain two or more hydroxymethylene groups in a molecule. When exposed to high temperature upon thermal curing, a crosslinking reaction proceeds through a dehydration reaction with the polymer according to the present invention.

Examples of the phenoplast compounds include 2,6-dihydroxymethyl-4-methylphenol, 2,4-dihydroxymethyl-6-methylphenol, bis(2-hydroxy-3-hydroxymethyl-5-methylphenyl)methane, bis(4-hydroxy-3-hydroxymethyl-5-methylphenyl)methane, 2,2-bis(4-hydroxy-3,5-dihydroxymethylphenyl)propane, bis(3-formyl-4-hydroxyphenyl)methane, bis(4-hydroxy-2,5-dimethylphenyl)formylmethane, α,α-bis(4-hydroxy-2,5-dimethylphenyl)-4-formyltoluene, and the like.

These phonoplast compounds are also available as commercial products. Specific examples include "26DMPC," "46DMOC," "DM-BIPC-F," "DM-BIOC-F," "DM-BIP-A," "RISA-F," "BI25X-DF" and "BI25X-TPA" (products of Asahi Organic Chemicals Industry Co., Ltd.); and the like.

These crosslinking agents may be used either singly or in combination. The crosslinking agent may be used in an amount of from 1 to 100 parts by mass per 100 parts by mass of the polymer.

Taking solvent resistance into consideration, its lower limit may be preferably 10 parts by mass, more preferably 20 parts by mass. Taking the control of refractive index into consideration, its upper limit may be preferably 50 parts by mass, more preferably 30 parts by mass.

The use of the crosslinking agent may be able to bring about advantageous effects such as an improvement in film density, an improvement in heat resistance and an improvement in heat-relieving capacity as a result of a reaction between the crosslinking agent and reactive terminal substituent groups which the polymer contains.

It is to be noted that the above-described other components may be added at the same time as the mixing of the polymer and the solvent or after the mixing without any particular limitation.

The film-forming composition according to the present invention can form a desired film by coating it onto a substrate and then heating the same as needed.

The coating method of the composition is optional. For example, it is possible to adopt a method such as spin coating, dip coating, flow coating, ink-jet coating, spray coating, bar coating, gravure coating, slit coating, roll coating, transfer printing, brush coating, blade coating or air-knife coating.

Substrates include silicon, glass with indium tin oxide (ITO) formed as a film thereon, glass with indium zinc oxide (IZO) formed as a film thereon, and substrates formed of polyethylene terephthalate (PET), plastics, glass, quartz, ceramics and the like. In addition, substrates having flexibility can also be used.

No particular limitation is imposed on the baking temperature insofar as the object to vaporize the solvent is concerned. For example, the baking can be performed at from 40 to 400° C. In this range, the baking temperature may be varied at two or more stages to exhibit film-forming properties of still higher uniformity or to allow a reaction to proceed on the substrate.

No particular limitation is imposed on the baking method. For example, the solvent may be vaporized under an appropriate atmosphere such as the atmosphere, an inert gas such as nitrogen or vacuum while using a hot plate or an oven.

Concerning the baking temperature and baking time, conditions suited to process steps for the intended electronic device can be selectively determined, and described specifically, baking conditions need to be selectively determined such that physical data of the resulting film meet properties required for the electronic device.

Films of the polymer according to the present invention, which have been obtained as described above, can achieve high heat resistance, high transparency, high refractive index, high solubility and low volume shrinkage by themselves, and therefore, can be suitably used as members upon fabrication of electronic devices such as liquid crystal displays, organic electroluminescence (EL) displays, optical semiconductor (LED) devices, solid-state imaging devices, organic thin-film solar cells, dye-sensitized solar cells, and organic thin-film transistors (TFT).

The polymer according to the present invention may also be used as a composition with another resin (thermoplastic resin or thermosetting resin).

Specific examples of such a resin include, but are not specifically limited to, as thermoplastic resins, for example, polyolefin resins such as PE (polyethylene), PP (polypropylene), EVA (ethylene-vinyl acetate copolymer) and EEA (ethylene-ethyl acrylate copolymer), polystyrene resins such as PS (polystyrene), HIPS (high-impact polystyrene), AS (acrylonitrile-styrene copolymer), ABS (acrylonitrile-butadiene-styrene copolymer) and MS (methyl methacrylate-styrene copolymer), polycarbonate resins, vinyl chloride resins, polyamide resins, polyimide resins, (meth)acrylic resins such as PMMA (polymethyl methacrylate), polyester resins such as PET (polyethylene terephthalate), polybutylene terephthalate, polyethylene naphthalate, polybutylene naphthalate, PLA (polylactic acid), poly-3-hydroxybutyric acid, polycaprolactone, polybutylene succinate and polyethylene succinate/adipate, polyphenylene ether resins, modified polyphenylene ether resins, polyacetal resins, polysulfone resins, polyphenylene sulfide resins, polyvinyl alcohol resins, polyglycolic acid, modified starches, cellulose acetate, cellulose triacetate, chitin, chitosan, lignin, and the like; and as thermosetting resins, for example, phenol resins, urea resins, melamine resins, unsaturated polyester resins, polyurethane resins, epoxy resins, and the like.

These resins may be used either singly or in combination. The resin may be used in an amount of preferably from 1 to 10,000 parts by mass, more preferably from 1 to 1,000 parts by mass per 100 parts by mass of the above-described polymer.

For example, a composition with a (meth)acrylic resin can be obtained by mixing a (meth)acrylate compound and the above-described polymer and polymerizing the (meth)acrylate compound.

Examples of the (meth)acrylate compound include methyl (meth)acrylate, ethyl (meth)acrylate, ethylene glycol di(meth)acrylate, tetraethylene glycol di(meth)acrylate, polyethylene glycol di(meth)acrylate, propylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, trimethylolpropanetrioxyethyl (meth)acrylate, tricyclodecanedimethanol di(meth)acrylate, tricyclodecanyl di(meth)acrylate, trimethylolpropanetrioxypropyl (meth)acrylate, tris-2-hydroxyethyl isocyanurate tri(meth)acrylate, tris-2-hydroxyethyl isocyanurate di(meth)acrylate, 1,9-nonanediol di(meth) acrylate, pentaerythritol di(meth)acrylate, glycerol methacrylate acrylate, pentaerythritol tri(meth)acrylate, trimethylolpropane trimethacrylate, allyl (meth)acrylate, vinyl (meth)acrylate, epoxy (meth)acrylates, polyester (meth)acrylates, urethane (meth)acrylates, and the like.

Polymerization of these (meth)acrylate compounds can be conducted by light irradiation or heating in the presence of a photoradical initiator or heat radical initiator.

Examples of the photoradical polymerization initiator include acetophenones, benzophenones, Michler's benzoyl benzoate, amyloxime ester, tetramethyl thiuram monosulfide, is thioxanthone, and the like.

Photocleavable photoradical polymerization initiators are particularly preferred. About photocleavable photoradical polymerization initiators, a description is found in TAKA-SUKI, Kazuhiro: "Latest UV Curing Technologies" (in Japanese), page 159, Technical Information Institute Co., Ltd. (1991).

Commercially-available, photoradical polymerization initiators include, for example, "IRGACURE 184, 369, 651, 500, 819, 907, 784, 2959, CGI1700, CGI1750, CGI1850, CG24-61" and "DAROCUR 1116, 1173," trade names, products of Ciba Japan; "LUCIRIN TPO," trade name, product of BASF SE; "UBECRYL P36," trade name, product of UCB S.A.; "EZACURE KIP150, KIP65LT, KIP100F, KT37, KT55, KT046, KIP75/B," trade names, products of Fratelli Lamberti S.p.A.; and the like.

Such a photopolymerization initiator may be used preferably in a range of from 0.1 to 15 parts by mass per 100 parts by mass of the (meth)acrylate compound, with a range of from 1 to 10 parts by mass being more preferred.

As solvents usable in the polymerization, similar solvents as those exemplified with respect to the film-forming composition can be mentioned.

The present invention also provides a polymer, which has a weight average molecular weight of from 500 to 500,000 and a refractive index at 550 nm of 1.70 or higher and contains no sulfur atom in its molecule.

Although the range of this refractive index varies depending on the use situation, the lower limit may be preferably 1.70 or higher, more preferably 1.75 or higher, still more preferably 1.80 or higher. The upper limit may be, but is not specifically limited to, approximately from 2.00 to 1.95, or lower.

This polymer has a structure that preferably contains no halogen atom.

Further, this polymer may preferably have the structure of a hyperbranched polymer. More preferably, this polymer is a hyperbranched polymer that contains in its structure amino groups having hydrogen atoms some of which are hydrogen-bonded to other sites.

The content of these hydrogen bonds can be calculated by infrared spectroscopy, and its lower limit may be preferably 0.3 or higher, more preferably 0.4 or higher.

The content of hydrogen bonds can be determined by reading the value ($I_H$) of a maximum absorbance of a peak for hydrogen-bonded NH and the value ($I_F$) of a maximum absorbance of a peak for NH which is not hydrogen-bonded, and conducting calculation in accordance with an equation, $I_H/I_F+I_H$.

This polymer may preferably have a structure that includes triazine rings.

Further, a composition of this polymer and a crosslinking agent is useful as a film-forming or like composition.

Specific examples of the crosslinking agent are similar to the crosslinking agents exemplified above.

This composition can be suitably used as lens members, and also, as members upon fabrication of electronic devices such as liquid crystal displays, organic electroluminescence (EL) displays, optical semiconductor (LED) devices, solid-state imaging devices, organic thin-film solar cells, dye-sensitized solar cells, and organic thin-film transistors (TFT). These members are required to have high refractive index without using any metal oxide.

The composition can be suitably used as members for solid-state imaging devices, said members being required to have particularly high refractive index, specifically as filling films and planarization films on photodiodes, front and rear planarization films for color filters, microlenses, and planarization films and conformal films on microlenses.

EXAMPLES

The present invention will hereinafter be described more specifically based on Examples and Comparative Examples, although the present invention shall not be limited to the following Examples. It is to be noted that individual measurement instruments used in the Examples are as will be described below.

[$^1$H-NMR]
  Instruments: "VARIAN NMR SYSTEM 400 NB" (400 MHz)
  "JEOL-ECA 700" (700 MHz)
  Measurement solvent: DMSO-d6
  Standard material: tetramethylsilane (TMS) (0.0 ppm)
[GPC]
  Instrument: "HLC-8200 GPC," manufactured by Tosoh Corporation
  Column: "SHODEX KF-804L+KF-805L"
  Column temperature: 40° C.
  Solvent: tetrahydrofuran (hereinafter "THF")
  Detector: UV (254 nm)
  Calibration curve: standard polystyrene
[Ultraviolet-Visible Spectrophotometer]
  Instrument: "SHIMADZU UV-3600," manufactured by Shimadzu Corporation
[Ellipsometer]
  Instrument: "VARIABLE ANGLE SPECTROSCOPIC ELLIPSOMETER VASE," manufactured by J.A. Woollam JAPAN Co., Inc.
[Differential Scanning Calorimeter (TG-DTA)]
  Instrument: "TG-8120," manufactured by Rigaku Corporation
  Ramp-up rate: 10° C./min
  Measurement temperature: 25 to 750° C.
[Electron Microscope]
  Instrument: "ELECTRON MICROSCOPE S-4800," manufactured by JEOL Ltd.

Example 1

Synthesis of High-Molecular Compound [3]

[Chemical Formula 31]

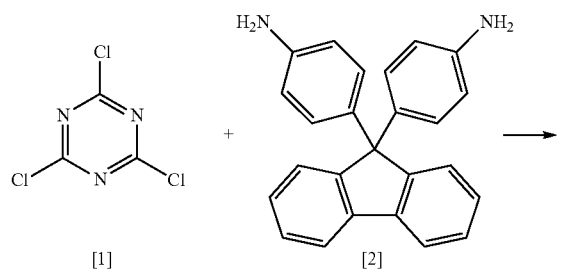

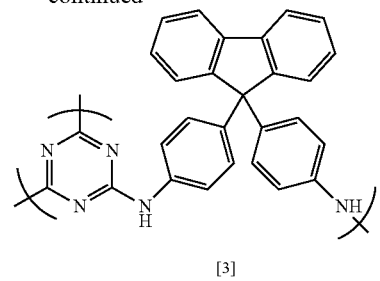

Under air and in a 200-mL, four-necked flask, 9,9-bis(4-aminophenyl)fluorene [2] (9.29 g, 0.027 mol, product of Aldrich Corporation) was placed and dissolved in N,N-dimethylacetamide (hereinafter "DMAc," 80 mL), followed by heating to 100° C. in an oil bath. Subsequently, a solution of 2,4,6-trichloro-1,3,5-triazine [1] (3.69 g, 0.02 mol, product of Tokyo Chemical Industry Co., Ltd.) in DMAc (20 mL) was added to initiate polymerization.

Five minutes later, aniline (3.34 g, 0.036 mol) was added, followed by stirring for 10 minutes to terminate the polymerization. After the resultant polymerization mixture was allowed to cool to room temperature, it was reprecipitated in an aqueous solution of potassium carbonate (15 g, 0.11 mol) in water (1,000 mL). The resulting precipitates were collected by filtration, redissolved in THF (50 mL), and then reprecipitated in a mixed solvent of hexane (540 mL) and ethanol (60 mL). The resulting precipitates were collected by filtration, and then dried at 40° C. for 6 hours in a vacuum dryer to obtain the target high-molecular compound [3] (hereinafter abbreviated as "HB-TFA90," 12.4 g).

The results of $^1$H-NMR spectrum measurement of HB-TFA90 are shown in FIG. 1. HB-TFA90 so obtained was a compound having structural units represented by the formula (1). The weight average molecular weight Mw of HB-TFA90 as measured by GPC and calibrated against standard polystyrene was 9,200, and the polydispersibility Mw/Mn was 2.33.

Example 2

Figure 2:
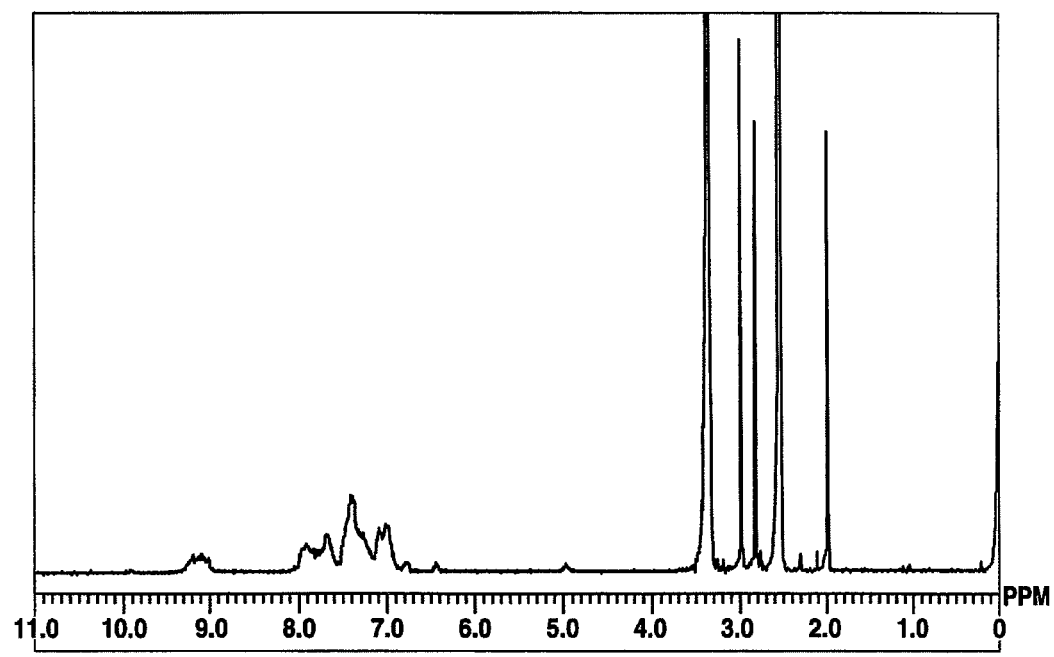
FIG. 2 is a diagram showing a $^1$H-NMR spectrum of the high-molecular compound [3] obtained in Example 2.

Using 9,9-bis(4-aminophenyl)fluorene [2] (8.37 g, 0.024 mol), 2,4,6-trichloro-1,3,5-triazine [1] (3.69 g, 0.02 mol) and aniline (5.64 g, 0.06 mol), synthesis was conducted in a similar manner as in Example 1 to obtain a high-molecular compound [3] (hereinafter abbreviated as "HB-TFA56," 11.5 g). The molecular weight of which was different from that of Example 1. The results of $^1$H-NMR spectrum measurement of HB-TFA56 are shown in FIG. 2. HB-TFA56 so obtained was a compound having structural units represented by the formula (1). The weight average molecular weight Mw of HB-TFA56 as measured by GPC and calibrated against standard polystyrene was 5,600, and the polydispersibility Mw/Mn was 2.67.

Example 3

Figure 3:
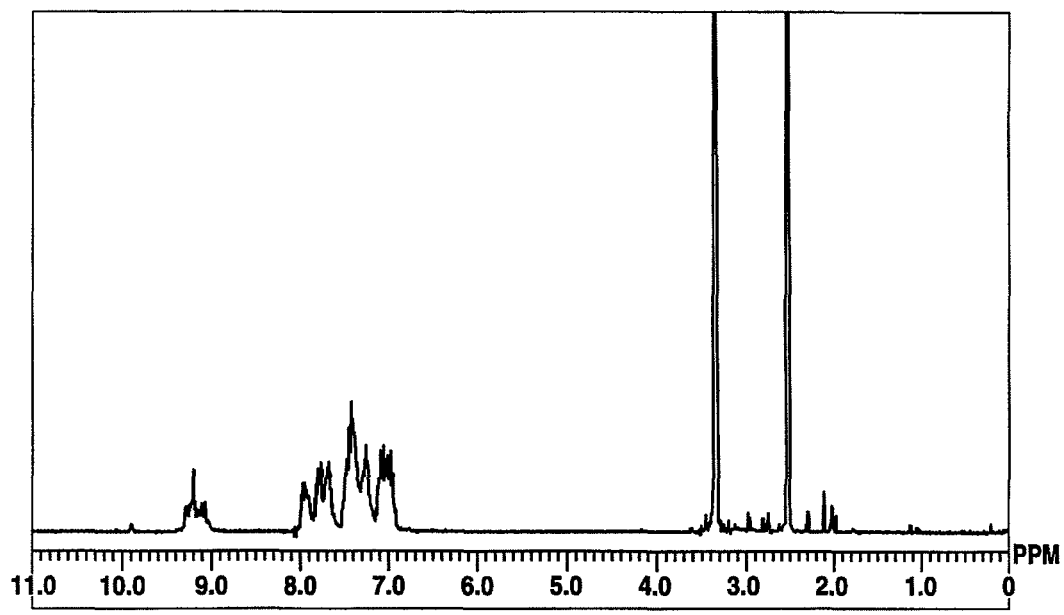
FIG. 3 is a diagram showing a $^1$H-NMR spectrum of the high-molecular compound [3] obtained in Example 3.

Using 9,9-bis(4-aminophenyl)fluorene [2] (7.32 g, 0.021 mol), 2,4,6-trichloro-1,3,5-triazine [1] (3.87 g, 0.01 mol) and aniline (5.64 g, 0.06 mol), synthesis was conducted in a similar manner as in Example 1 to obtain a high-molecular compound [3] (hereinafter abbreviated as "HB-TFA32," 10.9 g). The molecular weight of which was different from that of Example 1. The results of $^1$H-NMR spectrum measurement of HB-TFA32 are shown in FIG. 3. HB-TFA32 so obtained was a compound having structural units represented by the formula (1). The weight average molecular weight Mw of HB-TFA32 as measured by GPC and calibrated against standard polystyrene was 3,200, and the polydispersibility Mw/Mn was 2.02.

Example 4

Figure 4:
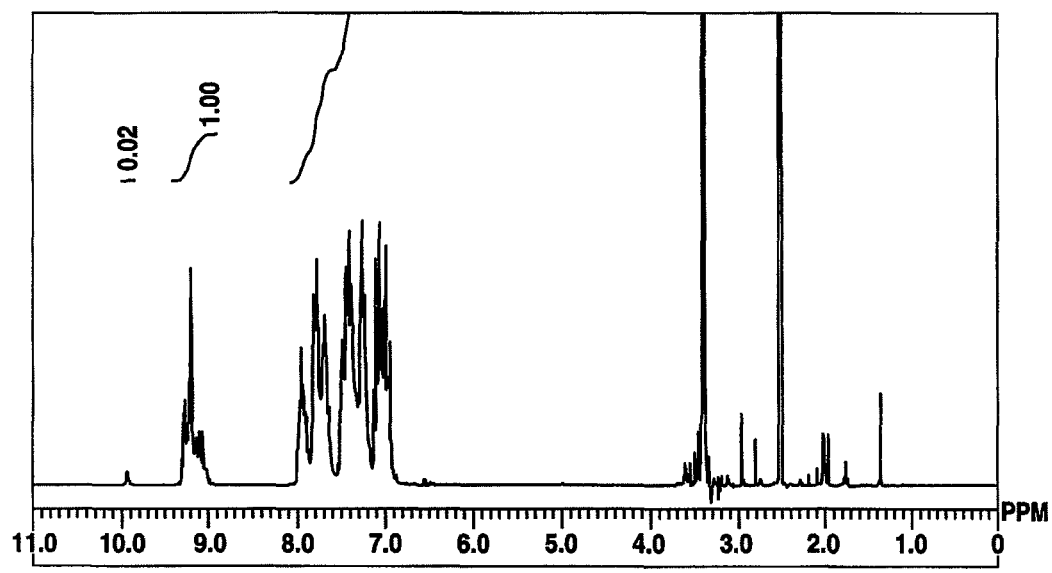
FIG. 4 is a diagram showing a $^1$H-NMR spectrum of the high-molecular compound [3] obtained in Example 4.

Using 9,9-bis(4-aminophenyl)fluorene [2] (6.48 g, 0.018 mol), 2,4,6-trichloro-1,3,5-triazine [1] (4.06 g, 0.022 mol) and aniline (5.64 g, 0.06 mol), synthesis was conducted in a similar manner as in Example 1 to obtain a high-molecular compound [3] (hereinafter abbreviated as "HB-TFA20," 10.8 g). The molecular weight of which was different from that of Example 1. The results of $^1$H-NMR spectrum measurement of HB-TFA20 are shown in FIG. 4. HB-TFA20 was a compound having structural units represented by the formula (1). The weight average molecular weight Mw of HB-TFA20 as measured by GPC and calibrated against standard polystyrene was 2,000, and the polydispersibility Mw/Mn was 1.58.

Example 5

Synthesis of High-Molecular Compound [5]

[Chemical Formula 32]

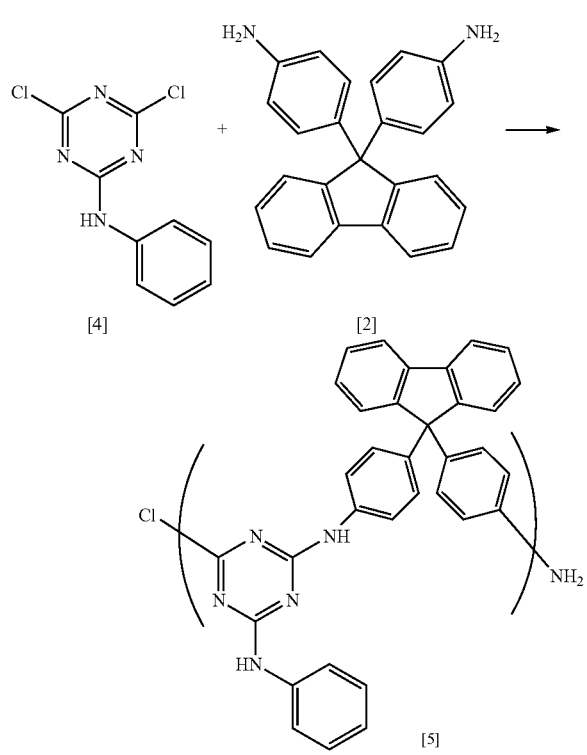

Figure 5:
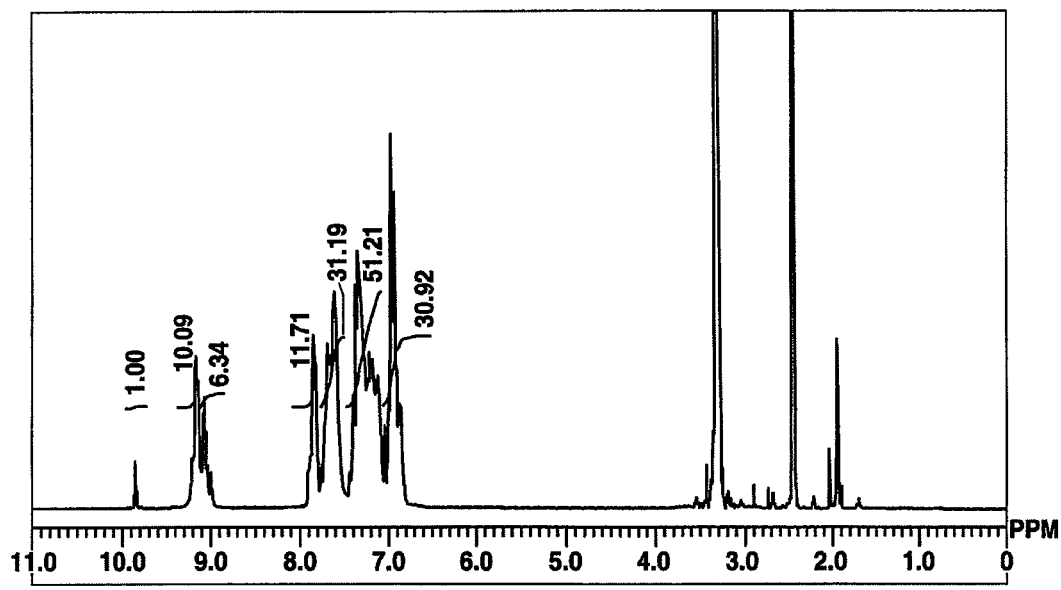
FIG. 5 is a diagram showing a $^1$H-NMR spectrum of the high-molecular compound [5] obtained in Example 5.

Using 4,6-dichloro-N-phenyl-1,3,5-triazin-2-amine [4] (6.48 g, 0.018 mol) in place of 2,4,6-trichloro-1,3,5-triazine, 9,9-bis(4-aminophenyl)fluorene [2] (6.48 g, 0.018 mol) and aniline (5.64 g, 0.06 mol), synthesis was conducted to obtain the target linear high-molecular compound [5] (hereinafter abbreviated as "L-TF39," 10.8 g). The results of $^1$H-NMR spectrum measurement of L-TF39 are shown in FIG. 5. L-TF39 so obtained was a compound having structural units represented by the formula (2). The weight average molecular weight Mw of L-TF39 as measured by GPC and calibrated against standard polystyrene was 3,900, and the polydispersibility Mw/Mn was 1.78.

<Preparation of Film-forming Compositions>

Example 6

Under air and in a 10-mL eggplant flask, HB-TFA90 (1.0000 g) obtained in Example 1 was placed, followed by the addition of cyclohexanone (3.9950 g) as a solvent. A 5% by mass solution (0.0100 g) of "MEGAFAC R-30" (trade name, product of DIC Corporation) in cyclohexanone was then added, and the resulting solution was stirred for 3 hours until homogeneous. After the stirring, the solute had been completely dissolved, and as a clear pale-yellow solution, a polymer varnish (hereinafter abbreviated as "HB-TFA90V") was obtained. The total percentage by mass of solids in HB-TFA90V was 10% by mass.

Example 7

A polymer varnish was prepared as in Example 6 except for the use of HB-TFA56 obtained in Example 2. As a clear pale-yellow solution, a polymer varnish (hereinafter abbreviated as "HB-TFA56V") was obtained. The total percentage by mass of solids in HB-TFA56V was 10% by mass.

Example 8

A polymer varnish was prepared as in Example 6 except for the use of HB-TFA32 obtained in Example 3. As a clear pale-yellow solution, a polymer varnish (hereinafter abbreviated as "HB-TFA32V") was obtained. The total percentage by mass of solids in HB-TFA32V was 10% by mass.

Example 9

A polymer varnish was prepared as in Example 6 except for the use of HB-TFA20 obtained in Example 4. As a clear pale-yellow solution, a polymer varnish (hereinafter abbreviated as "HB-TFA20V") was obtained. The total percentage by mass of solids in HB-TFA20V was 10% by mass.

Example 10

A polymer varnish was prepared as in Example 6 except for the use of L-TF39 obtained in Example 5. As a clear pale-yellow solution, a polymer varnish (hereinafter abbreviated as "L-TF39V") was obtained. The total percentage by mass of solids in L-TF39V was 10% by mass.

The polymer varnishes obtained in Examples 6 to 10 were homogeneous varnishes with their solutes dissolved completely therein. Even when left over for 1 month under conditions of 23° C. and 55% RH, the solutes did not precipitate so that the polymer varnishes were excellent in storage stability.

<Formation of Films and Refractive Indexes>

Example 11

Using a spin coater, HB-TFA90V obtained in Example 6 was spin-coated onto a silicon substrate to give a 500 nm thickness. Baking was then performed for 2 minutes on a hot plate controlled at 150° C. to obtain a film (hereinafter abbreviated as "HB-TFA90F1").

Example 12

Using a spin coater, HB-TFA90V obtained in Example 6 was spin-coated onto a silicon substrate to give a 500 nm thickness. On a hot plate controlled at 150° C., baking was performed for 2 minutes, followed by further baking at 200° C. for 5 minutes to obtain a film (hereinafter abbreviated as "HB-TFA90F2").

Example 13

Using a spin coater, HB-TFA90V obtained in Example 6 was spin-coated onto a silicon substrate to give a 500 nm thickness. On a hot plate controlled at 150° C., baking was performed for 2 minutes, followed by further baking at 250° C. for 5 minutes to obtain a film (hereinafter abbreviated as "HB-TFA90F3").

Example 14

Using a spin coater, HB-TFA90V obtained in Example 6 was spin-coated onto a silicon substrate to give a 500 nm thickness. On a hot plate controlled at 150° C., baking was performed for 2 minutes, followed by further baking at 300° C. for 5 minutes to obtain a film (hereinafter abbreviated as "HB-TFA90F4").

Example 15

Using a spin coater, HB-TFA56V obtained in Example 7 was spin-coated onto a silicon substrate to give a 500 nm thickness. Baking was then performed for 2 minutes on a hot plate controlled at 150° C. to obtain a film (hereinafter abbreviated as "HB-TFA56F1").

Example 16

Using a spin coater, HB-TFA56V obtained in Example 7 was spin-coated onto a silicon substrate to give a 500 nm thickness. On a hot plate controlled at 150° C., baking was performed for 2 minutes, followed by further baking at 200° C. for 5 minutes to obtain a film (hereinafter abbreviated as "HB-TFA56F2").

Example 17

Using a spin coater, HB-TFA56V obtained in Example 7 was spin-coated onto a silicon substrate to give a 500 nm thickness. On a hot plate controlled at 150° C., baking was performed for 2 minutes, followed by further baking at 250° C. for 5 minutes to obtain a film (hereinafter abbreviated as "HB-TFA56F3").

Example 18

Using a spin coater, HB-TFA56V obtained in Example 7 was spin-coated onto a silicon substrate to give a 500 nm thickness. On a hot plate controlled at 150° C., baking was performed for 2 minutes, followed by further baking at 300° C. for 5 minutes to obtain a film (hereinafter abbreviated as "HB-TFA56F4").

Example 19

Using a spin coater, HB-TFA32V obtained in Example 8 was spin-coated onto a silicon substrate to give a 500 nm thickness. Baking was then performed for 2 minutes on a hot plate controlled at 150° C. to obtain a film (hereinafter abbreviated as "HB-TFA32F1").

Example 20

Using a spin coater, HB-TFA32V obtained in Example 8 was spin-coated onto a silicon substrate to give a 500 nm thickness. On a hot plate controlled at 150° C., baking was performed for 2 minutes, followed by further baking at 200° C. for 5 minutes to obtain a film (hereinafter abbreviated as "HB-TFA32F2").

Example 21

Using a spin coater, HB-TFA32V obtained in Example 8 was spin-coated onto a silicon substrate to give a 500 nm thickness. On a hot plate controlled at 150° C., baking was performed for 2 minutes, followed by further baking at 250° C. for 5 minutes to obtain a film (hereinafter abbreviated as to "HB-TFA32F3").

Example 22

Using a spin coater, HB-TFA32V obtained in Example 8 was spin-coated onto a silicon substrate to give a 500 nm thickness. On a hot plate controlled at 150° C., baking was performed for 2 minutes, followed by further baking at 300° C. for 5 minutes to obtain a film (hereinafter abbreviated as "HB-TFA32F4").

Example 23

Using a spin coater, HB-TFA20V obtained in Example 9 was spin-coated onto a silicon substrate to give a 500 nm thickness. Baking was then performed for 2 minutes on a hot plate controlled at 150° C. to obtain a film (hereinafter abbreviated as "HB-TFA20F1").

Example 24

Using a spin coater, HB-TFA20V obtained in Example 9 was spin-coated onto a silicon substrate to give a 500 nm thickness. On a hot plate controlled at 150° C., baking was performed for 2 minutes, followed by further baking at 200° C. for 5 minutes to obtain a film (hereinafter abbreviated as "HB-TFA20F2").

Example 25

Using a spin coater, HB-TFA20V obtained in Example 9 was spin-coated onto a silicon substrate to give a 500 nm thickness. On a hot plate controlled at 150° C., baking was performed for 2 minutes, followed by further baking at 250° C. for 5 minutes to obtain a film (hereinafter abbreviated as "HB-TFA20F3").

Example 26

Using a spin coater, HB-TFA20V obtained in Example 9 was spin-coated onto a silicon substrate to give a 500 nm thickness. On a hot plate controlled at 150° C., baking was performed for 2 minutes, followed by further baking at 300° C. for 5 minutes to obtain a film (hereinafter abbreviated as "HB-TFA20F4").

Example 27

Using a spin coater, L-TF39V obtained in Example 10 was spin-coated onto a silicon substrate to give a 500 nm thickness. Baking was then performed for 2 minutes on a hot plate controlled at 150° C. to obtain a film (hereinafter abbreviated as "L-TF39F1").

Example 28

Using a spin coater, L-TF39V obtained in Example 10 was spin-coated onto a silicon substrate to give a 500 nm thickness. On a hot plate controlled at 150° C., baking was performed for 2 minutes, followed by further baking at 200° C. for 5 minutes to obtain a film (hereinafter abbreviated as "L-TF39F2").

Example 29

Using a spin coater, L-TF39V obtained in Example 10 was spin-coated onto a silicon substrate to give a 500 nm thickness. On a hot plate controlled at 150° C., baking was performed for 2 minutes, followed by further baking at 250° C. for 5 minutes to obtain a film (hereinafter abbreviated as "L-TF39F3").

Example 30

Using a spin coater, L-TF39V obtained in Example 10 was spin-coated onto a silicon substrate to give a 500 nm thickness. On a hot plate controlled at 150° C., baking was performed for 2 minutes, followed by further baking at 300° C. for 5 minutes to obtain a film (hereinafter abbreviated as "L-TF39F4").

The individual films formed above in Examples 11 to 30 were measured for refractive index and thickness. The results are presented in Table 1.

TABLE 1

| | | Refractive index | | Thickness |
|---|---|---|---|---|
| | Abbreviation | 550 nm | 633 nm | (nm) |
| Example 11 | HB-TFA90F1 | 1.7250 | 1.7025 | 531.3 |
| Example 12 | HB-TFA90F2 | 1.7287 | 1.7086 | 514.5 |
| Example 13 | HB-TFA90F3 | 1.7302 | 1.7098 | 510.9 |
| Example 14 | HB-TFA90F4 | 1.7310 | 1.7106 | 509.8 |
| Example 15 | HB-TFA56F1 | 1.7240 | 1.7068 | 522.1 |
| Example 16 | HB-TFA56F2 | 1.7300 | 1.7125 | 502.5 |
| Example 17 | HB-TFA56F3 | 1.7302 | 1.7130 | 499.5 |
| Example 18 | HB-TFA56F4 | 1.7301 | 1.7126 | 498.5 |
| Example 19 | HB-TFA32F1 | 1.7277 | 1.7104 | 539.1 |
| Example 20 | HB-TFA32F2 | 1.7335 | 1.7160 | 515.9 |
| Example 21 | HB-TFA32F3 | 1.7330 | 1.7156 | 511.5 |
| Example 22 | HB-TFA32F4 | 1.7310 | 1.7135 | 510.0 |
| Example 23 | HB-TFA20F1 | 1.7313 | 1.7139 | 541.3 |
| Example 24 | HB-TFA20F2 | 1.7377 | 1.7200 | 519.3 |
| Example 25 | HB-TFA20F3 | 1.7353 | 1.7177 | 514.4 |
| Example 26 | HB-TFA20F4 | 1.7398 | 1.7221 | 512.0 |
| Example 27 | L-TF39F1 | 1.7322 | 1.7149 | 521.7 |
| Example 28 | L-TF39F2 | 1.7354 | 1.7178 | 501.9 |
| Example 29 | L-TF39F3 | 1.7321 | 1.7147 | 501.1 |
| Example 30 | L-TF39F4 | 1.7305 | 1.7131 | 498.6 |

From the results of Table 1, it was found that the refractive index of HB-TFA90F1 in Example 11 was 1.7250 at 550 nm wavelength and 1.7025 at 633 nm wavelength and was hence very high as a polymer alone.

Comparing Examples 11 to 14, the refractive index was not lowered even when the baking step at 300° C. for 5 minutes in the atmosphere was added. It has, therefore, been confirmed that the stability of refractive index under heat is very high. Making a comparison in thickness between Example 12 and Example 14, there was only a small change of from 514.5 nm to 509.8 nm between the step at 200° C. and the step at 300° C. It has, accordingly, been found that the volume shrinkage rate is extremely small.

In Examples 15 to 18, Examples 19 to 22, Examples 23 to 26 and Examples 27 to 30, no large decrease in refractive index was confirmed either with a rise in baking temperature, and further, the volume shrinkage rate was also found to be small.

Concerning changes in refractive index depending on variations in the molecular weight of the polymer, a comparison was made among Example 12, Example 16, Example 20 and Example 24. The refractive indexes were 1.7287, 1.7300, 1.7335 and 1.7377, respectively, at 550 nm wavelength. It has, therefore, been found that a polymer of lower molecular weight tends to exhibit higher refractive index.

Comparing Example 19, in which the polymer having the highly-branched structure was used, with Example 27 in which the polymer having the linear structure was used, the refractive indexes were 1.7277 and 1.7322, respectively, at 550 nm wavelength. It has, therefore, been found that a polymer having a linear structure tends to exhibit higher refractive index.

<Formation of Films and Transmittances>

Example 31

Figure 6:
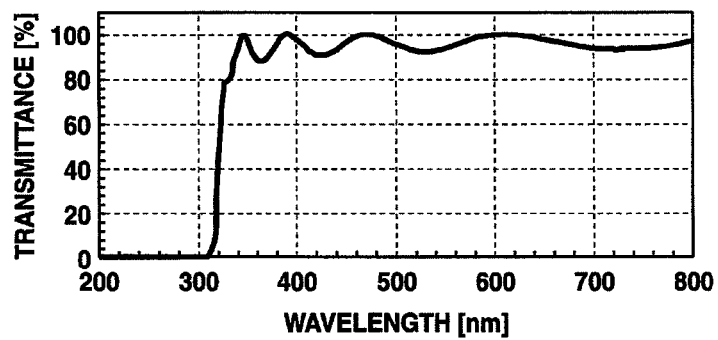
FIG. 6 is a diagram showing the transmittance of the film obtained in Example 31.

Using a spin coater, HB-TFA90V obtained in Example 6 was spin-coated onto a quartz substrate to give a 500 nm thickness. Baking was then performed for 2 minutes on a hot plate controlled at 150° C. to obtain HB-TFA90F1. The measurement results of transmittance of HB-TFA90F1 are shown in FIG. 6.

Example 32

Figure 7:
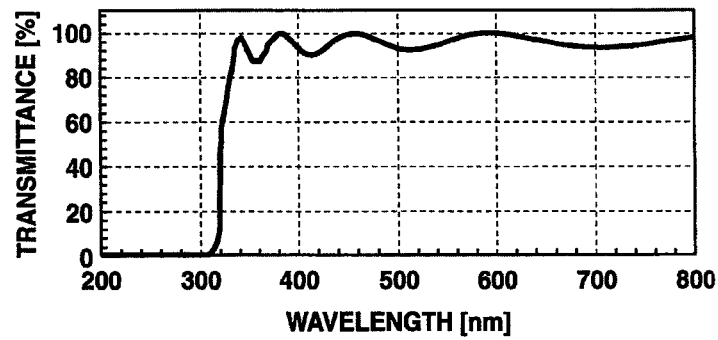
FIG. 7 is a diagram showing the transmittance of the film obtained in Example 32.

Using a spin coater, HB-TFA90V obtained in Example 6 was spin-coated onto a quartz substrate to give a 500 nm thickness. On a hot plate controlled at 150° C., baking was performed for 2 minutes, followed by further baking at 200° C. for 5 minutes to obtain HB-TFA90F2. The measurement results of transmittance of HB-TFA90F2 are shown in FIG. 7.

Example 33

Figure 8:
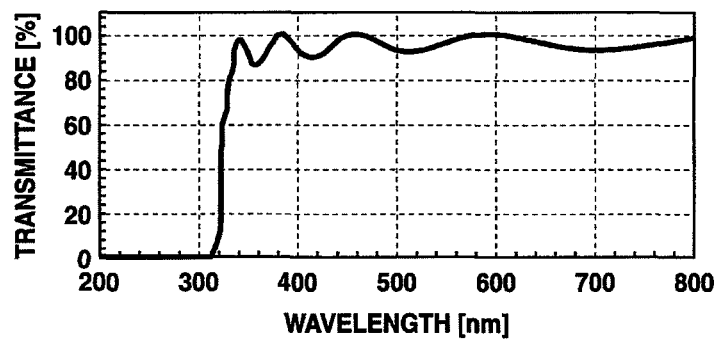
FIG. 8 is a diagram showing the transmittance of the film obtained in Example 33.

Using a spin coater, HB-TFA90V obtained in Example 6 was spin-coated onto a quartz substrate to give a 500 nm thickness. On a hot plate controlled at 150° C., baking was performed for 2 minutes, followed by further baking at 250° C. for 5 minutes to obtain HB-TFA90F3. The measurement results of transmittance of HB-TFA90F3 are shown in FIG. 8.

Example 34

Figure 9:
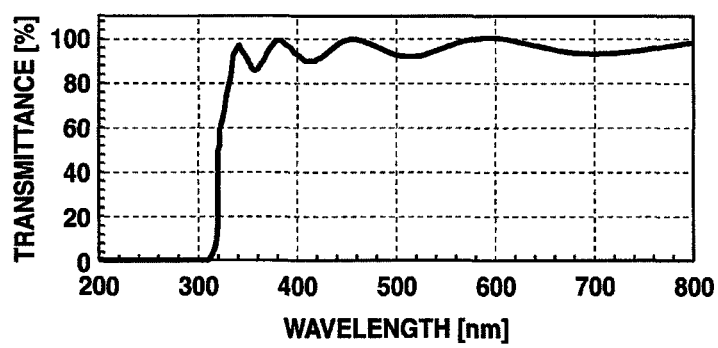
FIG. 9 is a diagram showing the transmittance of the film obtained in Example 34.

Using a spin coater, HB-TFA90V obtained in Example 6 was spin-coated onto a quartz substrate to give a 500 nm thickness. On a hot plate controlled at 150° C., baking was performed for 2 minutes, followed by further baking at 300° C. for 5 minutes to obtain HB-TFA90F4. The measurement results of transmittance of HB-TFA90F4 are shown in FIG. 9.

Example 35

Figure 10:
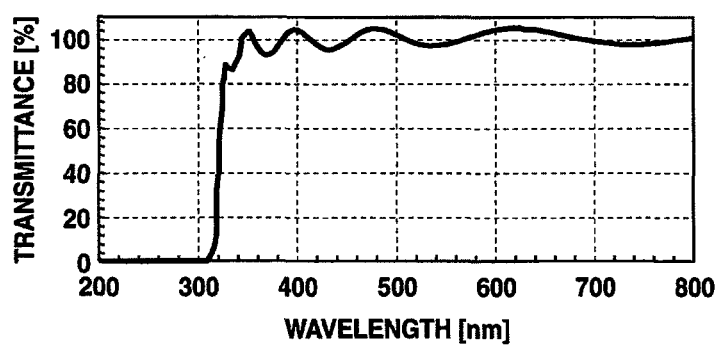
FIG. 10 is a diagram showing the transmittance of the film obtained in Example 35.

Using a spin coater, HB-TFA56V obtained in Example 7 was spin-coated onto a quartz substrate to give a 500 nm thickness. Baking was then performed for 2 minutes on a hot plate controlled at 150° C. to obtain HB-TFA56F1. The measurement results of transmittance of HB-TFA56F1 are shown in FIG. 10.

Example 36

Using a spin coater, HB-TFA56V obtained in Example 7 was spin-coated onto a quartz substrate to give a 500 nm thickness. On a hot plate controlled at 150° C., baking was performed for 2 minutes, followed by further baking at 200°

Figure 11:
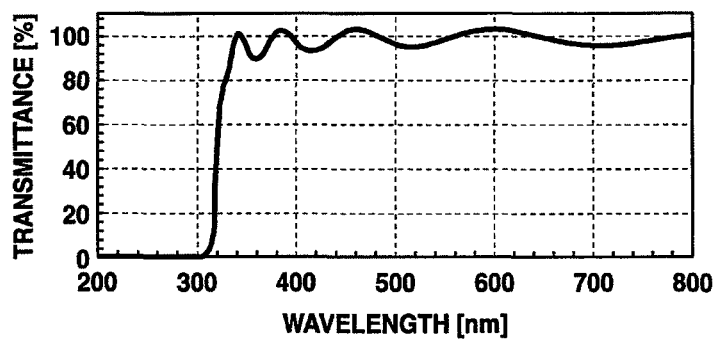
FIG. 11 is a diagram showing the transmittance of the film obtained in Example 36.

C. for 5 minutes to obtain HB-TFA56F2. The measurement results of transmittance of HB-TFA56F2 are shown in FIG. 11.

Example 37

Figure 12:
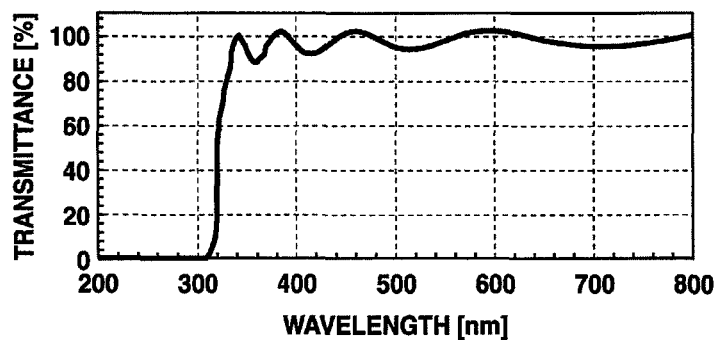
FIG. 12 is a diagram showing the transmittance of the film obtained in Example 37.

Using a spin coater, HB-TFA56V obtained in Example 7 was spin-coated onto a quartz substrate to give a 500 nm thickness. On a hot plate controlled at 150° C., baking was performed for 2 minutes, followed by further baking at 250° C. for 5 minutes to obtain HB-TFA56F3. The measurement results of transmittance of HB-TFA56F3 are shown in FIG. 12.

Example 38

Figure 13:
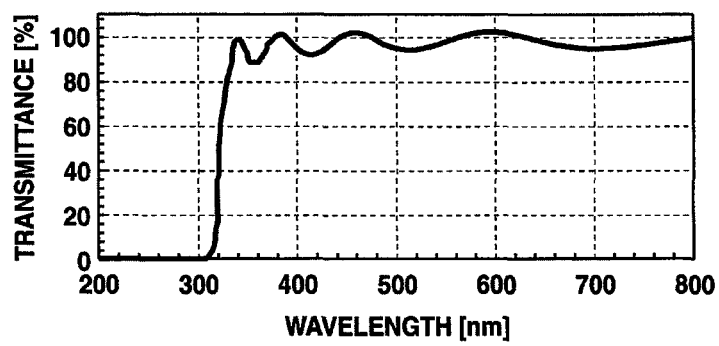
FIG. 13 is a diagram showing the transmittance of the film obtained in Example 38.

Using a spin coater, HB-TFA56V obtained in Example 7 was spin-coated onto a quartz substrate to give a 500 nm thickness. On a hot plate controlled at 150° C., baking was performed for 2 minutes, followed by further baking at 300° C. for 5 minutes to obtain HB-TFA56F4. The measurement results of transmittance of HB-TFA56F4 are shown in FIG. 13.

Example 39

Figure 14:
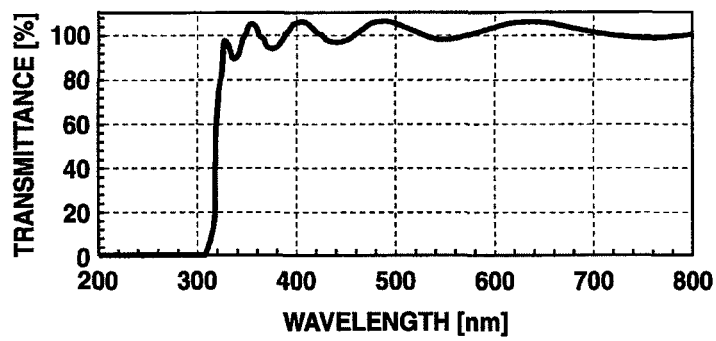
FIG. 14 is a diagram showing the transmittance of the film obtained in Example 39.

Using a spin coater, HB-TFA32V obtained in Example 8 was spin-coated onto a quartz substrate to give a 500 nm thickness. Baking was then performed for 2 minutes on a hot plate controlled at 150° C. to obtain HB-TFA32F1. The measurement results of transmittance of HB-TFA32F1 are shown in FIG. 14.

Example 40

Figure 15:
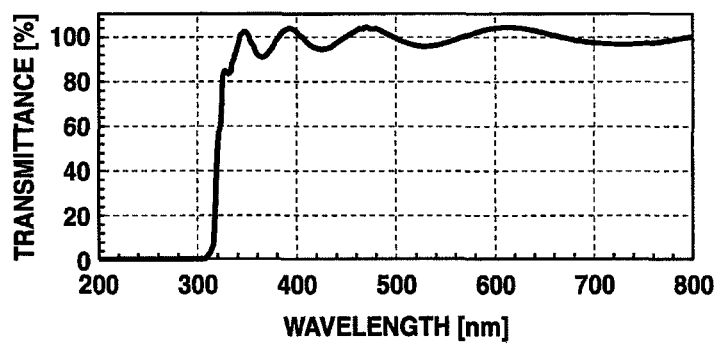
FIG. 15 is a diagram showing the transmittance of the film obtained in Example 40.

Using a spin coater, HB-TFA32V obtained in Example 8 was spin-coated onto a quartz substrate to give a 500 nm thickness. On a hot plate controlled at 150° C., baking was performed for 2 minutes, followed by further baking at 200° C. for 5 minutes to obtain HB-TFA32F2. The measurement results of transmittance of HB-TFA32F2 are shown in FIG. 15.

Example 41

Figure 16:
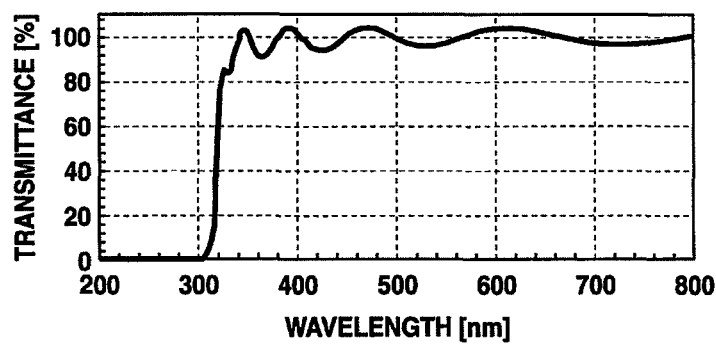
FIG. 16 is a diagram showing the transmittance of the film obtained in Example 41.

Using a spin coater, HB-TFA32V obtained in Example 8 was spin-coated onto a quartz substrate to give a 500 nm thickness. On a hot plate controlled at 150° C., baking was performed for 2 minutes, followed by further baking at 250° C. for 5 minutes to obtain HB-TFA32F3. The measurement results of transmittance of HB-TFA32F3 are shown in FIG. 16.

Example 42

Figure 17:
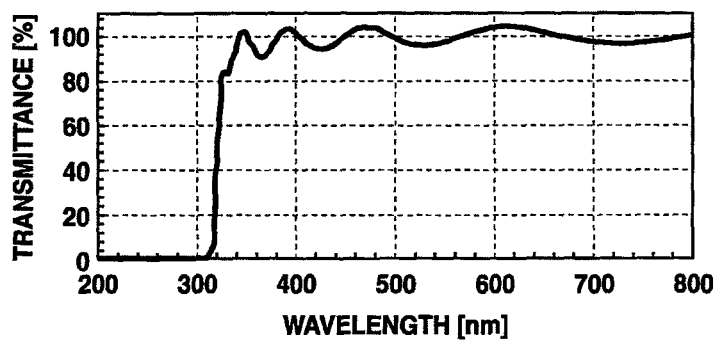
FIG. 17 is a diagram showing the transmittance of the film obtained in Example 42.

Using a spin coater, HB-TFA32V obtained in Example 8 was spin-coated onto a quartz substrate to give a 500 nm thickness. On a hot plate controlled at 150° C., baking was performed for 2 minutes, followed by further baking at 300° C. for 5 minutes to obtain HB-TFA32F4. The measurement results of transmittance of HB-TFA32F4 are shown in FIG. 17.

Example 43

Figure 18:
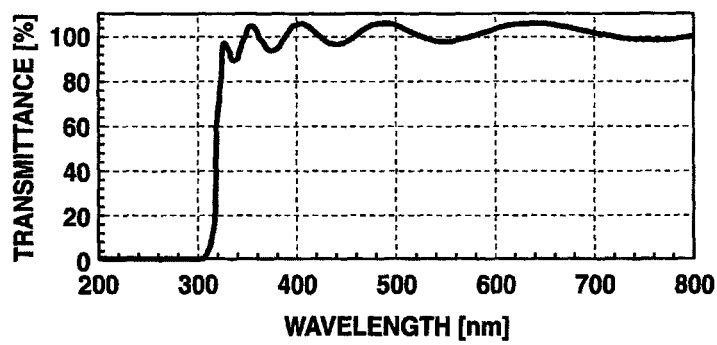
FIG. 18 is a diagram showing the transmittance of the film obtained in Example 43.

Using a spin coater, HB-TFA20V obtained in Example 9 was spin-coated onto a quartz substrate to give a 500 nm thickness. Baking was then performed for 2 minutes on a hot plate controlled at 150° C. to obtain HB-TFA20F1. The measurement results of transmittance of HB-TFA20F1 are shown in FIG. 18.

Example 44

Figure 19:
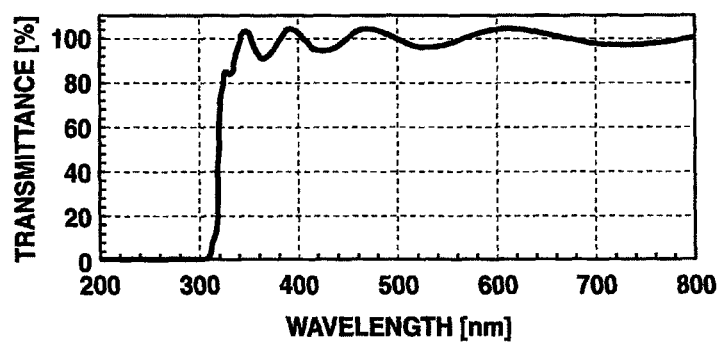
FIG. 19 is a diagram showing the transmittance of the film obtained in Example 44.

Using a spin coater, HB-TFA20V obtained in Example 9 was spin-coated onto a quartz substrate to give a 500 nm thickness. On a hot plate controlled at 150° C., baking was performed for 2 minutes, followed by further baking at 200° C. for 5 minutes to obtain HB-TFA20F2. The measurement results of transmittance of HB-TFA20F2 are shown in FIG. 19.

Example 45

Figure 20:
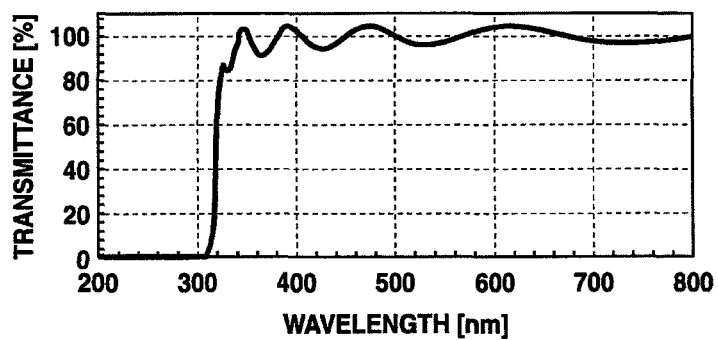
FIG. 20 is a diagram showing the transmittance of the film obtained in Example 45.

Using a spin coater, HB-TFA20V obtained in Example 9 was spin-coated onto a quartz substrate to give a 500 nm thickness. On a hot plate controlled at 150° C., baking was performed for 2 minutes, followed by further baking at 250° C. for 5 minutes to obtain HB-TFA20F3. The measurement results of transmittance of HB-TFA20F3 are shown in FIG. 20.

Example 46

Figure 21:
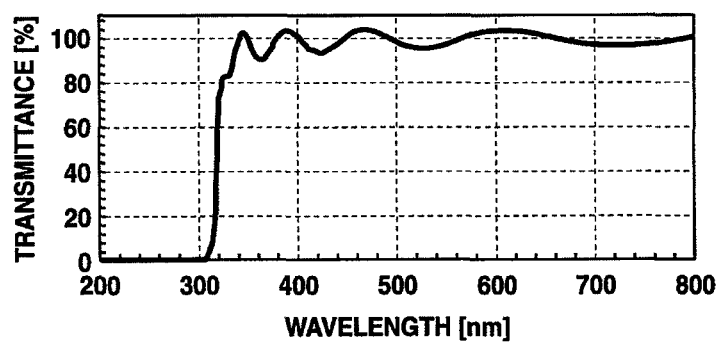
FIG. 21 is a diagram showing the transmittance of the film obtained in Example 46.

Using a spin coater, HB-TFA20V obtained in Example 9 was spin-coated onto a quartz substrate to give a 500 nm thickness. On a hot plate controlled at 150° C., baking was performed for 2 minutes, followed by further baking at 300° C. for 5 minutes to obtain HB-TFA20F4. The measurement results of transmittance of HB-TFA20F4 are shown in FIG. 21.

Example 47

Figure 22:
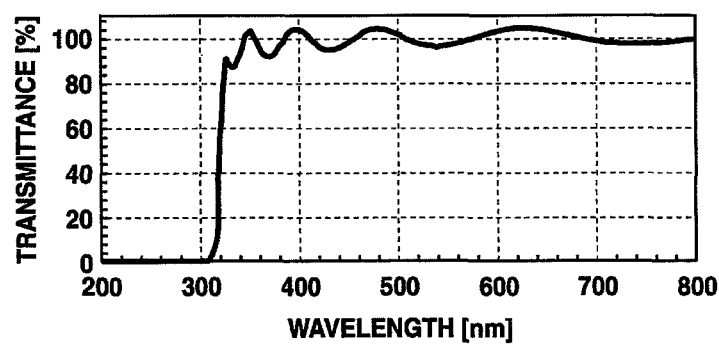
FIG. 22 is a diagram showing the transmittance of the film obtained in Example 47.

Using a spin coater, L-TF39V obtained in Example 10 was spin-coated onto a quartz substrate to give a 500 nm thickness. Baking was then performed for 2 minutes on a hot plate controlled at 150° C. to obtain L-TF39F1. The measurement results of transmittance of L-TF39F1 are shown in FIG. 22.

Example 48

Figure 23:
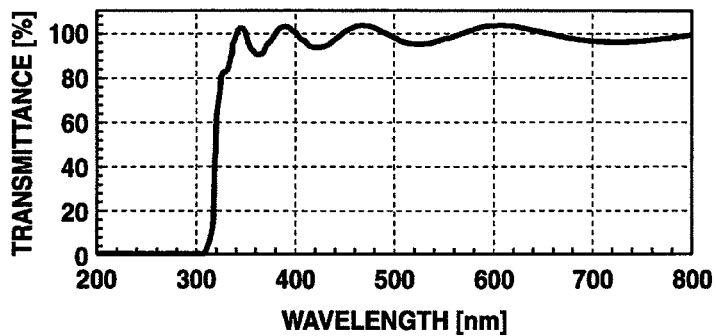
FIG. 23 is a diagram showing the transmittance of the film obtained in Example 48.

Using a spin coater, L-TF39V obtained in Example 10 was spin-coated onto a quartz substrate to give a 500 nm thickness. On a hot plate controlled at 150° C., baking was performed for 2 minutes, followed by further baking at 200° C. for 5 minutes to obtain L-TF39F2. The measurement results of transmittance of L-TF39F2 are shown in FIG. 23.

Example 49

Figure 24:
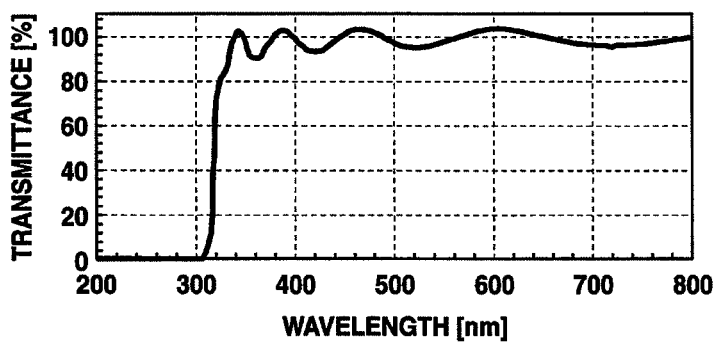
FIG. 24 is a diagram showing the transmittance of the film obtained in Example 49.

Using a spin coater, L-TF39V obtained in Example 10 was spin-coated onto a quartz substrate to give a 500 nm thickness. On a hot plate controlled at 150° C., baking was performed for 2 minutes, followed by further baking at 250° C. for 5 minutes to obtain L-TF39F3. The measurement results of transmittance of L-TF39F3 are shown in FIG. 24.

Example 50

Figure 25:
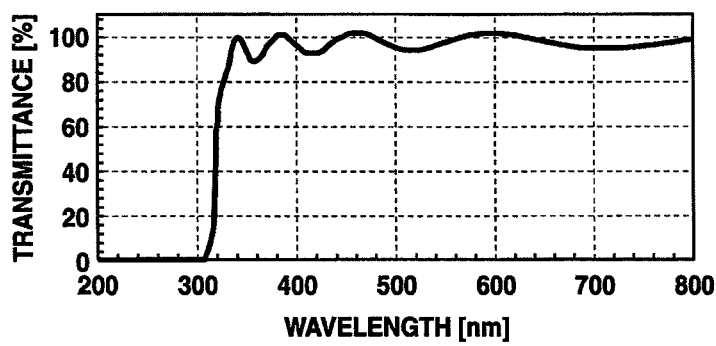
FIG. 25 is a diagram showing the transmittance of the film obtained in Example 50.

Using a spin coater, L-TF39V obtained in Example 10 was spin-coated onto a quartz substrate to give a 500 nm thickness. On a hot plate controlled at 150° C., baking was performed for 2 minutes, followed by further baking at 300° C.

for 5 minutes to obtain L-TF39F4. The measurement results of transmittance of L-TF39F4 are shown in FIG. 25.

With respect to the films obtained in Examples 31 to 34, Examples 35 to 38, Examples 39 to 42, Examples 43 to 46 and Examples 47 to 50, their transmittances ranging from 400 to 800 nm, that is, in the visible light range were compared. The transmittance was found to remain at 90% or higher without being lowered with a rise in baking temperature. As the refractive index was high, the transmittance hunted. Based on those transmittances, the average transmittance was calculated to be 95% or higher. It was, therefore, appreciated that extremely good transparency was exhibited.

<Light Resistance Test>

Light irradiation in a light resistance test was performed at the Japan Weathering Test Center. A xenon arc lamp the illuminance of which was 38.7 W/m² was used as a light source.

Example 51

Using the above-described light source, light was irradiated for 12.5 hours onto HB-TFA90F4 formed in Example 14. This light irradiation can be converted to a light irradiation quantity equivalent to one million Lux. One million Lux is widely known to be equivalent to one-year outdoor exposure.

The measurement results of refractive index and thickness of the film (hereinafter abbreviated as "HB-TFA90F4I") after the illumination of one million Lux are presented in Table 2.

TABLE 2

| | Abbreviation | Refractive index 550 nm | Refractive index 633 nm | Thickness (nm) |
|---|---|---|---|---|
| Example 14 | HB-TFA90F4 | 1.7310 | 1.7106 | 509.8 |
| Example 51 | HB-TFA90F4I | 1.7267 | 1.7068 | 508.8 |

As presented in Table 2, HB-TFA90F4 shrunk only as little as 1 nm in thickness by light irradiation of one million Lux although its refractive index was slightly lowered at 550 nm and 633 nm. HB-TFA90F4 was, therefore, found to have good light resistance.

Example 52

With respect to HB-TFA90F4 formed in Example 34, similar light irradiation as in Example 51 was performed to measure the transmittance. The results are shown in FIG. 26.

Figure 26:
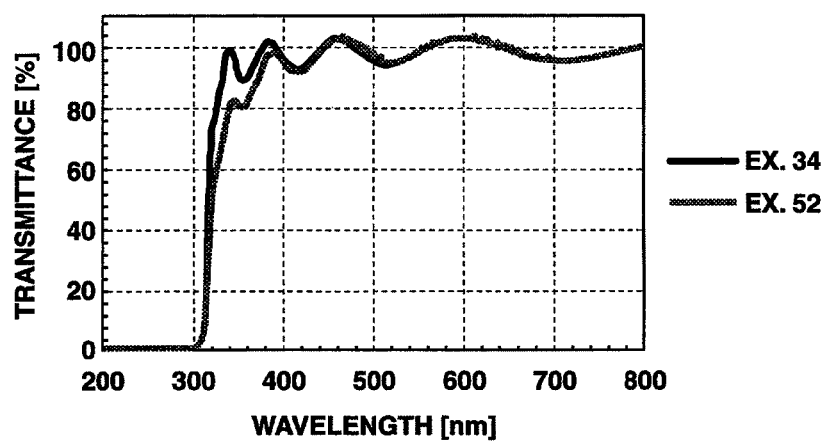
FIG. 26 is a diagram showing the measurement results of transmittance in Example 52.

As shown in FIG. 26, HB-TFA90F4 was found to undergo no change in transmittance in the visible light range by light irradiation of one million Lux.

Taking the results of Example 51 and Example 52 together, it was confirmed that HB-TFA90F4 underwent substantially no changes in refractive index, transmittance and thickness by light irradiation of one million Lux and was equipped with good heat resistance.

<Heat Resistance Test>

Example 53

5% Weight Loss Temperature Measurement of HB-TFA90

Figure 27:
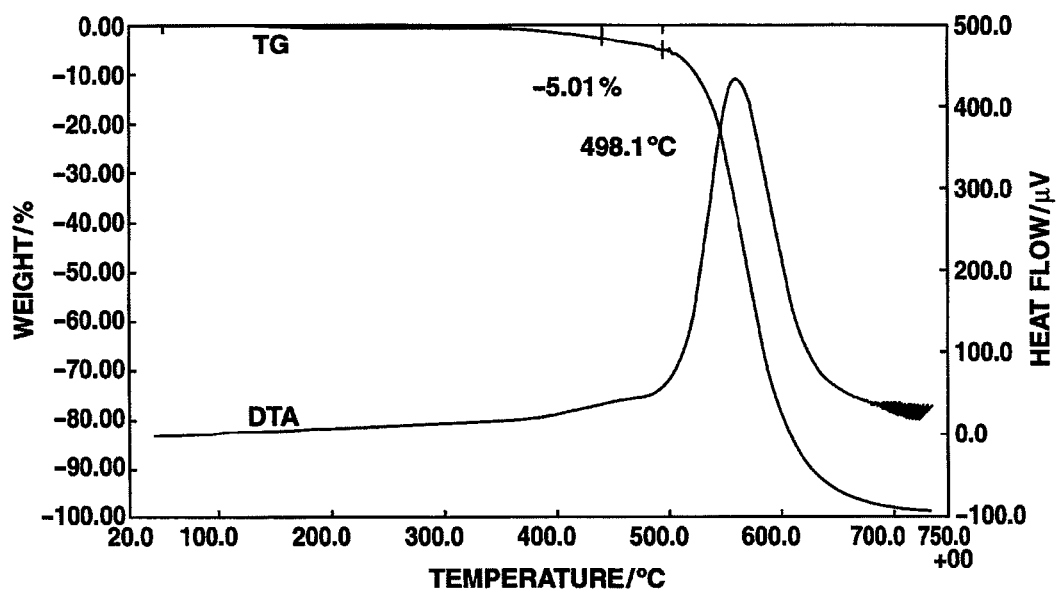
FIG. 27 is a diagram showing the results of TG-DTA measurement in Example 53.

The high-molecular compound [3] (3.57 mg) obtained in Example 1 was placed in a platinum pan, and was measured at a ramp-up rate of 15° C./min by TG-DTA. The results are shown in FIG. 27. The 5% weight loss temperature was 498° C. Further, its glass transition temperature was also measured by DSC. A transition point was observed at 289° C.

Example 54

5% Weight Loss Temperature Measurement of HB-TFA56

Figure 28:
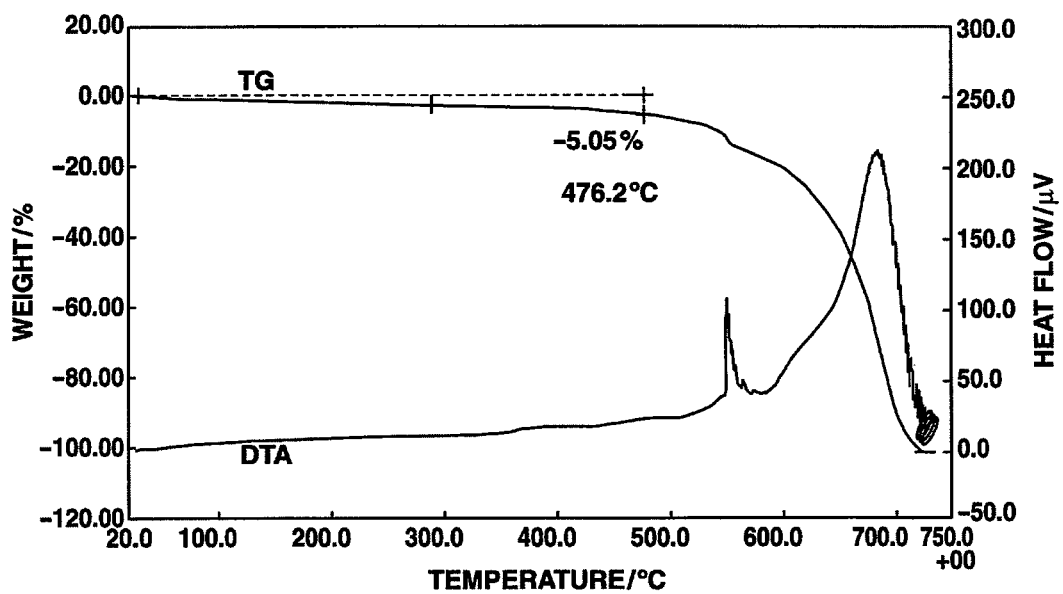
FIG. 28 is a diagram showing the results of TG-DTA measurement in Example 54.

As in Example 53, TG-DTA measurement of the high-molecular compound obtained in Example 2 was conducted. The 5% weight loss temperature was 476° C. The results are shown in FIG. 28.

Example 55

5% Weight Loss Temperature Measurement of HB-TFA32

Figure 29:
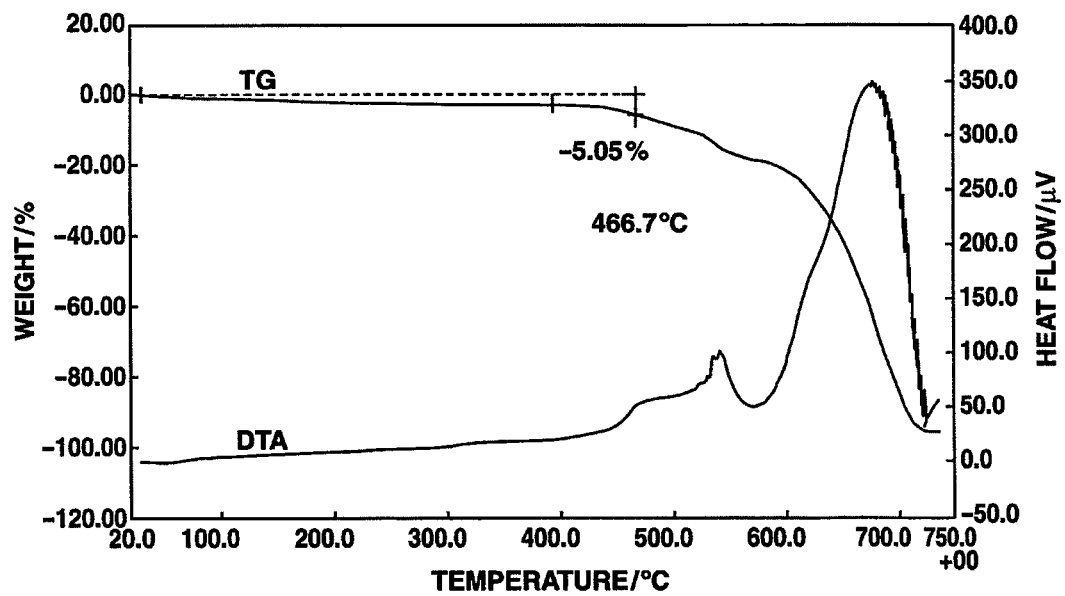
FIG. 29 is a diagram showing the results of TG-DTA measurement in Example 55.

As in Example 53, TG-DTA measurement of the high-molecular compound obtained in Example 3 was conducted. The 5% weight loss temperature was 466° C. The results are shown in FIG. 29.

Example 56

5% Weight Loss Temperature Measurement of HB-TFA20

Figure 30:
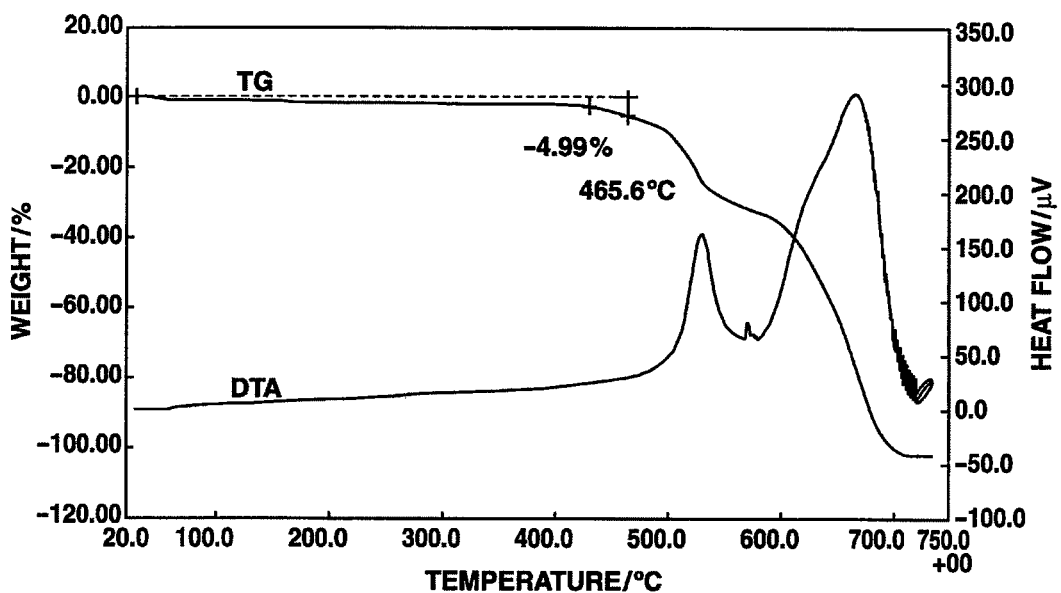
FIG. 30 is a diagram showing the results of TG-DTA measurement in Example 56.

As in Example 53, TG-DTA measurement of the high-molecular compound obtained in Example 4 was conducted. The 5% weight loss temperature was 465° C. The results are shown in FIG. 30.

Example 57

5% Weight Loss Temperature Measurement of L-TF39

Figure 31:
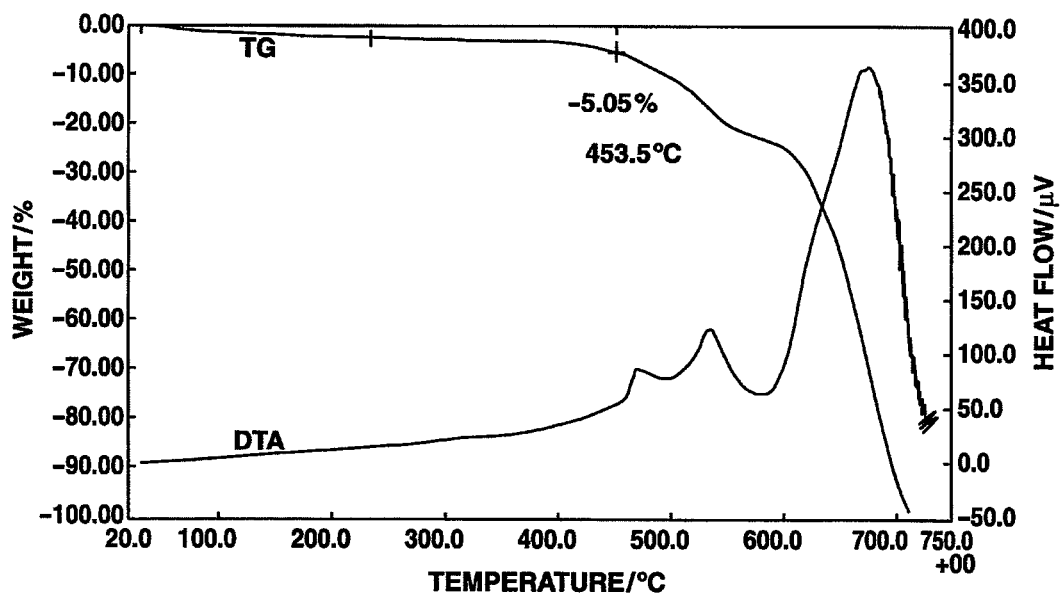
FIG. 31 is a diagram showing the results of TG-DTA measurement in Example 57.

As in Example 53, TG-DTA measurement of the high-molecular compound obtained in Example 5 was conducted. The 5% weight loss temperature was 465° C. The results are shown in FIG. 31.

<Filling Property Test>
<Preparation of Compositions for Filling Property Test>

Example 58

Under air, HB-TFA20 (2.0000 g) obtained in Example 4 was placed in a 10-mL eggplant flask, followed by the addition of cyclohexanone (8.0000 g) as a solvent. Using a wave rotor, HB-TFA20 was completely dissolved at room temperature to prepare a 20% by mass cyclohexanone solution of HB-TFA20. To an aliquot (1.0000 g) of the 20% by mass cyclohexanone solution, cyclohexanone (0.7220 g) was then added, and subsequently, a 10% by mass cyclohexanone solution of "EPOLEAD GT-401" (an epoxy-containing compound, product of Daicel Chemical Industries, Ltd.) as a crosslinking agent (0.1500 g; 75 parts by mass under the assumption that solids of the polymer amounted to 100 parts by mass) was added. Added further were a 2% by mass cyclohexanone solution of 3-glycidoxypropyltrimethoxysilane (product of Shin-Etsu Chemical Co., Ltd.) as an adhesion promoter (0.1000 g; 1 parts by mass per 100 parts by mass of the solids of the polymer) and a 0.1% by mass cyclohexanone solution of "MEGAFAC R-30" (trade name, product of DIC Corporation) as a surfactant (0.2000 g; 0.1 parts by mass under the assumption that the solids of the polymer amounted to 100 parts by mass). The resulting solution was stirred for 3 hours until homogeneous. After the stirring, the solute had been completely dissolved, and as a clear pale-yellow solution, a polymer varnish (hereinafter abbreviated as "HB-TFA20SV1") was obtained. The total percentage by mass of solids in HB-TFA20SV1 was 10% by mass.

Example 59

Under air, HB-TFA20 (2.0000 g) obtained in Example 4 was placed in a 10-mL eggplant flask, followed by the addition of cyclohexanone (8.0000 g) as a solvent. Using a wave rotor, HB-TFA20 was completely dissolved at room temperature to prepare a 20% by mass cyclohexanone solution of HB-TFA20. To an aliquot (1.0000 g) of the 20% by mass cyclohexanone solution, cyclohexanone (0.7220 g) was then added, and subsequently, a 10% by mass cyclohexanone solution of "VESTAGON B 1065" (a blocked isocyanato-containing compound, product of Degussa AG) as a crosslinking agent (0.1000 g; 5 parts by mass per 100 parts by mass of the solids of the polymer) was added. Added further were a 2% by mass cyclohexanone solution of 2-(3,4-epoxycyclohexyl) ethyltrimethoxysilane (product of Shin-Etsu Chemical Co., Ltd.) as an adhesion promoter (0.1000 g; 1 parts by mass per 100 parts by mass of the solids of the polymer) and a 0.1% by mass cyclohexanone solution of "MEGAFAC R-30" (trade name, product of DIC Corporation) as a surfactant (0.2000 g; 0.1 parts by mass per 100 parts by mass of the solids of the polymer). The resulting solution was stirred for 3 hours until homogeneous. After the stirring, the solute had been completely dissolved, and as a clear pale-yellow solution, a polymer varnish (hereinafter abbreviated as "HB-TFA20SV2") was obtained. The total percentage by mass of solids in HB-TFA20SV2 was 10% by mass.

Example 60

Using HB-TFA20V prepared in Example 9, a filling property test was performed. The material of a structural substrate employed in the filling property test was silicon, and the structural substrate had via holes of 1.6 μm depth and 400 nm diameter.

By the spin coating method, HB-TFA20V was applied onto the structural substrate to give a 500 nm thickness. Using a hot plate, baking was performed at 150° C. for 2 minutes, and then at 300° C. for 5 minutes.

After the baked structural substrate with a film formed thereon was scratched at an edge thereof with a diamond pen, the substrate was cleaved, followed by SEM observation. An observed image is shown in FIG. 32.

Figure 32:
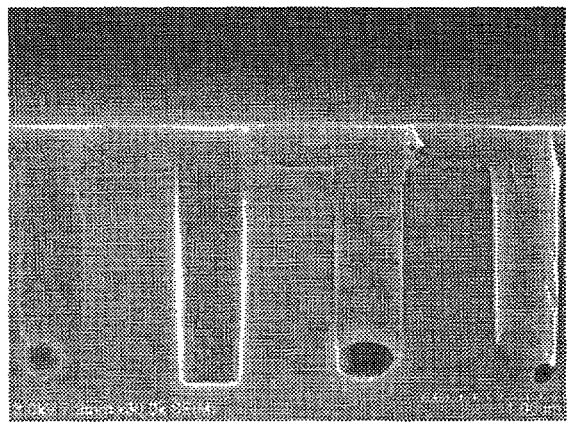
FIG. 32 is a picture showing an SEM image in a filling property test of Example 60.

As shown in FIG. 32, HB-TFA20V reached to the bottoms of the via holes. Although cracks were formed. Applicability of HB-TFA20 as a filling material was, therefore, suggested.

Example 61

A filling property test was performed as in Example 60 except for the use of HB-TFA20SV1 obtained in Example 58. An observed image is shown in FIG. 33.

Example 62

A filling property test was performed as in Example 61 except for the use of HB-TFA20SV2 obtained in Example 59. An observed image is shown in FIG. 34.

Figure 33:
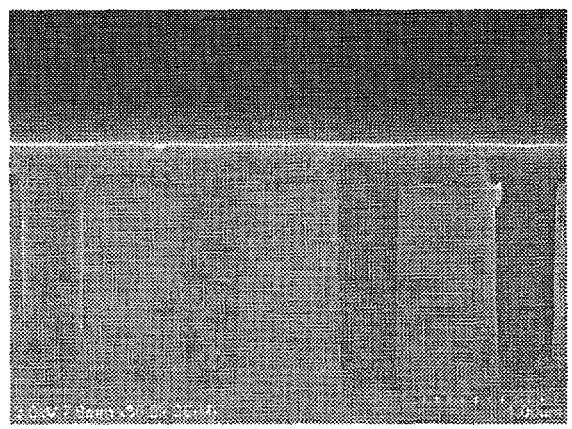
FIG. 33 is a picture showing an SEM image in a filling property test of Example 61.
Figure 34:
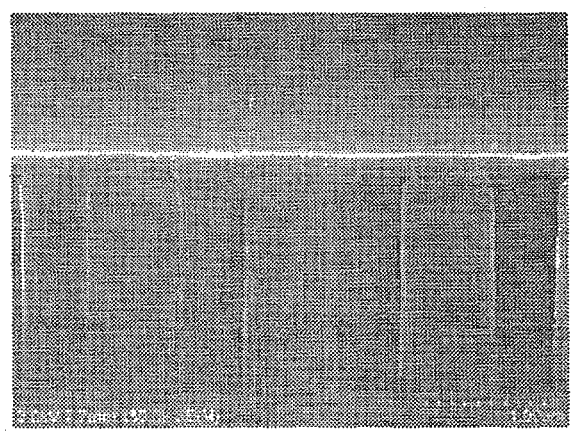
FIG. 34 is a picture showing an SEM image in a filling property test of Example 62.

Comparing FIG. 32, FIG. 33 and FIG. 34, it is appreciated that the addition of a crosslinking agent and an adhesion promoter leads to improvements in filling property. Described specifically, it is presumably suggested that by the addition of the crosslinking agent, terminal $NH_2$ groups of the polymer and epoxy or blocked isocyanato groups are crosslinked to form a high-molecular product and hence to provide improved crack resistance, and also that by the addition of the adhesion promoter, side slits are reduced.

As is understood from the foregoing, the selection of a crosslinking agent and an adhesion promoter makes it possible to control the crosslinking temperature and reflow temperature and hence to control the surface energy. It is, therefore, possible to select optimal filling materials for substrates having various surfaces, respectively.

These filling materials can be suitably used especially as planarizing materials (filling materials) on the photodiodes of solid-state imaging devices.

When the highly-branched polymer according to the present invention is used as a planarizing material on a photodiode, light can be guided to the photodiode based on the principle of optical waveguide owing to its refractive index as high as 1.7 or higher. The current via-hole diameter can, therefore, be set at a smaller value, thereby making it possible to fabricate high-definition, solid-state imaging devices.

Example 63

As in Example 14 except for the use of HB-TFA20SV1 obtained in Example 58, spin coating was conducted by a spin coater on a silicon substrate to give a 500 nm thickness. On a hot plate controlled at 150° C., baking was performed for 2 minutes, followed by further baking at 300° C. for 5 minutes to obtain a film (hereinafter abbreviated as "HB-TF20SVF1").

HB-TF20SVF1 was measured for refractive index and thickness. The refractive index at 550 nm was 1.7312 and the to refractive index at 633 nm was 1.7120, and the thickness was 510.5 nm.

Example 64

As in Example 14 except for the use of HB-TFA20SV2 obtained in Example 59, spin coating was conducted by a spin coater on a silicon substrate to give a 500 nm thickness. On a hot plate controlled at 150° C., baking was performed for 2 minutes, followed by further baking at 300° C. for 5 minutes to obtain a film (hereinafter abbreviated as "HB-TF20SVF2").

HB-TF20SVF2 was measured for refractive index and thickness. The refractive index at 550 nm was 1.7443 and the refractive index at 633 nm was 1.7242, and the thickness was 510.5 nm.

Comparing Examples 63 and 64 with Example 26, it was unable to confirm any substantial decrease in refractive index even by the addition of the crosslinking agent and adhesion promoter. As a crosslinking agent and adhesion promoter are generally materials of low refractive indexes, it has been confirmed that a highly-branched polymer is not lowered in refractive index within the content ranges of these additives in the examples and can be used as a material of high refractive index.

It has also been found from Example 64 that, when a crosslinking agent and adhesion promoter are added, the refractive index is improved than when they are not added. This tendency suggests that terminal amino groups of the highly-branched polymer and reactive groups of the crosslinking agent form crosslinks to provide a high-molecular product and this additive does not act as a component to lower the refractive index but acts as a component to retain or improve the refractive index.

Example 65

Using HB-TFA90 obtained in Example 1, a cured film was formed. Tricyclodecane dimethanol diacrylate as a polyfunctional acrylate (0.15 g, product of Shin-Nakamura Chemical Co., Ltd.), HB-TFA90 (0.15 g) and 2-methyl-1-(4-methylthiophenyl)-2-morpholinopropane-1-one (9.0 mg, "IRGACURE 907," trade name, product of Ciba Japan K.K.) were combined, and were dissolved in cyclohexanone (2.7 g). Using a spin coater, the prepared solution was spin-coated onto to a glass substrate at 200 rpm for 5 seconds and then at 1,000 rpm for 30 seconds, followed by heating at 120° C. for 20 minutes to remove the solvent. Subsequently, light illumination by a UV lamp (100 W high-pressure mercury vapor lamp, "HL-100" (manufactured by Sen Lights Co., Ltd.); illumination time: 20 minutes; distance from the light source: 5 cm; performed at room temperature) was performed, followed by baking at 160° C. for 5 minutes to obtain a cured film with HB-TFA90 incorporated therein.

The resultant cured film was measured for refractive index. Its refractive index at 550 nm was 1.7162.

Figure 35:
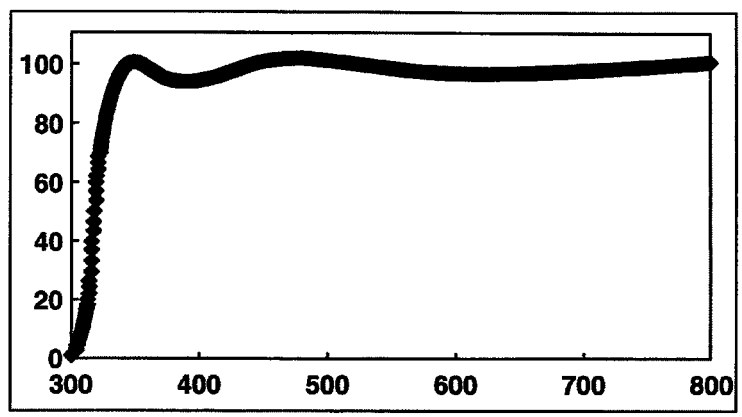
FIG. 35 is a diagram showing the transmittance of the film obtained in Example 65.

Further, the resultant film was measured for transmittance at from 400 to 800 nm. The results are shown in FIG. 35.

Example 66

A cured film was formed in a similar manner as in Example 65 except for the use of tricyclodecane dimethanol diacrylate (0.09 g) and HB-TFA90 (0.21 g).

The resultant cured film was measured for refractive index. Its refractive index at 550 nm was 1.7336.

Figure 36:
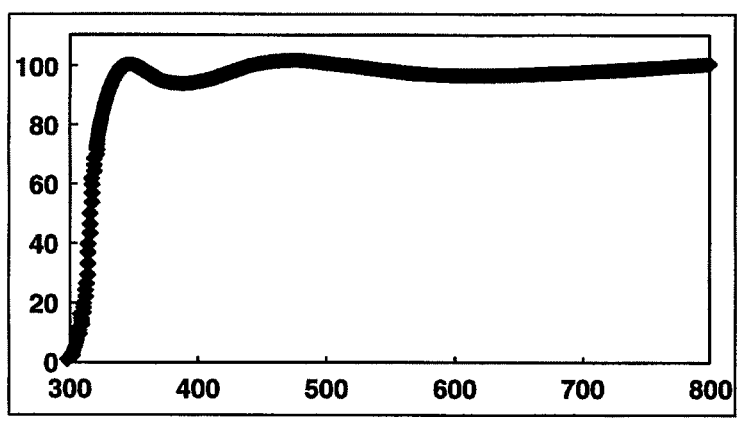
FIG. 36 is a diagram showing the transmittance of the film obtained in Example 66.

Further, the resultant film was measured for transmittance at from 400 to 800 nm. The results are shown in FIG. 36.

Comparing Examples 65 and 66 with Example 11, it has been found that a high refractive index close to that of a is film of HB-TFA90 alone is exhibited even when HB-TFA90 is added to a polyfunctional acrylate monomer of low refractive index. In general, a composition with a polyfunctional acrylate monomer tends to result in a lower refractive index. It has, however, been confirmed in the present invention that such a composition can be used as a material of high refractive index without inducing any substantial decrease in refractive index.

Example 67

Measurement of Refractive Index and Transmittance

HB-TFA90 (0.5 g) obtained in Example 1 was dissolved in cyclohexanone (4.5 g) to obtain a clear pale-yellow solution. Using a spin coater, the obtained polymer varnish was spin-coated onto a glass substrate at 100 rpm for 5 seconds and then at 500 rpm for 30 seconds, followed by baking at 150° C. for 5 minutes to remove the solvent so that a film was obtained. The resultant film was measured for refractive index. Its refractive index at 550 nm was 1.7428.

Figure 37:
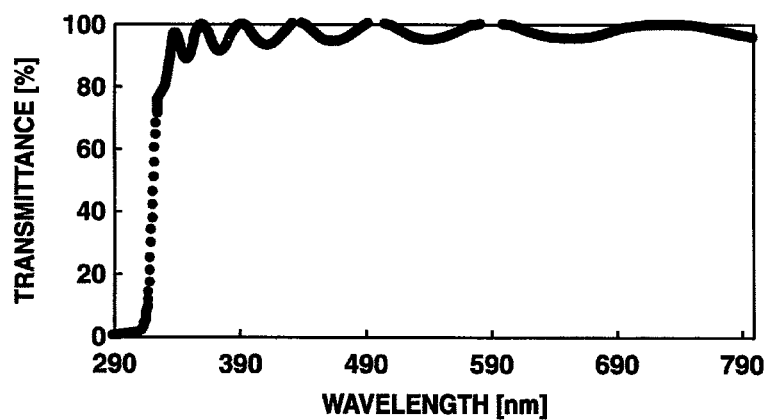
FIG. 37 is a diagram showing the transmittance of the film obtained in Example 67.

Further, the resultant film was measured for transmittance at from 400 to 800 nm. The results are shown in FIG. 37.

Example 68

Synthesis of High-Molecular Compound [7]

[Chemical Formula 33]

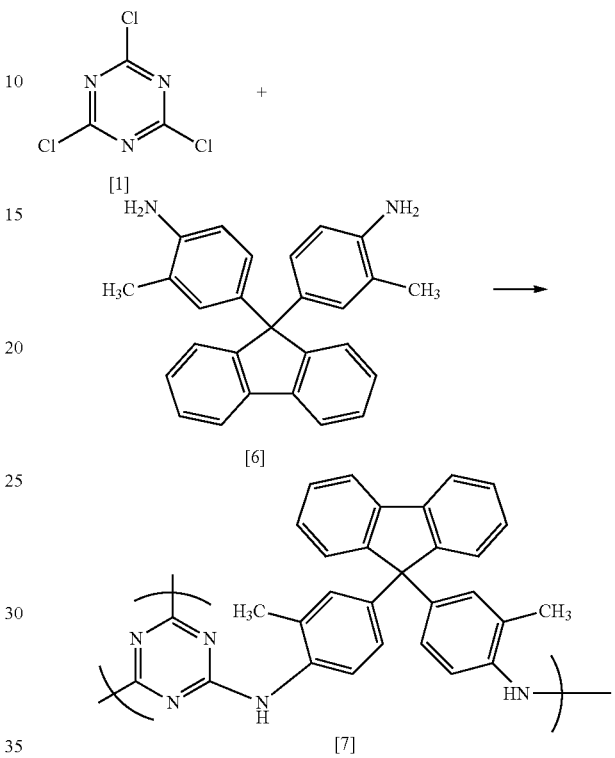

Figure 38:
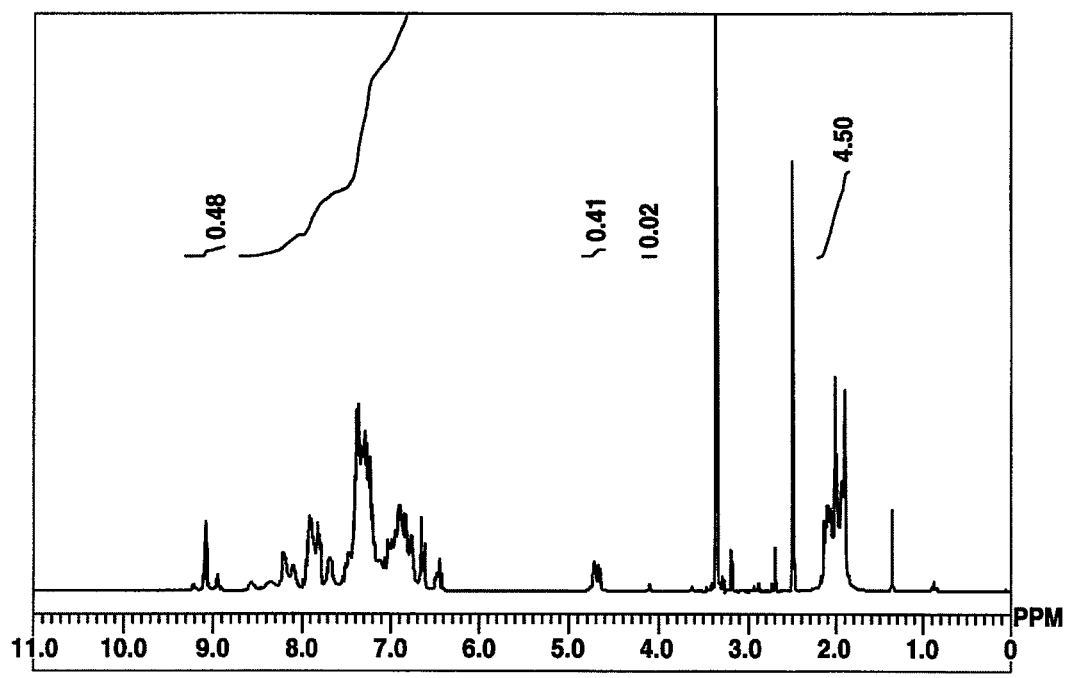
FIG. 38 is a diagram showing a $^1$H-NMR spectrum of the high-molecular compound [7] obtained in Example 68.

Using 9,9-bis(4-amino-3-methylphenyl)fluorene [6] (7.52 g, 0.02 mol, product of Tokyo Chemical Industry Co., Ltd.) in place of 9,9-bis(4-aminophenyl)fluorene, it was reacted to 2,4,6-trichloro-1,3,5-triazine [1] (2.74 g, 0.015 mol, product of Tokyo Chemical Industry Co., Ltd.) in a similar manner as in Example 1. Further, as in Example 1, aniline (4.29 g, 0.045 mol) was added to conduct treatment, whereby the target high-molecular compound [7] (hereinafter abbreviated as "HB-TFmA," 8.80 g) was obtained. A $^1$H-NMR spectrum of HB-TFmA is shown in FIG. 38. HB-TFmA so obtained was a compound having structural units represented by the formula (1). The weight average molecular weight Mw of HB-TFmA as measured by GPC and calibrated against standard polystyrene was 2,800, and the polydispersibility Mw/Mn was 2.09. It is to be noted that GPC measurement conditions in this example were as will be described below.
[GPC]
Instrument: "HLC-8200 GPC," manufactured by Tosoh Corporation
Column: "SHODEX OHPAK SB-803HQ+SB-804HQ"
Column temperature: 40° C.
Solvent: N,N-dimethylformamide (hereinafter "DMF")
Detector: UV (254 nm)
Calibration curve: standard polystyrene Example 69

Measurement of Refractive Index

HB-TFmA (1.0 g) obtained in Example 68 was dissolved in N-methylpyrrolidone (9.0 g) to obtain a clear pale-yellow solution. Using a spin coater, the obtained polymer varnish was spin-coated onto a glass substrate at 100 rpm for 5 seconds and then at 800 rpm for 30 seconds, followed by baking at 250° C. for 5 minutes to remove the solvent so that a film was obtained. The resultant film was measured for refractive index. Its refractive index at 550 nm was 1.7105.

Example 70

5% Weight Loss Temperature Measurement of HB-TFmA

Figure 39:
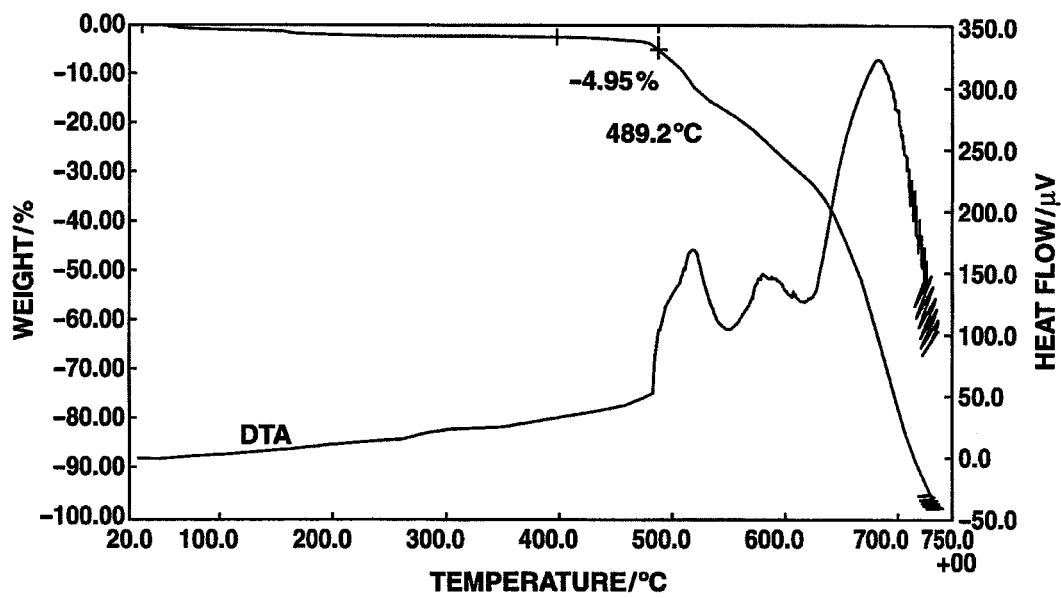
FIG. 39 is a diagram showing the results of TG-DTA measurement in Example 70.

As in Example 53, TG-DTA measurement of the high-molecular compound [7] obtained in Example 68 was conducted. The 5% weight loss temperature was 489° C. The results are shown in FIG. 39.

Example 71

Synthesis of High-Molecular Compound [9]

[Chemical Formula 34]

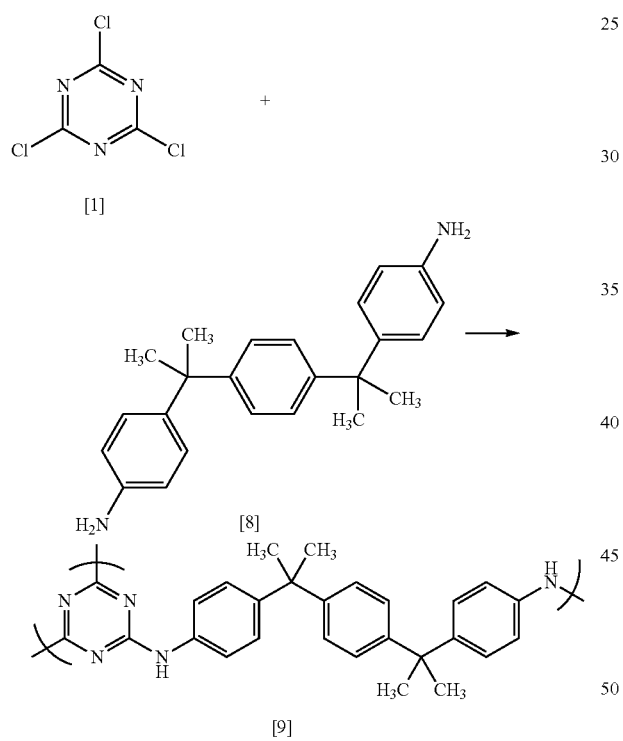

[9]

Using α,α'-bis(4-aminophenyl)-1,4-diisopropylbenzene [8] (4.59 g, 0.013 mol, product of Tokyo Chemical Industry Co., Ltd.) in place of 9,9-bis(4-aminophenyl)fluorene, it was reacted to 2,4,6-trichloro-1,3,5-triazine [1] (1.84 g, 0.010 mol, product of Tokyo Chemical Industry Co., Ltd.) in a similar manner as in Example 1. Further, as in Example 1, aniline (2.82 g, 0.03 mol) was added to conduct treatment, whereby the target high-molecular compound [9] (hereinafter abbreviated as "HB-TBA," 5.73 g) was obtained. HB-TBA so obtained was a compound having structural units represented by the formula (1). The weight average molecular weight Mw of HB-TBA as measured by GPC and calibrated against standard polystyrene was 15,900, and the polydispersibility Mw/Mn was 5.62.

Example 72

Measurement of Refractive Index

HB-TBA (1.0 g) obtained in Example 71 was dissolved in cyclohexanone (9.0 g) to obtain a clear pale-yellow solution. Using a spin coater, the obtained polymer varnish was spin-coated onto a glass substrate at 100 rpm for 5 seconds and then at 800 rpm for 30 seconds, followed by baking at 150° C. for 5 minutes to remove the solvent so that a film was obtained. The resultant film was measured for refractive index. Its refractive index at 550 nm was 1.6724.

Example 73

5% Weight Loss Temperature Measurement of HB-TBA

Figure 40:
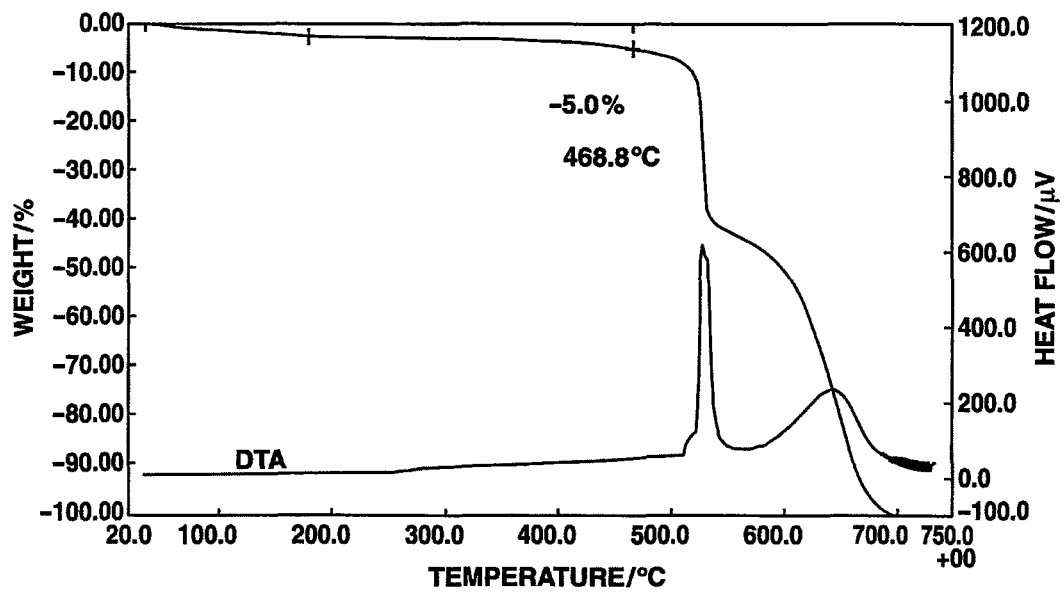
FIG. 40 is a diagram showing the results of TG-DTA measurement in Example 73.

As in Example 53, TG-DTA measurement of the high-molecular compound [9] obtained in Example 71 was conducted. The 5% weight loss temperature was 469° C. The results are shown in FIG. 40.

Example 74

Synthesis of High-Molecular Compound [11]

[Chemical Formula 35]

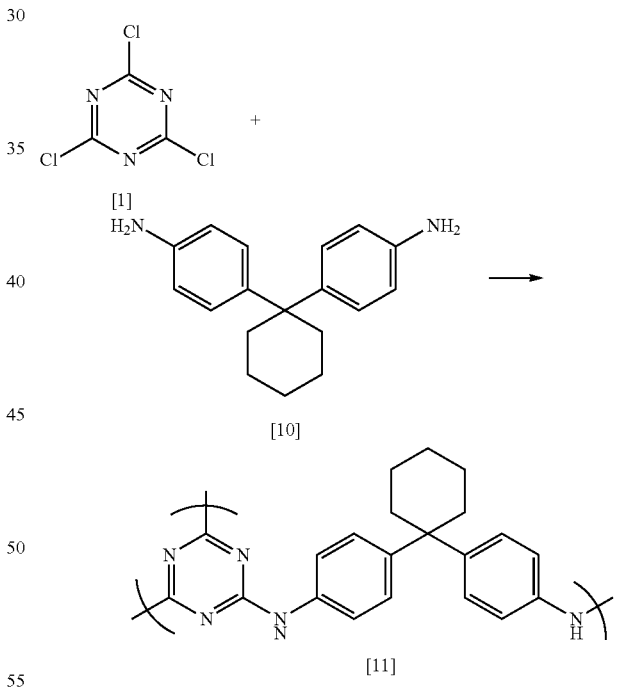

[11]

Figure 41:
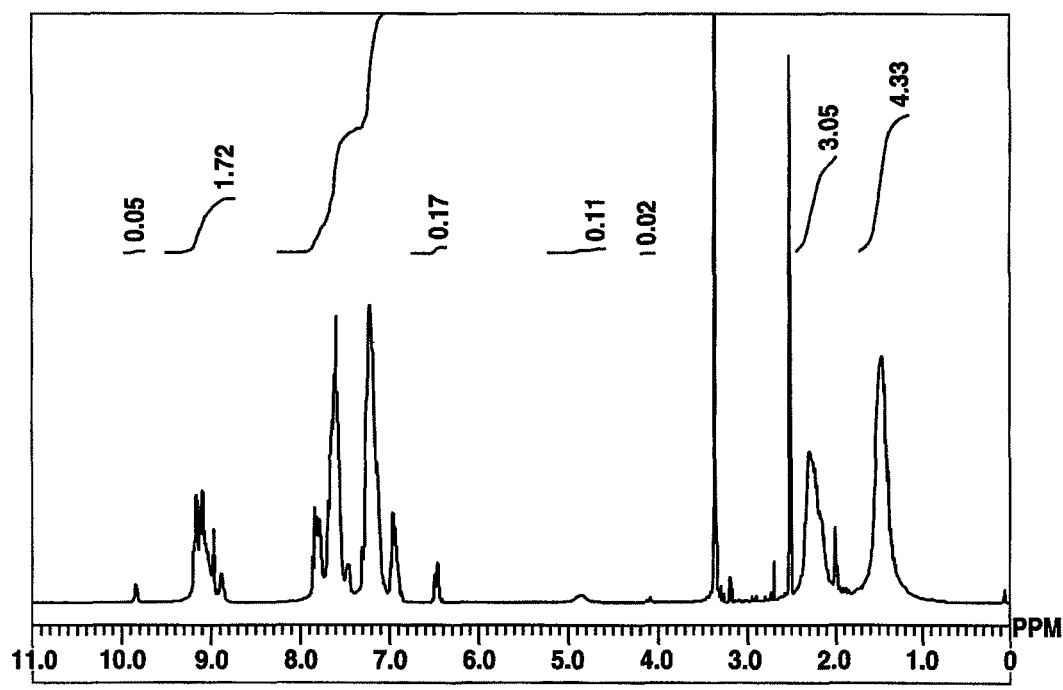
FIG. 41 is a diagram showing a $^1$H-NMR spectrum of the high-molecular compound [11] obtained in Example 74.

Using 1,1-bis(4-aminophenyl)cyclohexane [10] (3.57 g, 0.013 mol, product of Tokyo Chemical Industry Co., Ltd.) in place of 9,9-bis(4-aminophenyl)fluorene, it was reacted to 2,4,6-trichloro-1,3,5-triazine [1] (1.85 g, 0.010 mol, product of Tokyo Chemical Industry Co., Ltd.) in a similar manner as in Example 1. Further, as in Example 1, aniline (2.82 g, 0.03 mol) was added to conduct treatment, whereby the target high-molecular compound [1,1] (hereinafter abbreviated as "HB-TCA," 4.92 g) was obtained. A $^1$H-NMR spectrum of HB-TCA is shown in FIG. 41. HB-TCA so obtained was a compound having structural units represented by the formula (1). The weight average molecular weight Mw of HB-TCA as measured by GPC and calibrated against standard polystyrene was 3,100, and the polydispersibility Mw/Mn was 2.28.

Example 75

Measurement of Refractive Index

HB-TCA (1.0 g) obtained in Example 74 was dissolved in cyclohexanone (9.0 g) to obtain a clear brown solution. Using a spin coater, the obtained polymer varnish was spin-coated onto a glass substrate at 100 rpm for 5 seconds and then at 800 rpm for 30 seconds, followed by baking at 150° C. for 5 minutes to remove the solvent so that a film was obtained. The resultant film was measured for refractive index. Its refractive index at 550 nm was 1.7047.

Example 76

5% Weight Loss Temperature Measurement of HB-TCA

Figure 42:
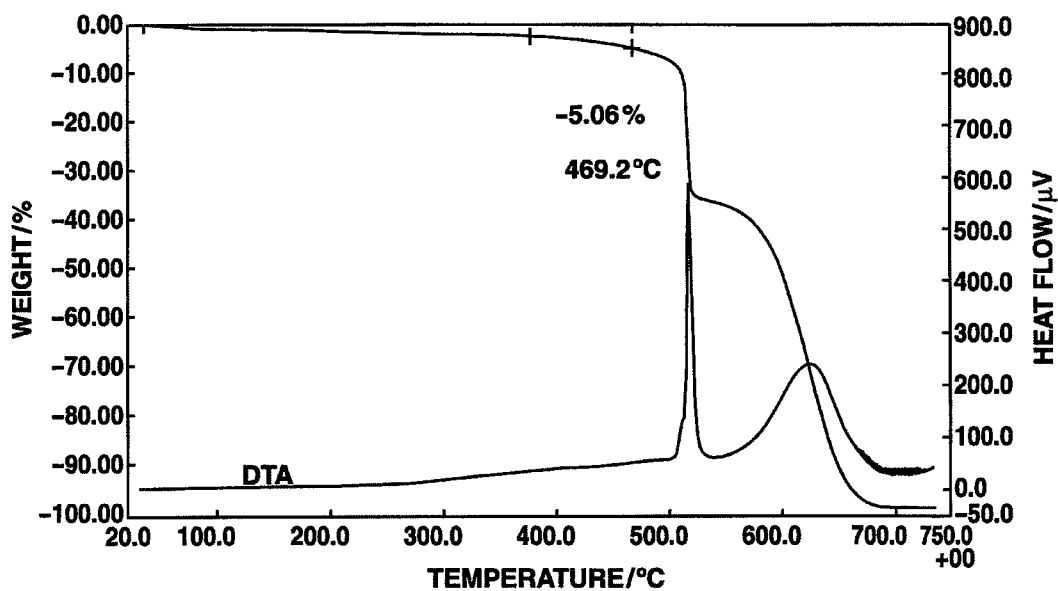
FIG. 42 is a diagram showing the results of TG-DTA measurement in Example 76.

As in Example 53, TG-DTA measurement of the high-molecular compound [1,1] obtained in Example 74 was conducted. The 5% weight loss temperature was 469° C. The results are shown in FIG. 42.

Example 77

Synthesis of High-Molecular Compound [13]

[Chemical Formula 36]

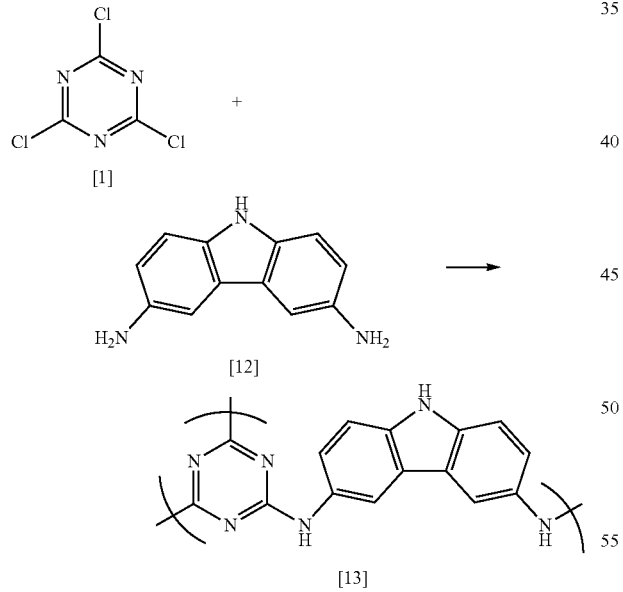

Figure 43:
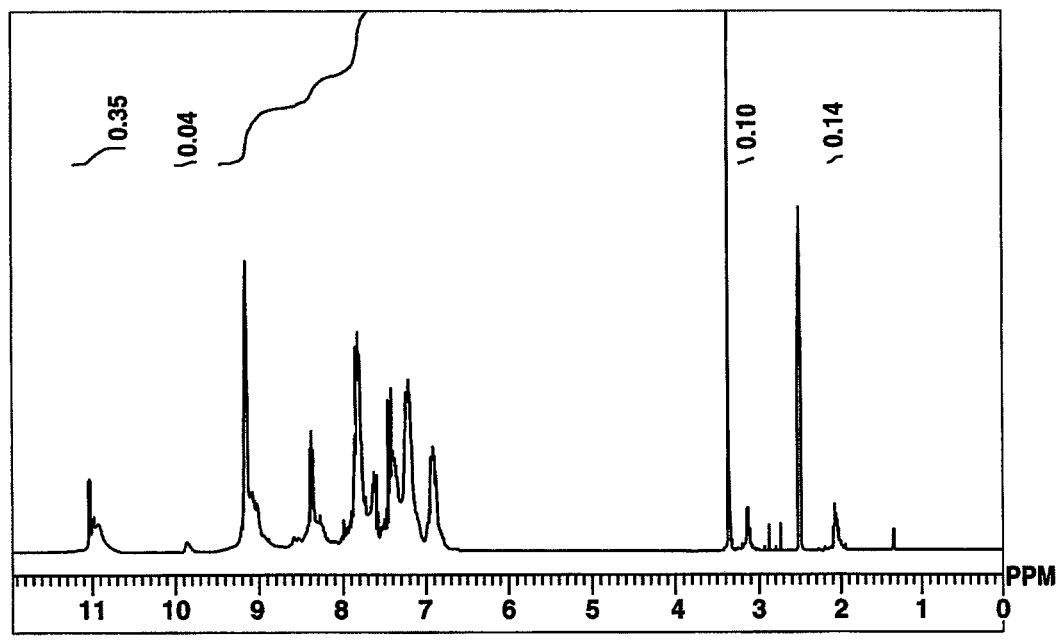
FIG. 43 is a diagram showing a $^1$H-NMR spectrum of the high-molecular compound [13] obtained in Example 77.

Using 3,6-diaminocarbazole [1,2] (0.52 g, 0.0025 mol, product of Tokyo Chemical Industry Co., Ltd.) in place of 9,9-bis(4-aminophenyl)fluorene, it was reacted to 2,4,6-trichloro-1,3,5-triazine [1] (0.56 g, 0.003 mol, product of Tokyo Chemical Industry Co., Ltd.) in a similar manner as in Example 1. Further, as in Example 1, aniline (0.87 g, 0.009 mol) was added to conduct treatment. Redissolution was conducted in DMF (13 mL), followed by reprecipitation to obtain the target high-molecular compound [13] (hereinafter abbreviated as "HB-TCzA," 0.87 g). A $^1$H-NMR spectrum of HB-TCzA so obtained is shown in FIG. 43. HB-TCzA so obtained was a compound having structural units represented by the formula (1).

The weight average molecular weight Mw of HB-TCzA as measured by GPC and calibrated against standard polystyrene was 3,200, and the polydispersibility Mw/Mn was 2.59. It is to be noted that the GPC measurement was conducted under the conditions of Example 68.

Example 78

Measurement of Refractive Index and Transmittance

Figure 44:
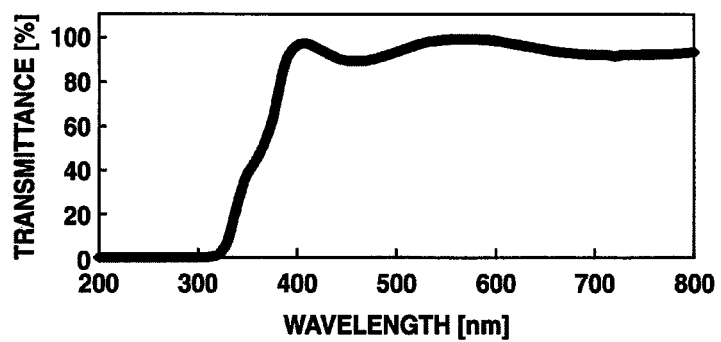
FIG. 44 is a diagram showing the transmittance of the film obtained in Example 78.

HB-TCzA (0.1 g) obtained in Example 77 was dissolved in N-methylpyrrolidone (0.9 g) to obtain a clear pale-yellow solution. Using a spin coater, the obtained polymer varnish was spin-coated onto a quartz substrate at 100 rpm for 5 seconds and then at 1,000 rpm for 30 seconds, followed by baking at 150° C. for 1 minute and then at 250° C. for 5 minutes to remove the solvent so that a film was obtained. The resultant film was measured for refractive index. Its refractive index at 550 nm was 1.8008. Further, the resultant film was measured for transmittance at from 400 to 800 nm. The results are shown in FIG. 44.

Example 79

5% Weight Loss Temperature Measurement of HB-TCzA

Figure 45:
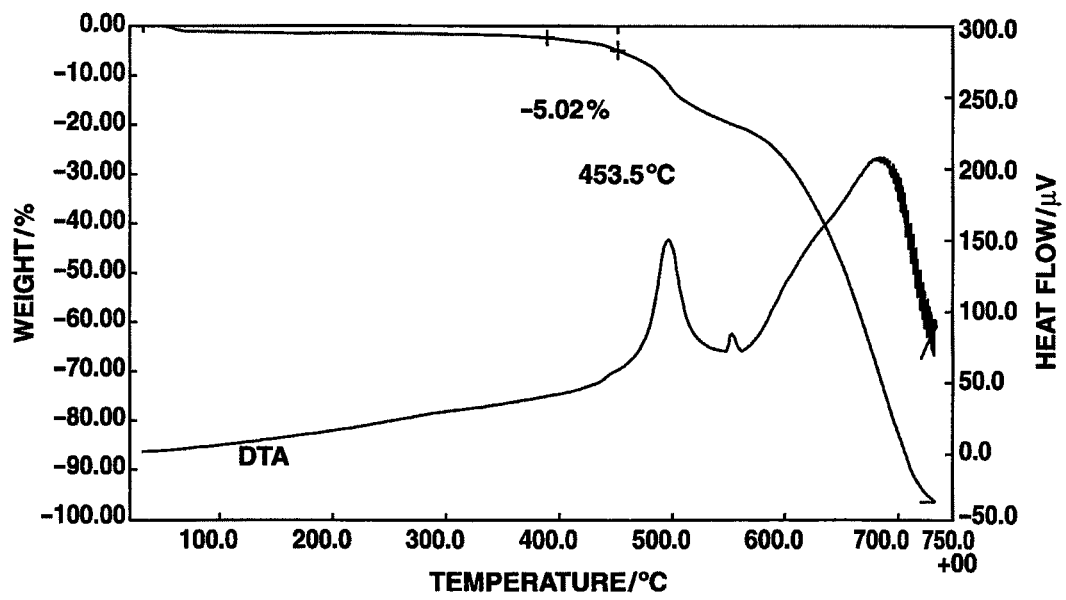
FIG. 45 is a diagram showing the results of TG-DTA measurement in Example 79.

As in Example 53, TG-DTA measurement of the high-molecular compound [13] obtained in Example 77 was conducted. The 5% weight loss temperature was 454° C. The results are shown in FIG. 45.

Example 80

Synthesis of High-Molecular Compound [15]

[Chemical Formula 37]

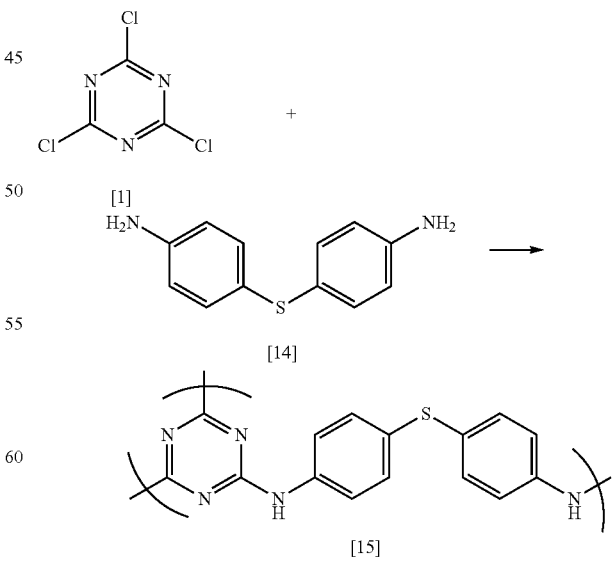

Figure 46:
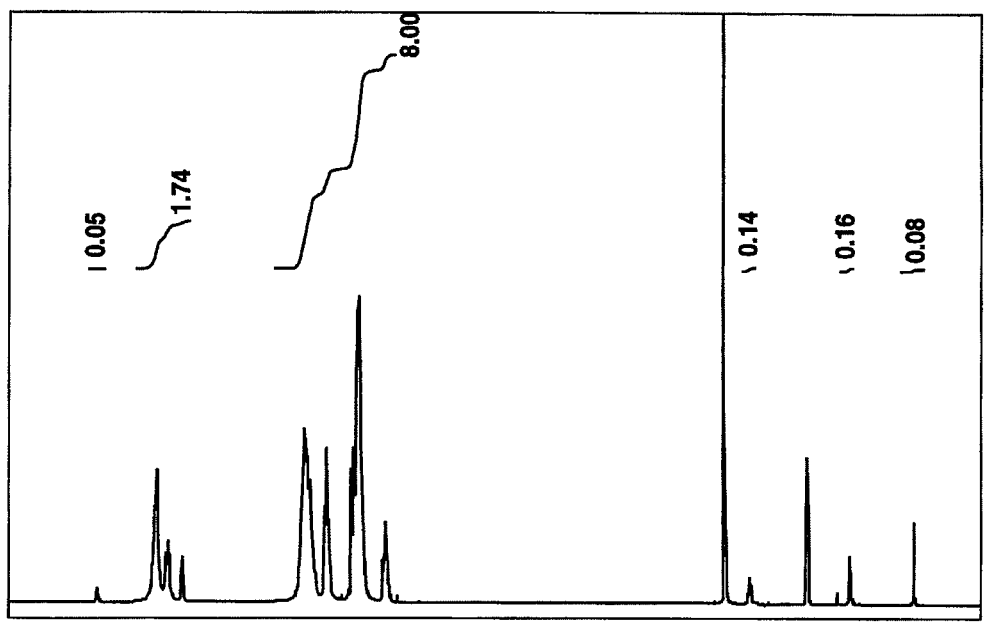
FIG. 46 is a diagram showing a $^1$H-NMR spectrum of the high-molecular compound [15] obtained in Example 80.

Using bis(4-aminophenyl) sulfide [1,4] (11.83 g, 0.06 mol, product of Tokyo Chemical Industry Co., Ltd.) in place of 9,9-bis(4-aminophenyl)fluorene, it was reacted to 2,4,6-trichloro-1,3,5-triazine [1] (0.56 g, 0.05 mol, product of Tokyo Chemical Industry Co., Ltd.) in a similar manner as in Example 1. Further, as in Example 1, aniline (14.1 g, 0.15 mol) was added to conduct treatment, whereby the target high-molecular compound [1,5] (hereinafter abbreviated as "HB-TTA," 16.85 g) was obtained. A $^1$H-NMR spectrum of HB-TTA is shown in FIG. 46. HB-TTA so obtained was a compound having structural units represented by the formula (1). The weight average molecular weight Mw of HB-TTA as measured by GPC and calibrated against standard polystyrene was 3,100, and the polydispersibility Mw/Mn was 2.30.

Example 81

Measurement of Refractive Index and Transmittance

HB-TTA (1.0 g) obtained in Example 80 was dissolved in N-methylpyrrolidone (9.0 g) to obtain a clear violet solution. Using a spin coater, the obtained polymer varnish was spin-coated onto a glass substrate at 100 rpm for 5 seconds and then at 1,000 rpm for 30 seconds, followed by baking at 150° C. for 1 minute and then at 250° C. for 5 minutes to remove the solvent so that a film was obtained. The resultant film was measured for refractive index. Its refractive index at 550 nm was 1.8008.

Figure 47:
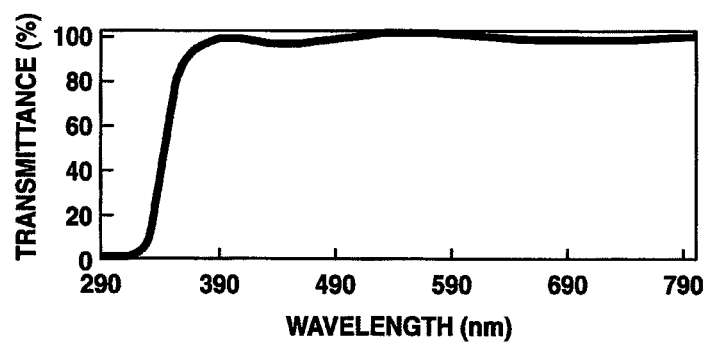
FIG. 47 is a diagram showing the transmittance of the film obtained in Example 81.

Further, the resultant film was measured for transmittance at from 400 to 800 nm. The results are shown in FIG. 47.

Example 82

5% Weight Loss Temperature Measurement of HB-TTA

Figure 48:
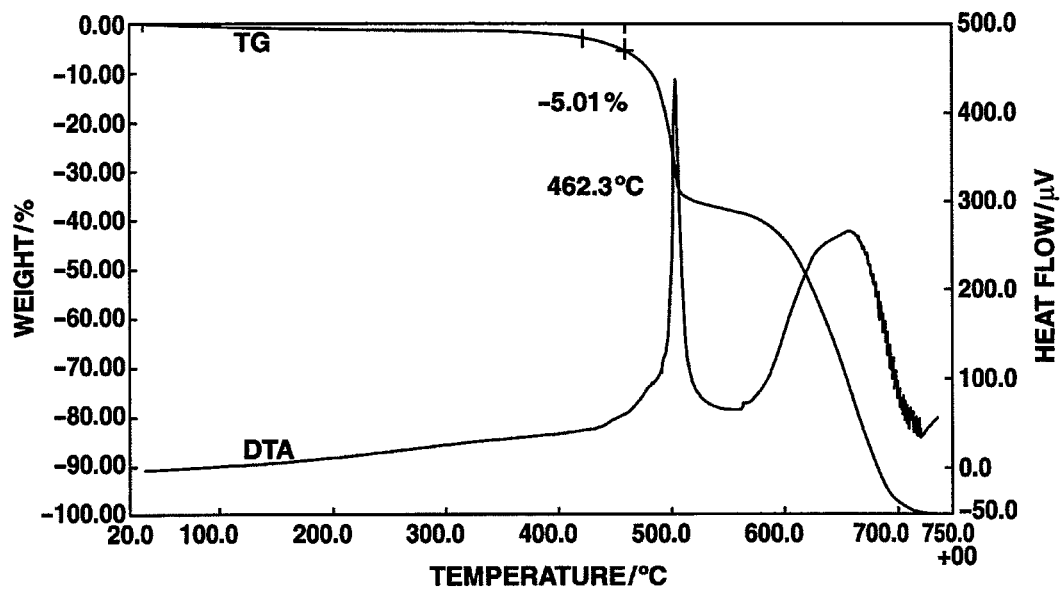
FIG. 48 is a diagram showing the results of TG-DTA measurement in Example 82.

As in Example 53, TG-DTA measurement of the high-molecular compound obtained in Example 80 was conducted. The 5% weight loss temperature was 452° C. The results are shown in FIG. 48.

Example 83

Synthesis of High-Molecular Compound [17]

[Chemical Formula 38]

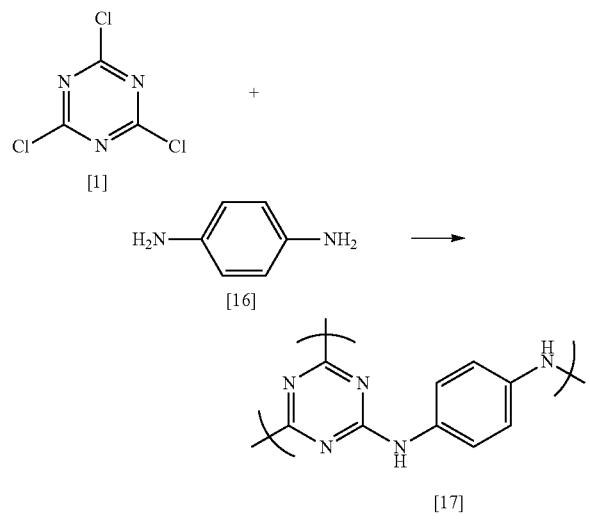

Figure 49:
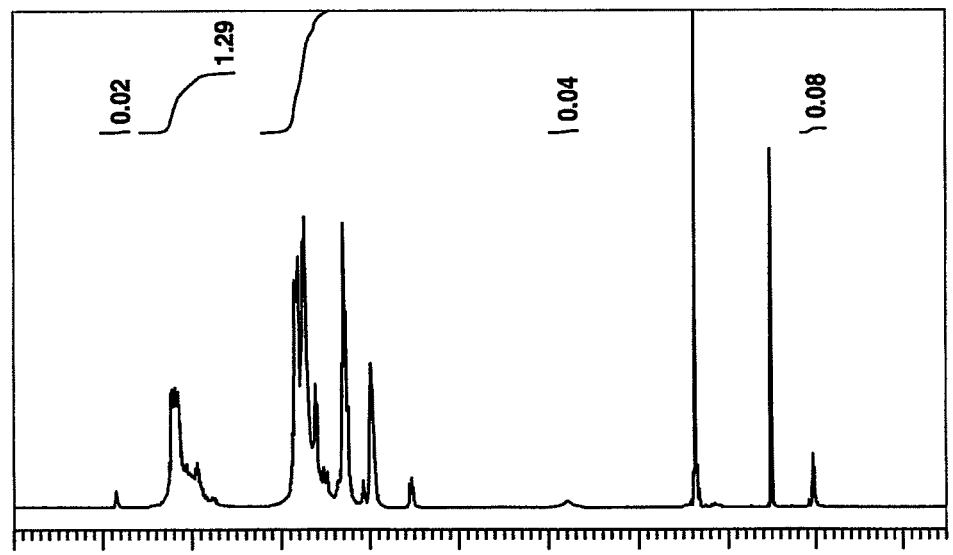
FIG. 49 is a diagram showing a $^1$H-NMR spectrum of the high-molecular compound [17] obtained in Example 83.

Using benzene-1,4-diamine [16] (2.70 g, 0.024 mol, product of Tokyo Chemical Industry Co., Ltd.) in place of 9,9-bis(4-aminophenyl)fluorene, it was reacted to 2,4,6-trichloro-1,3,5-triazine [1] (3.70 g, 0.02 mol, product of Tokyo Chemical Industry Co., Ltd.) in a similar manner as in Example 1. Further, as in Example 1, aniline (8.46 g, 0.09 mol) was added to conduct treatment. Redissolution was conducted in DMF (40 mL), followed by reprecipitation to obtain the target high-molecular compound [17] (hereinafter abbreviated as "HB-TDA," 0.87 g). A $^1$H-NMR spectrum of HB-TDA is shown in FIG. 49. HB-TDA so obtained was a compound having structural units represented by the formula (1). The weight average molecular weight Mw of HB-TDA as measured by GPC and calibrated against standard polystyrene was 14,900, and the polydispersibility Mw/Mn was 7.34. It is to be noted that the GPC measurement was conducted under the conditions of Example 68.

Example 84

Measurement of Refractive Index and Transmittance

HB-TDA (1.0 g) obtained in Example 83 was dissolved in N-methylpyrrolidone (9.0 g) to obtain a clear pale-brown solution. Using a spin coater, the obtained polymer varnish was spin-coated onto a glass substrate at 100 rpm for 5 seconds and then at 1,000 rpm for 30 seconds, followed by baking at 150° C. for 1 minute and then at 250° C. for 5 minutes to remove the solvent so that a film was obtained. The resultant film was measured for refractive index. Its refractive index at 550 nm was 1.8010.

Figure 50:
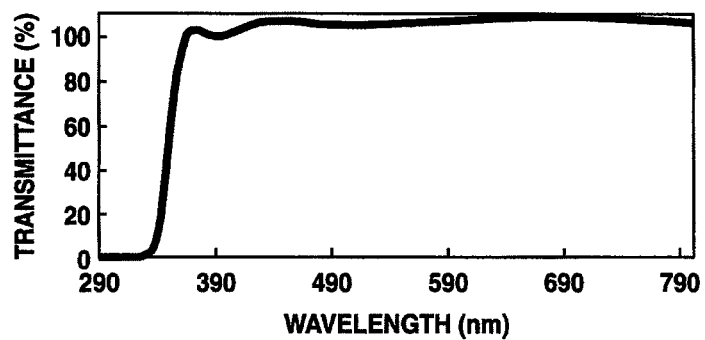
FIG. 50 is a diagram showing the transmittance of the film obtained in Example 84.

Further, the resultant film was measured for transmittance at from 400 to 800 nm. The results are shown in FIG. 50.

Example 85

5% Weight Loss Temperature Measurement of HB-TDA

Figure 51:
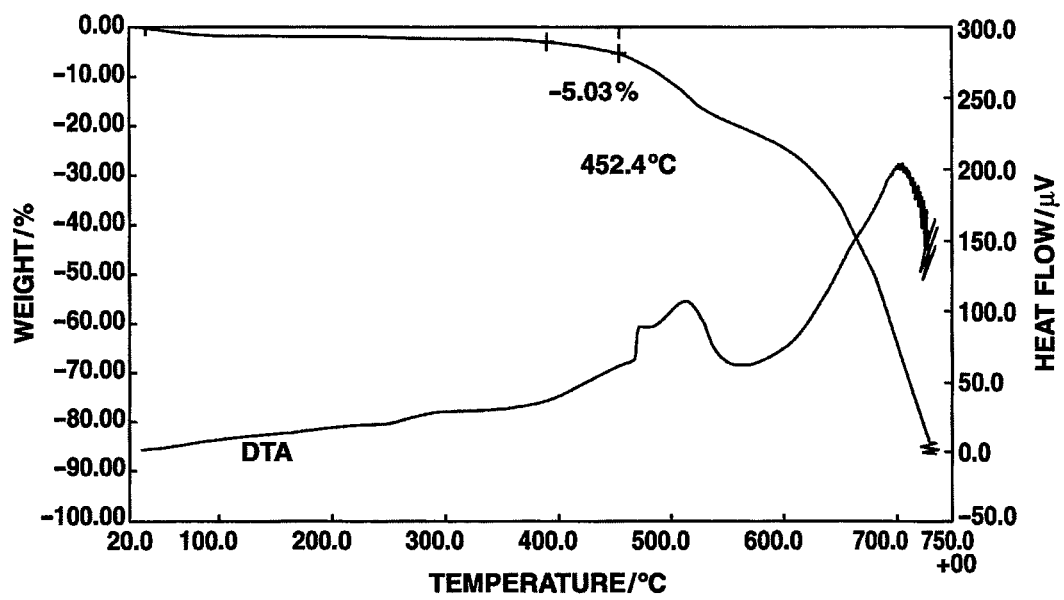
FIG. 51 is a diagram showing the results of TG-DTA measurement in Example 85.

As in Example 53, TG-DTA measurement of the high-molecular compound obtained in Example 83 was conducted. The 5% weight loss temperature was 452° C. The results are shown in FIG. 51.

Example 86

Synthesis of High-Molecular Compound [21]

[Chemical Formula 39]

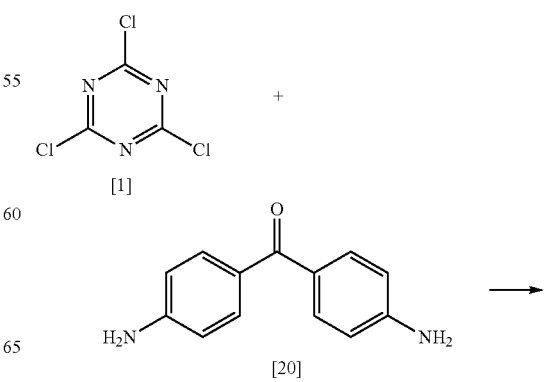

-continued

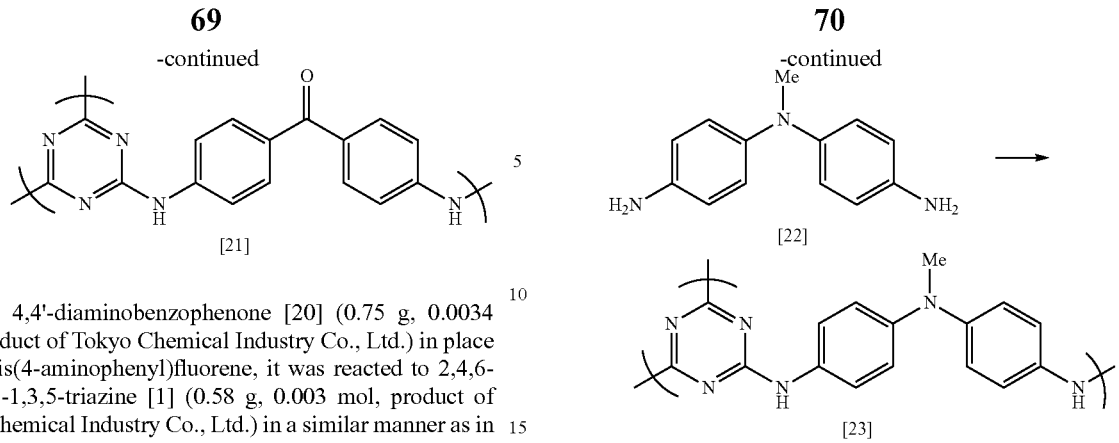

[21]

Figure 52:
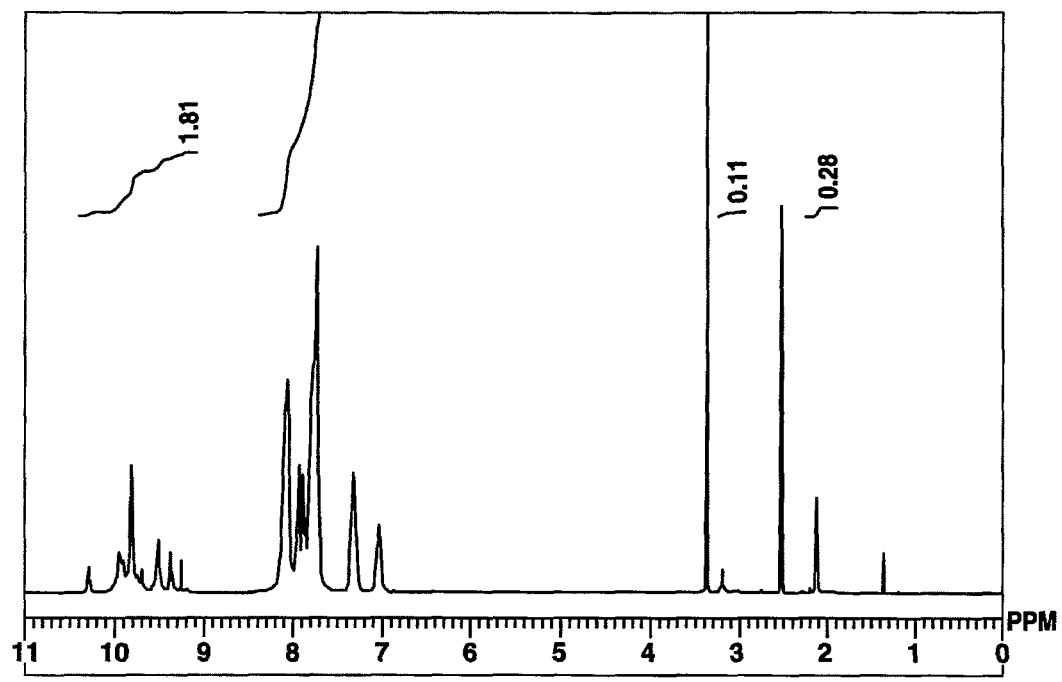
FIG. 52 is a diagram showing a $^1$H-NMR spectrum of the high-molecular compound [21] obtained in Example 86.

Using 4,4'-diaminobenzophenone [20] (0.75 g, 0.0034 mol, product of Tokyo Chemical Industry Co., Ltd.) in place of 9,9-bis(4-aminophenyl)fluorene, it was reacted to 2,4,6-trichloro-1,3,5-triazine [1] (0.58 g, 0.003 mol, product of Tokyo Chemical Industry Co., Ltd.) in a similar manner as in Example 1. Further, as in Example 1, aniline (0.87 g, 0.009 mol, product of Junsei Chemical Co., Ltd.) was added to conduct treatment so that the target high-molecular compound [21] (hereinafter abbreviated as "HB-TBpA," 1.05 g) was obtained. A $^1$H-NMR spectrum of HB-TBpA is shown in FIG. 52. HB-TBpA so obtained was a compound having structural units represented by the formula (1). The weight average molecular weight Mw of HB-TBpA as measured by GPC and calibrated against standard polystyrene was 3,200, and the polydispersibility Mw/Mn was 2.15.

Example 87

Measurement of Refractive Index and Transmittance

Figure 53:
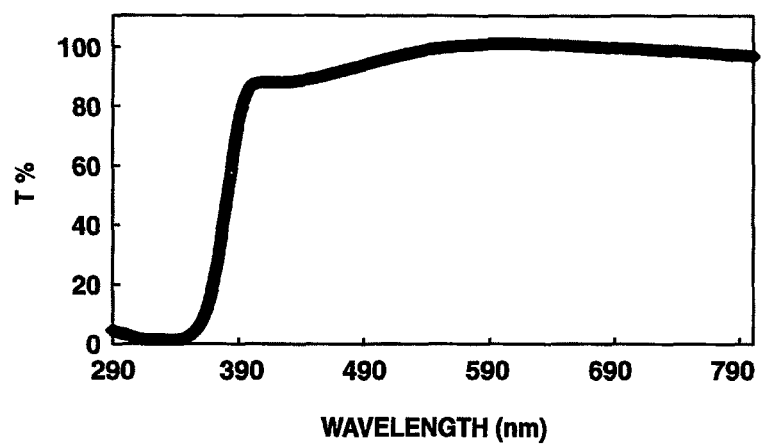
FIG. 53 is a diagram showing the transmittance of the film obtained in Example 87.

HB-TBpA (0.3 g) obtained in Example 86 was dissolved in N-methylpyrrolidone (2.7 g) to obtain a clear pale-yellow solution. Using a spin coater, the obtained polymer varnish was spin-coated onto a glass substrate at 200 rpm for 5 seconds and then at 2,000 rpm for 30 seconds, followed by baking at 150° C. for 2 minutes and then at 250° C. for 5 minutes to remove the solvent so that a film was obtained. The resultant film was measured for refractive index. Its refractive index at 550 nm was 1.8929. Further, the resultant film was measured for transmittance at from 400 to 800 nm. The results are shown in FIG. 53.

Example 88

5% Weight Loss Temperature Measurement of HB-TBpA

Figure 54:
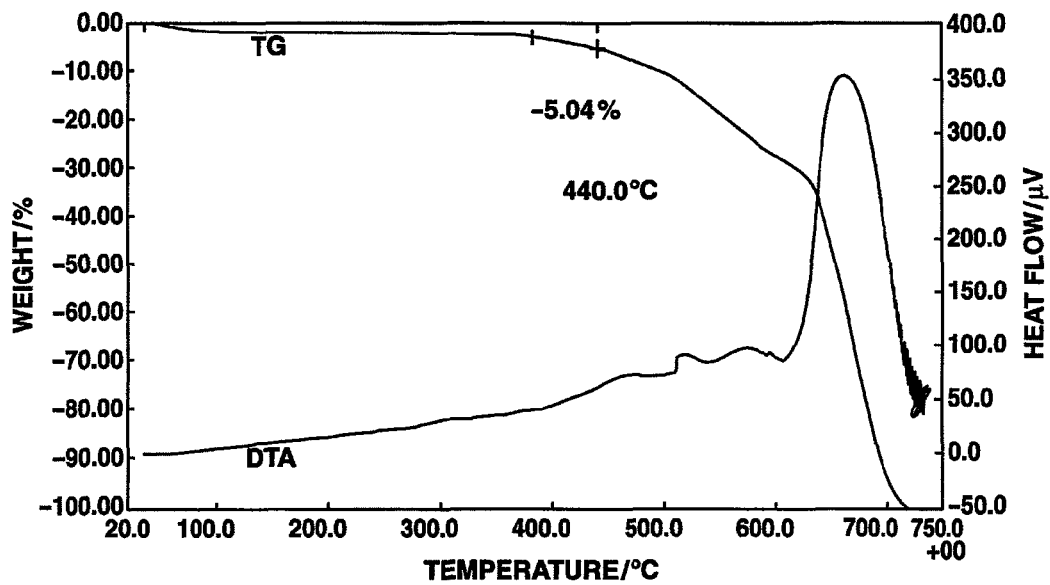
FIG. 54 is a diagram showing the results of TG-DTA measurement in Example 88.

As in Example 53, TG-DTA measurement of the high-molecular compound obtained in Example 86 was conducted. The 5% weight loss temperature was 453° C. The results are shown in FIG. 54.

Example 89

Synthesis of High-molecular Compound [23]

[Chemical Formula 40]

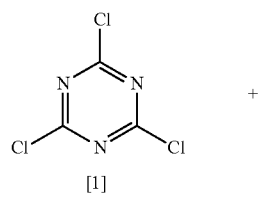

[1]

-continued

[22]

→

[23]

Figure 55:
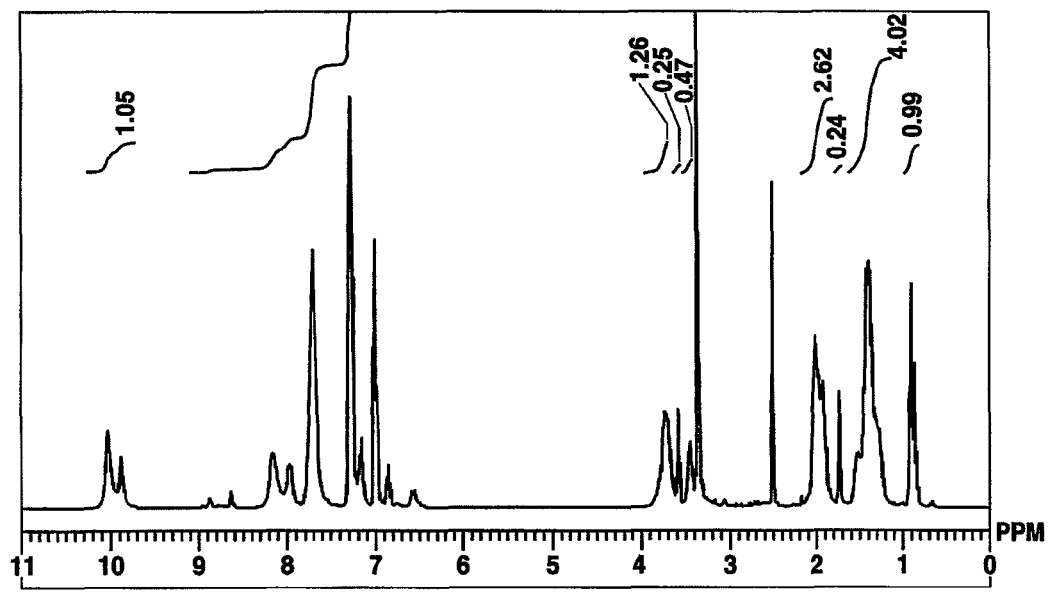
FIG. 55 is a diagram showing a $^1$H-NMR spectrum of the high-molecular compound [23] obtained in Example 89.

Using 4,4'-diamino-N-methyldiphenylamine [22] (3.56 g, 0.013 mol, produced following the procedure described in Macromolecules, 36(9), 3115-3127 (2003)) in place of 9,9-bis(4-aminophenyl)fluorene, it was reacted to 2,4,6-trichloro-1,3,5-triazine [1] (1.84 g, 0.010 mol, product of Tokyo Chemical Industry Co., Ltd.) in a similar manner as in Example 1. Further, as in Example 1, aniline (2.80 g, 0.03 mol, product of Junsei Chemical Co., Ltd.) was added to conduct treatment. Redissolution was conducted in DMF (100 mL), followed by reprecipitation to obtain the target high-molecular compound [23] (hereinafter abbreviated as "HB-TDMA," 1.77 g). The results of $^1$H-NMR spectrum measurement of HB-TDMA are shown in FIG. 55. HB-TDMA so obtained was a compound having structural units represented by the formula (1). The weight average molecular weight Mw of HB-TDMA as measured by GPC and calibrated against standard polystyrene was 7,800, and the polydispersibility Mw/Mn was 4.49. It is to be noted that the GPC measurement was conducted under the conditions of Example 68.

Example 90

Measurement of Refractive Index and Transmittance

HB-TDMA (0.3 g) obtained in Example 89 was dissolved in N-methylpyrrolidone (2.7 g) to obtain a clear pale-yellow solution. Using a spin coater, the obtained polymer varnish was spin-coated onto a glass substrate at 200 rpm for 5 seconds and then at 2,000 rpm for 30 seconds, followed by baking at 150° C. for 2 minutes and then at 250° C. for 5 minutes to remove the solvent so that a film was obtained. The resultant film was measured for refractive index. Its refractive index at 550 nm was 1.8034.

Figure 56:
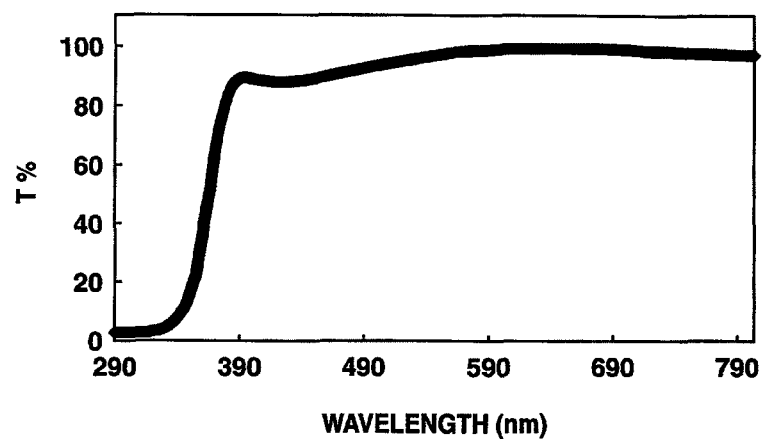
FIG. 56 is a diagram showing the transmittance of the film obtained in Example 90.

Further, the resultant film was measured for transmittance at from 400 to 800 nm. The results are shown in FIG. 56.

Example 91

5% Weight Loss Temperature Measurement of HB-TDMA

Figure 57:
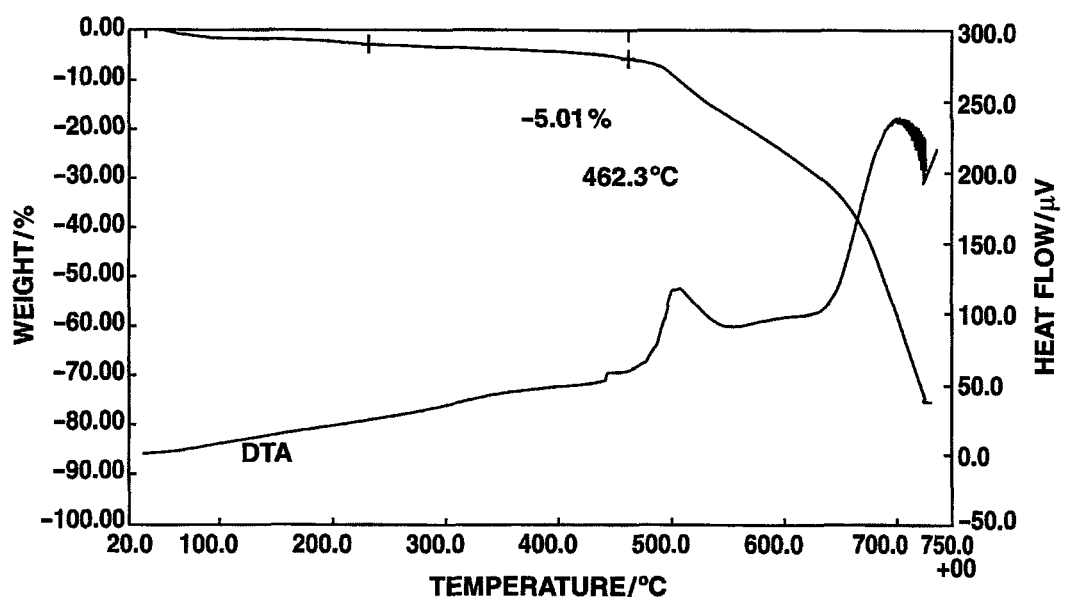
FIG. 57 is a diagram showing the results of TG-DTA measurement in Example 91.

As in Example 53, TG-DTA measurement of the high-molecular compound obtained in Example 89 was conducted. The 5% weight loss temperature was 462° C. The results are shown in FIG. 57.

Example 92

Synthesis of High-molecular Compound [3] by Low-temperature Charging Method

Under a nitrogen atmosphere and in a 50-mL, four-necked flask, 9,9-bis(4-aminophenyl)fluorene [2] (3.35 g, 0.0096 mol, product of Aldrich Corporation) was placed and dissolved in DMAc (23 g), followed by cooling to −10° C. Subsequently, 2,4,6-trichloro-1,3,5-triazine [1] (1.48 g, 0.08 mol, product of Tokyo Chemical Industry Co., Ltd.) was added little by little to prevent the temperature from rising to 0° C. or higher, followed by stirring for 30 minutes. Into a vessel provided beforehand by adding DMAc (23 g) to a 100-mL, four-necked flask and heating it to 85° C. in an oil bath, the resulting reaction mixture was added dropwise over 10 minutes by using a transfer tube. The resulting mixture was stirred for 1 hour to conduct polymerization.

Figure 58:
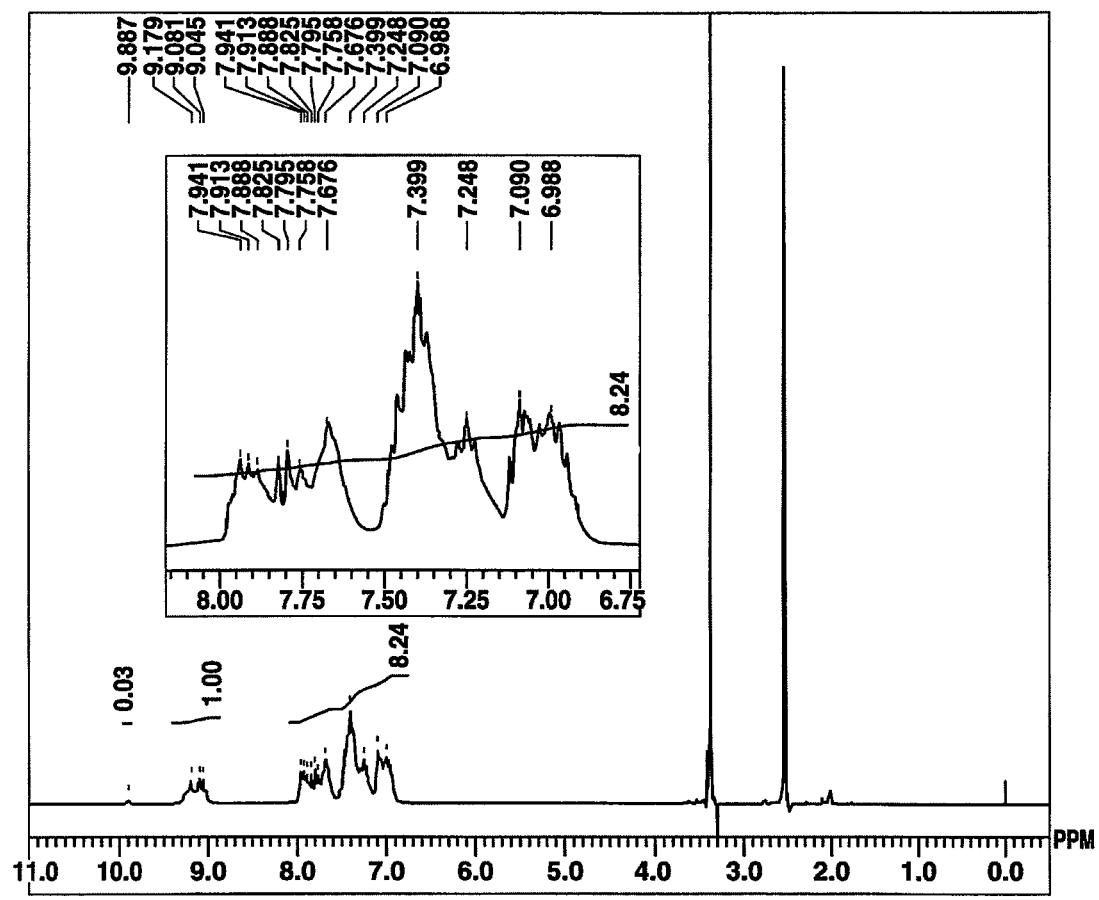
FIG. 58 is a diagram showing a $^1$H-NMR spectrum of the high-molecular compound [3] obtained in Example 92.

Subsequently, aniline (1.46 g, 0.024 mol) was added, followed by stirring for 1 hour to terminate the polymerization. After the resultant polymerization mixture was allowed to cool to room temperature, it was reprecipitated in a solution of 28% aqueous solution of ammonia (15 g, 0.024 mol) in a mixed solution of ion-exchanged water (181 g) and methanol (42 g). The resulting precipitates were collected by filtration, redissolved in THF (43 g), and then reprecipitated in ion-exchanged water (215 g). The resulting precipitates were collected by filtration, and then dried at 150° C. for 8 hours in a vacuum dryer to obtain the target high-molecular compound [3] (hereinafter abbreviated as "HB-TFA110," 4.43 g). The results of $^1$H-NMR spectrum measurement of HB-TFA110 are shown in FIG. 58. HB-TFA110 so obtained was a compound having structural units represented by the formula (1). The weight average molecular weight Mw of HB-TFA110 as measured by GPC and calibrated against standard polystyrene was 11,000, and the polydispersibility Mw/Mn was 3.30.

Example 93

Measurement of Refractive Index and Transmittance

HB-TFA110 (1.0 g) obtained in Example 92 was dissolved in cyclohexanone (9.0 g) to obtain a clear pale-yellow solution. Using a spin coater, the obtained polymer varnish was spin-coated onto a glass substrate at 500 rpm for 5 seconds and then at 3,000 rpm for 30 seconds, followed by baking at 150° C. for 2 minutes and then at 250° C. for 5 minutes to obtain a film. The resultant film was measured for refractive index. Its refractive index at 550 nm was 1.738.

Figure 59:
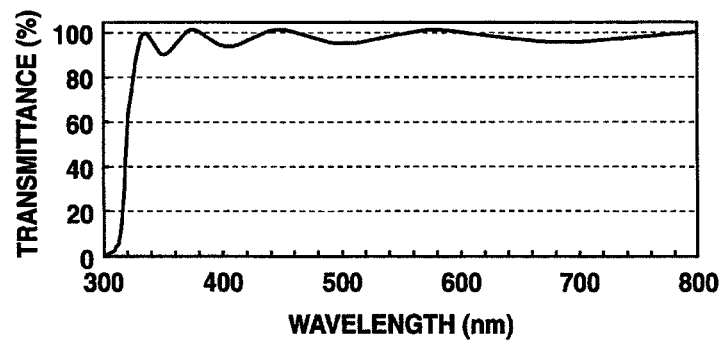
FIG. 59 is a diagram showing the transmittance of the film obtained in Example 93.

Further, the resultant film was measured for transmittance at from 400 to 800 nm. The results are shown in FIG. 59.

Example 94

5% Weight Loss Temperature Measurement of HB-TFA110

Figure 60:
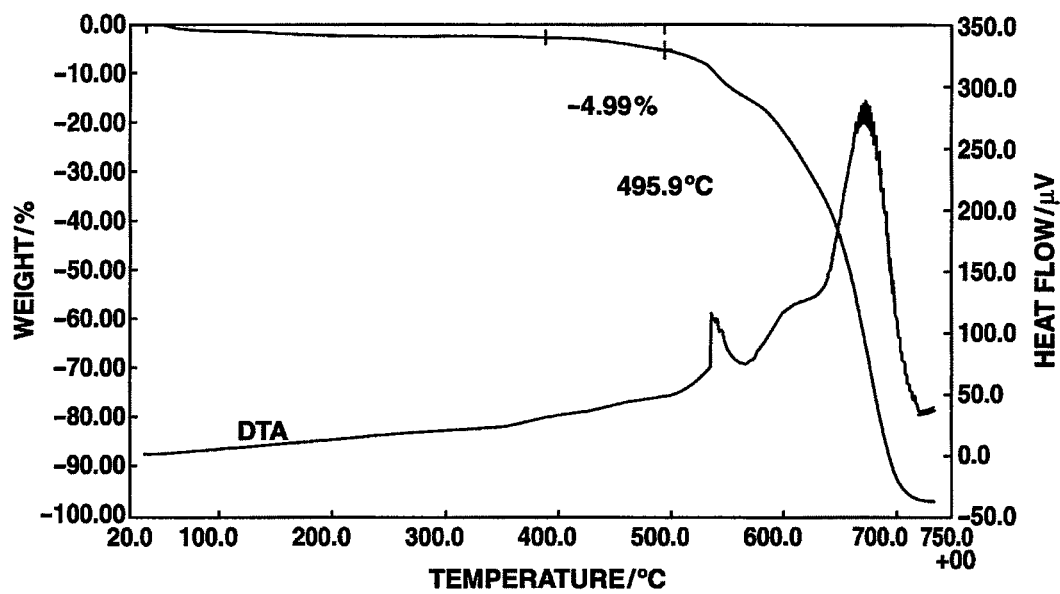
FIG. 60 is a diagram showing the results of TG-DTA measurement in Example 94.

HB-TFA110 (3.47 mg) obtained in Example 92 was placed in a platinum pan, and was measured at a ramp-up rate of 15° C./min by TG-DTA. The 5% weight loss temperature was 496° C. The results are shown in FIG. 60.

Example 95

Synthesis of High-molecular Compound [25]

[Chemical Formula 41]

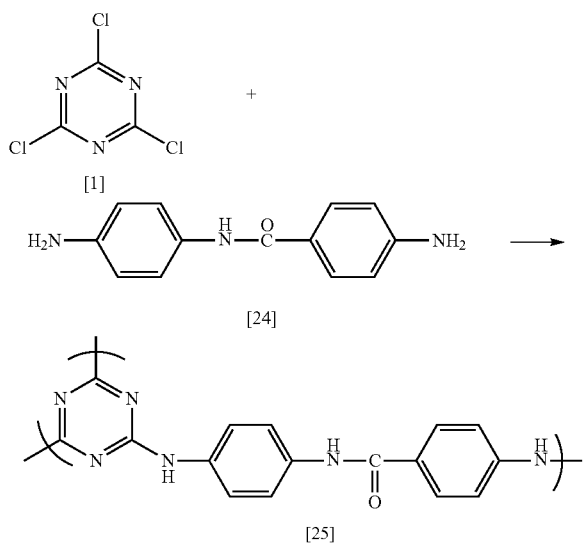

Using 4,4'-diaminobenzanilide [24] (4.18 g, 0.0184 mol, product of Tokyo Chemical Industry Co., Ltd.) in place of 9,9-bis(4-aminophenyl)fluorene, it was reacted to 2,4,6-trichloro-1,3,5-triazine [1] (2.67 g, 0.014 mol, product of Tokyo Chemical Industry Co., Ltd.) in a similar manner as in Example 1. Further, as in Example 1, aniline (4.00 g, 0.0425 mol) was added to conduct treatment. Redissolution was conducted using DMF (80 mL), followed by reprecipitation to obtain the target high-molecular compound [25] (hereinafter abbreviated as "HB-TAMA1," 6.30 g).

Figure 61:
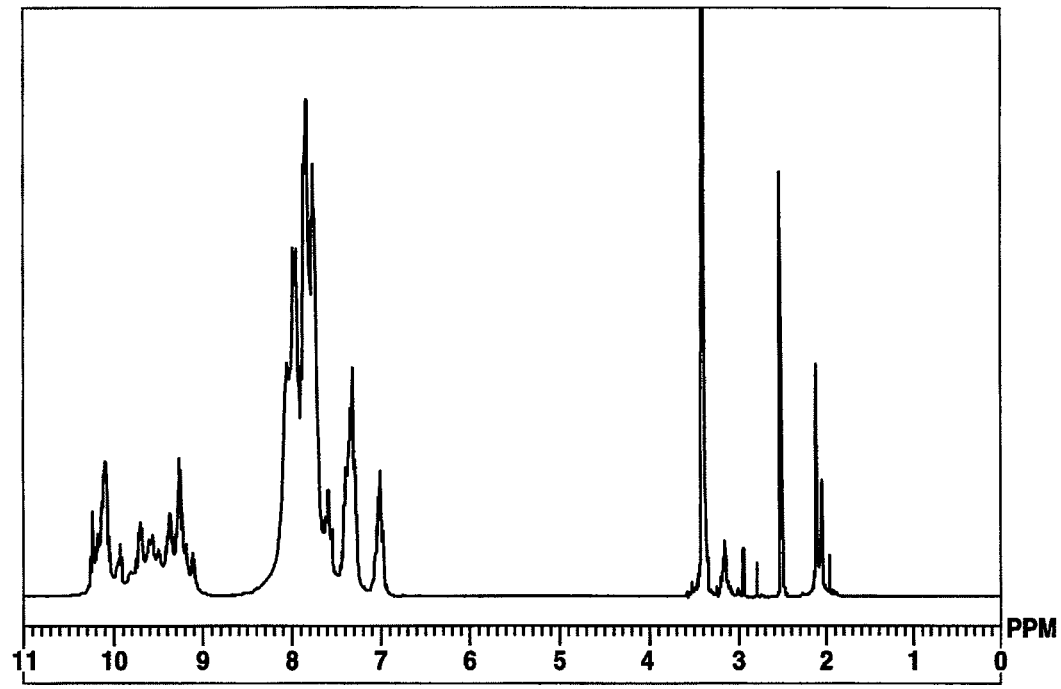
FIG. 61 is a diagram showing a $^1$H-NMR spectrum of the high-molecular compound [25] obtained in Example 95.

A $^1$H-NMR spectrum of HB-TAMA1 so obtained is shown in FIG. 61. HB-TAMA1 so obtained was a compound having structural units represented by the formula (1).

The weight average molecular weight Mw of HB-TAMA1 as measured by GPC and calibrated against standard polystyrene was 149,000, and the polydispersibility Mw/Mn was 44.0. It is to be noted that the GPC measurement was conducted under the conditions of Example 68.

Example 96

Measurement of Refractive Index and Transmittance

HB-TAMA1 (1.0 g) obtained in Example 95 was dissolved in N-methylpyrrolidone (9.0 g) to obtain a clear pale-yellow solution. Using a spin coater, the obtained polymer varnish was spin-coated onto a glass substrate at 200 rpm for 5 seconds and then at 2,000 rpm for 30 seconds, followed by baking at 150° C. for 2 minutes and then at 250° C. for 5 minutes to remove the solvent so that a film was obtained. The resultant film was measured for refractive index. Its refractive index at 550 nm was 1.9387.

Figure 62:
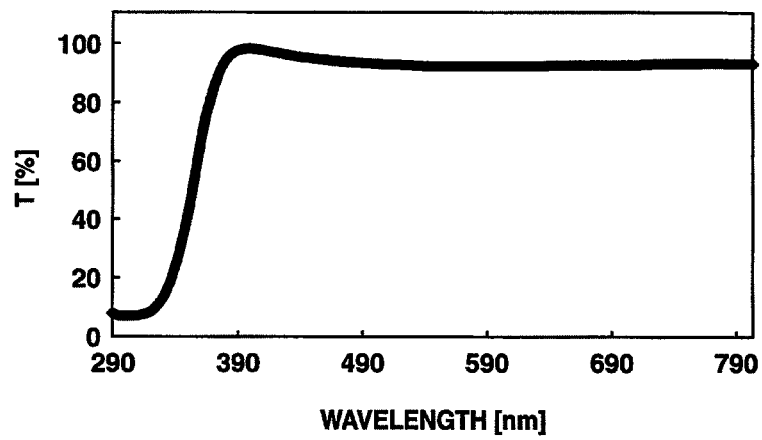
FIG. 62 is a diagram showing the transmittance of the film obtained in Example 96.

Further, the resultant film was measured for transmittance at from 400 to 800 nm. The results are shown in FIG. 62.

Example 97

5% Weight Loss Temperature Measurement of HB-TAMA1

Figure 63:
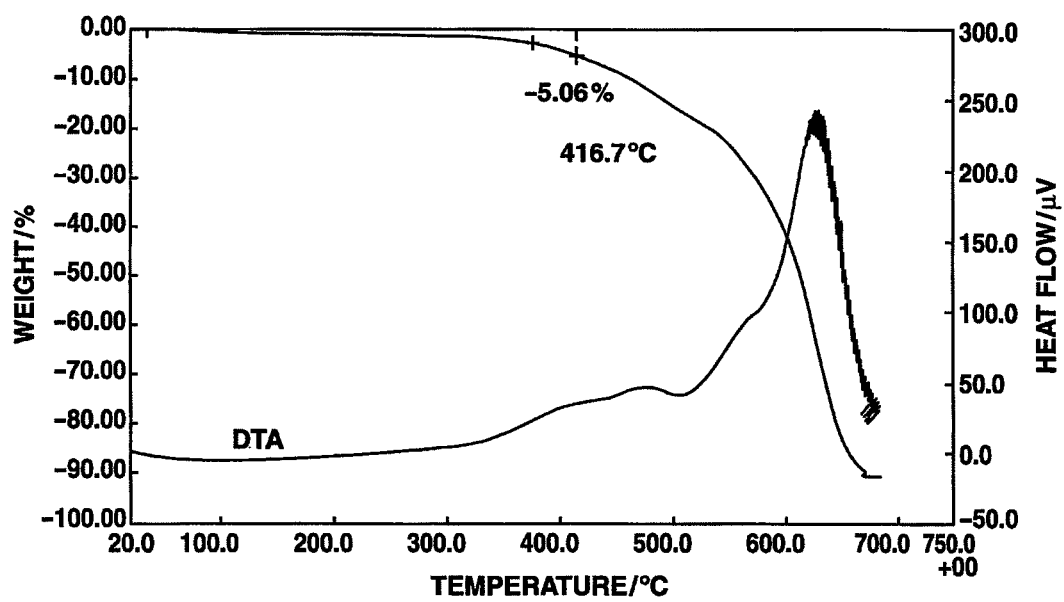
FIG. 63 is a diagram showing the results of TG-DTA measurement in Example 97.

As in Example 53, TG-DTA measurement of the high-molecular compound obtained in Example 95 was conducted. The 5% weight loss temperature was 416° C. The results are shown in FIG. 63.

Example 98

Synthesis of High-Molecular Compound [27]

[Chemical Formula 42]

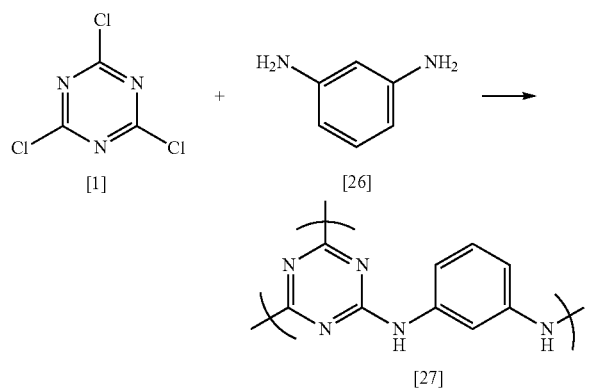

Under air and in a 1,000-mL, four-necked flask, m-phenylenediamine [26] (12.17 g, 0.12 mol, product of Aldrich Corporation) was placed and dissolved in DMAc (121 mL), followed by heating to 100° C. in an oil bath. Subsequently, a solution of 2,4,6-trichloro-1,3,5-triazine [1] (26.15 g, 0.14 mol, product of Tokyo Chemical Industry Co., Ltd.) in DMAc (261.5 mL) was added to initiate polymerization.

Fifty minutes later, aniline (30.6 g, 0.3 mol, product of Junsei Chemical Co., Ltd.) was added, followed by stirring for 1 hour to terminate the polymerization. After the resultant polymerization mixture was allowed to cool to room temperature, it was reprecipitated in a 28% aqueous solution of ammonia (30.4 g) in a mixed solvent of water (1,600 mL) and methanol (520 mL). The resulting precipitates were collected by filtration, redissolved in a mixed solvent of THF (400 mL) and DMF (15 mL), and then reprecipitated in ion-exchanged water (2,100 mL). The resulting precipitates were collected by filtration, and then dried at 150° C. for 6 hours in a vacuum dryer to obtain the target high-molecular compound [27] (hereinafter abbreviated as "HB-TmDA12," 19.94 g).

Figure 64:
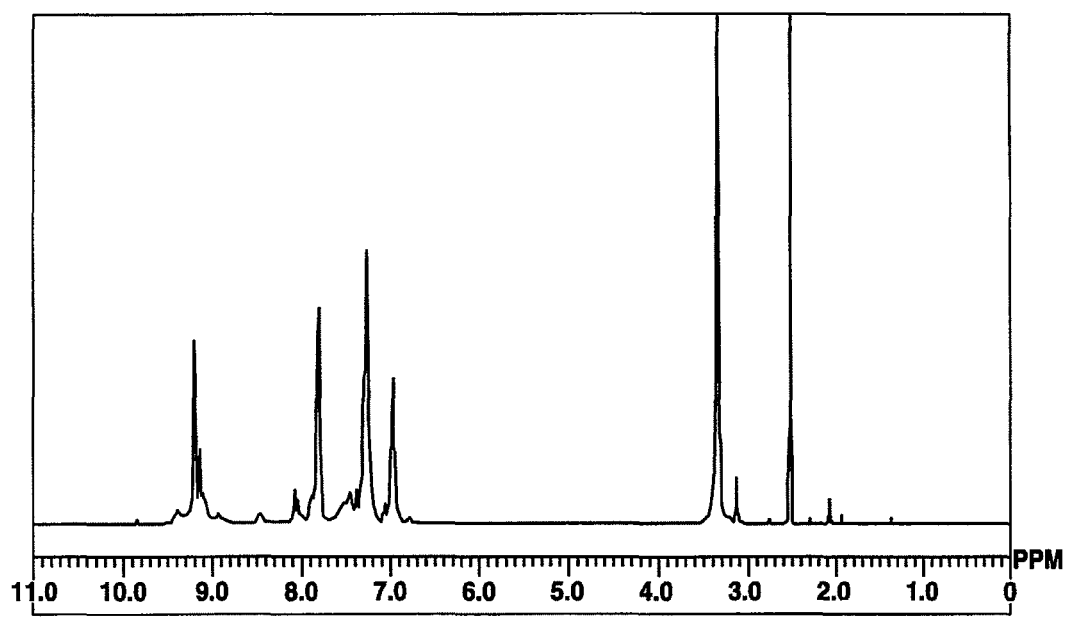
FIG. 64 is a diagram showing a $^1$H-NMR spectrum of the high-molecular compound [27] obtained in Example 98.

The results of $^1$H-NMR spectrum measurement of HB-TmDA12 are shown in FIG. 64. HB-TmDA12 so obtained was a compound having structural units represented by the formula (25). The weight average molecular weight Mw of HB-TmDA12 as measured by GPC and calibrated against standard polystyrene was 1,200, and the polydispersibility Mw/Mn was 1.23.

Example 99

Measurement of Refractive Index and Transmittance

HB-TmDA12 (1.0 g) obtained in Example 98 was dissolved in propylene glycol monomethyl ether (9.0 g) to obtain a clear pale-yellow solution. Using a spin coater, the obtained polymer varnish was spin-coated onto a quartz substrate at 200 rpm for 5 seconds and then at 2,000 rpm for 30 seconds, followed by baking at 150° C. for 2 minutes and then at 250° C. for 5 minutes to remove the solvent so that a film was obtained. The resultant film was measured for refractive index. Its refractive index at 550 nm was 1.7752.

Figure 65:
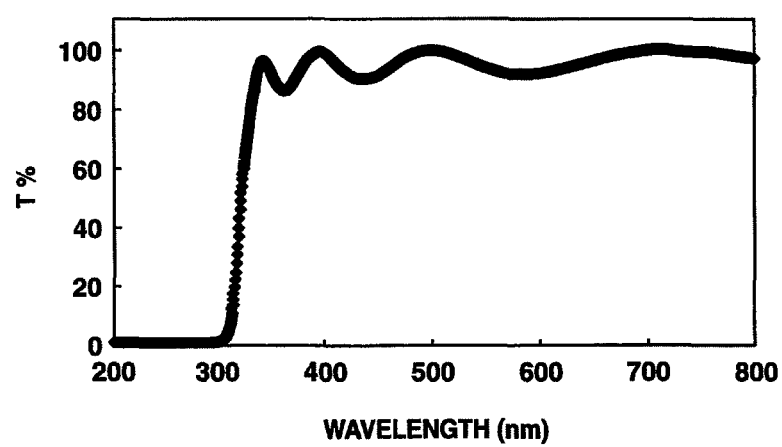
FIG. 65 is a diagram showing the transmittance of the film obtained in Example 99.

Further, the resultant film was measured for transmittance at from 400 to 800 nm. The results are shown in FIG. 65.

Example 100

5% Weight Loss Temperature Measurement of HB-TmDA12

Figure 66:
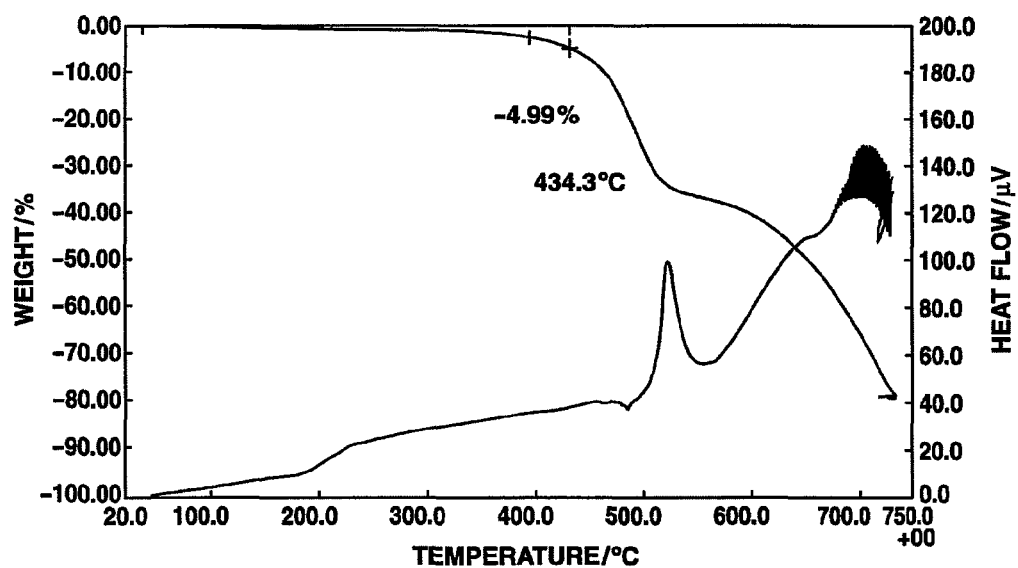
FIG. 66 is a diagram showing the results of TG-DTA measurement in Example 100.

The high-molecular compound [27] (3.57 mg) obtained in Example 98 was placed in a platinum pan, and was measured at a ramp-up rate of 15° C./min by TG-DTA. The 5% weight loss temperature was 434° C. The results are shown in FIG. 66.

Example 101

Synthesis of High-molecular Compound [27] Having Different Molecular Weight

Figure 67:
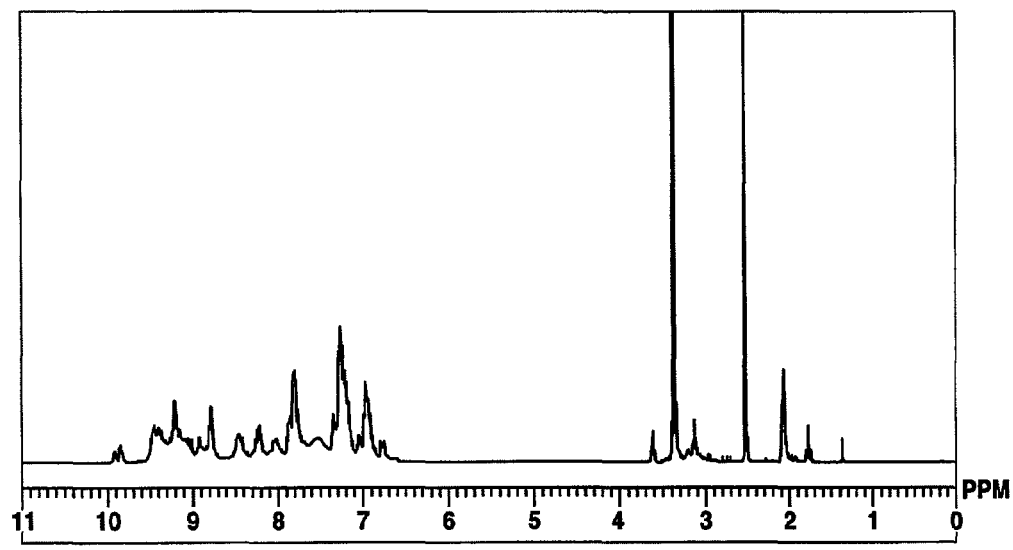
FIG. 67 is a diagram showing a $^1$H-NMR spectrum of the high-molecular compound [27] obtained in Example 101.

Using m-phenylenediamine [26] (28.94 g, 0.27 mol, product of Aldrich Corporation), 2,4,6-trichloro-1,3,5-triazine [1] (36.91 g, 0.20 mol, product of Tokyo Chemical Industry Co., Ltd.) and aniline (56.53 g, 0.6 mol, product of Junsei Chemical Co., Ltd.), synthesis was conducted in a similar manner as in Example 98 to obtain the target high-molecular compound [27] (hereinafter abbreviated as "HB-TmDA45," 49.78 g). The results of $^1$H-NMR spectrum measurement of HB-TmDA45 are shown in FIG. 67. HB-TmDA45 so obtained was a compound having structural units represented by the formula (25). The weight average molecular weight Mw of HB-TmDA45 as measured by GPC and calibrated against standard polystyrene was 4,600, and the polydispersibility Mw/Mn was 2.37.

Example 102

Measurement of Refractive Index and Transmittance

HB-TmDA45 (1.0 g) obtained in Example 101 was dissolved in cyclohexanone (9.0 g) to obtain a clear pale-yellow solution. Using a spin coater, the obtained polymer varnish was spin-coated onto a glass substrate at 200 rpm for 5 seconds and then at 2,000 rpm for 30 seconds, followed by baking at 150° C. for 2 minutes and then at 250° C. for 5 minutes to remove the solvent so that a film was obtained. The resultant film was measured for refractive index. Its refractive index at 550 nm was 1.8030.

Figure 68:
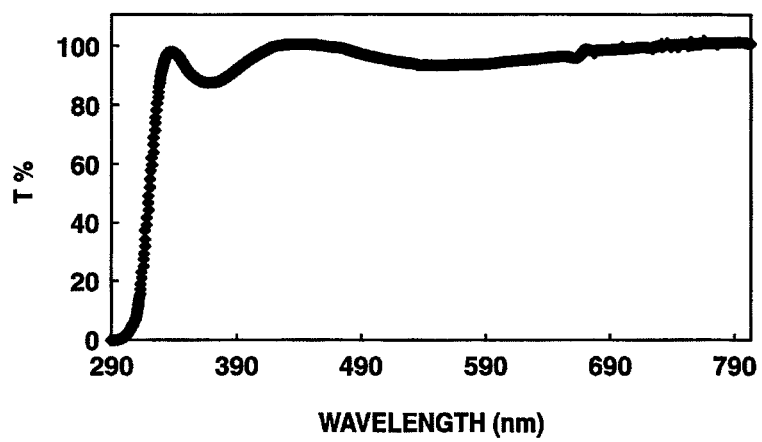
FIG. 68 is a diagram showing the transmittance of the film obtained in Example 102.

Further, the resultant film was measured for transmittance at from 400 to 800 nm. The results are shown in FIG. 68.

Example 103

5% Weight Loss Temperature Measurement of HB-TmDA45

Figure 69:
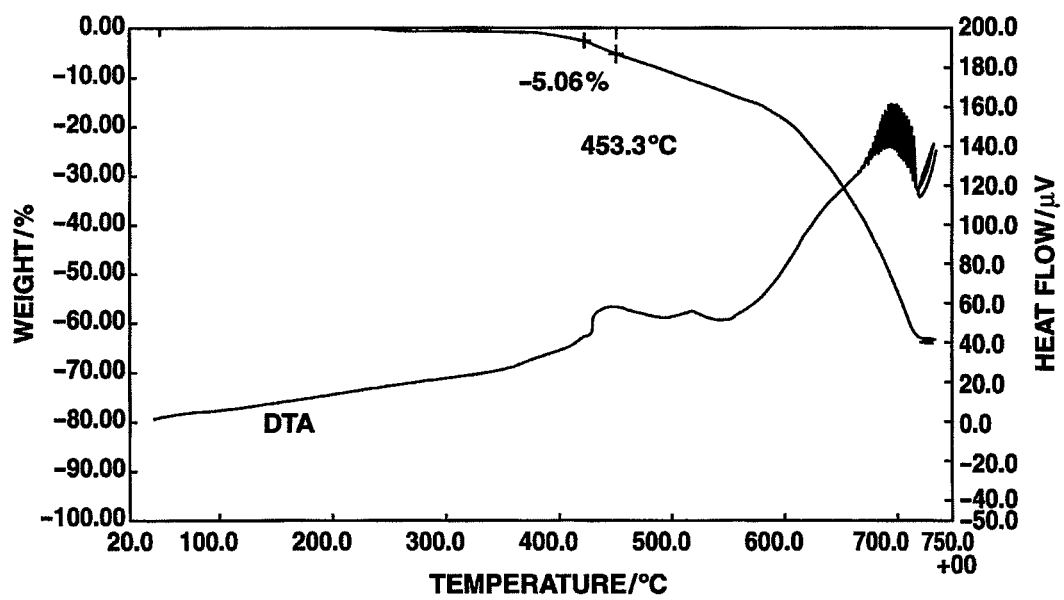
FIG. 69 is a diagram showing the results of TG-DTA measurement in Example 103.

As in Example 100, TG-DTA measurement of the high-molecular compound obtained in Example 101 was conducted. The 5% weight loss temperature was 453° C. The results are shown in FIG. 69.

As described above, the high-polymer compound represented by the formula [27] is appreciated to have a very high refractive index as a polymer by itself.

Example 104

[Chemical Formula 43]

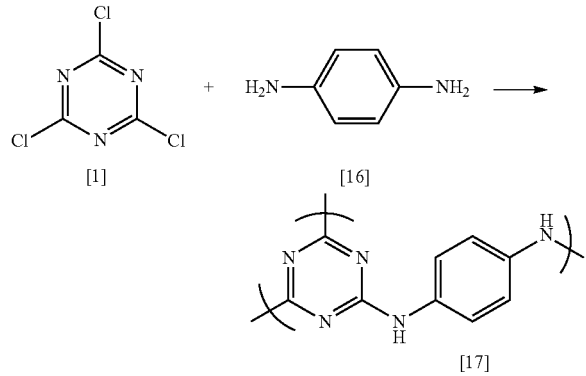

Figure 70:
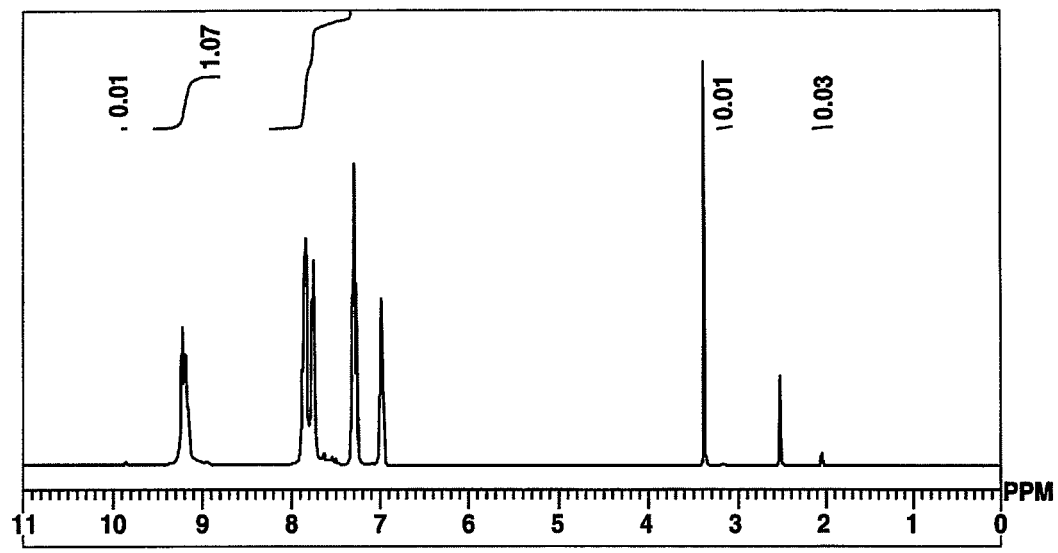
FIG. 70 is a diagram showing a $^1$H-NMR spectrum of the high-molecular compound [5] obtained in Example 104.

Using p-phenylenediamine [16] (7.49 g, 0.069 mol, product of Aldrich Corporation), 2,4,6-trichloro-1,3,5-triazine [1] (18.54 g, 0.1 mol, product of Tokyo Chemical Industry Co., Ltd.) and aniline (28.30 g, 0.3 mol, product of Junsei Chemical Co., Ltd.), synthesis was conducted in a similar manner as in Example 98. Redissolution was conducted with DMF (260 mL), followed by reprecipitation to obtain the target high-molecular compound [17] (hereinafter abbreviated as "HB-TpDA23," 49.78 g). The results of $^1$H-NMR spectrum measurement of HB-TpDA23 are shown in FIG. 70. The weight average molecular weight Mw of HB-TpDA23 as measured by GPC and calibrated against standard polystyrene was 2,300, and the polydispersibility Mw/Mn was 1.75. It is to be noted that the GPC measurement was performed under the conditions to be described below.
[GPC]
  Instrument: "HLC-8200 GPC," manufactured by Tosoh Corporation
  Column: "SHODEX OHPAK SB-803HQ+SB-804HQ"
  Column temperature: 40° C.
  Solvent: DMF
  Detector: UV (254 nm)
  Calibration curve: standard polystyrene
  Concerning the high-molecular compounds obtained above in Example 98 and Example 104, their solubility in the individual solvents presented in Table 3 was studied, and was evaluated in accordance with the below-described standards. It is to be noted that each solution was prepared to contain the corresponding high-molecular compound at 10% by mass and the solubility was visually determined at 25° C. an hour later.
  ○: Dissolved well into a clear solution
  x: Insoluble with settled precipitates

TABLE 3

| | Example 98 | Example 104 |
|---|---|---|
| Tetrahydrofuran | ○ | X |
| N-methylpyrrolidone | ○ | ○ |
| N,N-dimethylformamide | ○ | ○ |
| N,N-dimethylacetamide | ○ | ○ |
| Dimethyl sulfoxide | ○ | ○ |

TABLE 3-continued

| | Example 98 | Example 104 |
|---|---|---|
| Toluene | X | X |
| Cyclohexanone | ○ | X |
| Propylene glycol monomethyl ether | ○ | X |
| Propylene glycol monomethyl ether acetate | ○ | X |
| Propylene glycol monoethyl ether | ○ | X |
| Ethyl lactate | ○ | X |

As presented in Table 3, it is appreciated that the high-molecular compound obtained using m-phenylenediamine has better solubility in organic solvents than the high-molecular compound obtained using p-phenylenediamine, and is soluble well especially in cyclohexanone, propylene glycol monomethyl ether, propylene glycol monoethyl ether, propylene glycol monomethyl ether acetate, and the like, all of which are widely used in the field of electronic devices.
<Preparation of Film-forming Compositions>

Example 105

Under air, HB-TmDA45 (2.0000 g) obtained in Example 101 was placed in a 10-mL eggplant flask, followed by the addition of cyclohexanone (8.0000 g) as a solvent. Using a wave rotor, HB-TmDA45 was completely dissolved at room temperature to prepare a 20% by mass cyclohexanone solution of HB-TmDA45. To an aliquot (1.0000 g) of the 20% by mass cyclohexanone solution, cyclohexanone (0.9420 g) was then added, and subsequently, a 10% by mass cyclohexanone solution of "EPOLEAD GT-401" (an epoxy-containing compound, product of Daicel Chemical Industries, Ltd.) as a crosslinking agent (0.2000 g; 10.0 parts by mass per 100 parts by mass of the solids of the polymer) was added. Added further were a 5% by mass cyclohexanone solution of 3-glycidoxypropyltrimethoxysilane (product of Shin-Etsu Chemical Co., Ltd.) as an adhesion promoter (0.0400 g; 1 parts by mass under the assumption that the solids of the polymer amounted to 100 parts by mass) and a 0.5% by mass cyclohexanone solution of "MEGAFAC R-30" (trade name, product of DIC Corporation) as a surfactant (0.0400 g; 0.1 parts by mass under the assumption that the solids of the polymer amounted to 100 parts by mass). The resulting solution was stirred for 3 hours until homogeneous. After the stirring, the solute had been completely dissolved, and as a clear pale-yellow solution, a polymer varnish (hereinafter abbreviated as "HB-TmDA45SV1") was obtained. The total percentage by mass of solids in HB-TmDA45SV1 was 10% by mass.
<Formation of Film and Measurement of Transmittance>

Example 106

Using a spin coater, HB-TmDA45SV1 obtained in Example 105 was spin-coated onto a silicon substrate to give a 500 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TmDA45F1 as a film on the substrate. The measurement results of transmittance of HB-TmDA45F1 are shown in FIG. 71.

Figure 71:
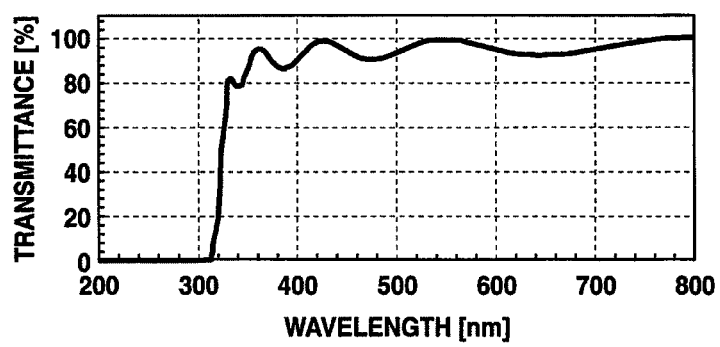
FIG. 71 is a diagram showing the transmittance of the film obtained in Example 106.

As shown in FIG. 71, HB-TmDA45F1 had good transmittance despite the baking at the temperature as high as 300° C. under the atmosphere. Described specifically, in the visible light range of from 400 to 800 nm, its average transmittance indicated a value of 95% or higher so that HB-TmDA45F1 was found to be a film of very high transparency.

Formation of Film and Refractive Index

Example 107

Using a spin coater, HB-TmDA45SV1 obtained in Example 105 was spin-coated onto a silicon substrate as in Example 106 to give a 500 nm thickness. Under the atmosphere, prebaking was performed for 1 minute on a hot plate controlled at 100° C. Under the atmosphere, final baking was then performed for 5 minutes on the hot plate controlled at 300° C. to obtain a film (hereinafter "HB-TmDA45F2").

HB-TmDA45F2 was measured for refractive index and thickness. The refractive index at 550 nm was 1.7604 and the refractive index at 633 nm was 1.7389, and the thickness was 508.2 nm.

As demonstrated above, the high-molecular compound according to the present invention has been found to permit realizing a very high refractive index exceeding 1.75 at 550 nm even in the form of a composition with a crosslinking agent and adhesion promoter added therein.

Solvent Resistance

Example 108

A solvent resistance test of HB-TmDA45F2 obtained in Example 107 was performed. The thickness of HB-TmDA45F2 after the final baking was 508.2 nm, which was recorded as an initial thickness. Samples of HB-TmDA45F2 were independently of each other immersed fully in propylene glycol monomethyl ether, propylene glycol monomethyl ether acetate, cyclohexanone, acetone and ethyl lactate, and left over for 5 minutes. Those samples were then dried in air, and baked for 1 minute on a hot plate controlled at 200° C. to completely vaporize any remaining solvent. Subsequently, their thicknesses were measured, and were compared with the initial thickness.

Assuming that the initial thickness was 100%, the thickness of HB-TmDA45F2 treated as described above was 97.5% against propylene glycol monomethyl ether, 99.9% against propylene glycol monomethyl ether acetate, 99.7% against cyclohexanone, 99.6% against acetone, and 99.3% against ethyl lactate. It was, therefore, found that HB-TmDA45F2 had good solvent resistance to the various organic solvents.

It is to be noted that the term "solvent resistance test" means a test to confirm whether or not a film after final baking has been insolubilized to its contact with a solvent. Solvent resistance is a property required upon addition of post-steps that a resist or the like is recoated on the film and the film is then patterned. Unless the film is equipped with solvent resistance, the film is dissolved in the resist solvent when recoated, so that the film is mixed with the resist and the inherent properties of the film may not be exhibited.

<Filling Property Test>

Example 109

Using HB-TmDA45SV1 prepared in Example 105, a filling property test was performed. The material of a structural substrate employed in the filling property test was silicon, and the structural substrate had via holes of 1.6 μm depth and 400 nm diameter.

By the spin coating method, HB-TmDA45SV1 was applied onto the structural substrate to give a 500 nm thickness. Prebaking was performed for 1 minute on a hot plate controlled at 100° C., followed by final baking for 5 minutes under the atmosphere on the hot plate controlled at 300° C.

After the baked structural substrate with a film formed thereon was scratched at an edge thereof with a diamond pen, the substrate was cleaved, followed by SEM observation. An observed image is shown in FIG. 72.

Figure 72:
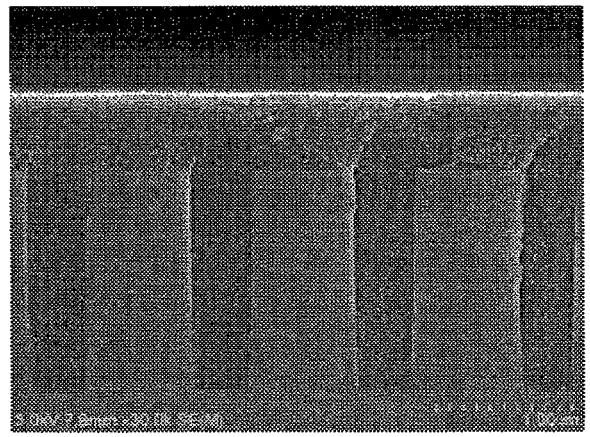
FIG. 72 is a picture showing an SEM image in a filling property test of Example 109.

As shown in FIG. 72, HB-TmDA45SV1 had good filling property. Applicability of HB-TmDA45SV1 as a filling material was, therefore, suggested.

When the highly-branched polymer according to the present invention is used as a planarizing material on a photodiode, light can be guided to the photodiode based on the principle of optical waveguide owing to its refractive index as high as 1.7 or higher. The current via-hole diameter can, therefore, be set at a smaller value, thereby making it possible to fabricate high-definition, solid-state imaging devices.

Example 110

Synthesis of High-molecular Compound [27] by Low-temperature Charging Method

Under nitrogen and in a 200-mL, four-necked flask, DMAc (50.41 g) was placed, followed by cooling to −10° C. in an ice bath with sodium chloride added therein, and 2,4,6-trichloro-1,3,5-triazine [1] (11.06 g, 0.06 mol, product of Aldrich Corporation) was added and dissolved. Subsequently, a solution of m-phenylenediamine [26] (8.43 g, 0.078 mol) in DMAc (41.24 g) was added dropwise. After the dropwise addition, the resulting mixture was stirred for 30 minutes. Into a vessel provided beforehand by adding DMAc (91.65 g) to a 300-mL, four-necked flask and heating it to 110° C. in an oil bath, the resulting reaction mixture was added dropwise by using a transfer tube. The resulting mixture was stirred for 1 hour to conduct polymerization.

Subsequently, aniline (1.46 g, 0.024 mol) was added, followed by stirring for 1 hour to terminate the polymerization. After the resultant polymerization mixture was allowed to cool to room temperature, it was reprecipitated in a mixed solution of 28% aqueous solution of ammonia (36.43 g) and ion-exchanged water (731 g). The resulting precipitates were collected by filtration, dried at 120° C. for 4 hours in a vacuum dryer, redissolved in a mixed solution of THF (95.5 g), DMF (35.1 g) and 28% aqueous solution of ammonia (3.64 g), and then reprecipitated in ion-exchanged water (1,365 g). The resulting precipitates were collected by filtration, and then dried at 120° C. for 8 hours in a vacuum dryer to obtain the target high-molecular compound [3] (hereinafter abbreviated as "HB-TmDA30," 17.3 g).

Figure 73:
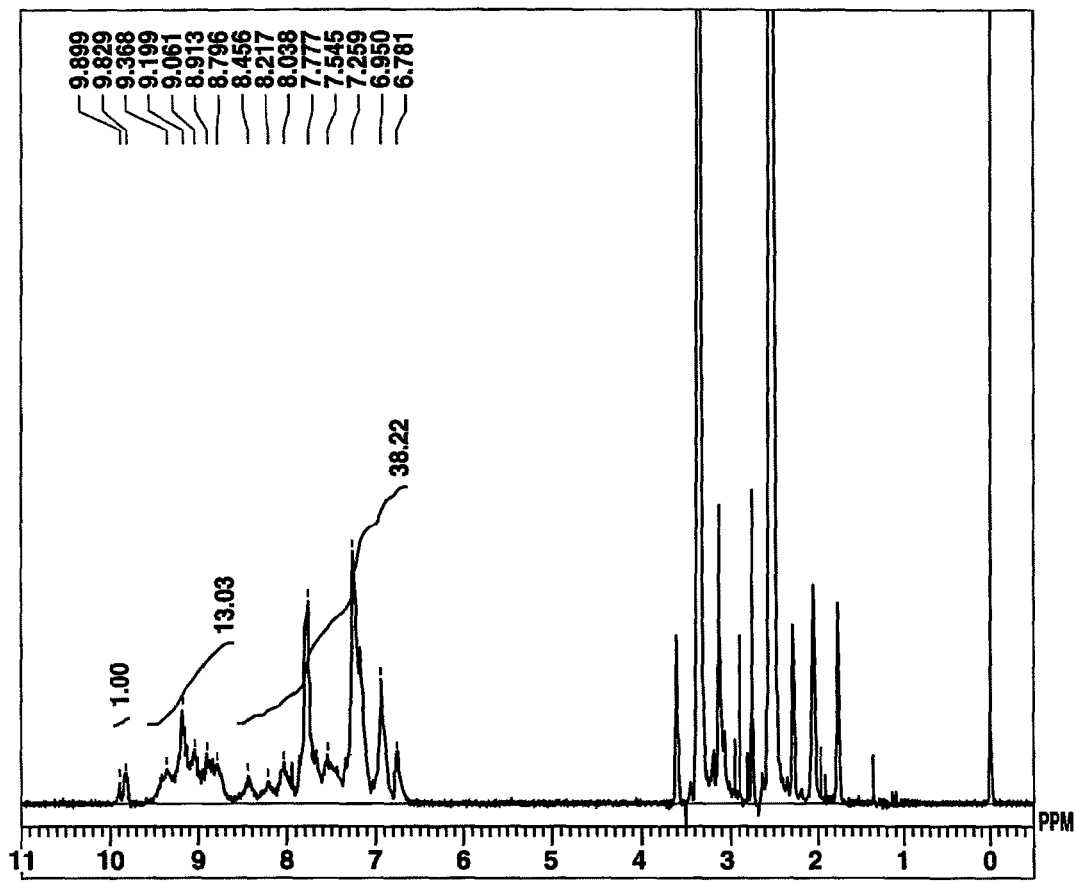
FIG. 73 is a diagram showing a $^1$H-NMR spectrum of the high-molecular compound [27] obtained in Example 110.

The results of $^1$H-NMR spectrum measurement of HB-TmDA30 are shown in FIG. 73. HB-TmDA30 so obtained was a compound having structural units represented by the formula (1). The weight average molecular weight Mw of HB-TmDA30 as measured by GPC and calibrated against standard polystyrene was 3,000, and the polydispersibility Mw/Mn was 2.99.

Example 111

5% Weight Loss Temperature Measurement of HB-TmDA30

Figure 74:
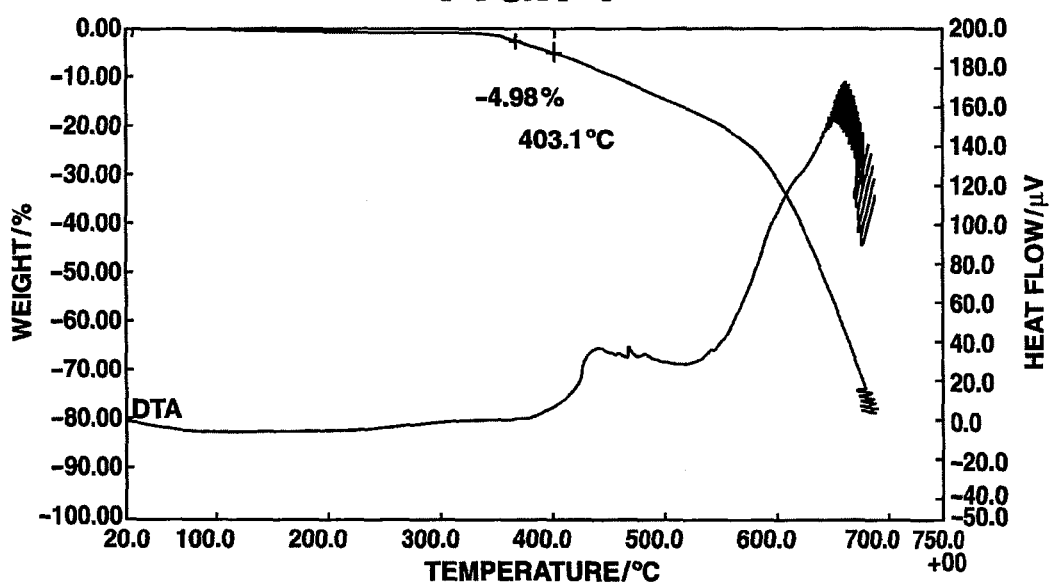
FIG. 74 is a diagram showing the results of TG-DTA measurement in Example 111.

As in Example 100, TG-DTA measurement of the high-molecular compound obtained in Example 110 was conducted. The 5% weight loss temperature was 403° C. The results are shown in FIG. 74.

Example 112

Synthesis of High-molecular Compound [27] by Concurrent Charging of Aniline Under nitrogen and in a 500-mL, four-necked flask, DMAc (300 g) was placed, followed by cooling to −10° C. in an ice bath with sodium chloride added therein, and 2,4,6-trichloro-1,3,5-triazine [1] (61.63 g, 0.33 mol, product of Aldrich Corporation) was added and dissolved. Subsequently, a solution of m-phenylenediamine [26] (97.55 g, 0.90 mol) and aniline (15.71 g, 0.17 mol) in DMAc (300 g) was added dropwise. After the dropwise addition, the resulting mixture was stirred for 30 minutes. Into a vessel provided beforehand by adding DMAc (895 g) to a 2,000-mL, four-necked flask and heating it to 110° C. in an oil bath, the resulting reaction mixture was added dropwise by using a transfer tube. The resulting mixture was stirred for 1 hour to conduct polymerization.

After the resultant polymerization mixture was allowed to cool to room temperature, it was reprecipitated in a mixed solution of 28% aqueous solution of ammonia (229.13 g) and ion-exchanged water (4,000 g). The resulting precipitates were collected by filtration, redissolved in a mixed solution of THF (550 g), DMF (50.8 g) and 28% aqueous solution of ammonia (20.2 g), and then reprecipitated in ion-exchanged water (4,000 g). The resulting precipitates were collected by filtration, and then dried at 120° C. for 8 hours in a vacuum dryer to obtain the target high-molecular compound [27] (hereinafter abbreviated as "HB-TmDA18NH2," 145.5 g).

Figure 75:
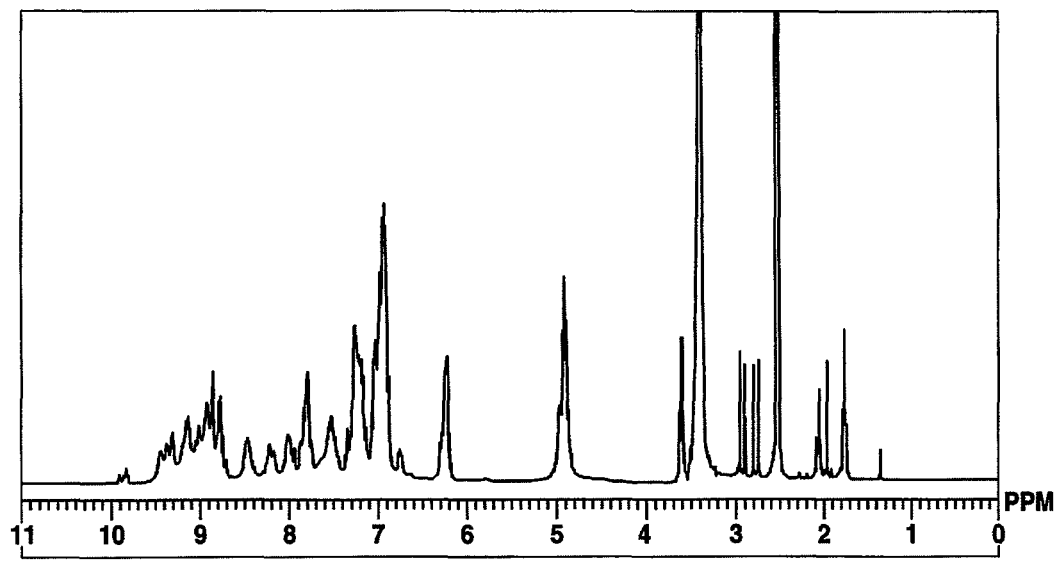
FIG. 75 is a diagram showing a $^1$H-NMR spectrum of the high-molecular compound [27] obtained in Example 112.

The results of $^1$H-NMR spectrum measurement of HB-TmDA18NH2 are shown in FIG. 75. A signal derived from the terminal NH2 of the high-molecular compound was observed around 5 ppm. HB-TmDA18NH2 so obtained was a compound having structural units represented by the formula (25). The weight average molecular weight Mw of HB-TmDA18NH2 as measured by GPC and calibrated against standard polystyrene was 2,200, and the polydispersibility Mw/Mn was 1.91.

Example 113

5% Weight Loss Temperature Measurement of HB-TmDA18NH2

Figure 76:
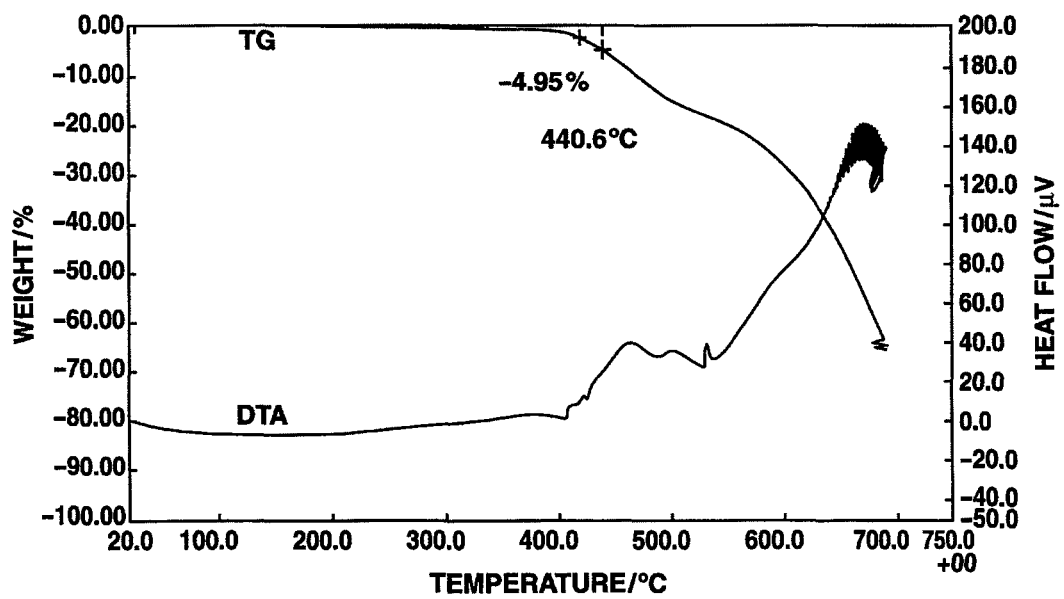
FIG. 76 is a diagram showing the results of TG-DTA measurement in Example 113.

As in Example 100, TG-DTA measurement of the high-molecular compound obtained in Example 112 was conducted. The 5% weight loss temperature was 440° C. The results are shown in FIG. 76.

Example 114

Synthesis of High-Molecular Compound [27] of Different Molecular Weight by Concurrent Charging of Aniline Under nitrogen and in a 200-mL, four-necked flask, m-phenylenediamine [26] (3.25 g, 0.03 mol, product of Aldrich Corporation) and aniline (0.82 g, 0.0085 mol) were placed, and then dissolved in DMAc (32 mL). The resulting solution was heated to 100° C. in an oil bath. Subsequently, a solution of 2,4,6-trichloro-1,3,5-triazine [1] (3.13 g, 0.017 mol, product of Tokyo Chemical Industry Co., Ltd.) in DMAc (31.3 mL) was added to initiate polymerization.

Sixty minutes later, aniline (3.99 g, 0.042 mol) was added further, followed by stirring for 60 minutes to terminate the polymerization. After the resultant polymerization mixture was allowed to cool to room temperature, it was reprecipitated in a mixed solution of 28% aqueous ammonia (5.29 g) and purified water (240 mL). The resulting precipitates were collected by filtration, redissolved in a mixed solvent of THF (60 mL) and DMF (10 mL), and then reprecipitated in purified water (420 mL). The resulting precipitates were collected by filtration, and then dried at 120° C. for 8 hours in a vacuum dryer to obtain the target high-molecular compound [27] (hereinafter abbreviated as "HB-TmDA25," 4.36 g).

Figure 77:
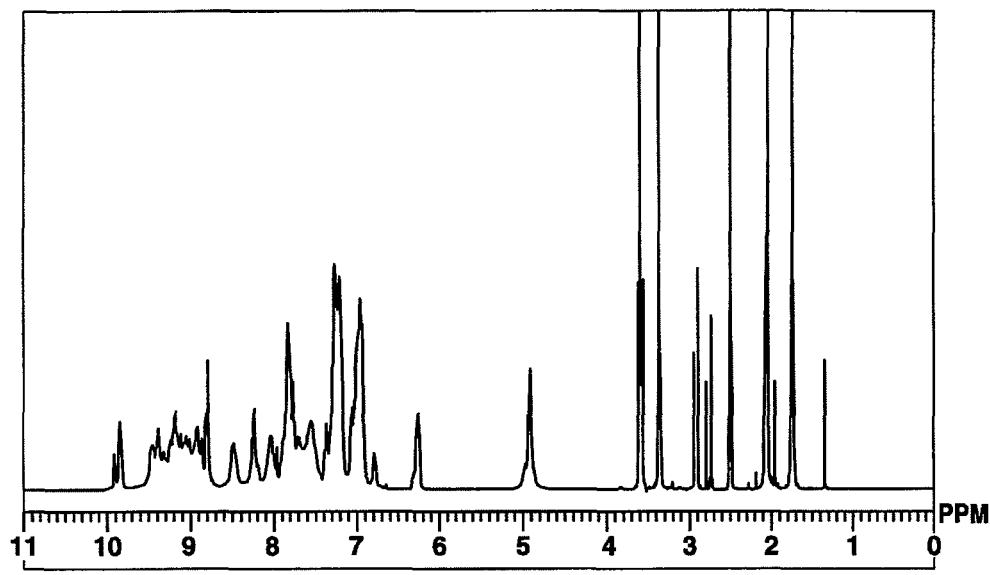
FIG. 77 is a diagram showing a $^1$H-NMR spectrum of the high-molecular compound [27] obtained in Example 114.

The results of $^1$H-NMR spectrum measurement of HB-TmDA25 are shown in FIG. 77. HB-TmDA25 so obtained was a compound having structural units represented by the formula (25). The weight average molecular weight Mw of HB-TmDA25 as measured by GPC and calibrated against standard polystyrene was 2,500, and the polydispersibility Mw/Mn was 1.87.

Example 115

Measurement of Refractive Index

HB-TmDA25 (0.5 g) obtained in Example 114 was dissolved in cyclohexanone (4.5 g) to obtain a clear pale-yellow solution. Using a spin coater, the obtained polymer varnish was spin-coated onto a glass substrate at 200 rpm for 5 seconds and then at 2,000 rpm for 30 seconds, followed by heating at 150° C. for 1 minute and then at 250° C. for 5 minutes to remove the solvent so that a film was obtained. The resultant film was measured for refractive index. Its refractive index at 550 nm was 1.7830.

Example 116

5% Weight Loss Temperature Measurement of HB-TmDA25

Figure 78:
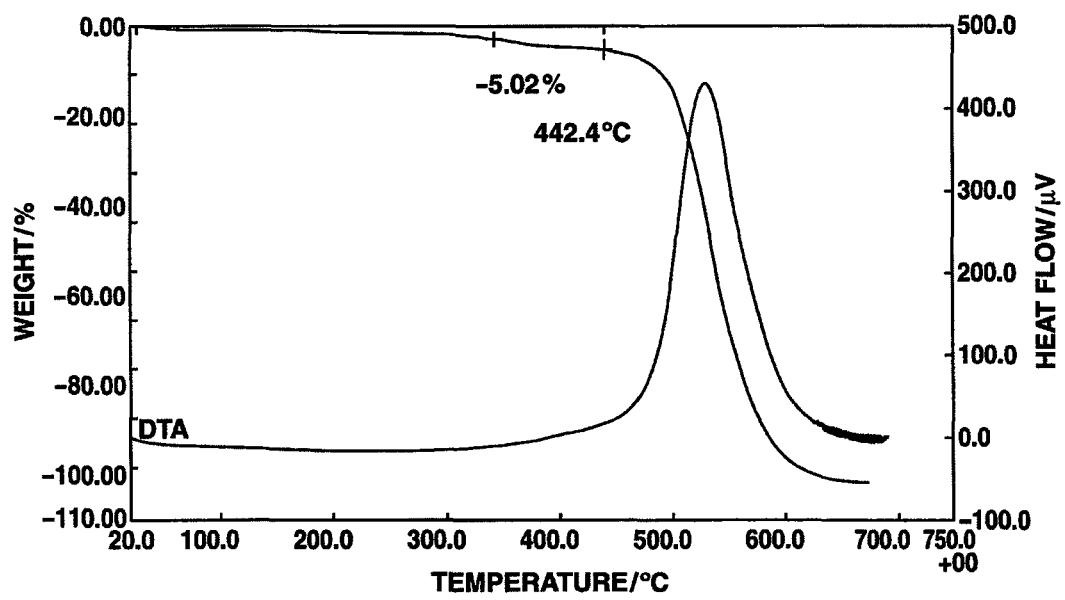
FIG. 78 is a diagram showing the results of TG-DTA measurement in Example 116.

As in Example 100, TG-DTA measurement of the high-molecular compound [27] obtained in Example 114 was conducted. The 5% weight loss temperature was 425° C. The results are shown in FIG. 78.

Example 117

Synthesis of High-molecular Compound [27] by Concurrent Charging of Aniline at Low Temperature Under nitrogen and in a 500-mL, four-necked flask, DMAc (223.05 g) was placed, followed by cooling to −10° C. in an acetone-dry ice bath, and 2,4,6-trichloro-1,3,5-triazine [1] (41.49 g, 0.225 mol, product of Evonik Degussa Japan Co., Ltd.) was added and dissolved. Subsequently, a solution of m-phenylenediamine [26] (30.41 g, 0.281 mol) and aniline (6.29 g, 0.068 mol) in DMAc (148.70 g) was added dropwise. After the dropwise addition, the resulting reaction mixture was stirred for 30 minutes. Into a vessel provided beforehand by adding DMAc (304.17 g) to a 1,000-mL, four-necked flask and heating it to 85° C. in an oil bath, the resulting reaction mixture was added dropwise over 1 hour by a feed pump. The resulting mixture was stirred for 1 hour to conduct polymerization.

Subsequently, aniline (56.58 g, 0.608 mol) was added, followed by stirring for 1 hour to terminate the reaction. After the resultant reaction mixture was allowed to cool to room temperature, it was reprecipitated in a mixed solution of 28% aqueous solution of ammonia (136.61 g) and ion-exchanged water (4,314 g). The resulting precipitates were collected by filtration, dried at 150° C. for 5 hours in a vacuum dryer, redissolved in THF (407.5 g), and then reprecipitated in ion-exchanged water (2,852 g). The resulting precipitates were collected by filtration, and then dried at 150° C. for 20 hours in a vacuum dryer to obtain the target high-molecular compound [27] (hereinafter abbreviated as "HB-TmDA30," 55.0 g).

Figure 79:
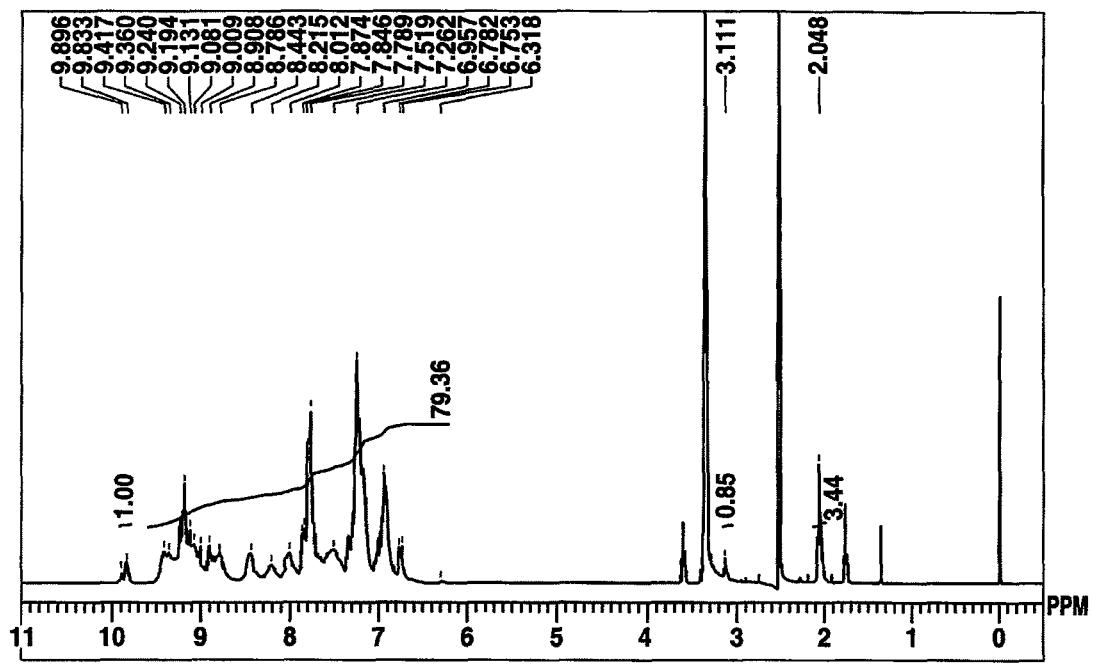
FIG. 79 is a diagram showing a $^1$H-NMR spectrum of the high-molecular compound [27] obtained in Example 117.

The results of $^1$H-NMR spectrum measurement of HB-TmDA30 are shown in FIG. 79. HB-TmDA30 so obtained was a compound having structural units represented by the formula (25). The weight average molecular weight Mw of HB-TmDA30 as measured by GPC and calibrated against standard polystyrene was 3,200, and the polydispersibility Mw/Mn was 2.62.

Example 118

5% Weight Loss Temperature Measurement of HB-TmDA30

Figure 80:
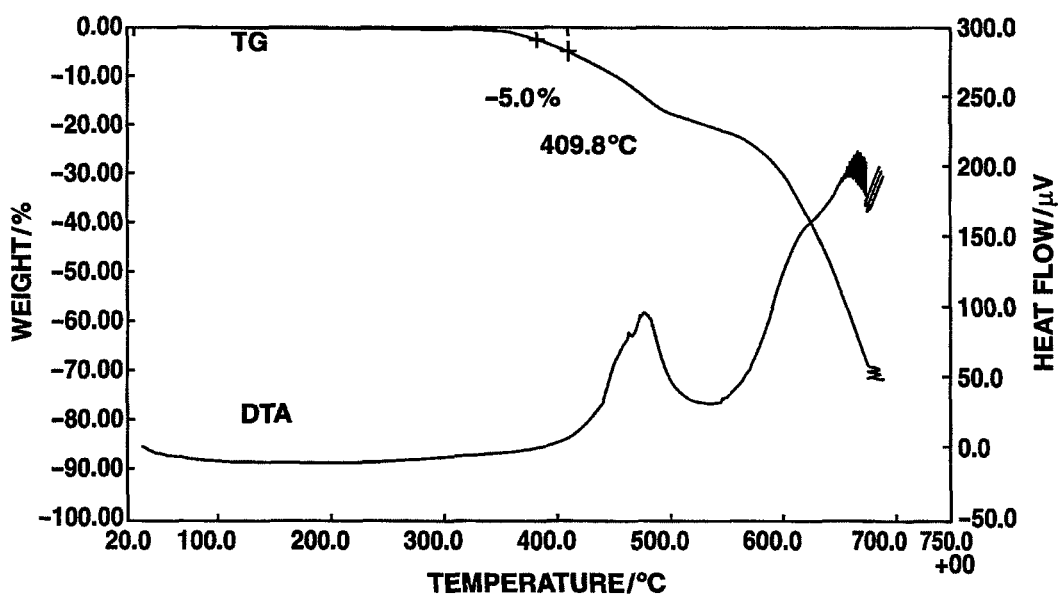
FIG. 80 is a diagram showing the results of TG-DTA measurement in Example 118.

As in Example 100, TG-DTA measurement of the high-molecular compound [27] obtained in Example 117 was conducted. The 5% weight loss temperature was 410° C. The results are shown in FIG. 80.

Example 119

Synthesis of High-molecular Compound [27] by Concurrent Charging of Aniline (an Example in which Aniline was Added In a Modified Proportion)

Under nitrogen and in a 500-mL, four-necked flask, m-phenylenediamine [26] (10.81 g, 0.10 mol, product of Aldrich Corporation) and aniline (5.40 g, 0.056 mol) were placed, and then dissolved in DMAc (108 mL). The resulting solution was heated to 100° C. in an oil bath. Subsequently, a solution of 2,4,6-trichloro-1,3,5-triazine [1] (10.48 g, 0.056 mol, product of Tokyo Chemical Industry Co., Ltd.) in DMAc (104 mL) was added to initiate polymerization.

Sixty minutes later, aniline (10.72 g, 0.114 mol) was added further, followed by stirring for 60 minutes to terminate the polymerization. After the resultant polymerization mixture was allowed to cool to room temperature, it was reprecipitated in a mixed solution of 28% aqueous ammonia (17.4 g) and purified water (800 mL). The resulting precipitates were collected by filtration, redissolved in a mixed solvent of THF (200 mL) and DMF (30 mL), and then reprecipitated in purified water (1,400 mL). The resulting precipitates were collected by filtration, and then dried at 120° C. for 8 hours in a vacuum dryer to obtain the target high-molecular compound [27] (hereinafter abbreviated as "HB-TmDA15," 16.36 g).

Figure 81:
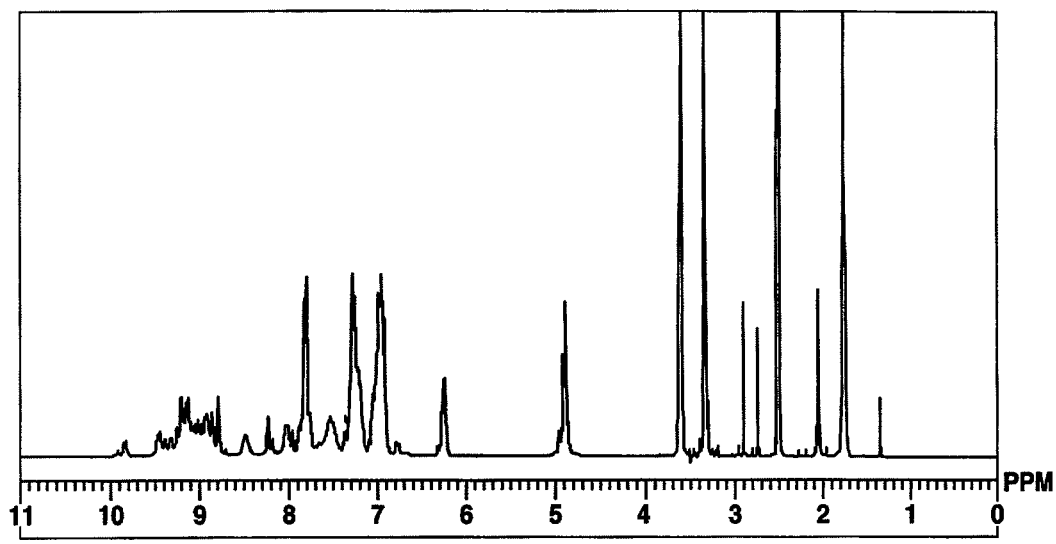
FIG. 81 is a diagram showing a $^1$H-NMR spectrum of the high-molecular compound [27] obtained in Example 119.

The results of $^1$H-NMR spectrum measurement of HB-TmDA15 are shown in FIG. 81. HB-TmDA15 so obtained was a compound having structural units represented by the formula (25). The weight average molecular weight Mw of HB-TmDA15 as measured by GPC and calibrated against standard polystyrene was 1,500, and the polydispersibility Mw/Mn was 1.47.

Example 120

Measurement of Refractive Index

HB-TmDA15 (0.5 g) obtained in Example 119 was dissolved in cyclohexanone (4.5 g) to obtain a clear pale-yellow solution. Using a spin coater, the obtained polymer varnish was spin-coated onto a glass substrate at 200 rpm for 5 seconds and then at 2,000 rpm for 30 seconds, followed by heating at 150° C. for 1 minute and then at 300° C. for 5 minutes to remove the solvent so that a film was obtained. The resultant film was measured for refractive index. Its refractive index at 550 nm was 1.7830.

Example 121

Synthesis of High-molecular Compound [27] by Concurrent Charging of Aniline at Low Temperature (an Example in Which Aniline was Added in a Modified Proportion)

Under nitrogen and in a 1,000-mL, four-necked flask, DMAc (456.02 g) was placed, followed by cooling to −10° C. in an acetone-dry ice bath, and 2,4,6-trichloro-1,3,5-triazine [1] (84.83 g, 0.460 mol, product of Evonik Degussa Japan Co., Ltd.) was added and dissolved. Subsequently, a solution of m-phenylenediamine [26] (62.18 g, 0.575 mol) and aniline (14.57 g, 0.156 mol) in DMAc (304.01 g) was added dropwise. After the dropwise addition, the resulting reaction mixture was stirred for 30 minutes. Into a vessel provided beforehand by adding DMAc (621.85 g) to a 2,000-mL, four-necked flask and heating it to 85° C. in an oil bath, the resulting reaction mixture was added dropwise over 1 hour by a feed pump. The resulting mixture was stirred for 1 hour to conduct polymerization.

Subsequently, aniline (113.95 g, 1.224 mol) was added, followed by stirring for 1 hour to terminate the reaction. After the resultant reaction mixture was cooled to room temperature in an ice bath, triethylamine (116.36 g, 1.15 mol) was added dropwise, and the resulting mixture was stirred for 30 minutes to quench hydrochloric acid. The precipitated hydrochloride salt was then filtered off. The filtered reaction mixture was reprecipitated in a mixed solution of 28% aqueous solution of ammonia (279.29 g) and ion-exchanged water (8,820 g). The resulting precipitates were collected by filtration, dried at 150° C. for 8 hours in a vacuum dryer, redissolved in THF (833.1 g), and then reprecipitated in ion-exchanged water (6,665 g). The resulting precipitates were collected by filtration, and then dried at 150° C. for 25 hours in a vacuum dryer to obtain the target high-molecular compound [27] (hereinafter abbreviated as "HB-TmDA40," 118.0 g).

Figure 82:
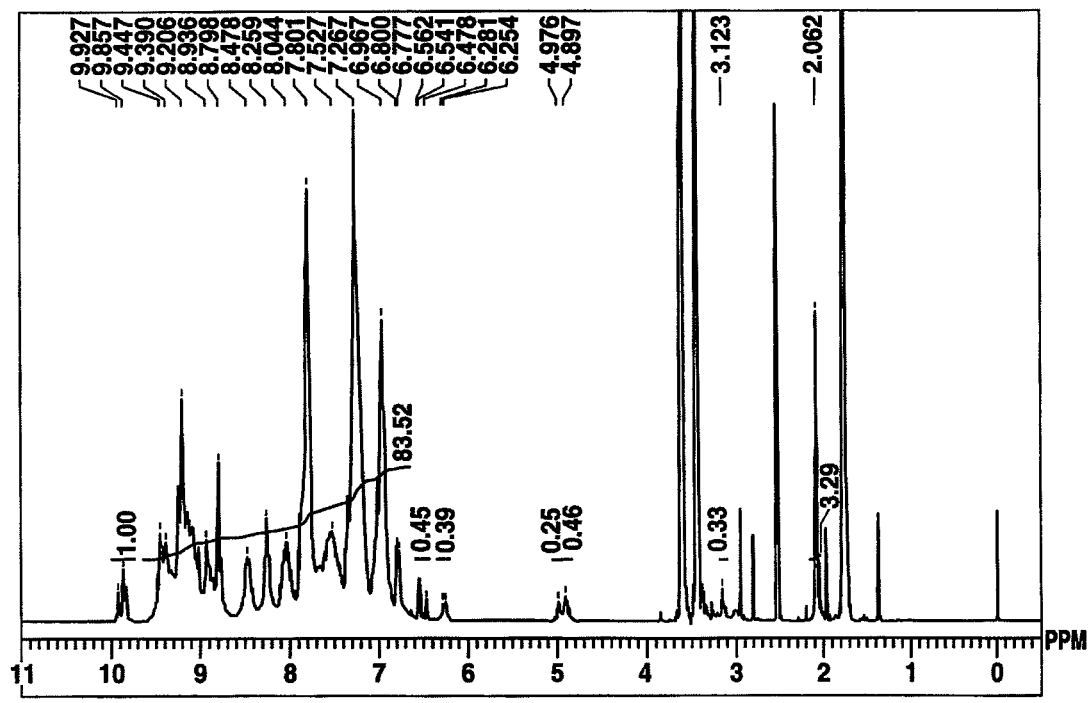
FIG. 82 is a diagram showing a $^1$H-NMR spectrum of the high-molecular compound [27] obtained in Example 121.

The results of $^1$H-NMR spectrum measurement of HB-TmDA40 are shown in FIG. 82. HB-TmDA40 so obtained was a compound having structural units represented by the formula (25). The weight average molecular weight Mw of HB-TmDA40 as measured by GPC and calibrated against standard polystyrene was 4,300, and the polydispersibility Mw/Mn was 3.44.

Example 122

Measurement of Refractive Index

HB-TmDA40 (0.5 g) obtained in Example 121 was dissolved in cyclohexanone (4.5 g) to obtain a clear pale-yellow solution. Using a spin coater, the obtained polymer varnish was spin-coated onto a glass substrate at 200 rpm for 5 seconds and then at 2,000 rpm for 30 seconds, followed by heating at 150° C. for 1 minute and then at 250° C. for 5 minutes to remove the solvent so that a film was obtained. The resultant film was measured for refractive index. Its refractive index at 550 nm was 1.790.

Example 123

5% Weight Loss Temperature Measurement of HB-TmDA40

Figure 83:
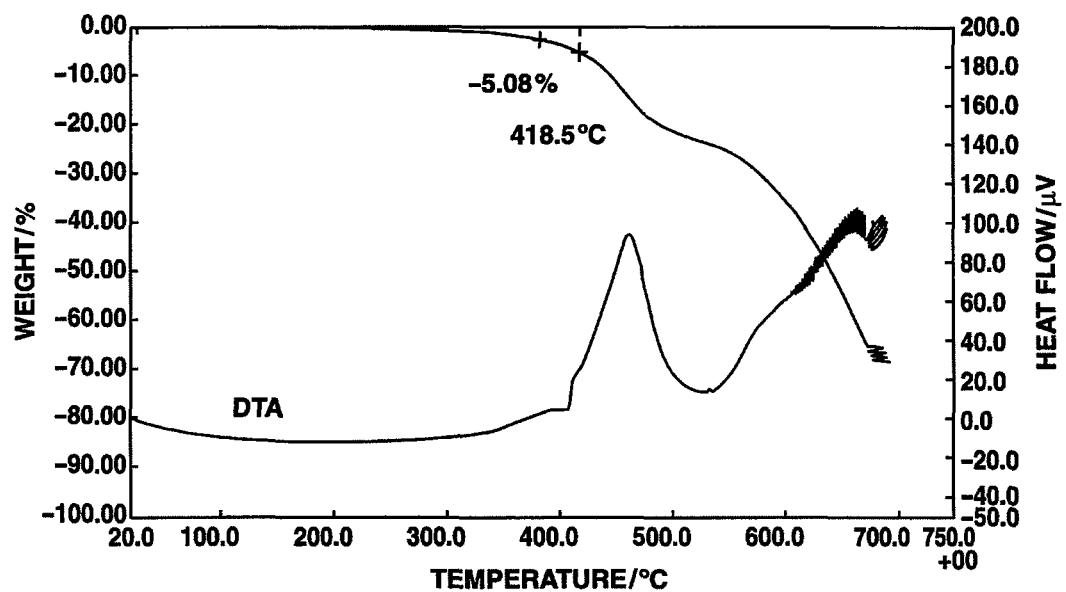
FIG. 83 is a diagram showing the results of TG-DTA measurement in Example 123.

As in Example 100, TG-DTA measurement of the high-molecular compound obtained in Example 121 was conducted. The 5% weight loss temperature was 419° C. The results are shown in FIG. 83.

Example 124

Figure 84:
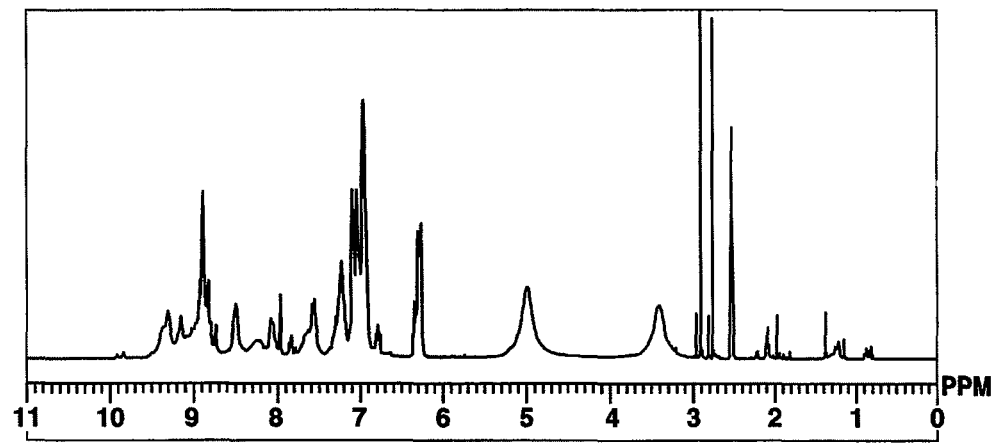
FIG. 84 is a diagram showing a $^1$H-NMR spectrum of the high-molecular compound [27] obtained in Example 124.

Synthesis of High-molecular Compound [27] by Concurrent Charging of 2-Ethylhexylamine at Low Temperature 2,4,6-Trichloro-1,3,5-triazine [1] (23.0 g, 0.125 mol, product of Tokyo Chemical Industry Co., Ltd.), m-phenylenediamine [26] (48.66 g, 0.45 mol, product of Aldrich Corporation) and 2-ethylhexylamine (6.46 g, 0.05 mol, product of Tokyo Chemical Industry Co., Ltd.) were combined together, and as in Example 117, a low-temperature reaction was conducted. Subsequently, polymerization was conducted in a reaction vessel controlled at 105° C. Sixty minutes later, 2-ethylhexylamine (37.45 g, 0.325 mol, product of Tokyo Chemical Industry Co., Ltd.) was added. Sixty minutes later, the resulting mixture was allowed to cool to room temperature, and by a similar procedure as in Example 117, purification was conducted to obtain the target high-molecular compound [27] (hereinafter abbreviated as "HB-TmEH," 74.24 g). The results of $^1$H-NMR spectrum measurement of HB-TmEH are shown in FIG. 84. HB-TmEH so obtained was a compound having structural units represented by the formula (25). The weight average molecular weight Mw of HB-TmEH as measured by GPC and calibrated against standard polystyrene was 2,500, and the polydispersibility Mw/Mn was 1.59.

HB-TmEH (0.5 g) so obtained was dissolved in cyclohexanone (4.5 g) to obtain a clear pale-yellow solution. Using a spin coater, the obtained polymer varnish was spin-coated onto a glass substrate at 200 rpm for 5 seconds and then at 2,000 rpm for 30 seconds, followed by heating at 150° C. for 1 minute and then at 250° C. for 5 minutes to remove the solvent so that a film was obtained. The resultant film was measured for refractive index. Its refractive index at 550 nm was 1.8153.

Figure 85:
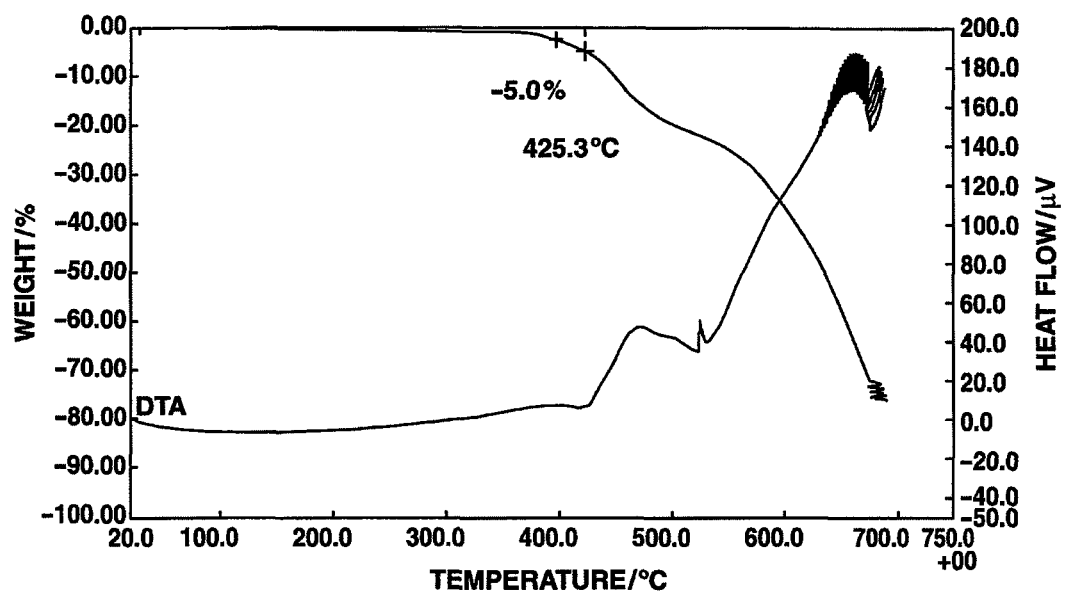
FIG. 85 is a diagram showing the results of TG-DTA measurement in Example 124.

As in Example 100, TG-DTA measurement of the resultant high-molecular compound was conducted. The 5% weight loss temperature was 469° C. The results are shown in FIG. 85.

Example 125

Synthesis of High-molecular Compound [29]

[Chemical Formula 44]

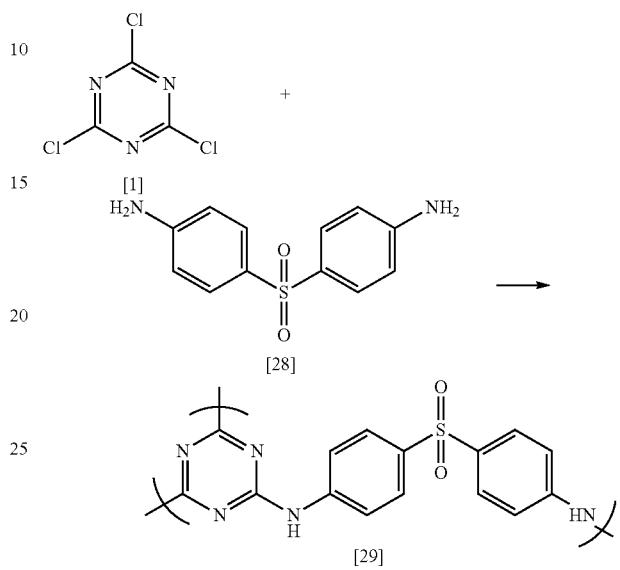

Figure 86:
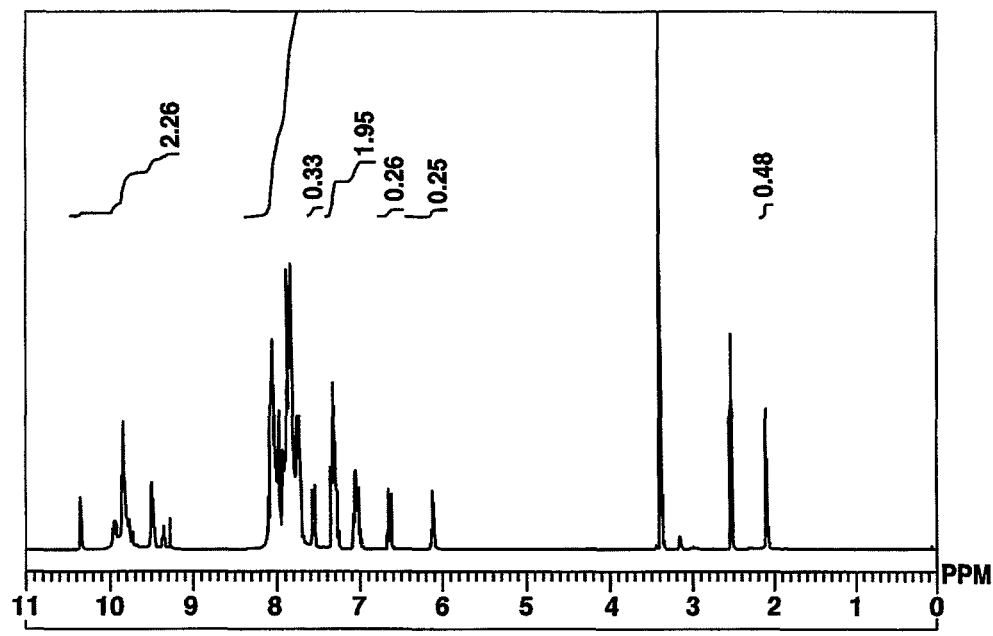
FIG. 86 is a diagram showing a $^1$H-NMR spectrum of the high-molecular compound [29] obtained in Example 125.

Using 4,4'-sulfonyldianiline [28] (7.45 g, 0.030 mol., product of Tokyo Chemical Industry Co., Ltd.) in place of 9,9-bis (4-aminophenyl)fluorene, it was reacted to 2,4,6-trichloro-1, 3,5-triazine [1] (4.64 g, 0.025 mol, product of Tokyo Chemical Industry Co., Ltd.) in a similar manner as in Example 1. Redissolution was conducted in DMF (120 mL), followed by reprecipitation to obtain the target high-molecular compound [29] (hereinafter abbreviated as "HB-TSdA," 10.30 g). The results of $^1$H-NMR spectrum measurement of HB-TSdA are shown in FIG. 86. HB-TSdA so obtained was a compound having structural units represented by the formula (1). The weight average molecular weight Mw of HB-TSdA as measured by GPC and calibrated against standard polystyrene was 3,200, and the polydispersibility Mw/Mn was 1.64.

Example 126

5% Weight Loss Temperature Measurement of HB-TSdA

Figure 87:
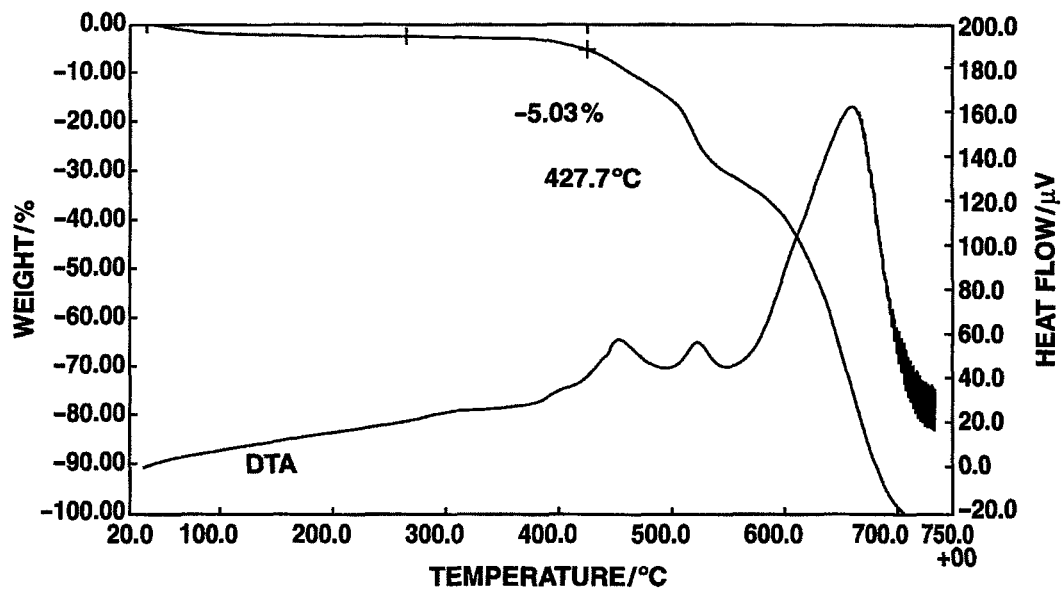
FIG. 87 is a diagram showing the results of TG-DTA measurement in Example 126.

As in Example 53, TG-DTA measurement of the high-molecular compound obtained in Example 125 was conducted. The 5% weight loss temperature was 427° C. The results are shown in FIG. 87.

Example 127

Synthesis of High-Molecular Compound [31]

[Chemical Formula 45]

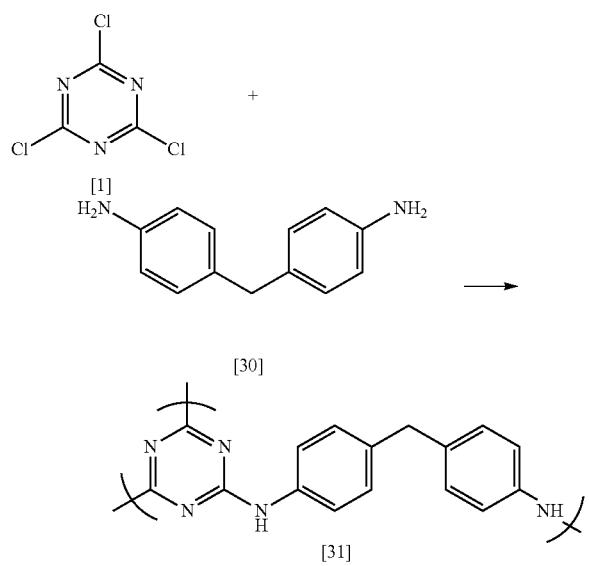

Figure 88:
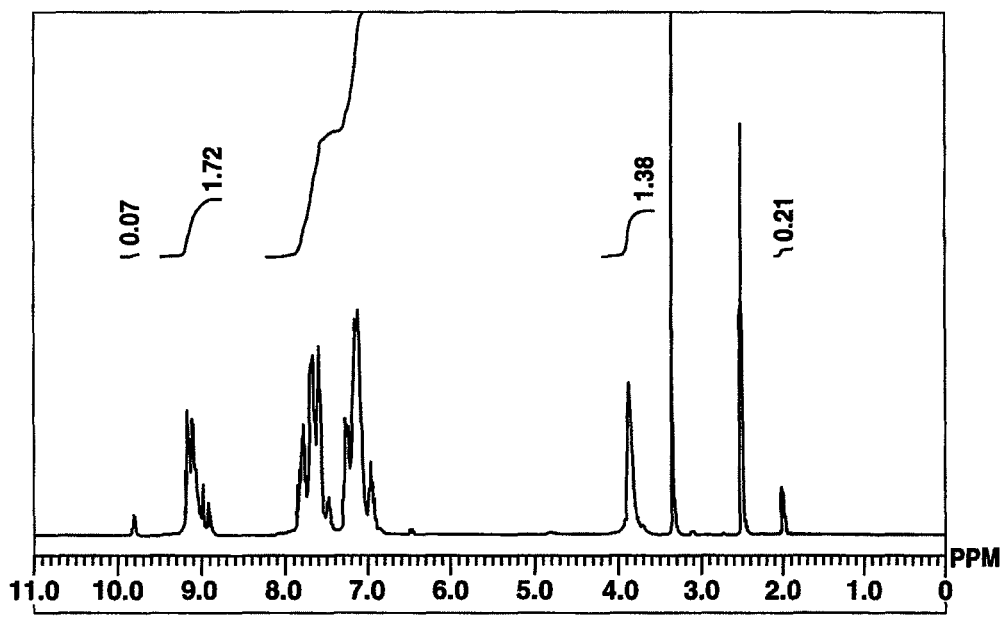
FIG. 88 is a diagram showing a $^1$H-NMR spectrum of the high-molecular compound [31] obtained in Example 127.

Using 4,4'-diaminophenylmethane [30] (11.90 g, 0.06 mol, product of Tokyo Chemical Industry Co., Ltd.) in place of 9,9-bis(4-aminophenyl)fluorene, it was reacted to 2,4,6-trichloro-1,3,5-triazine [1] (9.22 g, 0.05 mol, product of Tokyo Chemical Industry Co., Ltd.) in a similar manner as in Example 1. Redissolution was conducted in DMF (200 mL), followed by reprecipitation to obtain the target high-molecular compound [31] (hereinafter abbreviated as "HB-TMA," 15.86 g). The results of $^1$H-NMR spectrum measurement of HB-TMA are shown in FIG. 88. HB-TMA so obtained was a compound having structural units represented by the formula (1). The weight average molecular weight Mw of HB-TMA as measured by GPC and calibrated against standard polystyrene was 4,700, and the polydispersibility Mw/Mn was 2.93.

Example 128

5% Weight Loss Temperature Measurement of HB-TMA

Figure 89:
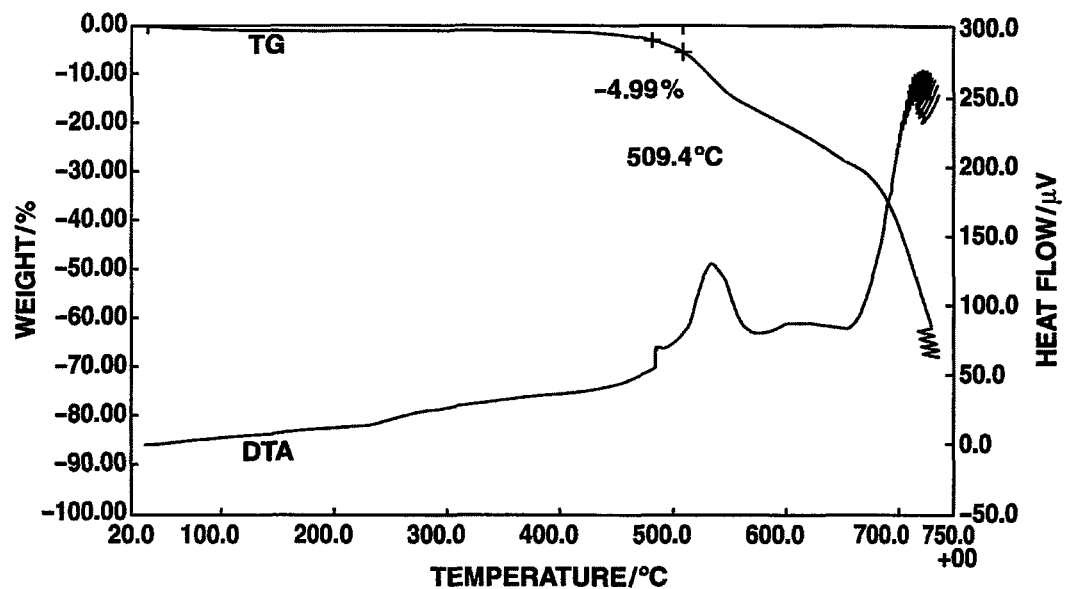
FIG. 89 is a diagram showing the results of TG-DTA measurement in Example 128.

As in Example 53, TG-DTA measurement of the high-molecular compound obtained in Example 127 was conducted. The 5% weight loss temperature was 509° C. The results are shown in FIG. 89.

Example 129

Synthesis of High-Molecular Compound [27] by Concurrent Charging (Low-Temperature Charging) with Aniline Placed Beforehand in Polymerization Vessel Under nitrogen and in a 50-mL, four-necked flask, DMAc (20.27 g) was placed, followed by cooling to −10° C. in an acetone-dry ice bath, and 2,4,6-trichloro-1,3,5-triazine [1] (3.69 g, 0.02 mol, product of Evonik Degussa Japan Co., Ltd.) was added and dissolved. Subsequently, a solution of m-phenylenediamine [26] (2.70 g, 0.025 mol) in DMAc (13.29 g) was added dropwise. After the dropwise addition, the resulting reaction mixture was stirred for 30 minutes. Into a vessel provided beforehand by adding dimethylacetamide (27.04 g) and aniline (0.63 g, 0.068 mol) to a 100-mL, four-necked flask and heating them to 85° C. in an oil bath, the resulting reaction mixture was added dropwise over 1 hour by a feed pump. The resulting mixture was then stirred for 1 hour to conduct polymerization.

Subsequently, aniline (4.95 g, 0.053 mol) was added, followed by stirring for 1 hour to terminate the reaction. After the resultant reaction mixture was cooled to room temperature in an ice bath, triethylamine (5.07 g, 0.05 mol) was added dropwise, and the resulting mixture was stirred for 30 minutes to quench hydrochloric acid. The precipitated hydrochloride salt was then filtered off. The filtered reaction mixture was reprecipitated in a mixed solution of 28% aqueous solution of ammonia (12.2 g) and ion-exchanged water (387 g). The resulting precipitates were collected by filtration, and the collected precipitates were redissolved in THF (39.3 g) and then reprecipitated in ion-exchanged water (306 g). The resulting precipitates were collected by filtration, and then dried at 150° C. for 25 hours in a vacuum dryer to obtain the target high-molecular compound [27] (hereinafter abbreviated as "HB-TmDA40H," 4.08 g).

Figure 90:
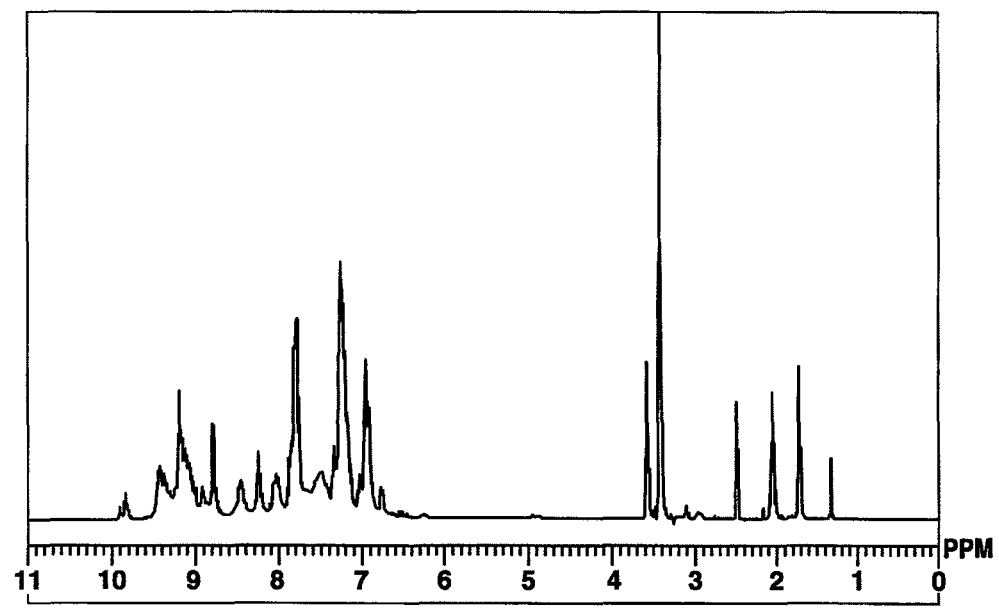
FIG. 90 is a diagram showing a $^1$H-NMR spectrum of the high-molecular compound [27] obtained in Example 129.

The results of $^1$H-NMR spectrum measurement of HB-TmDA40H are shown in FIG. 90. HB-TmDA40H so obtained was a compound having structural units represented by the formula (25). The weight average molecular weight Mw of HB-TmDA40H as measured by GPC and calibrated against standard polystyrene was 3,500, and the polydispersibility Mw/Mn was 2.21.

Example 130

Measurement of Refractive Index

HB-TmDA40H (0.5 g) obtained in Example 129 was dissolved in cyclohexanone (4.5 g) to obtain a clear pale-yellow solution. Using a spin coater, the obtained polymer varnish was spin-coated onto a glass substrate at 200 rpm for 5 seconds and then at 2,000 rpm for 30 seconds, followed by heating at 150° C. for 1 minute and then at 250° C. for 5 minutes to remove the solvent so that a film was obtained. The resultant film was measured for refractive index. Its refractive index at 550 nm was 1.7884.

Example 131

5% Weight Loss Temperature Measurement of HB-TmDA40H

Figure 91:
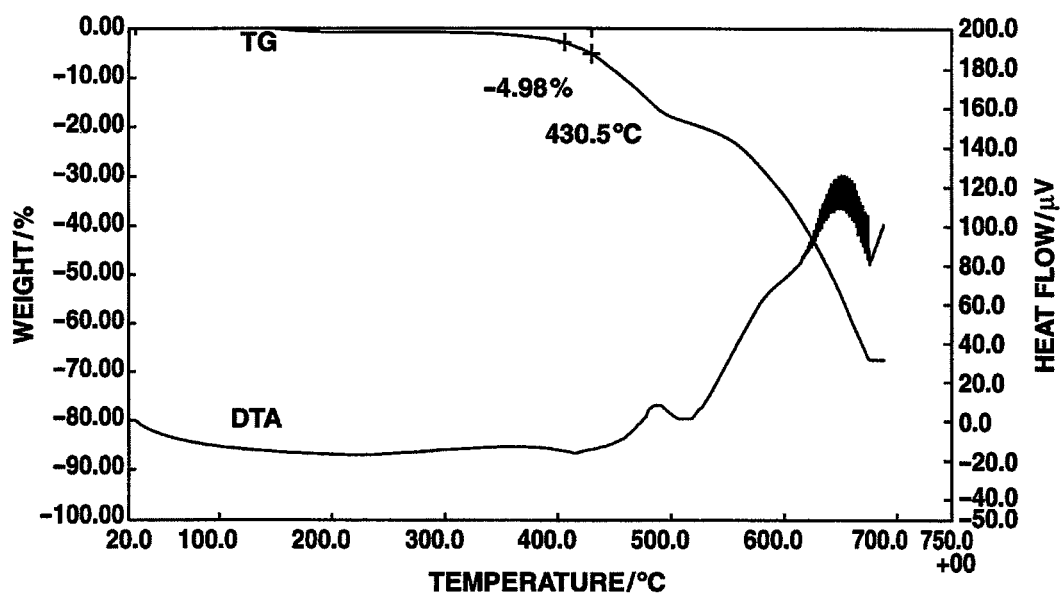
FIG. 91 is a diagram showing the results of TG-DTA measurement in Example 131.

As in Example 100, TG-DTA measurement of the high-molecular compound obtained in Example 129 was conducted. The 5% weight loss temperature was 430° C. The results are shown in FIG. 91.

Example 132

Synthesis of High-Molecular Compound [25] by Concurrent Charging of Aniline

Under nitrogen and in a 100-mL, four-necked flask, 4,4'-diaminobenzanilide (6.05 g, 0.027 mol) and aniline (0.67 g, 0.0072 mol) were added to dimethylacetamide (20.1 g), followed by cooling to −10° C. in an acetone-dry ice bath. Subsequently, a solution of 2,4,6-trichloro-1,3,5-triazine [1]

(3.69 g, 0.02 mol, product of Evonik Degussa Japan Co., Ltd.) in DMAc (30.2 g) which had been cooled to −10° C. beforehand was added dropwise. After the dropwise addition, the resulting reaction mixture was stirred for 30 minutes. Into a vessel provided beforehand by adding DMAc (41.19 g) to a 200-mL, four-necked flask and heating it to 85° C. in an oil bath, the resulting reaction mixture was added dropwise over 1 hour by a feed pump. The resulting mixture was then stirred for 1 hour to conduct polymerization.

Figure 92:
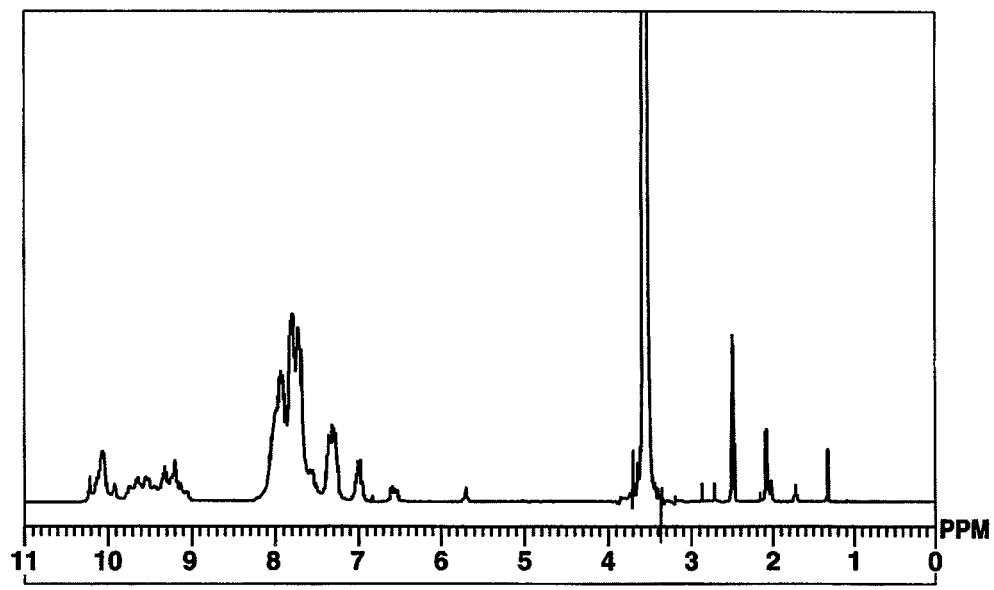
FIG. 92 is a diagram showing a $^1$H-NMR spectrum of the high-molecular compound [25] obtained in Example 132.

Subsequently, aniline (4.96 g, 0.053 mol) was added, followed by stirring for 1 hour to terminate the reaction. After the resultant reaction mixture was cooled to room temperature in an ice bath, triethylamine (5.07 g, 0.05 mol) was added dropwise, and the resulting mixture was stirred for 30 minutes to quench hydrochloric acid. The precipitated hydrochloride salt was then filtered off. The filtered reaction mixture was reprecipitated in a mixed solution of 28% aqueous solution of ammonia (12.3 g) and ion-exchanged water (585 g). The resulting precipitates were collected by filtration, and the collected precipitates were redissolved in THF (64.84 g) and then reprecipitated in ion-exchanged water (586.8 g). The resulting precipitates were collected by filtration, and then dried at 150° C. for 25 hours in a vacuum dryer to obtain the target high-molecular compound [25] (hereinafter abbreviated as "HB-TAMA40," 6.97 g). The results of $^1$H-NMR spectrum measurement of HB-TAMA40 are shown in FIG. 92. HB-TAMA40 so obtained was a compound having structural units represented by the formula (1). The weight average molecular weight Mw of HB-TAMA40 as measured by GPC and calibrated against standard polystyrene was 3,200, and the polydispersibility Mw/Mn was 2.40.

Example 133

Measurement of Refractive Index

HB-TAMA40 (0.5 g) obtained in Example 132 was dissolved in NMP (4.5 g) to obtain a clear pale-yellow solution. Using a spin coater, the obtained polymer varnish was spin-coated onto a glass substrate at 200 rpm for 5 seconds and then at 2,000 rpm for 30 seconds, followed by heating at 150° C. for 1 minute and then at 250° C. for 5 minutes to remove the solvent so that a film was obtained. The resultant film was measured for refractive index. Its refractive index at 550 nm was 1.8592.

Example 134

5% Weight Loss Temperature Measurement of HB-TAMA40

Figure 93:
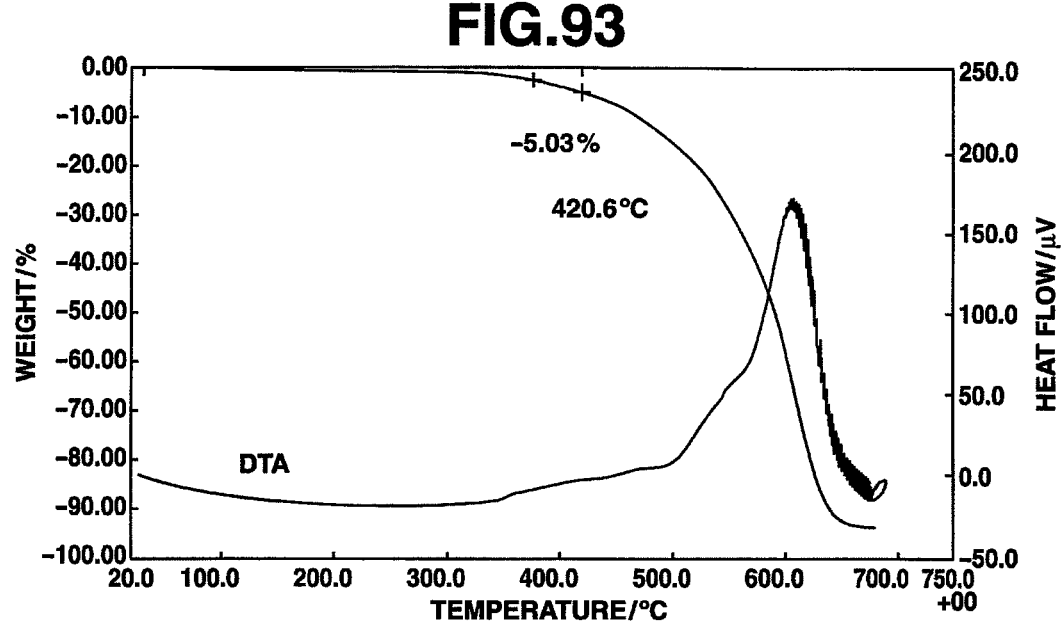
FIG. 93 is a diagram showing the results of TG-DTA measurement in Example 134.

As in Example 53, TG-DTA measurement of the high-molecular compound obtained in Example 132 was conducted. The 5% weight loss temperature was 420° C. The results are shown in FIG. 93.

Preparation of Film-Forming Compositions

Example 135

An aliquot (1.00 g) of HB-TSdA obtained in Example 125 was weighed in a 10-mL, single-necked, round-bottomed flask, followed by the addition of N-methylpyrrolidone (abbreviated as "NMP," 9.00 g). The resulting mixture was stirred at 23° C. for 24 hours to completely dissolve HB-TSdA to prepare a 10% NMP solution. In a 5-mL, single-necked, round-bottomed flask, an aliquot (0.50 g) of the 10% NMP solution of HB-TSdA was weighed, a 20% solution of "NK-OLIGO UA-53H" (product of Shin-Nakamura Chemical Co., Ltd.) diluted as a crosslinking agent in cyclohexanone (abbreviated as "CHN") (0.0750 g; 30 parts by mass under the assumption that solids of the polymer amounted to 100 parts by mass) was added, a 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TSdAV1") was prepared.

Example 136

As in Example 135 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TSdAV2") was prepared.

Example 137

As in Example 135 except that the crosslinking agent was changed from "NK-OLIGO UA-53H" to "EPOLEAD GT-401" (product of Daicel Chemical Industries, Ltd.), a varnish, specifically a varnish having a total solids content of 8.0% by mass (abbreviated as "HB-TSdAV3") was prepared.

Example 138

An aliquot (1.00 g) of HB-TMA obtained in Example 127 was weighed in a 10-mL, single-necked, round-bottomed flask, followed by the addition of NMP (9.00 g). The resulting mixture was stirred at 23° C. for 24 hours to completely dissolve HB-TMA to prepare a 10% NMP solution. In a 5-mL, single-necked, round-bottomed flask, an aliquot (0.50 g) of the 10% NMP solution of HB-TMA was weighed, the 20% solution of "NK-OLIGO UA-53H" (product of Shin-Nakamura Chemical Co., Ltd.) diluted as a crosslinking agent in CHN (0.0750 g; 30 parts by mass under the assumption that solids of the polymer amounted to 100 parts by mass) was added, the 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TMAV1") was prepared.

Example 139

As in Example 138 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TMAV2") was prepared.

Example 140

As in Example 138 except that the crosslinking agent was changed from "NK-OLIGO UA-53H" to "EPOLEAD GT-401" (product of Daicel Chemical Industries, Ltd.), a varnish, specifically a varnish having a total solids content of 8.0% by mass (abbreviated as "HB-TMAV3") was prepared.

Example 141

An aliquot (1.00 g) of HB-TMdA obtained in Example 71 was weighed in a 10-mL, single-necked, round-bottomed flask, followed by the addition of NMP (9.00 g). The resulting mixture was stirred at 23° C. for 24 hours to completely dissolve HB-TMdA to prepare a 10% NMP solution. In a 5-mL, single-necked, round-bottomed flask, an aliquot (0.50 g) of the 10% NMP solution of HB-TMdA was weighed, the 20% solution of "NK-OLIGO UA-53H" (product of Shin-Nakamura Chemical Co., Ltd.) diluted as a crosslinking agent in CHN (0.0750 g; 30 parts by mass under the assumption that solids of the polymer amounted to 100 parts by mass) was added, the 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TMdAV1") was prepared.

Example 142

As in Example 141 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TMdAV2") was prepared.

Example 143

As in Example 141 except that the crosslinking agent was changed from "NK-OLIGO UA-53H" to "EPOLEAD GT-401" (product of Daicel Chemical Industries, Ltd.), a varnish, specifically a varnish of 8.0% by mass in terms of total solids content (abbreviated as "HB-TMdAV3") was prepared.

Example 144

An aliquot (1.00 g) of HB-TAMA1 obtained in Example 95 was weighed in a 10-mL, single-necked, round-bottomed flask, followed by the addition of NMP (9.00 g). The resulting mixture was stirred at 23° C. for 24 hours to completely dissolve HB-TAMA1 to prepare a 10% NMP solution. In a 5-mL, single-necked, round-bottomed flask, an aliquot (0.50 g) of the 10% NMP solution of HB-TAMA1 was weighed, the 20% solution of "NK-OLIGO UA-53H" (product of Shin-Nakamura Chemical Co., Ltd.) diluted as a crosslinking agent in CHN (0.0750 g; 30 parts by mass under the assumption that solids of the polymer amounted to 100 parts by mass) was added, the 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TAMA1V1") was prepared.

Example 145

As in Example 144 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TAMA1V2") was prepared.

Example 146

As in Example 144 except that the crosslinking agent was changed from "NK-OLIGO UA-53H" to "EPOLEAD GT-401" (product of Daicel Chemical Industries, Ltd.), a varnish, specifically a varnish having a total solids content of 8.0% by mass (abbreviated as "HB-TAMA1V3") was prepared.

Example 147

An aliquot (1.00 g) of HB-TAMA40 obtained in Example 132 was weighed in a 10-mL, single-necked, round-bottomed flask, followed by the addition of NMP (9.00 g). The resulting mixture was stirred at 23° C. for 24 hours to completely dissolve HB-TAMA40 to prepare a 10% NMP solution. In a 5-mL, single-necked, round-bottomed flask, an aliquot (0.50 g) of the 10% NMP solution of HB-TAMA40 was weighed, the 20% solution of "NK-OLIGO UA-53H" (product of Shin-Nakamura Chemical Co., Ltd.) diluted as a crosslinking agent in CHN (0.0750 g; 30 parts by mass under the assumption that solids of the polymer amounted to 100 parts by mass) was added, the 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TAMA2V1") was prepared.

Example 148

As in Example 147 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TAMA2V2") was prepared.

Example 149

As in Example 147 except that the crosslinking agent was changed from "NK-OLIGO UA-53H" to "EPOLEAD GT-401" (product of Daicel Chemical Industries, Ltd.), a varnish, specifically a varnish having a total solids content of 8.0% by mass (abbreviated as "HB-TAMA2V3") was prepared.

Example 150

An aliquot (1.00 g) of HB-TCzA obtained in Example 77 was weighed in a 10-mL, single-necked, round-bottomed flask, followed by the addition of NMP (9.00 g). The resulting mixture was stirred at 23° C. for 24 hours to completely dissolve HB-TCzA to prepare a 10% NMP solution. In a 5-mL, single-necked, round-bottomed flask, an aliquot (0.50 g) of the 10% NMP solution of HB-TCzA was weighed, the 20% solution of "NK-OLIGO UA-53H" (product of Shin-Nakamura Chemical Co., Ltd.) diluted as a crosslinking agent in CHN (0.0750 g; 30 parts by mass under the assumption that solids of the polymer amounted to 100 parts by mass) was added, the 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TCzAV1") was prepared.

Example 151

As in Example 150 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TCzAV2") was prepared.

Example 152

As in Example 150 except that the crosslinking agent was changed from "NK-OLIGO UA-53H" to "EPOLEAD GT-401" (product of Daicel Chemical Industries, Ltd.), a varnish, specifically a varnish having a total solids content of 8.0% by mass (abbreviated as "HB-TCzAV3") was prepared.

Example 153

An aliquot (1.00 g) of HB-TDA obtained in Example 83 was weighed in a 10-mL, single-necked, round-bottomed flask, followed by the addition of NMP (9.00 g). The resulting mixture was stirred at 23° C. for 24 hours to completely dissolve HB-TDA to prepare a 10% NMP solution. In a 5-mL, single-necked, round-bottomed flask, an aliquot (0.50 g) of the 10% NMP solution of HB-TDA was weighed, the 20% solution of "NK-OLIGO UA-53H" (product of Shin-Nakamura Chemical Co., Ltd.) diluted as a crosslinking agent in CHN (0.0750 g; 30 parts by mass under the assumption that solids of the polymer amounted to 100 parts by mass) was added, the 1% solution of "MEGAFAC R-30" (product of DIC Corporation) diluted as a surfactant in CHN (0.0250 g; 0.05 parts by mass under the assumption that the solids of the polymer amounted to 100 parts by mass) was added, and further, CHN (0.2353 g) was added. The resulting solution was stirred at 23° C. for 1 hour. The solution was confirmed to become homogeneous so that a varnish having a total solids content of 8.0% by mass (abbreviated as "HB-TDAV1") was prepared.

Example 154

As in Example 153 except that the crosslinking agent was changed from "NK-OLIGO UA-53H" to "B-882N" (product of Mitsui Chemicals Polyurethanes Co., Ltd.), a varnish, specifically a varnish having a total solids content of 8.0% by mass (abbreviated as "HB-TDAV2") was prepared.

Example 155

As in Example 153 except that the crosslinking agent was changed from "NK-OLIGO UA-53H" to "EPOLEAD GT-401" (product of Daicel Chemical Industries, Ltd.), a varnish, is specifically a varnish having a total solids content of 8.0% by mass (abbreviated as "HB-TDAV3") was prepared.

Solvent Resistance Test

Example 156

Using a spin coater, a 10% NMP solution of HB-TSdA prepared in Example 135 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TSdA-F as a film on the substrate.

A solvent resistance test of the resultant HB-TSdA-F was performed. The thickness of HB-TSdA-F after the final baking was 198.5 nm, which was recorded as an initial thickness. In a thinner (hereinafter abbreviated as "Thinner 73") prepared by mixing propylene glycol monomethyl ether and propylene glycol monomethyl ether acetate at 7:3 (mass ratio) until complete homogeneous, HB-TSdA-F was immersed fully, and left over for 5 minutes. HB-TSdA-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TSdA-F after the immersion in Thinner 73 was reduced to 2.5%. It was, therefore, found that HB-TSdA-F was poor in solvent resistance.

Example 157

As in Example 156, a film ("HB-TCzA-F1") was prepared using HB-TSdAV1 obtained in Example 135, and its solvent resistance test was performed. Assuming that the initial thickness was 100%, the thickness of HB-TCzA-F1 after the immersion in Thinner 73 was 100%. It was, therefore, found that HB-TCzA-F1 was good in solvent resistance.

Example 158

As in Example 156, a film ("HB-TCzA-F2") was prepared using HB-TSdAV2 obtained in Example 136, and its solvent resistance test was performed. Assuming that the initial thickness was 100%, the thickness of HB-TCzA-F2 after the immersion in Thinner 73 was 100%. It was, therefore, found that HB-TCzA-F2 was good in solvent resistance.

Example 159

As in Example 156, a film ("HB-TCzA-F3") was prepared using HB-TSdAV3 obtained in Example 137, and its solvent resistance test was performed. Assuming that the initial thickness was 100%, the thickness of HB-TCzA-F3 after the immersion in Thinner 73 was 100%. It was, therefore, found that HB-TCzA-F3 was good in solvent resistance.

Example 160

Using a spin coater, a 10% NMP solution of HB-TMA prepared in Example 138 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TMA-F as a film on the substrate.

A solvent resistance test of the resultant HB-TMA-F was performed. The thickness of HB-TMA-F after the final baking was 202.5 nm, which was recorded as an initial thickness.

In Thinner 73, HB-TMA-F was immersed fully, and left over for 5 minutes. HB-TMA-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TMA-F after the immersion in Thinner 73 was reduced to 3.5%. It was, therefore, found that HB-TMA-F was poor in solvent resistance.

Example 161

As in Example 160, a film ("HB-TMA-F1") was prepared using HB-TMAV1 obtained in Example 138, and its solvent resistance test was performed. Assuming that the initial thickness was 100%, the thickness of HB-TMA-F1 after the immersion in Thinner 73 was 100%. It was, therefore, found that HB-TMA-F1 was good in solvent resistance.

Example 162

As in Example 160, a film ("HB-TMA-F2") was prepared using HB-TMAV2 obtained in Example 139, and its solvent resistance test was performed. Assuming that the initial thickness was 100%, the thickness of HB-TMA-F2 after the immersion in Thinner 73 was 100%. It was, therefore, found that HB-TMA-F2 was good in solvent resistance.

Example 163

As in Example 160, a film ("HB-TMA-F3") was prepared using HB-TMAV3 obtained in Example 140, and its solvent resistance test was performed. Assuming that the initial thickness was 100%, the thickness of HB-TMA-F3 after the immersion in Thinner 73 was 100%. It was, therefore, found that HB-TMA-F3 was good in solvent resistance.

Example 164

Using a spin coater, a 10% NMP solution of HB-TMdA prepared in Example 141 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TMdA-F as a film on the substrate.

A solvent resistance test of the resultant HB-TMdA-F was performed. The thickness of HB-TMdA-F after the final baking was 196.6 nm, which was recorded as an initial thickness. In Thinner 73, HB-TMdA-F was immersed fully, and left over for 5 minutes. HB-TMdA-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TMdA-F after the immersion in Thinner 73 was reduced to 1.5%. It was, therefore, found that HB-TMdA-F was poor in solvent resistance.

Example 165

As in Example 164, a film ("HB-TMdA-F1") was prepared using HB-TMdAV1 obtained in Example 141, and its solvent resistance test was performed. Assuming that the initial thickness was 100%, the thickness of HB-TMdA-F1 after the immersion in Thinner 73 was 100%. It was, therefore, found that HB-TMdA-F1 was good in solvent resistance.

Example 166

As in Example 164, a film ("HB-TMdA-F2") was prepared using HB-TMdAV2 obtained in Example 142, and its solvent resistance test was performed. Assuming that the initial thickness was 100%, the thickness of HB-TMdA-F2 after the immersion in Thinner 73 was 100%. It was, therefore, found that HB-TMdA-F2 was good in solvent resistance.

Example 167

As in Example 164, a film ("HB-TMdA-F3") was prepared using HB-TMdAV3 obtained in Example 143, and its solvent resistance test was performed. Assuming that the initial thickness was 100%, the thickness of HB-TMdA-F3 after the immersion in Thinner 73 was 100%. It was, therefore, found that HB-TMdA-F3 was good in solvent resistance.

Example 168

Using a spin coater, a 10% NMP solution of HB-TAMA1 prepared in Example 144 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TAMA1-F as a film on the substrate.

A solvent resistance test of the resultant HB-TAMA1-F was performed. The thickness of HB-TAMA1-F after the final baking was 198.4 nm, which was recorded as an initial thickness. In Thinner 73, HB-TAMA1-F was immersed fully, and left over for 5 minutes. HB-TAMA1-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TAMA1-F after the immersion in Thinner 73 was reduced to 5.6%. It was, therefore, found that HB-TAMA1-F was poor in solvent resistance.

Example 169

As in Example 168, a film ("HB-TAMA1-F1") was prepared using HB-TAMA1V1 obtained in Example 144, and its solvent resistance test was performed. Assuming that the initial thickness was 100%, the thickness of HB-TAMA1-F1 after the immersion in Thinner 73 was 100%. It was, therefore, found that HB-TAMA1-F1 was good in solvent resistance.

Example 170

As in Example 168, a film ("HB-TAMA1-F2") was prepared using HB-TAMA1V2 obtained in Example 145, and its solvent resistance test was performed. Assuming that the initial thickness was 100%, the thickness of HB-TAMA1-F2 after the immersion in Thinner 73 was 100%. It was, therefore, found that HB-TAMA1-F2 was good in solvent resistance.

Example 171

As in Example 168, a film ("HB-TAMA1-F3") was prepared using HB-TAMA1V3 obtained in Example 146, and its solvent resistance test was performed. Assuming that the initial thickness was 100%, the thickness of HB-TAMA1-F3 after the immersion in Thinner 73 was 100%. It was, therefore, found that HB-TAMA1-F3 was good in solvent resistance.

Example 172

Using a spin coater, a 10% NMP solution of HB-TAMA2 prepared in Example 147 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TAMA2-F as a film on the substrate.

A solvent resistance test of the resultant HB-TAMA2-F was performed. The thickness of HB-TAMA2-F after the final baking was 201.5 nm, which was recorded as an initial thickness. In Thinner 73, HB-TAMA2-F was immersed fully, and left over for 5 minutes. HB-TAMA2-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TAMA2-F after the immersion in Thinner 73 was reduced to 3.6%. It was, therefore, found that HB-TAMA2-F was poor in solvent resistance.

Example 173

As in Example 172, a film ("HB-TAMA2-F1") was prepared using HB-TAMA2V1 obtained in Example 147, and its solvent resistance test was performed. Assuming that the initial thickness was 100%, the thickness of HB-TAMA2-F1 after the immersion in Thinner 73 was 100%. It was, therefore, found that HB-TAMA2-F1 was good in solvent resistance.

Example 174

As in Example 172, a film ("HB-TAMA2-F2") was prepared using HB-TAMA2V2 obtained in Example 148, and its solvent resistance test was performed. Assuming that the initial thickness was 100%, the thickness of HB-TAMA2-F2 after the immersion in Thinner 73 was 100%. It was, therefore, found that HB-TAMA2-F2 was good in solvent resistance.

Example 175

As in Example 172, a film ("HB-TAMA2-F3") was prepared using HB-TAMA2V3 obtained in Example 149, and its solvent resistance test was performed. Assuming that the initial thickness was 100%, the thickness of HB-TAMA2-F3 after the immersion in Thinner 73 was 100%. It was, therefore, found that HB-TAMA2-F3 was good in solvent resistance.

Example 176

Using a spin coater, a 10% NMP solution of HB-TCzA prepared in Example 150 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TCzA-F as a film on the substrate.

A solvent resistance test of the resultant HB-TCzA-F was performed. The thickness of HB-TCzA-F after the final baking was 197.4 nm, which was recorded as an initial thickness. In Thinner 73, HB-TCzA-F was immersed fully, and left over for 5 minutes. HB-TCzA-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TCzA-F after the immersion in Thinner 73 was reduced to 2.2%. It was, therefore, found that HB-TCzA-F was poor in solvent resistance.

Example 177

As in Example 176, a film ("HB-TCzA-F1") was prepared using HB-TCzAV1 obtained in Example 150, and its solvent resistance test was performed. Assuming that the initial thickness was 100%, the thickness of HB-TCzA-F1 after the immersion in Thinner 73 was 100%. It was, therefore, found that HB-TCzA-F1 was good in solvent resistance.

Example 178

As in Example 176, a film ("HB-TCzA-F2") was prepared using HB-TCzAV2 obtained in Example 151, and its solvent resistance test was performed. Assuming that the initial thickness was 100%, the thickness of HB-TCzA-F2 after the immersion in Thinner 73 was 100%. It was, therefore, found that HB-TCzA-F2 was good in solvent resistance.

Example 179

As in Example 176, a film ("HB-TCzA-F3") was prepared using HB-TCzAV3 obtained in Example 152, and its solvent resistance test was performed. Assuming that the initial thickness was 100%, the thickness of HB-TCzA-F3 after the immersion in Thinner 73 was 100%. It was, therefore, found that HB-TCzA-F3 was good in solvent resistance.

Example 180

Using a spin coater, a 10% NMP solution of HB-TDA prepared in Example 153 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TDA-F as a film on the substrate.

A solvent resistance test of the resultant HB-TDA-F was performed. The thickness of HB-TDA-F after the final baking was 200.1 nm, which was recorded as an initial thickness. In Thinner 73, HB-TDA-F was immersed fully, and left over for 5 minutes. HB-TDA-F was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TDA-F after the immersion in Thinner 73 was reduced to 4.2%. It was, therefore, found that HB-TDA-F was poor in solvent resistance.

Example 181

As in Example 180, a film ("HB-TDA-F1") was prepared using HB-TDAV1 obtained in Example 153, and its solvent resistance test was performed. Assuming that the initial thickness was 100%, the thickness of HB-TDA-F1 after the immersion in Thinner 73 was 100%. It was, therefore, found that HB-TDA-F1 was good in solvent resistance.

Example 182

As in Example 180, a film ("HB-TDA-F2") was prepared using HB-TDAV2 obtained in Example 154, and its solvent resistance test was performed. Assuming that the initial thickness was 100%, the thickness of HB-TDA-F2 after the immersion in Thinner 73 was 100%. It was, therefore, found that HB-TDA-F2 was good in solvent resistance.

Example 183

As in Example 180, a film ("HB-TDA-F3") was prepared using HB-TDAV3 obtained in Example 155, and its solvent resistance test was performed. Assuming that the initial thickness was 100%, the thickness of HB-TDA-F3 after the immersion in Thinner 73 was 100%. It was, therefore, found that HB-TDA-F3 was good in solvent resistance.

It is to be noted that the term "solvent resistance test" means a test to confirm whether or not a film after final baking has been insolubilized to its contact with a solvent. Solvent resistance is a property required upon addition of post-steps that a resist or the like is recoated on the film and the film is then patterned. Unless the film is equipped with solvent resistance, the film is dissolved in the resist solvent when recoated, so that the film is mixed with the resist and the inherent properties of the film may not be exhibited. Solvent resistance is required to be 100%, and even at 99.5%, mixing takes place when recoated, thereby raising problems in that the film may become irregular in the substrate and the substrate may be provided with increased surface roughness.

As indicated above, each resin to which no crosslinking agent was added was poor in solvent resistance after formed into a film, but solvent resistance was exhibited by adding a crosslinking agent and applying heat to form crosslinks with bonding groups of the resin. The impart of solvent resistance may be chosen depending on the fabrication process for each intended device. When a general semiconductor fabrication process is used, however, it is a commonly-required performance that the solvent resistance is 100%.

Example 184

An aliquot (1.20 g) of HB-TmDA12 obtained in Example 98 was weighed in a 10-mL, single-necked, round-bottomed flask, followed by the addition of CHN (8.80 g). The resulting mixture was stirred at 23° C. for 24 hours to completely dissolve HB-TmDA12 to prepare a 12% CHN solution. In a 10-mL, single-necked, round-bottomed flask, an aliquot (5.00 g) of the 12% CHN solution of HB-TmDA12 was weighed, the 20% solution of "B-882N" (product of Mitsui Chemicals Polyurethanes Co., Ltd.) diluted as a crosslinking agent in CHN (0.60 g; 20 parts by mass under the assumption that solids of the polymer amounted to 100 parts by mass) was added, the 1% solution of "MEGAFAC R-30" (product of DIC Corporation) diluted as a surfactant in CHN (0.03 g; 0.05 parts by mass under the assumption that the solids of the polymer amounted to 100 parts by mass) was added, and further, CHN (0.5725 g) was added. The resulting solution was stirred at 23° C. for 1 hour. The solution was confirmed to become homogeneous so that a varnish having a total solids content of 12.0% by mass (abbreviated as "HB-TmDA-H1") was prepared.

Example 185

An aliquot (1.20 g) of HB-TmDA25 obtained in Example 114 was weighed in a 10-mL, single-necked, round-bottomed flask, followed by the addition of CHN (8.80 g). The resulting mixture was stirred at 23° C. for 24 hours to completely dissolve HB-TmDA25 to prepare a 12% CHN solution. In a 10-mL, single-necked, round-bottomed flask, an aliquot (5.00 g) of the 12% CHN solution of HB-TmDA25 was weighed, the 20% solution of "B-882N" (product of Mitsui Chemicals Polyurethanes Co., Ltd.) diluted as a crosslinking agent in CHN (0.60 g; 20 parts by mass under the assumption that solids of the polymer amounted to 100 parts by mass) was added, the 1% solution of "MEGAFAC R-30" (product of DIC Corporation) diluted as a surfactant in CHN (0.03 g; 0.05 parts by mass under the assumption that the solids of the polymer amounted to 100 parts by mass) was added, and further, CHN (0.5725 g) was added. The resulting solution was stirred at 23° C. for 1 hour. The solution was confirmed to become homogeneous so that a varnish having a total solids content of 12.0% by mass (abbreviated as "HB-TmDA-I1") was prepared.

Example 186

An aliquot (1.20 g) of HB-TAMA1 obtained in Example 95 was weighed in a 10-mL, single-necked, round-bottomed flask, followed by the addition of CHN (8.80 g). The resulting mixture was stirred at 23° C. for 24 hours to completely dissolve HB-TAMA1 to prepare a 12% CHN solution. In a 10-mL, single-necked, round-bottomed flask, an aliquot (5.00 g) of the 12% CHN solution of HB-TAMA1 was weighed, the 20% solution of "B-882N" (product of Mitsui Chemicals Polyurethanes Co., Ltd.) diluted as a crosslinking agent in CHN (0.60 g; 20 parts by mass under the assumption that solids of the polymer amounted to 100 parts by mass) was added, the 1% solution of "MEGAFAC R-30" (product of DIC Corporation) diluted as a surfactant in CHN (0.03 g; 0.05 parts by mass under the assumption that the solids of the polymer amounted to 100 parts by mass) was added, and further, CHN (0.5725 g) was added. The resulting solution was stirred at 23° C. for 1 hour. The solution was confirmed to become homogeneous so that a varnish having a total solids content of 12.0% by mass (abbreviated as "HB-TAMA-J1") was prepared.

Example 187

An aliquot (1.20 g) of HB-TAMA40 obtained in Example 132 was weighed in a 10-mL, single-necked, round-bottomed flask, followed by the addition of CHN (8.80 g). The resulting mixture was stirred at 23° C. for 24 hours to completely dissolve HB-TAMA40 to prepare a 12% CHN solution. In a 10-mL, single-necked, round-bottomed flask, an aliquot (5.00 g) of the 12% CHN solution of HB-TAMA40 was weighed, the 20% solution of "B-882N" (product of Mitsui Chemicals Polyurethanes Co., Ltd.) diluted as a crosslinking agent in CHN (0.60 g; 20 parts by mass under the assumption that solids of the polymer amounted to 100 parts by mass) was added, the 1% solution of "MEGAFAC R-30" (product of DIC Corporation) diluted as a surfactant in CHN (0.03 g; 0.05 parts by mass under the assumption that the solids of the polymer amounted to 100 parts by mass) was added, and further, CHN (0.5725 g) was added. The resulting solution was stirred at 23° C. for 1 hour. The solution was confirmed to become homogeneous so that a varnish having a total solids content of 12.0% by mass (abbreviated as "HB-TAMA-K1") was prepared.

Example 188

With respect to HB-TmDA-H1 obtained in Example 184, an edge bead rinse test was performed using a 4-inch silicon substrate. The term "edge bead rinse" means a step that removes a film on an edge portion of a substrate with a rinse solution after the formation of the film by spin coating on the substrate.

HB-TmDA-H1 was potted on a 4-inch silicon substrate under the following conditions: (1) rotational speed: 30 rpm, acceleration: 5,000 R/S, 3 seconds (pre-rotation), (2) rotational speed: 500 rpm, acceleration: 5,000 R/S, 1 second (pre-rotation), and (3) rotational speed: 1,500 rpm, acceleration: 5,000 R/S, 40 seconds (final rotation). To test whether or not edge bead rinse would be feasible on the substrate with the film formed thereon as described above, it was then successively subjected to: (4) edge bead rinse at rotational speed: 1,000 rpm and acceleration: 5,000 R/S for 30 seconds and (5) edge drying at rotational speed: 1,000 rpm and acceleration: 5,000 R/S for 20 seconds. As a rinse solution, Thinner 73 was used.

Figure 94:
FIG. 94 is a picture showing an optical microscope image of an edge portion of a substrate after edge bead rinse in Example 188.

The substrate after the above-described treatment was observed at an edge portion thereof at ×5 magnification under an optical microscope. The observation results are shown in FIG. 94.

Example 189

Figure 95:
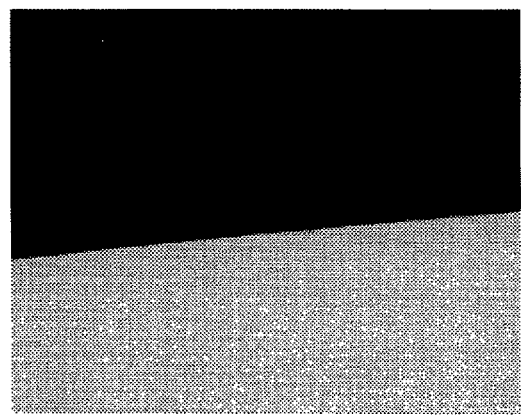
FIG. 95 is a picture showing an optical microscope image of an edge portion of a substrate after edge bead rinse in Example 189.

An edge bead rinse test was performed as in Example 188 except for the use of HB-TmDA-11 obtained in Example 185. The substrate after the treatment was observed at an edge portion thereof at ×5 magnification under an optical microscope. The observation results are shown in FIG. 95.

Example 190

Figure 96:
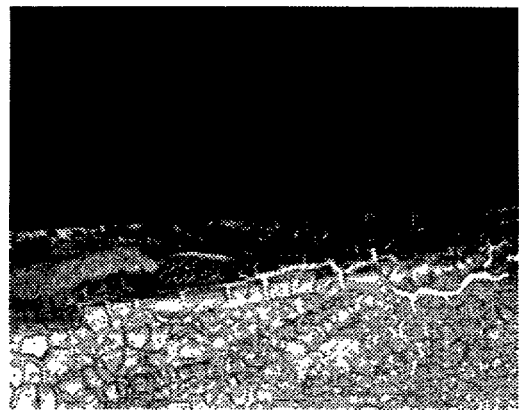
FIG. 96 is a picture showing an optical microscope image of an edge portion of a substrate after edge bead rinse in Example 190.

An edge bead rinse test was performed as in Example 188 except for the use of HB-TAMA-J1 obtained in Example 186 and CHN as a rise solution. The substrate after the treatment was observed at an edge portion thereof at ×5 magnification under an optical microscope. The observation results are shown in FIG. 96.

Example 191

Figure 97:
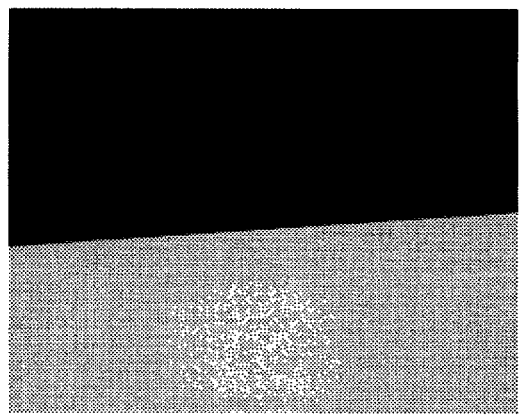
FIG. 97 is a picture showing an optical microscope image of an edge portion of a substrate after edge bead rinse in Example 191.

An edge bead rinse test was performed as in Example 188 except for the use of HB-TAMA-K1 obtained in Example 187 and CHN as a rise solution. The substrate after the treatment was observed at an edge portion thereof at ×5 magnification under an optical microscope. The observation results are shown in FIG. 97.

Comparing Example 188, Example 189, Example 190 and Example 191, it was appreciated that edge bead rinse was feasible in Examples 189 and 191 in which the polymers polymerized with concurrent charging of aniline were used, respectively. This result suggests that polymerization with concurrent charging of a primary amine provides the resulting polymer with a modified conformation, and hence, with improved solubility.

Upon fabrication of devices, a clean track is generally used. This clean track is an equipment which can consecutively perform treatments such as spin coating, edge bead rinse, back rinse and baking. This equipment automatically performs the conveyance of each substrate, so that the substrate needs edge bead rinse to avoid contaminating tweezer portions by which the substrate is held. Unless the film on the edge portion can be removed by the edge bead rinse, the tweezers may be contaminated and may hence become a case of particles to lower the yield of devices.

Whether edge bead rinse is feasible or not may be chosen depending on the fabrication process of an intended device. When a general semiconductor fabrication process is used, however, it is a commonly-required performance that any film remaining on an edge portion of each substrate can be removed by edge bead rinse.

Changes to the Species of Crosslinking Agent

Example 192

Synthesis of High-Molecular Compound [27] Having Many Amine Terminals

Under nitrogen and in a 500-mL, four-necked flask, DMAc (280 mL) was cooled to −10° C. in a ice bath with sodium chloride mixed therein, and 2,4,6-trichloro-1,3,5-triazine [1] (43.08 g, 0.23 mol, product of Aldrich Corporation) was added and dissolved. Subsequently, a solution of m-phenylenediamine [26] (75.80 g, 0.70 mol) in DMAc (390 g) was added dropwise. After the dropwise addition, the resulting mixture was stirred for 30 minutes. Into a vessel provided beforehand by adding DMAc (446 g) to a 2,000-mL, four-necked flask and heating it to 110° C. in an oil bath, the resulting reaction mixture was added dropwise by using a transfer tube. The resulting mixture was stirred for 1 hour to conduct polymerization. Subsequently, aniline (21.73 g, 0.23 mol) was added, followed by stirring for 1 hour to terminate the polymerization. After the resultant polymerization mixture was allowed to cool to room temperature, it was reprecipitated in a mixed solution of 28% aqueous solution of ammonia (70.83 g) and deionized water (4,000 g). The resulting precipitates were collected by filtration, redissolved in a mixed solvent of THF (600 g) and DMF (600 g), and then reprecipitated in deionized water (3,500 g). The resulting precipitates were collected by filtration, and then dried at 120° C. for 8 hours in a vacuum dryer to obtain the target high-molecular compound [27] (hereinafter abbreviated as "HB-TmDA20NH2," 70.0 g).

Example 193

Crosslinking Agent: None

Under air, HB-TmDA20NH2 (1.0000 g) obtained in Example 192 was placed in a 10-mL eggplant flask, followed by the addition of propylene glycol monomethyl ether (abbreviated as "PGME," 9.0000 g) as a solvent. Using a wave rotor, HB-TmDA20NH2 was completely dissolved at room temperature to prepare a 10% by mass PGME solution of HB-TmDA20NH2.

Example 194

Crosslinking Agent: "B-882N"

Under air, HB-TmDA20NH2 (2.0000 g) obtained in Example 192 was placed in a 10-mL eggplant flask, followed by the addition of PGME (8.0000 g). Using a wave rotor, HB-TmDA20NH2 was completely dissolved at room temperature to prepare a 20% by mass PGME solution of HB-TmDA20NH2. To an aliquot (1.0000 g) of the 20% by mass PGME solution, PGME (0.5083 g) was then added, and subsequently, a 10% by mass PGME solution of "B-882N" (a blocked isocyanato-group containing compound, product of Mitsui Chemicals Polyurethanes Co., Ltd.) as a crosslinking agent (0.4000 g; 20.0 parts by mass per 100 parts by mass of the solids of the polymer) was added. Added further was a 1.0% by mass PGME solution of "MEGAFAC R-30" (trade name, product of DIC Corporation) as a surfactant (0.1000 g; 0.5 parts by mass per 100 parts by mass of the solids of the polymer). The resulting solution was stirred for 3 hours until homogeneous. After the stirring, the solute had been completely dissolved, and as a clear pale-yellow solution, a polymer varnish (hereinafter abbreviated as "HB-TmDA20NH2SV1") was obtained. The total percentage by mass of solids in HB-TmDA20NH2SV1 was 12% by mass.

Example 195

Crosslinking Agent: "GT-401"

As in Example 194 except for the use of "EPOLEAD GT-401" (an epoxy-containing compound, product of Daicel Chemical Industries, Ltd.) as a crosslinking agent, a varnish was prepared to obtain a polymer varnish (hereinafter abbreviated as "HB-TmDA20NH2SV2").

Example 196

Crosslinking Agent: "CELLOXIDE 2021"

As in Example 194 except for the use of "CELLOXIDE 2021" (an epoxy-containing compound, product of Daicel Chemical Industries, Ltd.) as a crosslinking agent, a varnish was prepared to obtain a polymer varnish (hereinafter abbreviated as "HB-TmDA20NH2SV3").

Example 197

Crosslinking Agent: "EHPE3150"

As in Example 194 except for the use of "EHPE3150" (an epoxy-containing compound, product of Daicel Chemical Industries, Ltd.) as a crosslinking agent, a varnish was prepared to obtain a polymer varnish (hereinafter abbreviated as "HB-TmDA20NH2SV4").

Example 198

Crosslinking Agent: "CYMEL303"

As in Example 194 except for the use of "CYMEL (registered trademark) 303" (a methoxymethylene-containing compound, product of Nihon Cytec Industries, Inc.) as a crosslinking agent, a varnish was prepared to obtain a polymer varnish (hereinafter abbreviated as "HB-TmDA20NH2SV5").

Example 199

Crosslinking Agent: "UA-53H"

As in Example 194 except for the use of "UA-53H" (an acryl-containing compound, product of Shin-Nakamura Chemical Co., Ltd.) as a crosslinking agent, a varnish was prepared to obtain a polymer varnish (hereinafter abbreviated as "HB-TmDA20NH2SV6").

Example 200

Crosslinking Agent: "B-830"

As in Example 194 except for the use of "B-830" (a blocked polyisocyanato-containing compound, product of Mitsui Chemicals Polyurethane Co., Ltd.) as a crosslinking agent, a varnish was prepared to obtain a polymer varnish (hereinafter abbreviated as "HB-TmDA20NH2SV7").

Example 201

Crosslinking Agent: "B-5010"

As in Example 194 except for the use of "B-5010" (a blocked polyisocyanato-containing compound, product of Mitsui Chemicals Polyurethanes Co., Ltd.) as a crosslinking agent, a varnish was prepared to obtain a polymer varnish (hereinafter abbreviated as "HB-TmDA20NH2SV8").

Example 202

Crosslinking Agent: "B-7075"

As in Example 194 except for the use of "B-7075" (a blocked polyisocyanato-containing compound, product of Mitsui Chemicals Polyurethanes Co., Ltd.) as a crosslinking agent, a varnish was prepared to obtain a polymer varnish (hereinafter abbreviated as "HB-TmDA20NH2SV9").

Example 203

Crosslinking Agent: "KAYARAD DPHA"

As in Example 194 except for the use of "KAYARAD (registered trademark) DPHA" (an acryl-containing compound, product of Nippon Kayaku Co., Ltd.) as a crosslinking agent, a varnish was prepared to obtain a polymer varnish (hereinafter abbreviated as "HB-TmDA20NH2SV10").

Example 204

Crosslinking Agent: "TM-BIP-A"
As in Example 194 except for the use of "TM-BIP-A" (a hydroxymethylene-containing compound, product of Asahi Organic Chemicals Industry Co., Ltd.) as a crosslinking agent, a varnish was prepared to obtain a polymer varnish (hereinafter abbreviated as "HB-TmDA20NH2SV11").

Example 205

Crosslinking Agent: "OXT-221"

As in Example 194 except for the use of "OXT-221" (an oxetane skeleton-containing compound, product of Toagosei Co., Ltd.) as a crosslinking agent, a varnish was prepared to obtain a polymer varnish (hereinafter abbreviated as "HB-TmDA20NH2SV12").

Example 206

Crosslinking Agent: "OX-SQ-H"

As in Example 194 except for the use of "OX-SQ-H" (an oxetane skeleton-containing compound, product of Toagosei Co., Ltd.) as a crosslinking agent, a varnish was prepared to obtain a polymer varnish (hereinafter abbreviated as "HB-TmDA20NH2SV13").

Example 207

Crosslinking Agent: "OX-SC"

As in Example 194 except for the use of "OX-SC" (an oxetane skeleton-containing compound, product of Toagosei Co., Ltd.) as a crosslinking agent, a varnish was prepared to obtain a polymer varnish (hereinafter abbreviated as "HB-TmDA20NH2SV14").

Solvent Resistance Test

Example 208

Using a spin coater, a 10% by mass PGME solution of HB-TmDA20NH2 obtained in Example 193 was spin-coated onto a silicon substrate to give a 200 nm thickness. Under the atmosphere, prebaking was performed for 1 minute on a hot plate controlled at 100° C. Under the atmosphere, final baking was then performed for 5 minutes on the hot plate controlled at 300° C. to obtain HB-TmDA20NH2-F0 as a film on the substrate.

A solvent resistance test of the resultant HB-TmDA20NH2-F0 was performed. The thickness of HB-TmDA20NH2-F0 after the final baking was 198.4 nm, which was recorded as an initial thickness. In Thinner 73, HB-TmDA20NH2-F0 was immersed fully, and left over for 5 minutes. HB-TmDA20NH2-F0 was then dried in air, and baked for 1 minute on a hot plate controlled at 200° C. to completely vaporize any remaining solvent. Subsequently, its thickness was measured, and was compared with the initial thickness.

Assuming that the initial thickness was 100%, the thickness of HB-TmDA20NH2-F0 after the immersion in Thinner 73 was reduced to 0.0%. It was, therefore, found that HB-TmDA20NH2-F0 was poor in solvent resistance.

Example 209

As in Example 208, a film ("HB-TmDA20NH2-F1") was prepared using HB-TmDA20NH2SV1 obtained in Example 194, and its solvent resistance test was performed. Assuming that the initial thickness was 100%, the thickness of HB-TmDA20NH2-F1 after the immersion in Thinner 73 was 100%. It was, therefore, found that HB-TmDA20NH2-F1 was good in solvent resistance.

Example 210

As in Example 208, a film ("HB-TmDA20NH2-F2") was prepared using HB-TmDA20NH2SV2 obtained in Example 195, and its solvent resistance test was performed. Assuming that the initial thickness was 100%, the thickness of HB-TmDA20NH2-F2 after the immersion in Thinner 73 was 100%. It was, therefore, found that HB-TmDA20NH2-F2 was good in solvent resistance.

Example 211

As in Example 208, a film ("HB-TmDA20NH2-F3") was prepared using HB-TmDA20NH2SV3 obtained in Example 196, and its solvent resistance test was performed. Assuming that the initial thickness was 100%, the thickness of HB-TmDA20NH2-F3 after the immersion in Thinner 73 was 90.5%. It was, therefore, found that HB-TmDA20NH2-F3 was poor in solvent resistance.

Example 212

As in Example 208, a film ("HB-TmDA20NH2-F4") was prepared using HB-TmDA20NH2SV4 obtained in Example 197, and its solvent resistance test was performed. Assuming that the initial thickness was 100%, the thickness of HB-TmDA20NH2-F4 after the immersion in Thinner 73 was 100%. It was, therefore, found that HB-TmDA20NH2-F4 was good in solvent resistance.

Example 213

As in Example 208, a film ("HB-TmDA20NH2-F5") was prepared using HB-TmDA20NH2SV5 obtained in Example 198, and its solvent resistance test was performed. Assuming that the initial thickness was 100%, the thickness of HB-TmDA20NH2-F5 after the immersion in Thinner 73 was 100%. It was, therefore, found that HB-TmDA20NH2-F5 was good in solvent resistance.

Example 214

As in Example 208, a film ("HB-TmDA20NH2-F6") was prepared using HB-TmDA20NH2SV6 obtained in Example 199, and its solvent resistance test was performed. Assuming that the initial thickness was 100%, the thickness of HB-TmDA20NH2-F6 after the immersion in Thinner 73 was 100%. It was, therefore, found that HB-TmDA20NH2-F6 was good in solvent resistance.

Example 215

As in Example 208, a film ("HB-TmDA20NH2-F7") was prepared using HB-TmDA20NH2SV7 obtained in Example 200, and its solvent resistance test was performed. Assuming that the initial thickness was 100%, the thickness of HB-TmDA20NH2-F7 after the immersion in Thinner 73 was 99.9%. It was, therefore, found that HB-TmDA20NH2-F7 was good in solvent resistance.

Example 216

As in Example 208, a film ("HB-TmDA20NH2-F8") was prepared using HB-TmDA20NH2SV8 obtained in Example 201, and its solvent resistance test was performed. Assuming that the initial thickness was 100%, the thickness of HB-TmDA20NH2-F8 after the immersion in Thinner 73 was 95.6%. It was, therefore, found that HB-TmDA20NH2-F8 was poor in solvent resistance.

Example 217

As in Example 208, a film ("HB-TmDA20NH2-F9") was prepared using HB-TmDA20NH2SV9 obtained in Example 202, and its solvent resistance test was performed. Assuming that the initial thickness was 100%, the thickness of HB-TmDA20NH2-F9 after the immersion in Thinner 73 was 100%. It was, therefore, found that HB-TmDA20NH2-F9 was good in solvent resistance.

Example 218

As in Example 208, a film ("HB-TmDA20NH2-F10") was prepared using HB-TmDA20NH2SV10 obtained in Example 203, and its solvent resistance test was performed. Assuming that the initial thickness was 100%, the thickness of HB-TmDA20NH2-F10 after the immersion in Thinner 73 was 100%. It was, therefore, found that HB-TmDA20NH2-F10 was good in solvent resistance.

Example 219

As in Example 208, a film ("HB-TmDA20NH2-F11") was prepared using HB-TmDA20NH2SV11 obtained in Example 204, and its solvent resistance test was performed. Assuming that the initial thickness was 100%, the thickness of HB-TmDA20NH2-F11 after the immersion in Thinner 73 was 100%. It was, therefore, found that HB-TmDA20NH2-F11 was good in solvent resistance.

Example 220

As in Example 208, a film ("HB-TmDA20NH2-F12") was prepared using HB-TmDA20NH2SV12 obtained in Example 205, and its solvent resistance test was performed. Assuming that the initial thickness was 100%, the thickness of HB-TmDA20NH2-F12 after the immersion in Thinner 73 was 12.6%. It was, therefore, found that HB-TmDA20NH2-F12 was poor in solvent resistance.

Example 221

As in Example 208, a film ("HB-TmDA20NH2-F13") was prepared using HB-TmDA20NH2SV13 obtained in Example 206, and its solvent resistance test was performed. Assuming that the initial thickness was 100%, the thickness of HB-TmDA20NH2-F13 after the immersion in Thinner 73 was 15.6%. It was, therefore, found that HB-TmDA20NH2-F13 was poor in solvent resistance.

Example 222

As in Example 208, a film ("HB-TmDA20NH2-F14") was prepared using HB-TmDA20NH2SV14 obtained in Example 207, and its solvent resistance test was performed. Assuming that the initial thickness was 100%, the thickness of HB-TmDA20NH2-F14 after the immersion in Thinner 73 was 14.5%. It was, therefore, found that HB-TmDA20NH2-F14 was poor in solvent resistance.

From the results of Examples 209 to 222, it has been suggested that the inclusion of one or more epoxy, blocked isocyanato, acryl, methoxymethylene or hydroxymethylene groups in a crosslinking agent provides solvent resistance of 100% and that a crosslinking agent having an oxetane skeleton is poor in solvent resistance and results in a low crosslink density.

Among these crosslinking agents, those containing one or more methoxymethylene or hydroxymethylene groups may be colored to lower the transmittance when the resulting film is used in a devices required to have robustness and weatherability, for example, when the fabrication process includes a high-temperature step such as baking at 300° C. or when the resulting film is required to have light resistance of 1 million Lux or higher. In contrast, crosslinking agents containing one or more epoxy, blocked isocyanato or acryl groups have a post-crosslinking structure stable to heat and light, do not reduce the transmittance of films when employed in devices required to have robustness and weatherability, and therefore, are preferred.

Filling Property Test

Example 223

Using HB-TmDA20NH2SV1 prepared in Example 196, filling property test was performed. The material of structural substrates employed in the filling property test is was silicon, and the structural substrates each had via holes of 1.6 μm depth and 400 nm or 750 nm diameter.

By the spin coating method, HB-TmDA20NH2SV1 was applied onto the respective structural substrates to give a 500 nm thickness. Prebaking was performed for 1 minute on a hot plate controlled at 100° C., followed by final baking for 5 minutes under the atmosphere on the hot plate controlled at 300° C.

Figure 98:
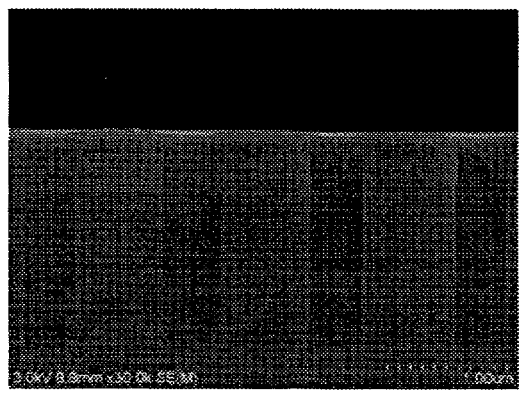
FIG. 98 is a picture showing an SEM image obtained by observing 400 nm via portions in a filling property test of Example 223.
Figure 99:
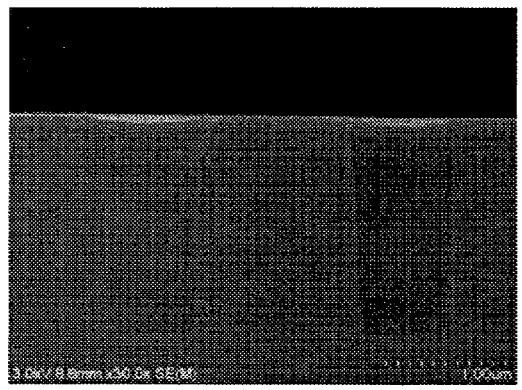
FIG. 99 is a picture showing an SEM image obtained by observing 750 nm via portions in a filling property test of Example 223.

After the baked structural substrates with films formed thereon, respectively, were scratched at edges thereof with a diamond pen, the substrates were cleaved, followed by SEM observation. An observed image of 400 nm via portions is shown in FIG. 98, while an observed image of 750 nm via portions is shown in FIG. 99.

Example 224

Figure 100:
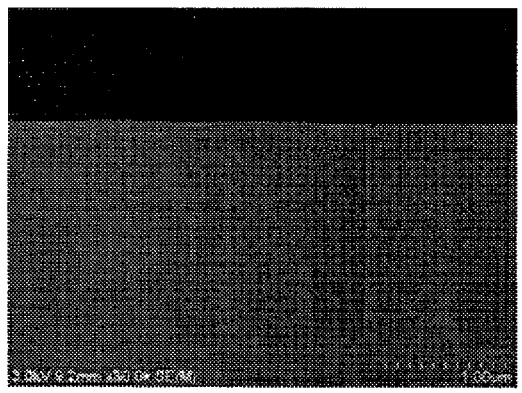
FIG. 100 is a picture showing an SEM image obtained by observing 400 nm via portions in a filling property test of Example 224.
Figure 101:
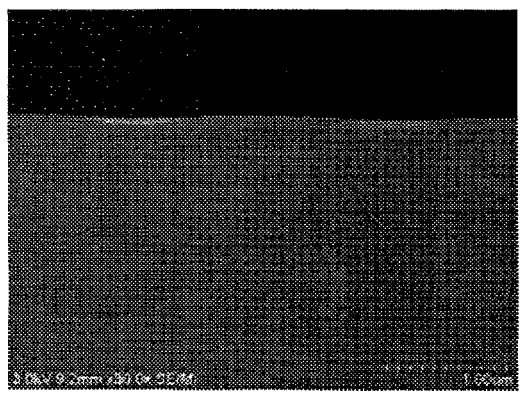
FIG. 101 is a picture showing an SEM image obtained by observing 750 nm via portions in a filling property test of Example 224.

As in Example 223, a filling property test was performed using HB-TmDA20NH2SV2 prepared in Example 195. An observed image of 400 nm via portions is shown in FIG. 100, while an observed image of 750 nm via portions is shown in FIG. 101.

Example 225

Figure 102:
FIG. 102 is a picture showing an SEM image obtained by observing 400 nm via portions in a filling property test of Example 225.
Figure 103:
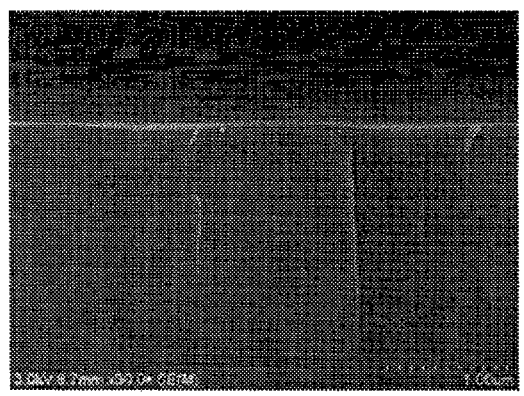
FIG. 103 is a picture showing an SEM image obtained by observing 750 nm via portions in a filling property test of Example 225.

As in Example 223, a filling property test was performed using HB-TmDA20NH2SV3 prepared in Example 196. An observed image of 400 nm via portions is shown in FIG. 102, while an observed image of 750 nm via portions is shown in FIG. 103.

Example 226

Figure 104:
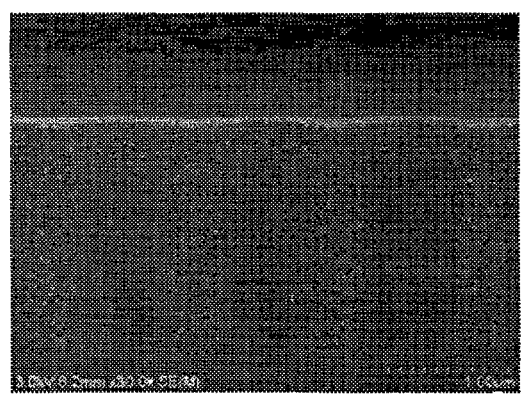
FIG. 104 is a picture showing an SEM image obtained by observing 400 nm via portions in a filling property test of Example 226.
Figure 105:
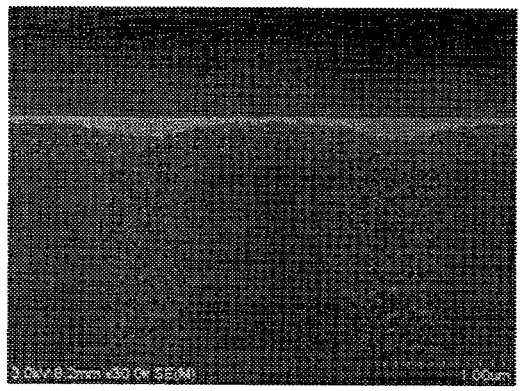
FIG. 105 is a picture showing an SEM image obtained by observing 750 nm via portions in a filling property test of Example 226.

As in Example 223, a filling property test was performed using HB-TmDA20NH2SV4 prepared in Example 197. An observed image of 400 nm via portions is shown in FIG. 104, while an observed image of 750 nm via portions is shown in FIG. 105.

Example 227

Figure 106:
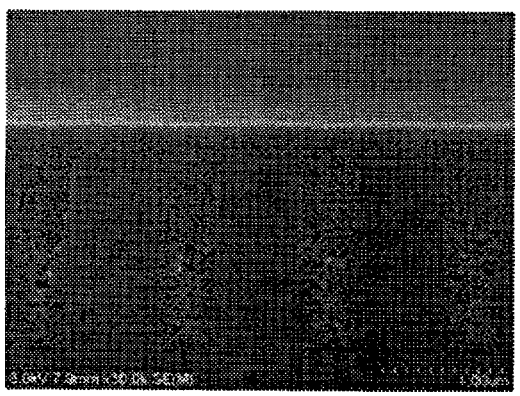
FIG. 106 is a picture showing an SEM image obtained by observing 400 nm via portions in a filling property test of Example 227.
Figure 107:
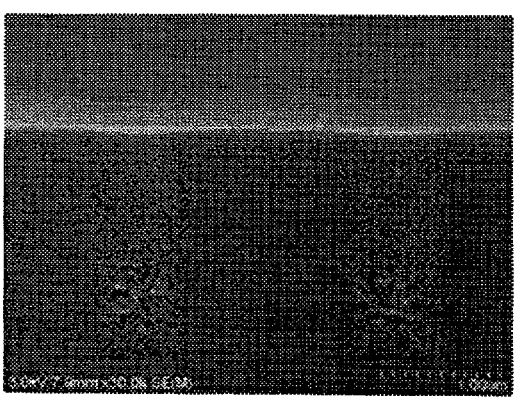
FIG. 107 is a picture showing an SEM image obtained by observing 750 nm via portions in a filling property test of Example 227.

As in Example 223, a filling property test was performed using HB-TmDA20NH2SV5 prepared in Example 198. An observed image of 400 nm via portions is shown in FIG. 106, while an observed image of 750 nm via portions is shown in FIG. 107.

Example 228

Figure 108:
FIG. 108 is a picture showing an SEM image obtained by observing 400 nm via portions in a filling property test of Example 228.
Figure 109:
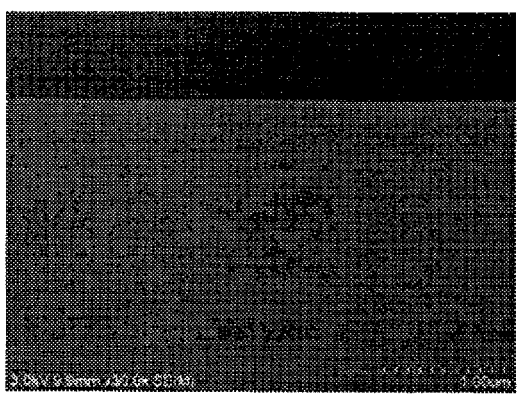
FIG. 109 is a picture showing an SEM image obtained by observing 750 nm via portions in a filling property test of Example 228.

As in Example 223, a filling property test was performed using HB-TmDA20NH2SV6 prepared in Example 199. An observed image of 400 nm via portions is shown in FIG. 108, while an observed image of 750 nm via portions is shown in FIG. 109.

Example 229

Figure 110:
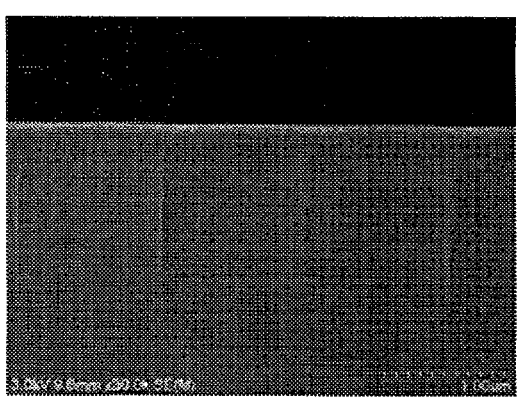
FIG. 110 is a picture showing an SEM image obtained by observing 400 nm via portions in a filling property test of Example 229.
Figure 111:
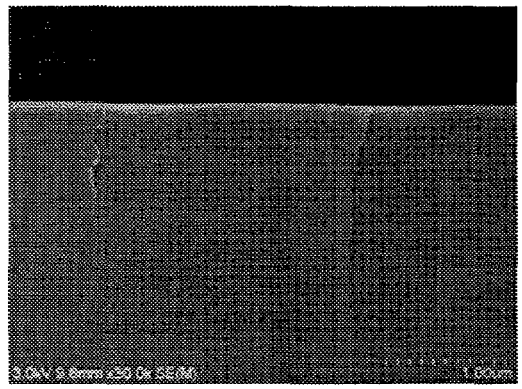
FIG. 111 is a picture showing an SEM image obtained by observing 750 nm via portions in a filling property test of Example 229.

As in Example 223, a filling property test was performed using HB-TmDA20NH2SV7 prepared in Example 200. An observed image of 400 nm via portions is shown in FIG. 110, while an observed image of 750 nm via portions is shown in FIG. 111.

Example 230

Figure 112:
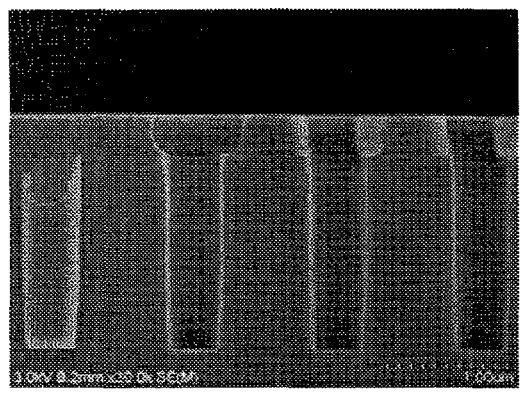
FIG. 112 is a picture showing an SEM image obtained by observing 400 nm via portions in a filling property test of Example 230.
Figure 113:
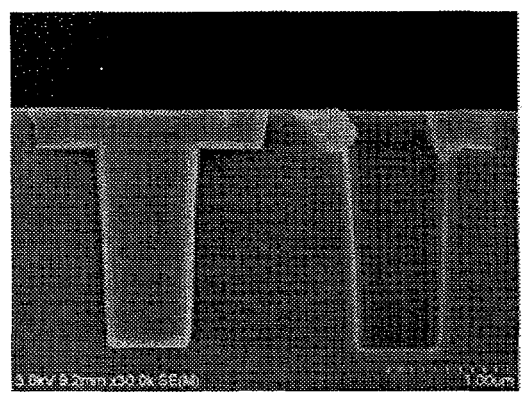
FIG. 113 is a picture showing an SEM image obtained by observing 750 nm via portions in a filling property test of Example 230.

As in Example 223, a filling property test was performed using HB-TmDA20NH2SV8 prepared in Example 201. An observed image of 400 nm via portions is shown in FIG. 112, while an observed image of 750 nm via portions is shown in FIG. 113.

Example 231

Figure 114:
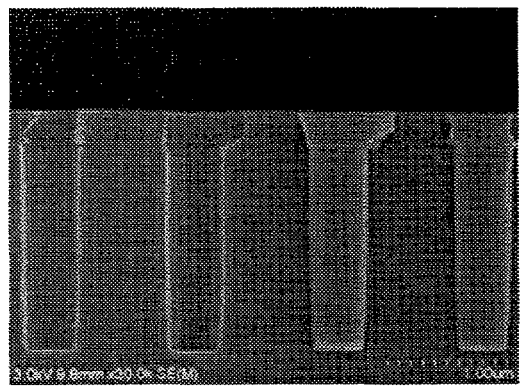
FIG. 114 is a picture showing an SEM image obtained by observing 400 nm via portions in a filling property test of Example 231.
Figure 115:
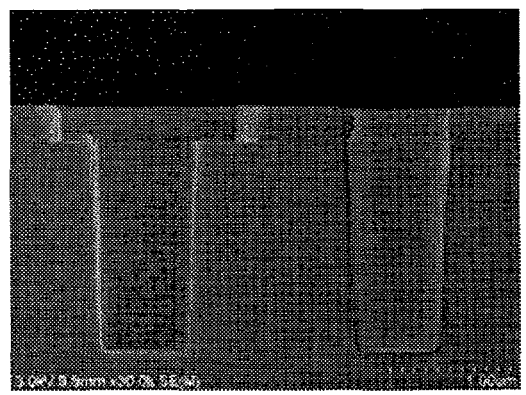
FIG. 115 is a picture showing an SEM image obtained by observing 750 nm via portions in a filling property test of Example 231.

As in Example 223, a filling property test was performed using HB-TmDA20NH2SV9 prepared in Example 202. An observed image of 400 nm via portions is shown in FIG. 114, while an observed image of 750 nm via portions is shown in FIG. 115.

Example 232

Figure 116:
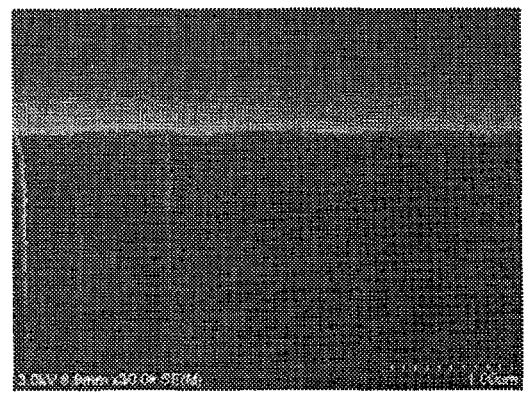
FIG. 116 is a picture showing an SEM image obtained by observing 400 nm via portions in a filling property test of Example 232.
Figure 117:
FIG. 117 is a picture showing an SEM image obtained by observing 750 nm via portions in a filling property test of Example 232.

As in Example 223, a filling property test was performed using HB-TmDA20NH2SV10 prepared in Example 203. An observed image of 400 nm via portions is shown in FIG. 116, while an observed image of 750 nm via portions is shown in FIG. 117.

As shown in FIGS. 98 to 117, it has been found that the filling property has a tendency depending on the kind of the crosslinking agent and the use of "B-5010" or "B-7075" as a crosslinking agent results in poor filling property.

On the other hand, it has been found that the use of "B-882N," "GT-401," "CELLOXIDE 2021P," "EHPE3150," "CYMEL 303," "UA-53H," "B-830," "DPHA" or "TM-BIP-A" can exhibit good filling property.

When the polymer according to the present invention is used as a planarizing material on a photodiode, light can be guided to the photodiode based on the principle of optical waveguide owing to its refractive index as high as 1.7 or higher. The current via-hole diameter can, therefore, be set at a smaller value, thereby making it possible to fabricate high-definition, solid-state imaging devices.

Further, required performance can be selectively determined depending on an intended device, thereby making it possible to control the solvent resistance, the feasibility/infeasibility of edge bead rinse, and/or the filling property. To exhibit sufficient function especially as a filling material on a photodiode of a solid-state imaging device, it is required that the solvent resistance is 100%, edge bead rinse is feasible, and the filling property is good. The use of the composition according to the present invention can meet these requirements. To exhibit sufficient function as a lens for a solid-state imaging device, on the other hand, it is required to have solvent resistance and to permit edge bead rinse. The use of the composition according to the present invention can also meet these requirements.

Example 233

Measurement of Infrared Absorption Spectrum

Figure 118:
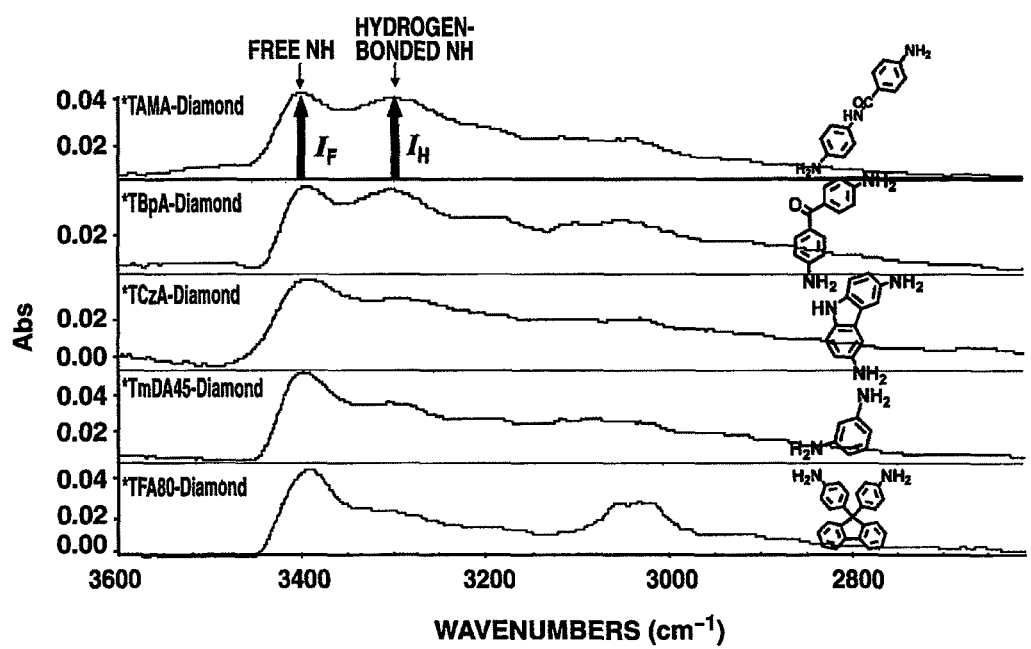
FIG. 118 is a diagram showing an infrared absorption spectrum of a polymer with modified diaminoaryl moieties in Example 233.
Figure 119:
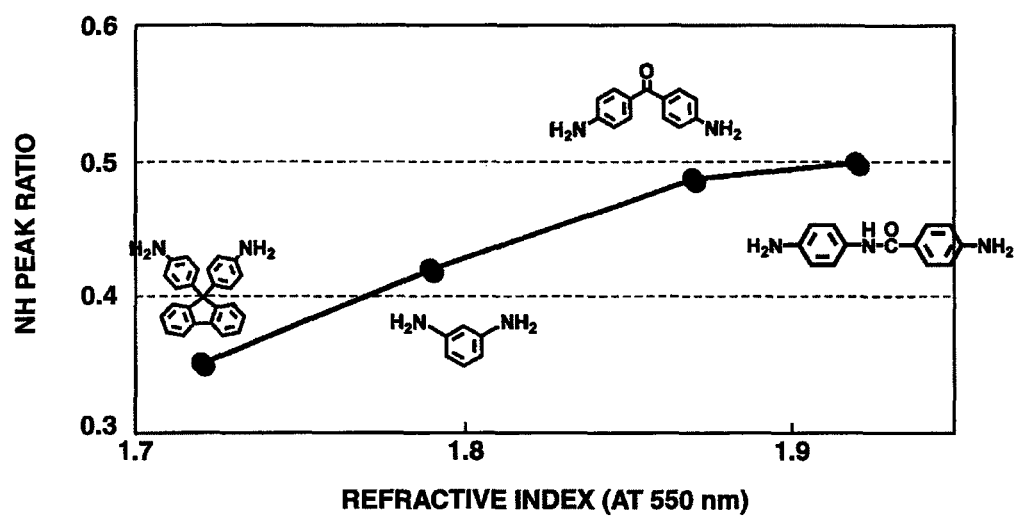
FIG. 119 is a diagram showing a correlation between NH peak ratio and refractive index in Example 233.

Infrared absorption spectra of polymers according to the present invention, diaminoaryl units of which had been modified, were measured. Described specifically, the high-molecular compound [25] (amide type) obtained in Example 95, the high-molecular compound [21] (benzophenone type) obtained in Example 86, the high-molecular compound [13] (carbazole type) obtained in Example 77, the high-molecular compound [27] (m-phenylenediamine type) obtained in Example 101 and the high-molecular compound [3] (bisaminophenylfluorene type) obtained in Example 1 were measured for infrared absorption spectrum. The results so obtained are shown in FIG. 118, and a correlation between NH peak ratio and refractive index is shown in FIG. 119.

It is to be noted that the measurement was conducted under the below-described conditions immediately after each polymer was dried at 60° C. for 6 hours in a vacuum.
Measurement instrument: "NICOLET 6700" (manufactured by Thermo Fisher Scientific K.K.); single-bounce ATR method (with a diamond head)
Cumulative scans: 64 scans Example 234

Synthesis of High-molecular Compound [17] by Concurrent Charging of Aniline

Under nitrogen and in a 200-mL, four-necked flask, p-phenylenediamine [16] (4.52 g, 0.042 mol, product of Tokyo Chemical Industry Co., Ltd.) and aniline (1.10 g, 0.012 mol) were placed, and then dissolved in DMAc (45 mL). The resulting solution was heated to 100° C. in an oil bath. Subsequently, a solution of 2,4,6-trichloro-1,3,5-triazine [1] (5.55 g, 0.03 mol, product of Tokyo Chemical Industry Co., Ltd.) in DMAc (55 mL) was added to initiate polymerization.

Thirty minutes later, aniline (7.33 g, 0.078 mol) was added further, followed by stirring for 60 minutes to terminate the polymerization. After the resultant polymerization mixture was allowed to cool to room temperature, it was reprecipitated in a mixed aqueous solution of 28% aqueous ammonia (9.1 g) and purified water (400 mL). The resulting precipitates were collected by filtration, redissolved in DMF (200 mL), and then reprecipitated in purified water (800 mL). The resulting precipitates were collected by filtration, and then dried at 120° C. for 8 hours in a vacuum dryer to obtain the target high-molecular compound [17] (hereinafter abbreviated as "HB-TpDA600," 7.58 g).

Figure 120:
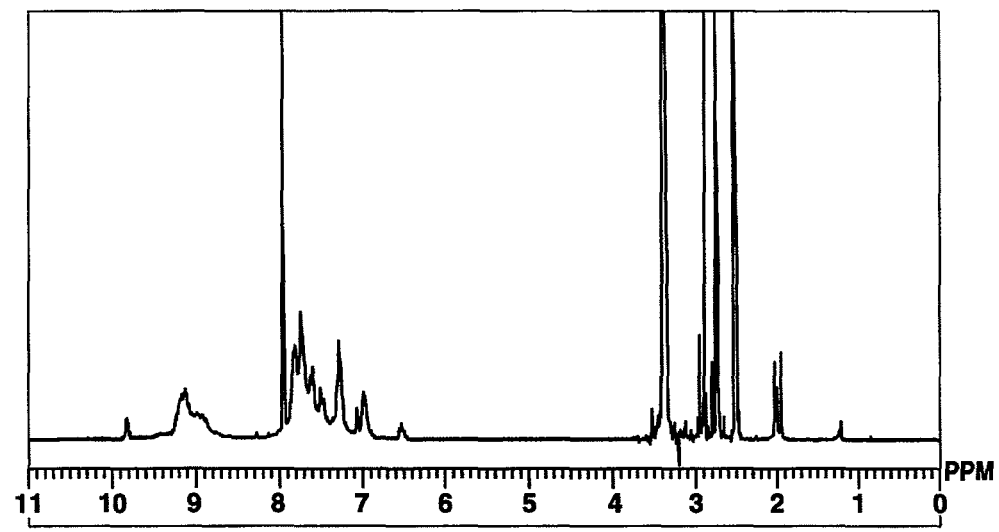

The results of $^1$H-NMR spectrum measurement of HB-TpDA600 are shown in FIG. 120. HB-TpDA600 so obtained was a compound having structural units represented by the formula (1). The weight average molecular weight Mw of HB-TpDA600 as measured by GPC and calibrated against standard polystyrene was 66,000, and the polydispersibility Mw/Mn was 60.4.

[GPC]
Instrument: "HLC-8200 GPC," manufactured by Tosoh Corporation
Column: "SHODEX OHPAK SB-803HQ+SB-804HQ"
Column temperature: 40° C.
Solvent: DMF
Detector: UV (254 nm)
Calibration curve: standard polystyrene As has been described above, the polymer according to the present invention is excellent in transparency and heat resistance, has high refractive index, and moreover, is superb in the solubility in various solvents. Therefore, the polymer according to the present invention can be applied as protective films for liquid crystal display devices, planarization films for TFT arrays, overcoat and spacer materials for color filters and the like, light extraction-enhancing films for EL displays, light intake-enhancing films for imaging devices, light retrieval-enhancing layers for LED devices, and the like.

What is claimed is:

1. A triazine ring-containing polymer characterized by comprising repeating unit structures represented by the following formula (2):

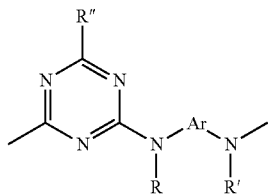
(2)

wherein R and R' independently from each other mean a hydrogen atom or an alkyl, alkoxy, aryl or aralkyl group, R" means an alkyl, aralkyl, aryl, alkylamino, alkoxysilyl-containing alkylamino, aralkylamino, arylamino, alkoxy, aralkyloxy or aryloxy group, and Ar means at least one selected from the group consisting of groups represented by the following formulas (6) to (12) and (14) to (19):

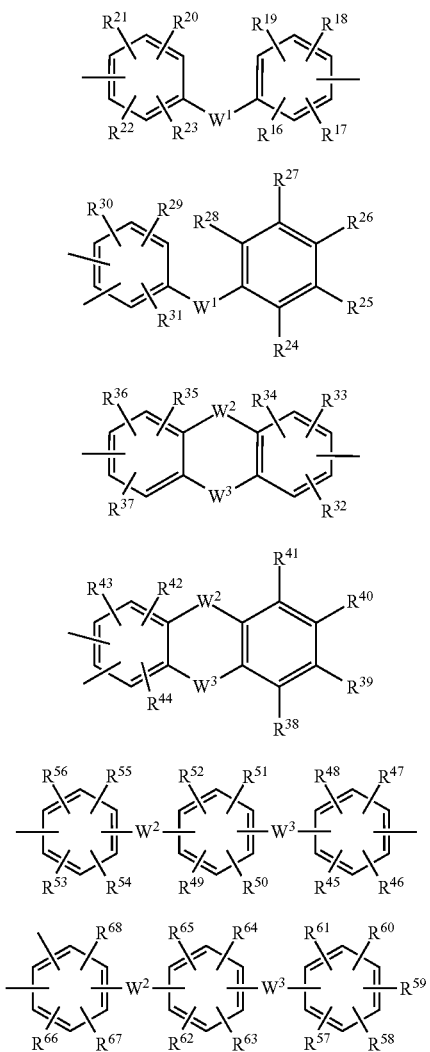

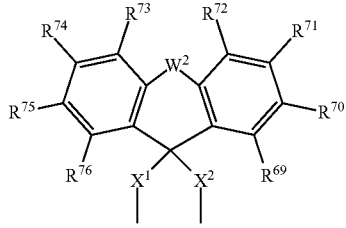
(12)

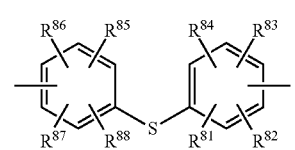
(14)

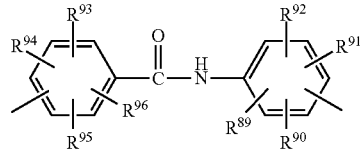
(15)

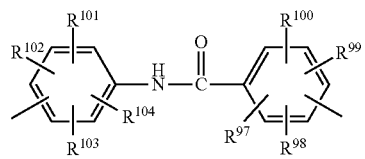
(16)

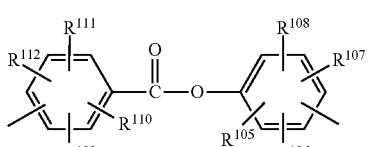
(17)

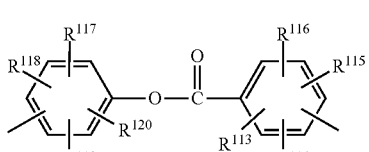
(18)

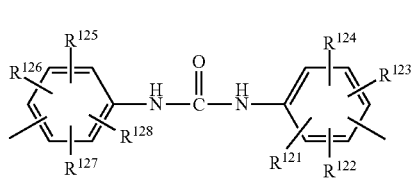
(19)

wherein $R^{16}$ to $R^{76}$ and $R^{81}$ to $R^{128}$ independently from each other mean a hydrogen or halogen atom, or a carboxyl, sulfone, branched or unbranched C1 to C10 alkyl or branched or unbranched C1 to C10 alkoxy group, $W^1$ means $NR^{129}$ in which $R^{129}$ means a hydrogen atom or a branched or unbranched C1 to C10 alkyl group, $W^2$ and $W^3$ independently from each other mean a single bond, $CR^{130}R^{131}$ in which $R^{130}$ and $R^{131}$ independently from each other mean a hydrogen atom or a branched or unbranched C1 to C10 alkyl group with a proviso that these alkyl groups may be fused together to form a ring, $C=O$, $S$, $SO$, $SO_2$, or $NR^{129}$ in which $R^{129}$ has the same meaning as defined above, $X^1$ and $X^2$ independently from each other mean a single bond, a branched or unbranched C1 to C10 alkylene group, or the following formula (20):

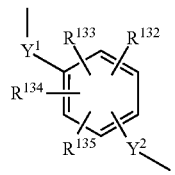

(20)

wherein $R^{132}$ to $R^{135}$ independently from each other mean a hydrogen or halogen atom, or a carboxyl, sulfone, branched or unbranched C1 to C10 alkyl or branched or unbranched C1 to C10 alkoxy group, and $Y^1$ and $Y^2$ independently from each other mean a single bond, or a branched or unbranched C1 to C10 alkylene group.

2. The triazine ring-containing polymer of claim 1, wherein Ar is at least one selected from the group consisting of the groups represented by the formulas (6) to (12).

3. The triazine ring-containing polymer of claim 1, wherein Ar is at least one selected from the group consisting of the groups represented by the formulas (8), (9) and (12).

4. The triazine ring-containing polymer of claim 1, wherein Ar is at least one selected from the group consisting of the groups represented by the formulas (6) and (15) to (19).

5. The triazine ring-containing polymer of claim 1, wherein Ar is represented by the following formula (21) or (22):

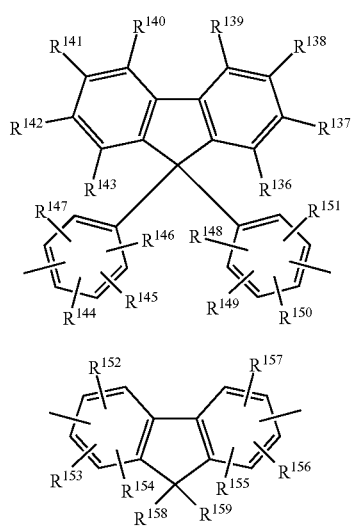

(21)

(22)

wherein $R^{136}$ to $R^{159}$ independently from each other mean a hydrogen or halogen atom, a carboxyl or sulfone group, a branched or unbranched C1 to C10 alkyl group with a proviso that $R^{158}$ and $R^{159}$ may be fused together to form a ring, or a branched or unbranched C1 to C10 alkoxy group.

6. The triazine ring-containing polymer of claim 1, wherein the repeating unit structures are represented by the following formula (24):

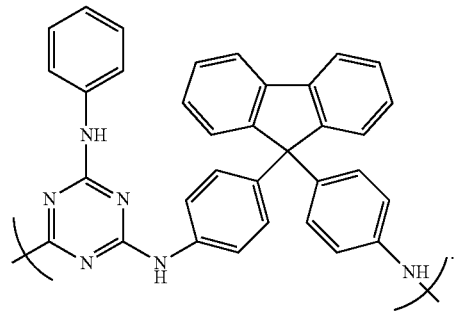

(24)

7. The triazine ring-containing polymer according to any one of claims 1 to 6, wherein at least one end thereof is capped by alkyl, aralkyl, aryl, alkylamino, alkoxysilyl-containing alkylamino, aralkylamino, arylamino, alkoxy, aralkyloxy, aryloxy or ester groups.

8. The triazine ring-containing polymer of claim 7, comprising at least one terminal triazine ring, which is capped by alkyl, aralkyl, aryl, alkylamino, alkoxysilyl-containing alkylamino, aralkylamino, arylamino, alkoxy, aralkyloxy, aryloxy or ester groups.

9. A film-forming composition comprising the triazine ring-containing polymer according to claim 1.

10. A film comprising the triazine ring-containing polymer according to claim 1.

11. An electronic device provided with a substrate and the film of claim 10 formed on the substrate.

12. An optical member provided with a substrate and the film of claim 10 formed on the substrate.

13. A solid-state imaging device comprising a charge-coupled device or complementary metal oxide film semiconductor provided with at least one film of claim 10.

14. A solid-state imaging device provided with the film of claim 10 as a planarization layer on a color filter.

* * * * *